US012493045B2

(12) United States Patent
Wang et al.

(10) Patent No.: US 12,493,045 B2
(45) Date of Patent: Dec. 9, 2025

(54) MULTI-TARGET CROSSLINKERS AND USES THEREOF

(71) Applicant: The Regents of the University of California, Oakland, CA (US)

(72) Inventors: Lei Wang, San Francisco, CA (US); Bing Yang, San Francisco, CA (US); Haifan Wu, San Francisco, CA (US); William DeGrado, San Francisco, CA (US); Jun Liu, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 1203 days.

(21) Appl. No.: 17/281,179

(22) PCT Filed: Oct. 2, 2019

(86) PCT No.: PCT/US2019/054336
§ 371 (c)(1),
(2) Date: Mar. 29, 2021

(87) PCT Pub. No.: WO2020/072674
PCT Pub. Date: Apr. 9, 2020

(65) Prior Publication Data

US 2022/0107327 A1 Apr. 7, 2022

Related U.S. Application Data

(60) Provisional application No. 62/740,079, filed on Oct. 2, 2018.

(51) Int. Cl.

| | |
|---|---|
| ***G01N 33/68*** | (2006.01) |
| ***C07D 207/46*** | (2006.01) |
| ***C07D 295/192*** | (2006.01) |

(52) U.S. Cl.
CPC ....... *G01N 33/6845* (2013.01); *C07D 207/46* (2013.01); *C07D 295/192* (2013.01); *G01N 33/6848* (2013.01)

(58) Field of Classification Search
None
See application file for complete search history.

(56) References Cited

U.S. PATENT DOCUMENTS

| | | | |
|---|---|---|---|
| 2020/0010411 | A1 | 1/2020 | Wang et al. |
| 2021/0002325 | A1 | 1/2021 | Wang et al. |
| 2022/0371986 | A1 | 11/2022 | Wang |

OTHER PUBLICATIONS

Aoki, T. et al. (2014). "Bi-functional cross-linking reagents efficiently capture protein-DNA complexes in *Drosophila* embryos," *Fly* (*Austin*) 8(1):43-51.

(Continued)

*Primary Examiner* — Xiaoyun R Xu
(74) *Attorney, Agent, or Firm* — Mintz, Levin, Cohn, Ferris, Glovsky and Popeo, P.C.

(57) ABSTRACT

Disclosed herein, inter alia, are compositions and methods for cross-linking biomolecules. In an aspect is provided a method of detecting a covalently conjugated molecule, the method including i) contacting a first biomolecule and a second biomolecule with a crosslinking agent to form a covalently conjugated biomolecule; ii) identifying a first point of attachment of the crosslinking agent to the first biomolecule using mass spectroscopy; and iii) identifying a second point of attachment of the crosslinking agent to the second biomolecule using mass spectroscopy; thereby detecting a covalently conjugated molecule.

30 Claims, 55 Drawing Sheets

Specification includes a Sequence Listing.

NHSF

(56) References Cited

OTHER PUBLICATIONS

Bai, W-J. et al. (Dec. 16, 2014). "The domestication of ortho-quinone methides," *Acc Chem Res* 47(12):3655-3664.
Brodie, N.I. et al. (Apr. 6, 2015). "Isotopically-coded short-range hetero-bifunctional photo-reactive crosslinkers for studying protein structure," *J Proteomics* 118:12-20.
Chavez, J.D. et al. (Feb. 2019). "Chemical cross-linking with mass spectrometry: a tool for systems structural biology," *Curr Opin Chem Biol* 48:8-18.
Chen, X-H. et al. ((Sep. 19, 2014). "Genetically encoding an electrophilic amino acid for protein stapling and covalent binding to native receptors," *ACS Chem Biol* 9(9):1956-1961.
Devaraj, N.K. (Aug. 22, 2018). "The Future of Bioorthogonal Chemistry," *ACS Cent Sci* 4(8):952-959.
Dong, J. et al. (Sep. 1, 2014). "Sulfur(VI) fluoride exchange (SuFEx): another good reaction for click chemistry," *Angew Chem Int Ed Engl* 53(36):9430-9448.
Götze, M. et al. (Jan. 2012). "StavroX—a software for analyzing crosslinked products in protein interaction studies," *J Am Soc Mass Spectrom* 23(1):76-87.
Gutierrez, C.B. et al. (Aug. 16, 2016). "Developing an Acidic Residue Reactive and Sulfoxide-Containing MS-Cleavable Homobifunctional Cross-Linker for Probing Protein-Protein Interactions," *Anal Chem* 88(16):8315-22.
Herzog, F. et al. (Sep. 14, 2012). "Structural probing of a protein phosphatase 2A network by chemical cross-linking and mass spectrometry," *Science* 337(6100):1348-1352.
Hoffman, E.A. et al. (Oct. 30, 2015). "Formaldehyde crosslinking: a tool for the study of chromatin complexes," *J Biol Chem* 290(44):26404-26411.
Hoppmann, C. et al. (Apr. 14, 2016). "Proximity-enabled bioreactivity to generate covalent peptide inhibitors of p53-Mdm4," *Chem Commun* 52(29):5140-5143.
Hoppmann, C. et al. (Sep. 9, 2015). "In Situ Formation of an Azo Bridge on Proteins Controllable by Visible Light," *J Am Chem Soc* 137(35):11218-11221.
International Search Report mailed on Feb. 6, 2020, for PCT Application No. PCT/US2019/054336, filed Oct. 2, 2019, 9 pages.
Leitner, A. et al. (Jul. 1, 2014). Chemical cross-linking/mass spectrometry targeting acidic residues in proteins and protein complexes *PNAS USA* 111(26):9455-9460.
Liu, J. et al. (Jun. 19, 2019). "Genetically Encoding Photocaged Quinone Methide to Multitarget Protein Residues Covalently in Vivo," *J Am Chem Soc* 141(24):9458-9462.
Lossl, P. et al. (2016). "Combining Amine-Reactive Cross-Linkers and Photo-Reactive Amino Acids for 3D-Structure Analysis of Proteins and Protein Complexes," *Methods Mol Biol* 1394:109-127.
Lu, S. et al. (Apr. 2015). "Mapping native disulfide bonds at a proteome scale," *Nat Methods* 12(4):329-331.
Merkley, E.D. et al. (Jun. 2014). "Distance restraints from crosslinking mass spectrometry: mining a molecular dynamics simulation database to evaluate lysine-lysine distances," *Protein Sci* 23(6):747-759.
Mikkelsen, R.B. et al. (Dec. 10, 1976). "Photoactivated cross-linking of proteins within the erythrocyte membrane core," *J Biol Chem* 251(73):7413-7416.
Mukherjee, H. et al. (Nov. 22, 2017). "A study of the reactivity of S (VI)-F containing warheads with nucleophilic amino-acid side chains under physiological conditions," *Org Biomol Chem* 15(45):9685-9695.
Narayanan, A. et al. (May 1, 2015). "Sulfonyl fluorides as privileged warheads in chemical biology," 6(5):2650-2659.
Novak, P. et al. (2008). "Intra-molecular cross-linking of acidic residues for protein structure studies," *Eur J Mass Spectrom* 14(6):355-365.
Nowak, D.E. et al. (Nov. 2005). "Two-step cross-linking method for identification of NF-κb gene network by chromatin immunoprecipitation," *Biotechniques* 39(5):715-725.
Santi, D.V. et al. (1974). "Peptidyl-tRNA analogs as affinity labeling agents," *Methods of Enzymology* 29:695-706.
Shi, Y. et al. (Dec. 2015). "A strategy for dissecting the architectures of native macromolecular assemblies," *Nat Methods* 12(12):1135-1138.
Sinz, A. (May 28, 2018). "Cross-Linking/Mass Spectrometry for Studying Protein Structures and Protein-Protein Interactions: Where Are We Now and Where Should We Go from Here?," *Angew Chem Int Ed Engl* 57(22):6390-6396.
Steen, H. et al. (Oct. 2001). "Mass spectrometric analysis of a UV-cross-linked protein-DNA complex: tryptophans 54 and 88 of *E. coli* SSB cross-link to DNA," *Protein Sci* 10(10):1989-2001.
Suchanek, M. et al. (Apr. 2005). "Photo-leucine and photo-methionine allow identification of protein-protein interactions in living cells," *Nat Methods* 2(4):261-267.
Wang, L. (Sep. 25, 2017). "Genetically encoding new bioreactivity," *N Biotechnol* 38(Pt A):16-25.
Wang, N. et al. (Apr. 18, 2018). "Genetically Encoding Fluorosulfate-l-tyrosine To React with Lysine, Histidine, and Tyrosine via SuFEx in Proteins in Vivo," *J Am Chem Soc* 140(15):4995-4999.
Woltjer, R.L. et al. (Aug. 18, 1992). "High-yield covalent attachment of epidermal growth factor to its receptor by kinetically controlled, stepwise affinity cross-linking," *Biochemistry* 31(32):7341-7346.
Written Opinion mailed on Feb. 6, 2020, for PCT Application No. PCT/US2019/054336, filed Oct. 2, 2019, 11 pages.
Xiang, Z. et al. (Sep. 2013). "Adding an unnatural covalent bond to proteins through proximity-enhanced bioreactivity," *Nat Methods* 10(9):885-888.
Xiang, Z. et al. (Feb. 17, 2014). "Proximity-enabled protein crosslinking through genetically encoding haloalkane unnatural amino acids," *Angew Chem Int Ed Engl* 53(8):2190-2193.
Xuan, W. et al. (Apr. 24, 2017). "Protein Crosslinking by Genetically Encoded Noncanonical Amino Acids with Reactive Aryl Carbamate Side Chains," *Angew Chem Int Ed Engl* 56(18):5096-5100.
Yang, B. et al. (Sep. 2012). "Identification of cross-linked peptides from complex samples," *Nat Methods* 9(9):904-906.
Yang, B. et al. (Dec. 21, 2017). "Spontaneous and specific chemical cross-linking in live cells to capture and identify protein interactions," *Nat Commun* 8(1):2240.
Yang, B. et al. (Oct. 30, 2018). "Proximity-enhanced SuFEx chemical cross-linker for specific and multitargeting cross-linking mass spectrometry," *PNAS USA* 115(44):11162-11167.
Young, M.M. et al. (May 23, 2000). "High throughput protein fold identification by using experimental constraints derived from intramolecular cross-links and mass spectrometry," *PNAS USA* 97(11):5802-5806.
Yu, C. et al. (Jan. 2, 2018). "Cross-Linking Mass Spectrometry: An Emerging Technology for Interactomics and Structural Biology," *Anal Chem* 90(1):144-165.

NHSF

BS2G

NHSF

| Accession # | Gene | Description | **Cross-linked peptides** (cross-linked sites underlined) |
|---|---|---|---|
| P43319 | yraK | Uncharacterized fimbrial-like protein | MSDKIIHLTDDSFDTDVLK - GAWVDGMGSPSTGDFHDLVK |
| P36566 | cmoM | tRNA 5-carboxymethoxyuridine methyltransferase | MSDKIIHLTDDSFDTDVLK - YCRQEPYITLGR |
| P16918 | rhsC | May involved in natural ecology of cell | EAAGEFSGEITGVTDGAGRHFR - SDKIIHLTDDSFDTDVLK |
| C4ZUA4 | menC | o-succinylbenzoate synthase | GIPTLLLFKNGEVAATK - EKVAK |
| P55138 | ygcE | Uncharacterized sugar kinase YgcE | GIPTLLLFKNGEVAATK - GYGIR |
| P0AGA2 | secY | Protein translocase subunit | GIPTLLLFKNGEVAATK - KANLK |
| P0AGC3 | slt | Soluble lytic murein transglycosylase | NGEVAATK - DLFKR |

FIG. 6B

| No. | Cross-linked site | Cross-linked peptides (Cross-linked residues underlined) | Cα-Cα distance (Å) |
| --- | --- | --- | --- |
| 1 | $14\text{-}3\text{-}3^{15}\text{-}14\text{-}3\text{-}3^{74}$ | LAEQAER(4)-VVSSIEQKTEGAEKK(14) | 18.0 |
| 2 | $14\text{-}3\text{-}3^{68}\text{-}14\text{-}3\text{-}3^{75}$ | VVSSIEQKTEGAEKK(8)-KQQMAR(1) | 11.2 |
| 3 | $14\text{-}3\text{-}3^{66}\text{-}14\text{-}3\text{-}3^{75}$ | VVSSIEQKTEGAEKK(6)-KQQMAR(1) | 8.3 |
| 4 | $14\text{-}3\text{-}3^{57}\text{-}14\text{-}3\text{-}3^{138}$ | SSWRVVSSIEQKTEGAEKK(1)-YLAEVAAGDDKK(11) | 20.0 |
| 5 | $14\text{-}3\text{-}3^{56}\text{-}14\text{-}3\text{-}3^{139}$ | NVVGARRSSWRVVSSIEQK(17)-KGIVDQSQQAYQEAFEISK(1) | 23.7 |
| 6 | $14\text{-}3\text{-}3^{102}\text{-}14\text{-}3\text{-}3^{122}$ | IETELRDICNDVLSLLEK(17)-MKGDYYRYLAEVAAGDDKK(2) | 8.7 |
| 7 | $14\text{-}3\text{-}3^{56}\text{-}14\text{-}3\text{-}3^{139}$ | NVVGARRSSWRVVSSIEQK(7)-KGIVDQSQQAYQEAFEISK(1) | 19.8 |
| 8 | $14\text{-}3\text{-}3^{9}\text{-}14\text{-}3\text{-}3^{59}$ | NELVQKAK(6)-NVVGAR(1) | 16.8 |

FIG. 10A

NHQM3C

| No. | Cross-linked site | Cross-linked peptides (Cross-linked residues underlined) | Cα-Cα distance (Å) |
|---|---|---|---|
| 1 | 14-3-3$^{67}$-14-3-3$^{122}$ | VVSSIEQK(7)-MKGDYYR(2) | 29.7 |
| 2 | 14-3-3$^{73}$-14-3-3$^{122}$ | TEGAEK(5)-MKGDYYR(2) | 37.7 |
| 3 | 14-3-3$^{11}$-14-3-3$^{69}$ | AKLAEQAER(2)-TEGAEK(1) | 14.6 |
| 4 | 14-3-3$^{11}$-14-3-3$^{149}$ | AKLAEQAER(2)-GIVDQSQQAYQEAFEISK(10) | 29.3 |
| 5 | 14-3-3$^{69}$-14-3-3$^{85}$ | TEGAEK(1)-EKIETELR(2) | 18.8 |
| 6 | 14-3-3$^{22}$-14-3-3$^{75}$ | LAEQAERYDDMAACMK(11)-KQQMAR(1) | 16.4 |
| 7 | 14-3-3$^{11}$-14-3-3$^{136}$ | AKLAEQAER(2)-YLAEVAAGDDK(9) | 32.2 |
| 8 | 14-3-3$^{11}$-14-3-3$^{14}$ | AKLAEQAER(2)-AKLAEQAER(5) | 29.1 |

FIG. 13A (HoQM)

(NHQM)

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION

<400> SEQUENCE: 1

Ala Ala Ala Lys Ala Ala Arg
1               5


<210> SEQ ID NO 2
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 2

gttgttcata tgaaattgtt ctacaaaccg ggtgcctgc                            39
```

<210> SEQ ID NO 3
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 3
gttgttaagc ttttaatggt gatggtgatg gtgctttaag ccttccgctg acag 54

<210> SEQ ID NO 4
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 4
tgtagctgtt gatctaagtt gtagctgttg atctaagttg tagctgttga tctaagt 57

<210> SEQ ID NO 5
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 5
aattcgccaa tgacaagacg ctgggcgggg ccggatccat catcatcatc tagaagct 58

<210> SEQ ID NO 6
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 6
gttgttcata tggataaaaa tgaactagta caaaaggcta agttg 45

<210> SEQ ID NO 7
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 7
gttgttaagc ttttagtgat ggtgatggtg atggttttca ccaccctcac ccgcctc 57

<210> SEQ ID NO 8
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 8
catatggata aaaatgaact agtacaaaag gctaagcagc agcgtcaagc tgagcgctac 60

<210> SEQ ID NO 9
<211> LENGTH: 40
<212> TYPE: DNA
<213> ORGANISM: Artificial Sequence
<220> FEATURE:
<223> OTHER INFORMATION: Synthetic polynucleotide -continued

<400> SEQUENCE: 9
gttgttaagc ttgccaccat ggataaaaat gaactagtac 40

<210> SEQ ID NO 10
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 10
ggtggtctcg agttagtgat ggtgatggtg atggttttca c 41

MULTI-TARGET CROSSLINKERS AND USES THEREOF

CROSS-REFERENCES TO RELATED APPLICATIONS

This application is the national stage filing under 35 U.S.C. § 371 of International Application No. PCT/US2019/054336 filed Oct. 2, 2019, which claims the benefit of U.S. Provisional Application No. 62/740,079, filed Oct. 2, 2018, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. R01 GM118384, R35 GM122603, and MI 14079 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-627N01US_Sequence_Listing_ST25.txt, created Mar. 22, 2021, 2,413 bytes, machine format IBM-PC, MS Windows operating system, is hereby incorporated by reference.

BACKGROUND

Chemical cross-linking mass spectrometry is a powerful method to identify protein interaction partners. The cross-links also provide approximate inter-residue distances, which can help model the structures of complexes. However, current cross-linking reagents react with only a limited set of amino acid residues and their very high reactivity can induce cross-links between sites that are distant in the native state of the interrogated proteins. Chemical cross-linking mass spectrometry (CXMS) is being increasingly used to study protein assemblies and complex protein interaction networks. Existing CXMS chemical crosslinkers target only Lys, Cys, Glu, and Asp residues, limiting the information measurable. Described herein, inter alia, are solutions to these and other problems in the art.

BRIEF SUMMARY

In an aspect is provided a method of detecting a covalently conjugated molecule, the method including i) contacting a first biomolecule and a second biomolecule with a crosslinking agent to form a covalently conjugated biomolecule; ii) identifying a first point of attachment of the crosslinking agent to the first biomolecule using mass spectroscopy; and iii) identifying a second point of attachment of the crosslinking agent to the second biomolecule using mass spectroscopy; thereby detecting a covalently conjugated molecule. The crosslinking agent has the formula: $R^1$-$L^1$-$R^2$ (I). $R^1$ is a bioconjugate reactive moiety capable of bonding to the first biomolecule. $R^2$ is a proximity enhanced bioconjugate reactive moiety capable of bonding to the second biomolecule. $L^1$ is a covalent linker. The bonding reactivity of $R^1$ with the first molecule is greater than the bonding reactivity of $R^2$ with the second biomolecule.

In an aspect is provided a method of detecting a covalently conjugated biomolecule, the method including i) contacting a first biomolecule and a second biomolecule with a crosslinking agent to form the covalently conjugated biomolecule; ii) identifying a first point of attachment of the crosslinking agent to the first biomolecule; and iii) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a bioconjugate reactive moiety; $R^2$ is a proximity enhanced bioconjugate reactive moiety; $L^1$ is a covalent linker; and the bonding reactivity of $R^1$ with the first biomolecule is greater than the bonding reactivity of $R^2$ with the second biomolecule.

In an aspect is provided a method of detecting an intramolecular crosslinked protein, the method including: i) contacting the protein with a crosslinking agent, wherein the crosslinking agent bonds to a first amino acid of the protein and a second amino acid of the protein to form the intramolecular crosslinked protein; ii) identifying a first point of attachment of the crosslinking agent to the protein using mass spectroscopy; and iii) identifying a second point of attachment of the crosslinking agent to the protein using mass spectroscopy. The crosslinking agent has the formula: $R^1$-$L^1$-$R^2$ (I). $R^1$ is a bioconjugate reactive moiety capable of bonding with the first amino acid. $R^2$ is a proximity enhanced bioconjugate reactive moiety capable of bonding with the second amino acid. $L^1$ is a covalent linker. The bonding reactivity of $R^1$ with the first amino acid is greater than the bonding reactivity of $R^2$ with the second amino acid.

In an aspect is provided a method of detecting an intramolecular crosslinked protein, the method including: i) contacting the protein with a crosslinking agent, wherein the crosslinking agent bonds to a first amino acid of the protein and a second amino acid of the protein to form the intramolecular crosslinked protein; ii) identifying a first point of attachment of the crosslinking agent to the protein; and iii) identifying a second point of attachment of the crosslinking agent to the protein and thereby detecting the intramolecular crosslinked protein. The crosslinking agent has the formula: $R^1$-$L^1$-$R^2$ (I); wherein $R^1$ is a bioconjugate reactive moiety; $R^2$ is a proximity enhanced bioconjugate reactive moiety; $L^1$ is a covalent linker; and the bonding reactivity of $R^1$ with the first amino acid is greater than the bonding reactivity of $R^2$ with the second amino acid.

In an aspect is provided a method of detecting a covalently conjugated biomolecule including a first biomolecule conjugated to a second biomolecule, the method including i) contacting the first biomolecule with a crosslinking agent to form an activated biomolecule; ii) contacting the activated biomolecule with radiation in the presence of the second biomolecule thereby forming the covalently conjugated biomolecule; iii) identifying a first point of attachment of the crosslinking agent to the first biomolecule; and iv) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a bioconjugate reactive moiety; $R^2$ is a photo-activated bioconjugate reactive moiety; $L^1$ is a covalent linker; and the bonding reactivity of $R^2$ with the second biomolecule after contact of $R^2$ with radiation is greater than the bonding reactivity of $R^2$ with the second biomolecule prior to contact of $R^2$ with radiation.

In an aspect is provided a method of detecting a covalently conjugated biomolecule including a first biomolecule conjugated to a second biomolecule, the method including i)

contacting a crosslinking agent with a first radiation in the presence of the first biomolecule, thereby forming an activated biomolecule; ii) contacting the activated biomolecule with an optionally different second radiation in the presence of the second biomolecule thereby forming a covalently conjugated biomolecule; (iii) identifying a first point of attachment of the crosslinking agent to the first biomolecule; and iv) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a first photo-activated bioconjugate reactive moiety; $R^2$ is a second photo-activated bioconjugate reactive moiety; $L^1$ is a covalent linker; the bonding reactivity of $R^1$ with the first biomolecule after contact of $R^1$ with the first radiation is greater than the bonding reactivity of $R^1$ with the first biomolecule prior to contact of $R^1$ with the first radiation; and the bonding reactivity of $R^2$ with the second biomolecule after contact of $R^2$ with the second radiation is greater than the bonding reactivity of $R^2$ with the second biomolecule prior to contact of $R^2$ with the second radiation.

In an aspect is provided a crosslinking agent having the formula: $R^1$-$L^1$-$R^2$ (I). $R^1$ is a bioconjugate reactive moiety capable of bonding to a first biomolecule. $R^2$ is a proximity enhanced bioconjugate reactive moiety capable of bonding to a second biomolecule or a second location of the first biomolecule. $L^1$ is a covalent linker. The bonding reactivity of $R^1$ with the first molecule is greater than the bonding reactivity of $R^2$ with the second biomolecule or second location of the first biomolecule.

In an aspect is provided a crosslinking agent having the formula: $R^1$-$L^1$-$R^2$ wherein $R^1$ is a bioconjugate reactive moiety; $R^2$ is a proximity enhanced bioconjugate reactive moiety; $L^1$ is a covalent linker; and the bonding reactivity of $R^1$ with a first biomolecule is greater than the bonding reactivity of $R^2$ with a second biomolecule or second location of the first biomolecule.

In an aspect is provided a crosslinking agent having the formula: $R^1$-$L^1$-$R^2$ (I); wherein $R^1$ is a bioconjugate reactive moiety; $R^2$ is a photo-activated bioconjugate reactive moiety; $L^1$ is a covalent linker; and the bonding reactivity of $R^2$ with a second biomolecule after contact of $R^2$ with radiation is greater than the bonding reactivity of $R^2$ with the second biomolecule prior to contact of $R^2$ with radiation.

In an aspect is provided a crosslinking agent having the formula: $R^1$-$L^1$-$R^2$ (I); wherein $R^1$ is a first photo-activated bioconjugate reactive moiety; $R^2$ is a second photo-activated bioconjugate reactive moiety; $L^1$ is a covalent linker; the bonding reactivity of $R^1$ with a first biomolecule after contact of $R^1$ with radiation is greater than the bonding reactivity of $R^1$ with the first biomolecule prior to contact of $R^1$ with radiation; and the bonding reactivity of $R^2$ with a second biomolecule after contact of $R^2$ with radiation is greater than the bonding reactivity of $R^2$ with the second biomolecule prior to contact of $R^2$ with radiation.

BRIEF DESCRIPTION OF THE DRAWINGS

(FIG. 1A) The plant-and-cast strategy. (FIG. 1B) Structure of NHSF. (FIG. 1C) NHSF cross-links Lys with various nucleophilic residues via proximity-enhanced SuFEx reaction for CXMS.

(FIG. 2A) Structures of BS2G and NHSF. Mass spectra of peptide 7KR (Ac-AAAKAAR (SEQ ID NO:1)) (FIG. 2B), BS2G treated 7KR (Ac-AAAKAAR (SEQ ID NO:1)) (FIG. 2C), and NHSF treated 7KR (Ac-AAAKAAR (SEQ ID NO:1)) (FIG. 2D).

(FIG. 3A) Total number of identified cross-linked peptides from BS2G or NHSF cross-linked BSA. (FIG. 3B) New types of cross-linking sites identified from the NHSF cross-linked BSA sample, with numbers indicated on top. (FIG. 3C) Distribution of Cα-Cα distance of cross-linked residues from BSA samples (left column in each pair is BS2GT and right column in each pair (except >25) is NHSF). (FIG. 3D) Identified cross-links mapped onto the crystal structures of BSA (PDB 3V03). The Cα-Cα distances of cross-links are color-coded.

(FIG. 4A) SDS-PAGE (left) and Western blot (right) analyses of GST cross-linking. (FIG. 4B) Total number of identified cross-linked peptides from BS2G or NHSF cross-linked GST. (FIG. 4C) New types of cross-linking sites identified from the NHSF cross-linked GST sample, with numbers indicated on top. Nt represents N-terminal $NH_2$. (FIG. 4D) Distribution of Cα-Cα distance of cross-linked residues from GST samples (5-10 column (3), 10-15 column (2), and 15-20 column (4) are NGSF, others BS2G). (FIG. 4E) Identified cross-links mapped onto the crystal structures of GST (PDB 1N2A). The Cα-Cα distances of cross-links are color-coded.

(FIG. 5A) Total number of identified cross-linked peptides. (FIG. 5B) Types and numbers of cross-links identified from the NHSF-treated sample. Nt represents N-terminal $NH_2$. (FIG. 5C-5G) Representative tandem mass spectra for each cross-link generated by NHSF.

FIGS. 6A-6B. GECX followed by NHSF cross-linking increases the number of identifiable cross-linked proteins. (FIG. 6A) Scheme showing the combined procedures for identifying Trx-interacting proteins in *E. coli* cells. (FIG. 6B) Seven new Trx-interacting proteins identified with NHSF cross-linking.

(FIG. 7A) Scheme showing NHQM structure and photo-controlled crosslinking mechanism. Upon UV activation, a highly reactive ortho-quinone methide was generated capable of reacting with multiple nucleophilic amino acids. (FIG. 7B) Protein 14-3-3 forms a homodimer (PDB code: 4N7Y). (FIG. 7C) SDS-PAGE analysis of 14-3-3 dimeric crosslinking by NHQM. (FIG. 7D) SDS-PAGE analysis of NHQM-mediated dimeric crosslinking of 14-3-3 with different UV exposure time.

(FIGS. 9A-9B) Scheme showing that NHQM should crosslink the WT 14-3-3 dimer into a covalent dimeric form, but not the monomeric QQR mutant, which can be distinguished readily on SDS-PAGE or Western. (FIG. 9C) Titration of the NHQM amount required for crosslinking 14-3-3 WT in vitro on SDS-PAGE. (FIG. 9D) Under the same conditions in FIG. 9C, NHQM didn't crosslink 14-3-3(QQR) mutant into dimeric form, as observed by SDS-PAGE. (FIG. 9E) Titration of the NHQM amount required for crosslinking 14-3-3 WT in *E. coli* cell lysate. 14-3-3 was detected using Western blot with an anti-His×6 antibody. (FIG. 9F) Under the same conditions in FIG. 9E, NHQM did not crosslink 14-3-3 (QQR) mutant into dimeric form detected using Western blot.

FIGS. 10A-10C. NHQM and NHQM3C multi-target a total of ten nucleophilic amino acid residues in protein crosslinking. (FIG. 10A) CXMS analysis of WT 14-3-3 crosslinked by NHQM. (FIG. 10B) Representative tandem mass spectrum for crosslinked peptide showing crosslinking of Lys with Gln. Others are shown in FIGS. 11A-11E and FIG. 13. (FIG. 10C) Structure of crosslinker NHQM3C and its crosslinking mechanism.

FIGS. 13A-13G. NHQM3C crosslinked multiple nucleophilic residues when crosslinking the WT 14-3-3 protein into dimeric form. (FIG. 13A) CXMS analysis of WT 14-3-3 protein crosslinked by NHQM3C, showing the crosslinked sites, residues, and their Cα-Ca distance. (FIGS. 13B-13G) Tandem mass spectra for crosslinked peptides identified from NHQM3C-crosslinked WT 14-3-3 protein, showing crosslinking of Lys with Met, Glu, Thr, Tyr, Glu, Asp, respectively.

(FIG. 18A) Schematic show of NHQM-mediated EGFR dimeric crosslinking upon UV activation. (FIG. 18B) Western blot analysis showed that EGFR dimeric crosslinking was detected only in the presence of NHQM and UV activation.

(FIG. 19A) Scheme showing HoQM structure and crosslinking mechanism. Upon UV activation, o-QM was generated at both ends of the crosslinker to react with nucleophilic amino acids. (FIG. 19B) Western blot analysis of HoQM mediated 14-3-3 crosslinking in *E. coli* cells. (FIG. 19C) Western blot analysis of HoQM mediated 14-3-3 crosslinking in mammalian cells. HoQM (0.6 mM) was added to HEK293T cells for 4 or 8 hr followed by photoactivation (λ=365 nm) for 10 min.

(FIG. 21A) Denaturing TBE-urea gel shift assay of NHQM mediated crosslinking of the SSB protein with 19(3×) or ATC(4×) DNA. The upshifted crosslinked DNA band is indicated by a *. (FIG. 21B) Denaturing TBE-urea gel shift assay of NHQM mediated crosslinking of the SSB protein with the viral M13mp18 DNA. After crosslinking the minor form of M13mp18 was upshifted into the well and thus disappeared from the original position. In both experiments crosslinker $BS^3$ was included as a negative control.

(FIG. 22A) TBE-urea gel shift assay of NHQM mediated crosslinking of the SSB protein with the viral M13mp18 DNA. The SSB protein was first reconstituted with M13mp18, and then they were treated with or without 1 mM NHQM, followed by with or without UV activation (λ=365 nm) for 15 min. The samples were run in 5% TBE-urea gel. (FIG. 22B) Same to FIG. 22A except the DNA used was 19(3×) or ATC(4×) for protein-DNA complex reconstitution (* indicates the crosslinked protein-DNA band). The results shown here are consistent with those shown in FIGS. 21A-21B, with more controls added: [SSB+/M13mp18+/UV+] in FIG. 22A; [SSB+/19(3×)+/UV+] and [SSB+/ATC(4×)+/UV+] in FIG. 22B, which indicate that UV (λ=365 nm) alone without NHQM did not crosslink protein to DNA.

DETAILED DESCRIPTION

I. Definitions

Figure 1A:
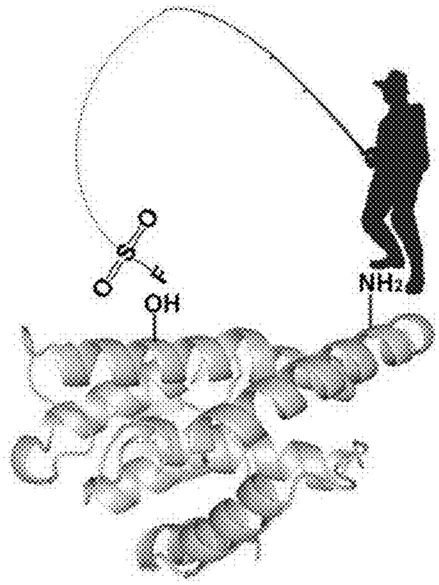
FIGS. 1A-1C. A "plant-and-cast" strategy for developing specific, multi-targeting NHSF crosslinker.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. An unsaturated alkyl group is one having one or more double bonds or triple bonds. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. The term "alkylene," by itself or as part of another substituent, means, unless otherwise stated, a divalent radical derived from an alkyl. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). In embodiments, the bridged or fused bicyclic cycloalkyl is attached to the parent molecular moiety through any carbon atom contained within the monocyclic cycloalkyl ring. In embodiments, the multicyclic cycloalkyl is attached to the parent molecular moiety through any carbon atom contained within the base ring.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). In embodiments, the bridged or fused bicyclic cycloalkenyl is attached to the parent molecular moiety through any carbon atom contained within the monocyclic cycloalkenyl ring. In embodiments, the multicyclic cycloalkenyl is attached to the parent molecular moiety through any carbon atom contained within the base ring.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. The heterocyclyl bicyclic heterocycle is connected to the parent molecular moiety through any carbon atom or any nitrogen atom contained within the monocyclic heterocycle portion of the bicyclic ring system. The multicyclic heterocyclyl is attached to the parent molecular moiety through any carbon atom or nitrogen atom contained within the base ring.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A heteroaryl group can be attached to the remainder of the molecule through a carbon or heteroatom. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "$\sim\sim\sim$" denotes the point of attachment of a chemical moiety to the remainder of a molecule or chemical formula.

The term "oxo," as used herein, means an oxygen that is double bonded to a carbon atom.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), or heteroaryl (e.g., 5 to 10 membered heteroaryl, 5 to 9 membered heteroaryl, or 5 to 6 membered heteroaryl), substituted with at least one substituent selected from:

(i) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), or heteroaryl (e.g., 5 to 10 membered heteroaryl, 5 to 9 membered heteroaryl, or 5 to 6 membered heteroaryl), substituted with at least one substituent selected from:

(a) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_5$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_5$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_5$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), or heteroaryl (e.g., 5 to 10 membered heteroaryl, 5 to 9 membered heteroaryl, or 5 to 6 membered heteroaryl), substituted with at least one substituent selected from: oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_5$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure. The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" or "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH2, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the bioconjugate reactive moiety is capable of bonding to a biomolecule. In embodiments, the first bioconjugate reactive moiety is capable of bonding to a first biomolecule. In embodiments, the second bioconjugate reactive moiety is capable of bonding to a second biomolecule. In embodiments, the bioconjugate reactive moiety is capable of bonding to a protein. In embodiments, the first bioconjugate reactive moiety is capable of bonding to a protein. In embodiments, the second bioconjugate reactive moiety is capable of bonding to a protein. In embodiments, the bioconjugate reactive moiety is capable of bonding to a nucleotide or nucleic acid. In embodiments, the first bioconjugate reactive moiety is capable of bonding to a nucleotide or nucleic acid. In embodiments, the second bioconjugate reactive moiety is capable of bonding to a nucleotide or nucleic acid. In embodiments, the bioconjugate reactive moiety is capable of bonding to a glycan. In embodiments, the first bioconjugate reactive moiety is capable of bonding to a glycan. In embodiments, the second bioconjugate reactive moiety is capable of bonding to a glycan. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine). Additional bioconjugate reactive moieties are described in detail in Patterson et al (ACS Chem. Biol. 2014, 9, 592-605) and Deveraj ACS Cent. Sci. 2018, 4, 952-959, both of which are incorporated herein by reference in their entirety for all purposes.

The term "glycan" or "polysaccharide" as used herein refer to a molecule consisting of monosaccharides linked together via glycosidic linkages. In embodiments, glycan refers to the carbohydrate portion of a biomolecule.

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex. The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

As used herein, the term "proximity enhanced bioconjugate reactive moiety" or "proximity enhanced bioconjugate reactive group" refers to a bioconjugate reactive moiety or bioconjugate reactive group that is less reactive with a second functional group (e.g., a functional group on a second biomolecule or a second amino acid) relative to the reactivity of a bioconjugate reactive moiety or bioconjugate reactive group or photo-activated bioconjugate reactive moiety or photo-activated bioconjugate reactive group to a first functional group (e.g., a functional group on a first biomolecule or a first amino acid), when the photo-activated bioconjugate reactive moiety or photo-activated bioconjugate reactive group is activated by radiation. In embodiments, the proximity enhanced bioconjugate reactive moiety is more reactive after being brought into close proximity to a compatible functional group of a biomolecule. In embodiments, the proximity enhanced bioconjugate reactive moiety is reactive with a functional group at a distance from about 5 to about 50 Å. In embodiments, the proximity enhanced bioconjugate reactive moiety is reactive with a functional group at a distance from about 5 to about 25 Å. In embodiments, the proximity enhanced bioconjugate reactive moiety is reactive with a functional group at a distance from about 15 to about 25 Å. In embodiments, the proximity enhanced bioconjugate reactive moiety is reactive with a functional group at a distance from about 20 Å. In embodiments, the proximity enhanced bioconjugate reactive moiety is reactive with a functional group at a distance of about 20 Å. In embodiments, when the proximity enhanced bioconjugate reactive moiety is within proximity of a compatible functional group of a biomolecule such that the proximity enhanced bioconjugate reactive moiety is more reactive, as described herein above, the distance between the proximity enhanced bioconjugate reactive moiety and the compatible functional group of a biomolecule is from 5 to 50 Å. In embodiments, when the proximity enhanced bioconjugate reactive moiety is within proximity of a compatible functional group of a biomolecule such that the proximity enhanced bioconjugate reactive moiety is more reactive, as described herein above, the distance between the proximity enhanced bioconjugate reactive moiety and the compatible functional group of a biomolecule is less than 50 Å (e.g., less than 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 Å). When the proximity enhanced bioconjugate reactive moiety is placed in proximity to its weakly reactive target functional group in the biomolecule, the increased local effective concentration facilitates the reaction (e.g., increases the rate of reaction compared to the rate of reaction when not in proximity, increases reaction rate by at least 1.1, 1.2, 1.3, 1.4, 1.5, 1.6, 1.7, 1.8, 1.9, 2, 3, 4, 5, 6, 7, 8, 9, 10, 100, 1000, 10,000, 100,000, or 1,000,000 fold compared to the rate of reaction when not in proximity, increases the ratio of reacted bioconjugate product relative to proximity enhanced bioconjugate reactive moiety compared to the ratio of reacted bioconjugate product relative to proximity enhanced bioconjugate reactive moiety when not in proximity, increases the ratio of bioconjugate product relative to proximity enhanced bioconjugate reactive moiety compared to the ratio of bioconjugate product relative to proximity enhanced bioconjugate reactive moiety when not in proximity by at least 1.1, 1.2, 1.3, 1.4, 1.5, 1.6, 1.7, 1.8, 1.9, 2, 3, 4, 5, 6, 7, 8, 9, 10, 100, 1000, 10,000, 100,000, or 1,000,000 fold, increases equilibrium amount of reacted bioconjugate product by at least 1.1, 1.2, 1.3, 1.4, 1.5, 1.6, 1.7, 1.8, 1.9, 2, 3, 4, 5, 6, 7, 8, 9, 10, 100, 1000, 10,000, 100,000, or 1,000,000 fold) of the proximity enhanced bioconjugate reactive moiety with the target functional group to form a covalent bond. In embodiments, the proximity increases the rate of a first order reaction.

As used herein, the term "photo-activated bioconjugate reactive moiety" or "photo-activated bioconjugate reactive group" refers to a bioconjugate reactive moiety or bioconjugate reactive group that is more reactive after contact with radiation. In embodiments, the radiation is UV radiation. In embodiments, the radiation has a wavelength of from about 300 nm to about 400 nm. In embodiments, the radiation has a wavelength of about 365 nm.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a substance, compound, element, molecule, or composition detectable by appropriate means such as spectroscopic, photochemical, biochemical, immunochemical, chemical, magnetic resonance imaging, or other physical means. For example, useful detectable agents include $^{18}F$, $^{32}P$ $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$. $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}F$, $^{32}p$, $^{33}P$, $^{45}Ti$, $^{47}Sc$, $^{52}Fe$, $^{59}Fe$, $^{62}Cu$, $^{64}Cu$, $^{67}Cu$, $^{67}Ga$ $^{68}Ga$, $^{77}As$, $^{86}Y$ $^{90}Y$. $^{89}Sr$, $^{89}Zr$, $^{94}Tc$, $^{94}Tc$, $^{99m}Tc$, 99Mo, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}I$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $-CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. The term "modulate" is used in accordance with its plain ordinary meaning and refers to the act of changing or varying one or more properties. "Modulation" refers to the process of changing or varying one or more properties.

The term "associated" or "associated with" in the context of a substance or substance activity or function associated with a disease means that the disease is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "disease" or "condition" refer to a state of being or health status of a patient or subject capable of being treated with the compounds or methods provided herein.

As used herein, the term "cancer" refers to all types of cancer, neoplasm or malignant tumors found in mammals (e.g. humans), including leukemias, lymphomas, carcinomas and sarcomas.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. A "stem cell" is a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Specific", "specifically", "specificity", or the like of a compound refers to the compound's ability to cause a particular action, such as inhibition, to a particular molecular target with minimal or no action to other proteins in the cell.

The term "electrophilic chemical moiety" or "electrophilic moiety" is used in accordance with its plain ordinary chemical meaning and refers to a chemical group (e.g., monovalent chemical group) that is electrophilic.

The term "irreversible covalent bond" is used in accordance with its plain ordinary meaning in the art and refers to the resulting association between atoms or molecules of (e.g., electrophilic chemical moiety and nucleophilic moiety) wherein the probability of dissociation is low. In embodiments, the irreversible covalent bond does not easily dissociate under normal biological conditions. In embodiments, the irreversible covalent bond is formed through a chemical reaction between two species (e.g., electrophilic chemical moiety and nucleophilic moiety).

The term "capable of binding" as used herein refers to a moiety (e.g. a compound as described herein) that is able to measurably bind to a target (e.g., a E3 Ubiquitin ligase binder is capable of forming a covalent bond with a cysteine of an E3 Ubiquitin ligase). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

The term "covalent cysteine modifier moiety" as used herein refers to a monovalent electrophilic moiety that is able to measurably bind to a cysteine amino acid. In embodiments, the covalent cysteine modifier moiety binds via an irreversible covalent bond. In embodiments, the covalent cysteine modifier moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

The term "biomolecule" is used in accordance with its plain ordinary meaning and refers to a molecule or substance (e.g., a compound, ligand, or protein) that may be found within an organism. In embodiments, a biomolecule is a protein, carbohydrate, lipid, protein, or nucleic acid. In embodiments, the biomolecule is a ligand. In embodiments, the biomolecule is a heme. In embodiments, the biomolecule is a protein. In embodiments, the biomolecule is a carbohydrate. In embodiments, the biomolecule is a lipid. In embodiments, the biomolecule is a nucleic acid. In embodiments, the biomolecule is a metabolite.

The term "crosslinking agent" as used herein refers to a molecule capable of linking (e.g., covalently binding) at least two points of attachment of a biomolecule (e.g., within the same biomolecule or two independent biomolecules).

The term "activated biomolecule" as used herein refers to a biomolecule (e.g., protein) bound to a crosslinking agent at a first point of attachment.

The term "covalently conjugated biomolecule" as used herein refers to a biomolecule (e.g., a protein) which includes a first biomolecule and a second biomolecule bound together via a crosslinking agent.

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "bonding reactivity" as used herein refers to the intrinsic rate (e.g., second order rate constant) with which a bioconjugate reactive moiety of the crosslinker is able to react with a point of attachment of the biomolecule (e.g., a sidechain, an amino-terminus, a posttranslational modification (e.g., saccharides), a C-terminal carboxylate, or protein backbone). In embodiments, when the bonding reactivity of one bioconjugate reactive moiety is characterized as greater than the bonding reactivity of a second bioconjugate reactive moiety, the bonding reactivities of both bioconjugate reactive moieties being compared are the intrinsic (e.g., predicted, empirically measured, or calculated) bond reactivities of the bioconjugate reactive moieties under identical or comparable conditions, for example the second order rate constants for each bioconjugate reactive moiety with the same point of attachment or with their predicted respective points of attachment with identical or comparable reaction conditions (e.g., solvent, temperature, or reactant concentrations).

II. Compounds

In an aspect is provided a crosslinking agent having the formula: $R^1$-$L^1$-$R^2$ (I). $R^1$ is a bioconjugate reactive moiety, a proximity enhanced bioconjugate reactive moiety, or a photo-activated bioconjugate reactive moiety. $R^2$ is bioconjugate reactive moiety, a proximity enhanced bioconjugate reactive moiety, or a photo-activated bioconjugate reactive moiety. $L^1$ is a covalent linker.

In an aspect is provided a crosslinking agent having the formula: $R^1$-$L^1$-$R^2$ (I). $R^1$ is a bioconjugate reactive moiety capable of bonding to a first biomolecule. $R^2$ is a proximity enhanced bioconjugate reactive moiety capable of bonding to a second biomolecule or a second location of the first biomolecule. $L^1$ is a covalent linker. The bonding reactivity of $R^1$ with the first molecule is greater than the bonding reactivity of $R^2$ with the second biomolecule or second location of the first biomolecule.

In an aspect is provided a crosslinking agent having the formula: $R^1$-$L^1$-$R^2$ (I); wherein $R^1$ is a bioconjugate reactive moiety; $R^2$ is a proximity enhanced bioconjugate reactive moiety; $L^1$ is a covalent linker; and the bonding reactivity of $R^1$ with a first biomolecule is greater than the bonding reactivity of $R^2$ with a second biomolecule or second location of the first biomolecule.

In an aspect is provided a crosslinking agent having the formula: $R^1$-$L^1$-$R^2$ (I). $R^1$, $L^1$, and $R^2$ are as described herein. $R^1$ is a bioconjugate reactive moiety. $R^2$ is a proximity enhanced bioconjugate reactive moiety. $L^1$ is a covalent linker. The bonding reactivity of $R^1$ with a first biomolecule is greater than the bonding reactivity of $R^2$ with a second biomolecule or second location of the first biomolecule.

In embodiments, $R^1$ is a bioconjugate reactive moiety capable of bonding to a first biomolecule. In embodiments, $R^2$ is a proximity enhanced bioconjugate reactive moiety capable of bonding to a second biomolecule or a second location of the first biomolecule.

In embodiments, $R^1$ is

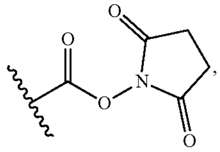,
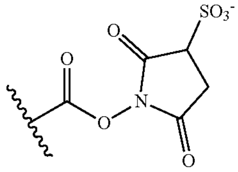,
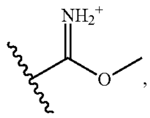,
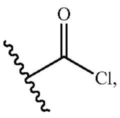, or
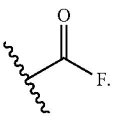

In embodiments, $R^1$ is

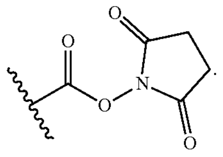 [SMILES: *C(=O)ON1C(=O)CCC1=O]

In embodiments, $R^1$ is
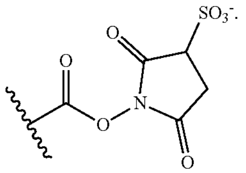
In embodiments, $R^1$ is
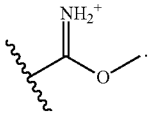 [SMILES: *C(=[NH2+])OC]
In embodiments, $R^1$ is
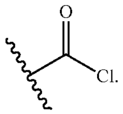 [SMILES: *C(=O)Cl]
In embodiments, $R^1$ is
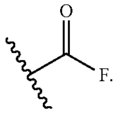 [SMILES: *C(=O)F]
In embodiments, $R^2$ is
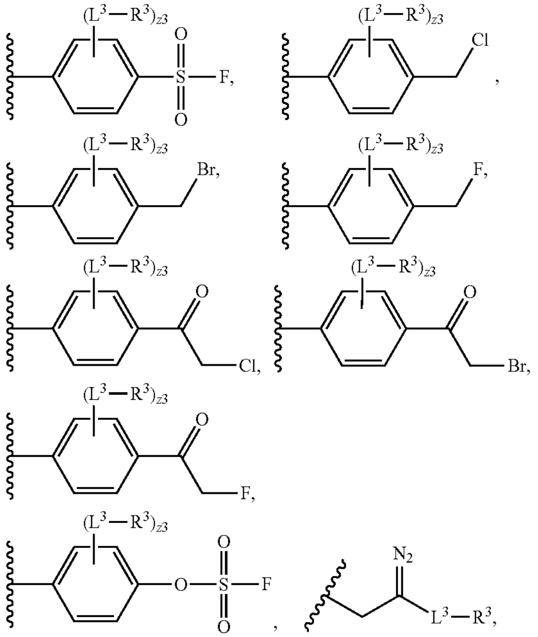
-continued
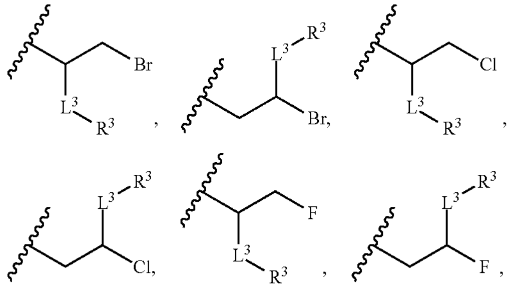
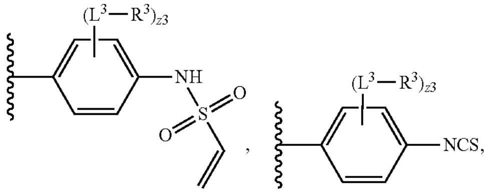
or
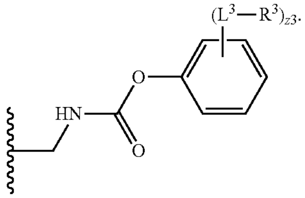
$L^3$, $R^3$, and z3 are as described herein, including in embodiments.
In embodiments, $R^2$ is
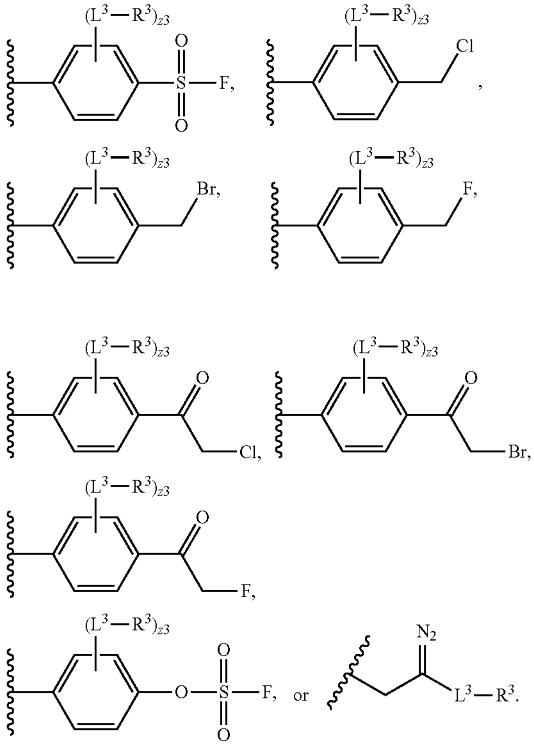
$L^3$, $R^3$, and z3 are as described herein, including in embodiments.

In embodiments, $R^2$ is independently

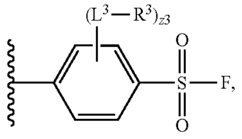

wherein $L^3$, $R^3$, and z3 are as described herein, including in embodiments. In embodiments, $R^2$ is independently

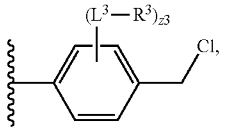

wherein $L^3$, $R^3$, and z3 are as described herein, including in embodiments. In embodiments, $R^2$ is independently

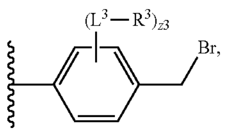

wherein $L^3$, $R^3$, and z3 are as described herein, including in embodiments. In embodiments, $R^2$ is independently

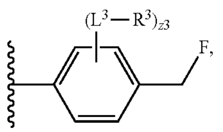

wherein $L^3$, $R^3$, and z3 are as described herein, including in embodiments. In embodiments, $R^2$ is independently

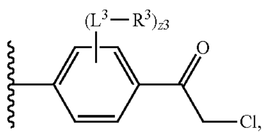

wherein $L^3$, $R^3$, and z3 are as described herein, including in embodiments. In embodiments, $R^2$ is independently

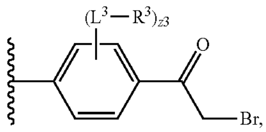

wherein $L^3$, $R^3$, and z3 are as described herein, including in embodiments. In embodiments, $R^2$ is independently

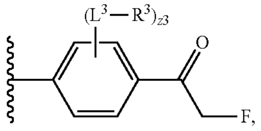

wherein $L^3$, $R^3$, and z3 are as described herein, including in embodiments. In embodiments, $R^2$ is independently

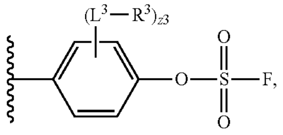

wherein $L^3$, $R^3$, and z3 are as described herein, including in embodiments. In embodiments, $R^2$ is independently

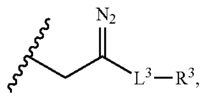

wherein $L^3$ and $R^3$ are as described herein, including in embodiments. In embodiments, $R^2$ is independently

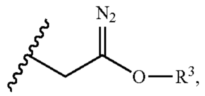

wherein $R^3$ is as described herein, including in embodiments. In embodiments, $R^2$ is independently

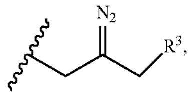

wherein $R^3$ is as described herein, including in embodiments. In embodiments, $R^2$ is independently

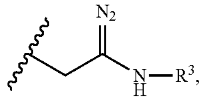

wherein $R^3$ is as described herein, including in embodiments. In embodiments, $R^2$ is independently

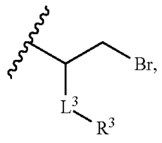

wherein $L^3$ and $R^3$ are as described herein, including in embodiments. In embodiments, $R^2$ is independently

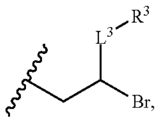

wherein $L^3$ and $R^3$ are as described herein, including in embodiments. In embodiments, $R^2$ is independently

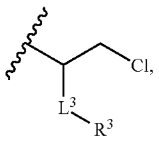

wherein $L^3$ and $R^3$ are as described herein, including in embodiments. In embodiments, $R^2$ is independently

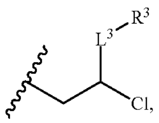

wherein $L^3$ and $R^3$ are as described herein, including in embodiments. In embodiments, $R^2$ is independently

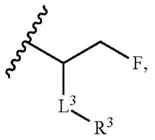

wherein $L^3$ and $R^3$ are as described herein, including in embodiments. In embodiments, $R^2$ is independently

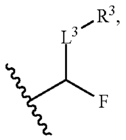

wherein $L^3$ and $R^3$ are as described herein, including in embodiments. In embodiments, $R^2$ is independently

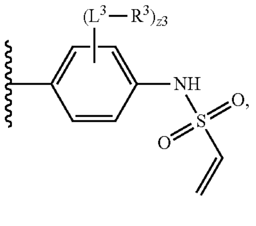

wherein $L^3$ and $R^3$ are as described herein, including in embodiments. In embodiments, $R^2$ is independently

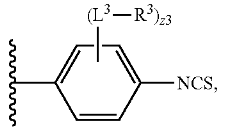

wherein $L^3$ and $R^3$ are as described herein, including in embodiments. In embodiments, $R^2$ is independently

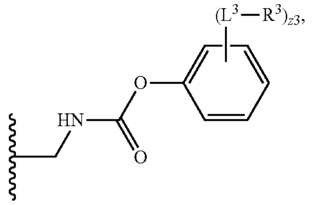

wherein $L^3$ and $R^3$ are as described herein, including in embodiments. In embodiments, $R^2$ is independently

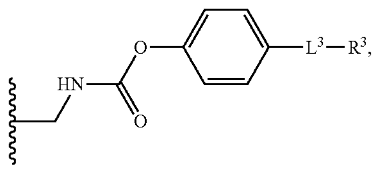

wherein $L^3$ and $R^3$ are as described herein, including in embodiments. In embodiments, $R^3$ is independently substituted or unsubstituted alkyl. In embodiments, $R^3$ is independently substituted or unsubstituted aryl.

In embodiments, $R^2$ is

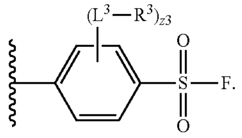

In embodiments, $R^2$ is

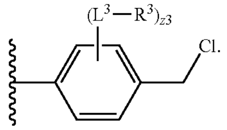

In embodiments, $R^2$ is

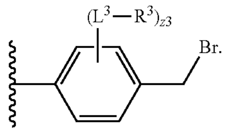

In embodiments, $R^2$ is

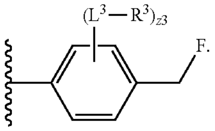

In embodiments, $R^2$ is

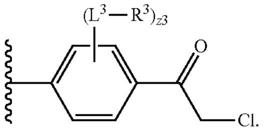

In embodiments, $R^2$ is

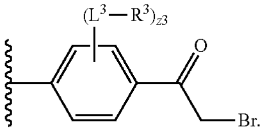

In embodiments, $R^2$ is

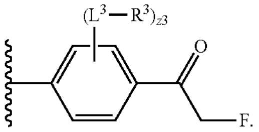

In embodiments, $R^2$ is

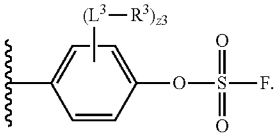

In embodiments, $R^2$ is

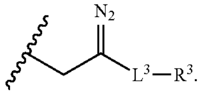

In embodiments, $R^2$ is

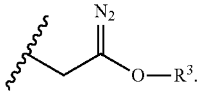

In embodiments, $R^2$ is

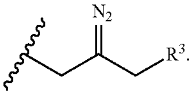

In embodiments, $R^2$ is

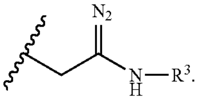

In embodiments, $R^3$ is substituted or unsubstituted alkyl. In embodiments, $R^3$ is substituted or unsubstituted aryl.

In embodiments, $R^2$ is independently

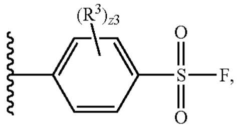 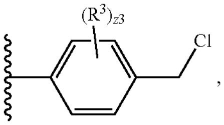

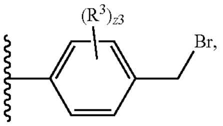 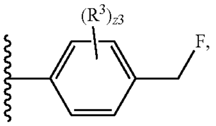

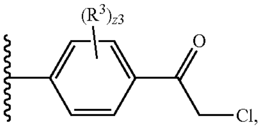 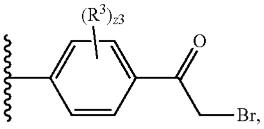

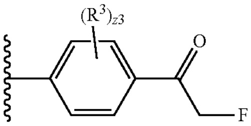 , 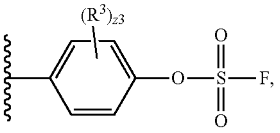

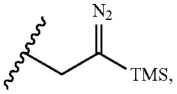 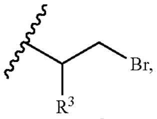 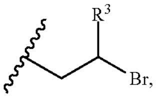

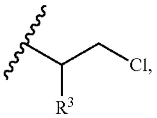 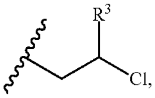 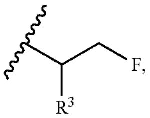

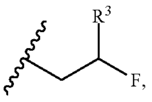 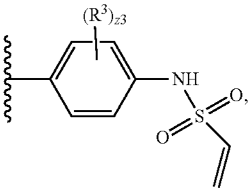

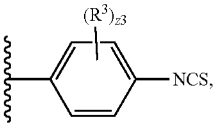 or 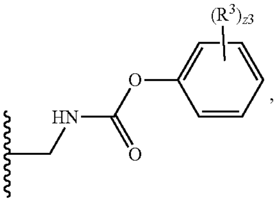

wherein $R^3$ and z3 are as described herein.

In embodiments, $R^2$ is independently
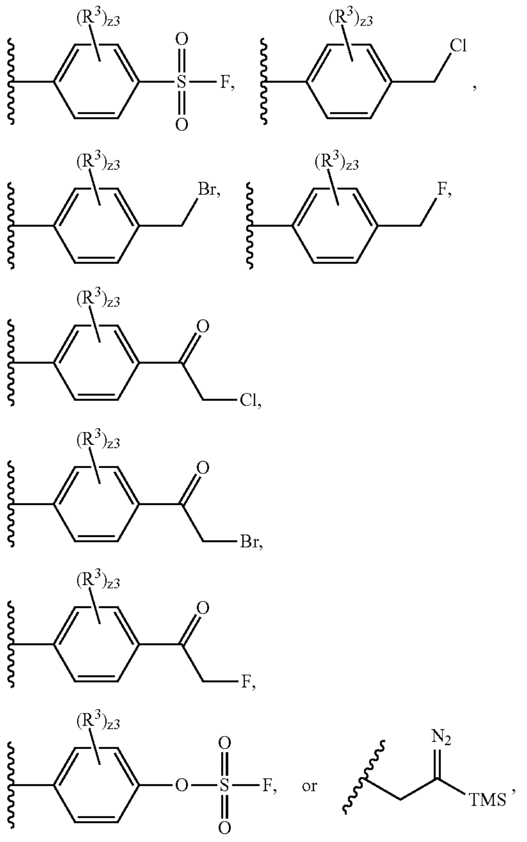
wherein $R^3$ and z3 are as described herein.
In embodiments, $R^2$ is independently
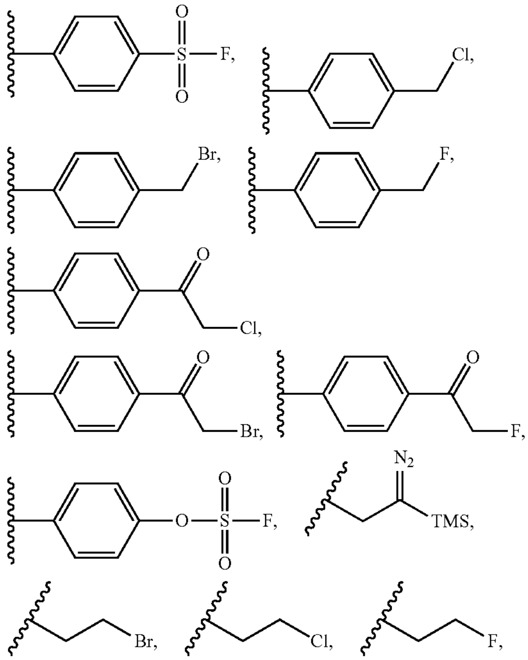
-continued
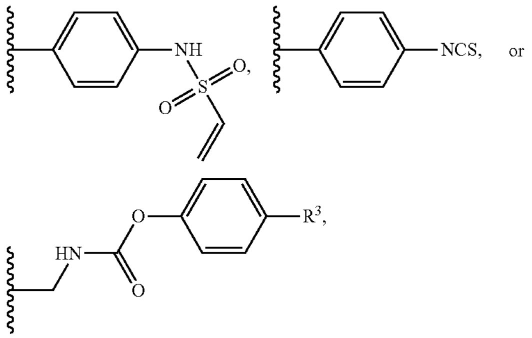
wherein $R^3$ is as described herein, including in embodiments.
In embodiments, $R^2$ is independently
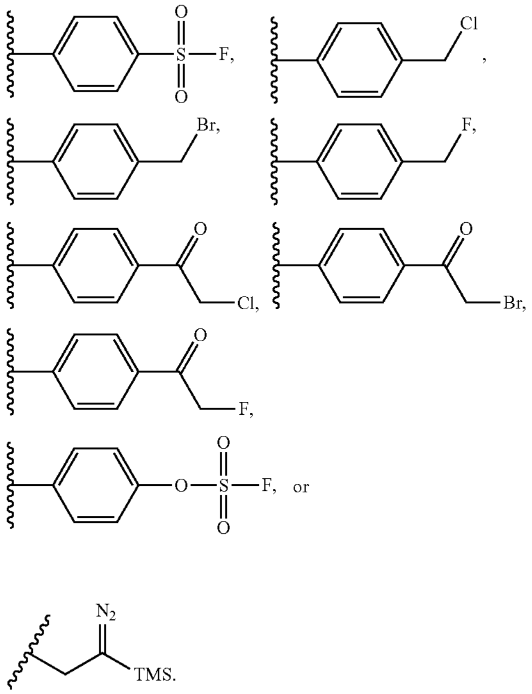
In embodiments, $R^2$ is independently
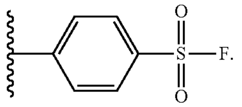 [SMILES: *c1ccc(S(=O)(=O)F)cc1]
In embodiments, $R^2$ is independently
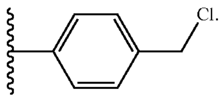 [SMILES: *c1ccc(CCl)cc1]

In embodiments, $R^2$ is independently

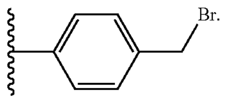 [SMILES: *c1ccc(CBr)cc1]

In embodiments, $R^2$ is independently

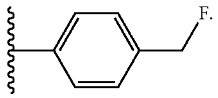 [SMILES: *c1ccc(CF)cc1]

In embodiments, $R^2$ is independently

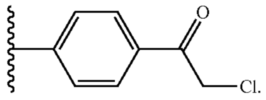 [SMILES: *c1ccc(C(=O)CCl)cc1]

In embodiments, $R^2$ is independently

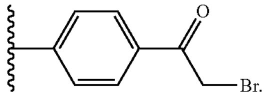 [SMILES: *c1ccc(C(=O)CBr)cc1]

In embodiments, $R^2$ is independently

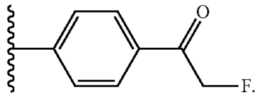 [SMILES: *c1ccc(C(=O)CF)cc1]

In embodiments, $R^2$ is independently

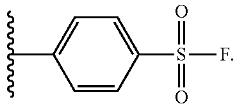 [SMILES: *c1ccc(S(=O)(=O)F)cc1]

In embodiments, $R^2$ is independently

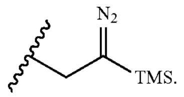

$L^3$ is independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^3$ is independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^3$ is independently a bond, —$S(O)_2$—, —NH—, —O—, —S—, —C(O)—, —C(O)NH—, —NHC(O)—, —NHC(O)NH—, —C(O)O—, —OC(O)—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene.

In embodiments, a substituted $L^3$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^3$ is substituted with a plurality of groups selected from substituent groups, size-limited substituent groups, and lower substituent groups; each substituent group, size-limited substituent group, and/or lower substituent group may optionally be different. In embodiments, when $L^3$ is substituted, it is substituted with at least one substituent group. In embodiments, when $L^3$ is substituted, it is substituted with at least one size-limited substituent group. In embodiments, when $L^3$ is substituted, it is substituted with at least one lower substituent group.

In embodiments, $L^3$ is independently a bond, —$S(O)_2$—, —NH—, —O—, —S—, —C(O)—, —C(O)NH—, —NHC(O)—, —NHC(O)NH—, —C(O)O—, —OC(O)—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, 2 to 3 membered, or 4 to 5 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 8 membered, 3 to 6 membered, 4 to 6 membered, 4 to 5 membered, or 5 to 6 membered), unsubstituted arylene (e.g., $C_6$-$C_{10}$ or phenylene), or unsubstituted heteroarylene (e.g., 5 to 10 membered, 5 to 9 membered, or 5 to 6 membered).

$R^3$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety. The symbol z3 is an integer from 0 to 4.

A person of ordinary skill in the art would understand that the substituent $—SO_3H$ may exist as $—SO_3^-$ under conditions that favor the ionized form over the non-ionized form. The substituent $—SO_3H$ describes $—SO_3H$, $—SO_3^-$, or the combination of both $—SO_3H$ and $—SO_3^-$. Similarly, a person of ordinary skill in the art would understand that the substituent —COOH may exist as $—COO^-$ under conditions that favor the ionized form over the non-ionized form. The substituent —COOH describes —COOH, $—COO^-$, or the combination of both —COOH and $—COO^-$.

In embodiments, $R^3$ is independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^3$ is independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^3$ is independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^3$ is independently a substituted or unsubstituted alkynyl, $—N_3$, or a bioconjugate reactive moiety. In embodiments, $R^3$ is independently a substituted or unsubstituted alkynyl. In embodiments, $R^3$ is independently $—N_3$. In embodiments, $R^3$ is independently a bioconjugate reactive moiety.

In embodiments, z3 is 0. In embodiments, z3 is 1. In embodiments, z3 is 2. In embodiments, z3 is 3. In embodiments, z3 is 4.

In embodiments, $L^1$ has the formula: $-L^{1A}-L^{1B}-L^{1C}-L^{1D}-$. $L^{1A}$ is connected directly to $R^1$. $L^{1A}$, $L^{1B}$, $L^{1C}$, and $L^{1D}$ are each independently a bond, $—N(R^{10})—$, —C(O)—, $—C(O)N(R^{10})—$, $—N(R^{10})C(O)—$, —N(H)—, —C(O)N(H)—, —N(H)C(O)—, —C(O)O—, —OC(O)—, $—S(O)_2—$, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

In embodiments, $L^{1A}$, $L^{1B}$, $L^{1C}$, and $L^{1D}$ are each independently a bond, $—N(R^{10})—$, —C(O)—, $—C(O)N(R^{10})—$, $—N(R^{10})C(O)—$, —N(H)—, —C(O)N(H)—, —N(H)C(O)—, —C(O)O—, —OC(O)—, $—S(O)_2—$, —S(O)—, —O—, —S—, —NHC(O)NH—, $R^{10}$-substituted or unsubstituted alkylene, $R^{10}$-substituted or unsubstituted heteroalkylene, $R^{10}$-substituted or unsubstituted cycloalkylene, $R^{10}$-substituted or unsubstituted heterocycloalkylene, $R^{10}$-substituted or unsubstituted arylene, or $R^{10}$-substituted or unsubstituted heteroarylene, or a bioconjugate linker.

In embodiments, $L^{1A}$, $L^{1B}$, $L^{1C}$, and $L^{1D}$ are each independently a bond, $—S(O)_2—$, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^{1A}$, $L^{1B}$, $L^{1C}$, and $L^{1D}$ are each independently a bond, —$S(O)_2$—, —NH—, —O—, —S—, —C(O)—, —C(O)NH—, —NHC(O)—, —NHC(O)NH—, —C(O)O—, —OC(O)—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene.

In embodiments, a substituted $L^{1A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{1A}$ is substituted with a plurality of groups selected from substituent groups, size-limited substituent groups, and lower substituent groups; each substituent group, size-limited substituent group, and/or lower substituent group may optionally be different. In embodiments, when $L^{1A}$ is substituted, it is substituted with at least one substituent group. In embodiments, when $L^{1A}$ is substituted, it is substituted with at least one size-limited substituent group. In embodiments, when $L^{1A}$ is substituted, it is substituted with at least one lower substituent group.

In embodiments, a substituted $L^{1B}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{1B}$ is substituted with a plurality of groups selected from substituent groups, size-limited substituent groups, and lower substituent groups; each substituent group, size-limited substituent group, and/or lower substituent group may optionally be different. In embodiments, when $L^{1B}$ is substituted, it is substituted with at least one substituent group. In embodiments, when $L^{1B}$ is substituted, it is substituted with at least one size-limited substituent group. In embodiments, when $L^{1B}$ is substituted, it is substituted with at least one lower substituent group.

In embodiments, a substituted $L^{1C}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{1C}$ is substituted with a plurality of groups selected from substituent groups, size-limited substituent groups, and lower substituent groups; each substituent group, size-limited substituent group, and/or lower substituent group may optionally be different. In embodiments, when $L^{1C}$ is substituted, it is substituted with at least one substituent group. In embodiments, when $L^{1C}$ is substituted, it is substituted with at least one size-limited substituent group. In embodiments, when $L^{1C}$ is substituted, it is substituted with at least one lower substituent group.

In embodiments, a substituted LD (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted LD is substituted with a plurality of groups selected from substituent groups, size-limited substituent groups, and lower substituent groups; each substituent group, size-limited substituent group, and/or lower substituent group may optionally be different. In embodiments, when LD is substituted, it is substituted with at least one substituent group. In embodiments, when LD is substituted, it is substituted with at least one size-limited substituent group. In embodiments, when LD is substituted, it is substituted with at least one lower substituent group.

$R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, $R^{11}$-substituted or unsubstituted alkyl (e.g., $C_1$-$C_8$ alkyl, $C_1$-$C_6$ alkyl, or $C_1$-$C_4$ alkyl), $R^{11}$-substituted or unsubstituted heteroalkyl (e.g., 2 to 8 membered heteroalkyl, 2 to 6 membered heteroalkyl, or 2 to 4 membered heteroalkyl), $R^{11}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11}$-substituted or unsubstituted aryl (e.g., $C_6$-$C_{10}$ aryl, $C_{10}$ aryl, or phenyl), or $R^{11}$-substituted or unsubstituted heteroaryl (e.g., 5 to 10 membered heteroaryl, 5 to 9 membered heteroaryl, or 5 to 6 membered heteroaryl).

In embodiments, $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, unsubstituted alkyl, unsubstituted heteroalkyl, unsubstituted cycloalkyl, unsubstituted heterocycloalkyl, unsubstituted aryl, or unsubstituted heteroaryl.

$R^{11}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, $R^{12}$-substituted or unsubstituted alkyl (e.g., $C_1$-$C_5$ alkyl, $C_1$-$C_6$ alkyl, or $C_1$-$C_4$ alkyl), $R^{12}$-substituted or unsubstituted heteroalkyl (e.g., 2 to 8 membered heteroalkyl, 2 to 6 membered heteroalkyl, or 2 to 4 membered heteroalkyl), $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12}$-substituted or unsubstituted aryl (e.g., $C_6$-$C_{10}$ aryl, $C_{10}$ aryl, or phenyl), or $R^{12}$-substituted or unsubstituted heteroaryl (e.g., 5 to 10 membered heteroaryl, 5 to 9 membered heteroaryl, or 5 to 6 membered heteroaryl).

In embodiments, $R^{11}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, unsubstituted alkyl, unsubstituted heteroalkyl, unsubstituted cycloalkyl, unsubstituted heterocycloalkyl, unsubstituted aryl, or unsubstituted heteroaryl.

$R^{12}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, unsubstituted alkyl (e.g., $C_1$-$C_5$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{12}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, unsubstituted alkyl, unsubstituted heteroalkyl, unsubstituted cycloalkyl, unsubstituted heterocycloalkyl, unsubstituted aryl, or unsubstituted heteroaryl.

In embodiments, $L^1$ is a bond, —N($R^{10}$)—, —C(O)—, —C(O)N($R^{10}$)—, —N($R^{10}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

In embodiments, $L^1$ is a bond, —N($R^{10}$)—, —C(O)—, —C(O)N($R^{10}$)—, —N($R^{10}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, $R^{10}$-substituted or unsubstituted alkylene, $R^{10}$-substituted or unsubstituted heteroalkylene, $R^{10}$-substituted or unsubstituted cycloalkylene, $R^{10}$-substituted or unsubstituted heterocycloalkylene, $R^{10}$-substituted or unsubstituted arylene, or $R^{10}$-substituted or unsubstituted heteroarylene, or a bioconjugate linker.

In embodiments, $L^1$ is a bond, —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^1$ is a bond, —S(O)$_2$—, —NH—, —O—, —S—, —C(O)—, —C(O)NH—, —NHC(O)—, —NHC(O)NH—, —C(O)O—, —OC(O)—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene.

In embodiments, a substituted $L^1$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^1$ is substituted with a plurality of groups selected from substituent groups, size-limited substituent groups, and lower substituent groups; each substituent group, size-limited substituent group, and/or lower substituent group may optionally be different. In embodiments, when $L^1$ is substituted, it is substituted with at least one substituent group. In embodiments, when $L^1$ is substituted, it is substituted with at least one size-limited substituent group. In embodiments, when $L^1$ is substituted, it is substituted with at least one lower substituent group.

In embodiments, $L^1$ is cleavable by mass spectroscopy. In embodiments, $L^1$ is

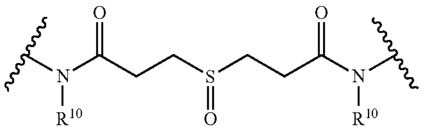

or

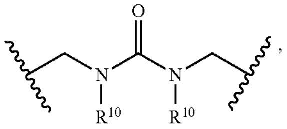

, wherein $R^{10}$ is as described herein. In embodiments, $L^1$ is

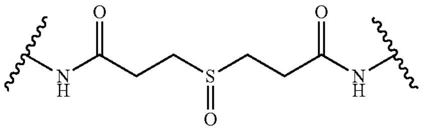

or

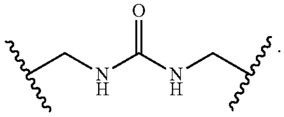

.

In embodiments, $L^1$ is a bond or substituted or unsubstituted $C_1$-$C_4$ alkylene. In embodiments, $L^1$ is an unsubstituted $C_1$-$C_4$ alkylene.

In embodiments, $L^1$ is

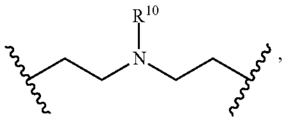

, wherein $R^{10}$ is as described herein. In embodiments, $L^1$ is

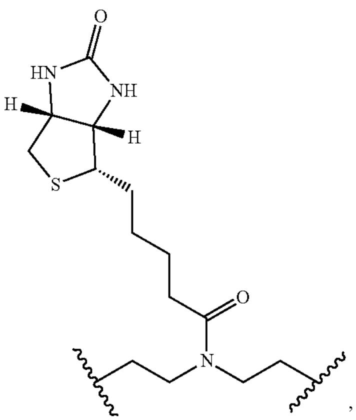

,

-continued

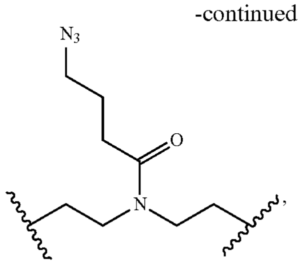

or

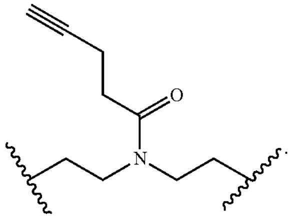

In embodiments, $L^1$ is

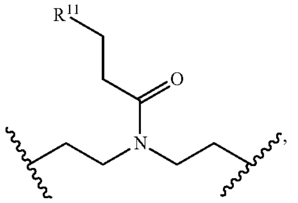

wherein $R^{11}$ is as described herein. In embodiments, $R^{10}$ is independently a bioconjugate reactive moiety. In embodiments, $R^{10}$ is independently an alkyne. In embodiments, $R^{10}$ is independently a cycloalkyne. In embodiments, $R^{10}$ is independently a strained alkyne. In embodiments, $R^{10}$ is independently

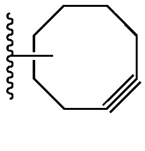

or

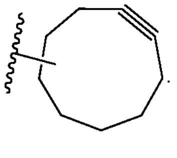

In embodiments, $R^{10}$ is independently an azide. In embodiments, $R^{10}$ is independently a bioconjugate reactive moiety as described in in Patterson et al (ACS Chem. Biol. 2014, 9, 592-605) and Deveraj ACS Cent. Sci. 2018, 4, 952-959, both of which are incorporated herein by reference in their entirety for all purposes. In embodiments, $R^{11}$ is independently a bioconjugate reactive moiety. In embodiments, $R^{11}$ is independently an alkyne. In embodiments, $R^{11}$ is independently a cycloalkyne. In embodiments, $R^{11}$ is independently a strained alkyne. In embodiments, $R^{11}$ is independently

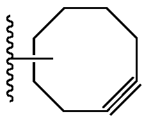

or

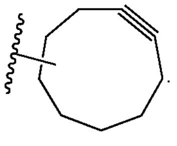

In embodiments, $R^{11}$ is independently an azide. In embodiments, $R^{11}$ is independently a bioconjugate reactive moiety as described in in Patterson et al (ACS Chem. Biol. 2014, 9, 592-605) and Deveraj ACS Cent. Sci. 2018, 4, 952-959, both of which are incorporated herein by reference in their entirety for all purposes.

In an aspect is provided a crosslinking agent having the formula: $R^1$-$L^1$-$R^2$ (I); wherein $R^1$ is a bioconjugate reactive moiety; $R^2$ is a photo-activated bioconjugate reactive moiety; $L^1$ is a covalent linker; the bonding reactivity of $R^2$ with a second biomolecule after contact of $R^2$ with radiation is greater than the bonding reactivity of $R^2$ with the second biomolecule prior to contact of $R^2$ with radiation.

In an aspect is provided a crosslinking agent having the formula: $R^1$-$L^1$-$R^2$ (I). $R^1$, $L^1$, and $R^2$ are as described herein. $R^1$ is a bioconjugate reactive moiety. $R^2$ is a photo-activated bioconjugate reactive moiety. $L^1$ is a covalent linker. The bonding reactivity of $R^2$ with a second biomolecule after contact of $R^2$ with radiation is greater than the bonding reactivity of $R^2$ with the second biomolecule prior to contact of $R^2$ with radiation.

In embodiments, $R^1$ is a bioconjugate reactive moiety capable of bonding to a first biomolecule. In embodiments, $R^2$ is a photo-activated bioconjugate reactive moiety capable of bonding to a second biomolecule or a second location of the first biomolecule.

In embodiments, $R^2$ is independently

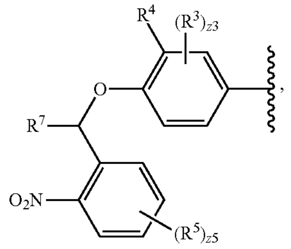

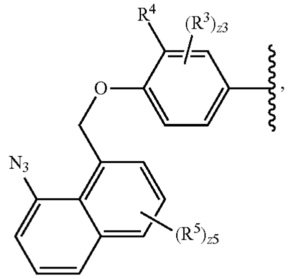

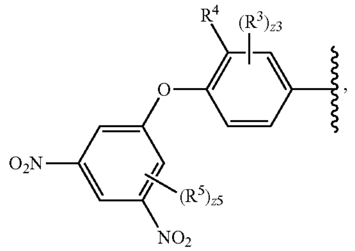

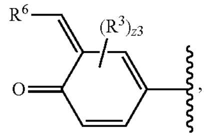

-continued
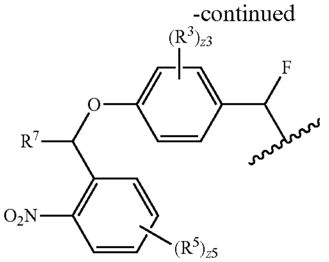,
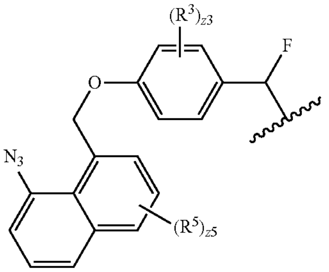,
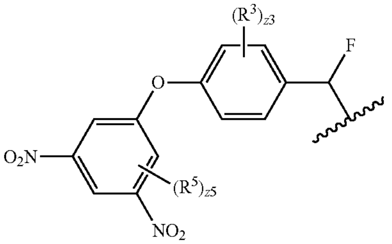,
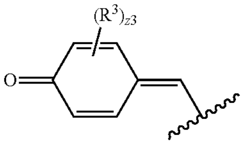,
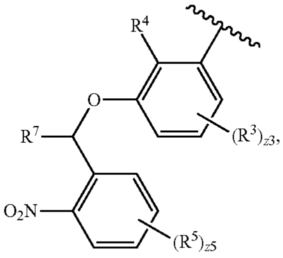,
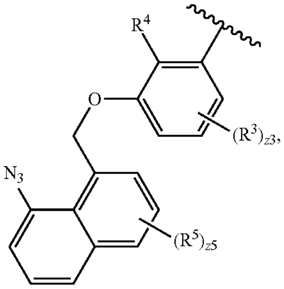,
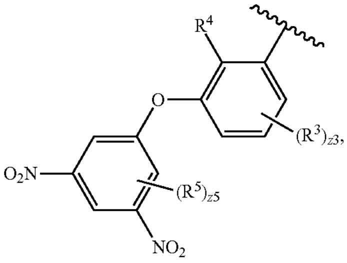,
-continued
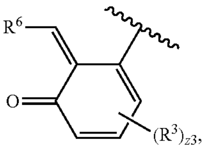,
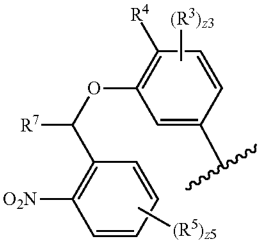,
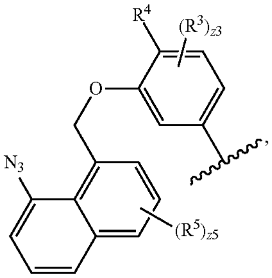,
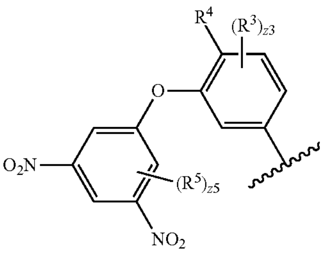,
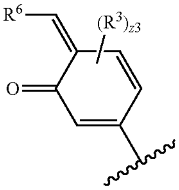,
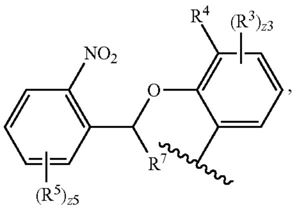,
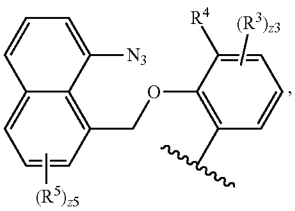, -continued

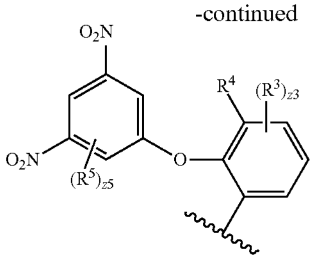

, or

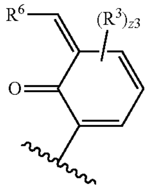

, wherein $R^3$ and z3 are as described herein, including in embodiments. $R^4$, $R^6$, and $R^7$ are each independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety. $R^5$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety. The symbol z5 is an integer from 0 to 6.

In embodiments, $R^4$, $R^6$, and $R^7$ are each independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is independently

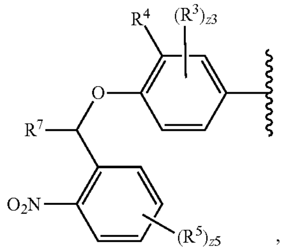

, wherein $R^3$, $R^4$, $R^5$, $R^7$, z3, and z5 are as described herein, including in embodiments. In embodiments, $R^2$ is independently

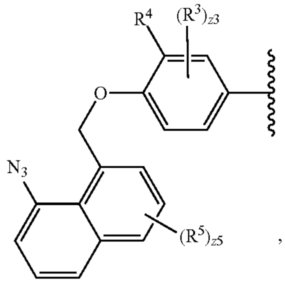

, wherein $R^3$, $R^4$, $R^5$, z3, and z5 are as described herein, including in embodiments. In embodiments, $R^2$ is independently

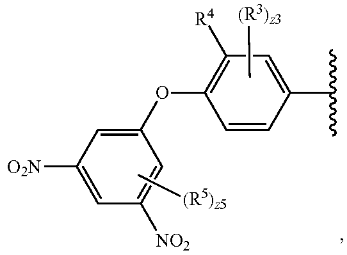

, wherein $R^3$, $R^4$, $R^5$, z3, and z5 are as described herein, including in embodiments. In embodiments, $R^2$ is independently

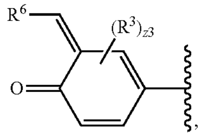

, wherein $R^3$, $R^6$, and z3 are as described herein, including in embodiments. In embodiments, $R^2$ is independently

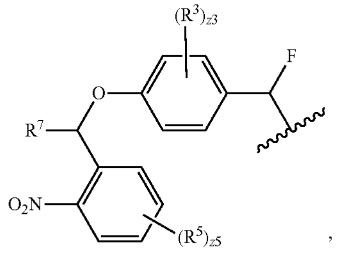

wherein $R^3$, $R^5$, $R^7$, z3, and z5 are as described herein, including in embodiments. In embodiments, $R^2$ is independently

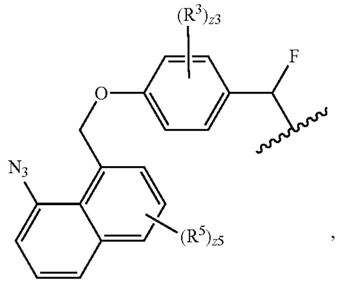

wherein $R^3$, $R^5$, z3, and z5 are as described herein, including in embodiments. In embodiments, $R^2$ is independently

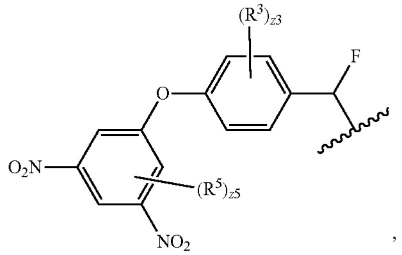

wherein $R^3$, $R^5$, z3, and z5 are as described herein, including in embodiments. In embodiments, $R^2$ is independently

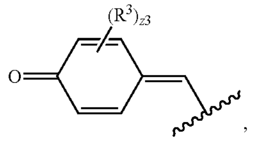

wherein $R^3$ and z3 are as described herein, including in embodiments. In embodiments, $R^2$ is independently

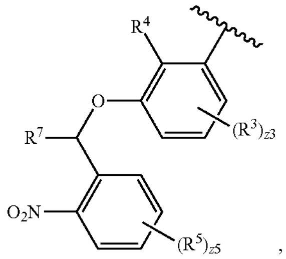

wherein $R^3$, $R^4$, $R^5$, $R^7$, z3, and z5 are as described herein, including in embodiments. In embodiments, $R^2$ is independently

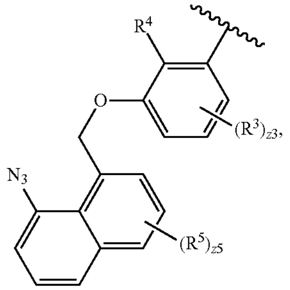

wherein $R^3$, $R^4$, $R^5$, z3, and z5 are as described herein, including in embodiments. In embodiments, $R^2$ is independently

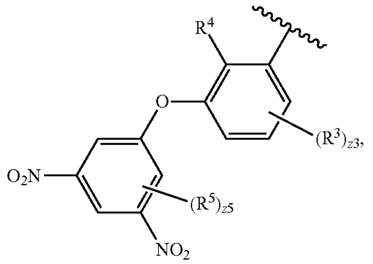

wherein $R^3$, $R^4$, $R^5$, z3, and z5 are as described herein, including in embodiments. In embodiments, $R^2$ is independently

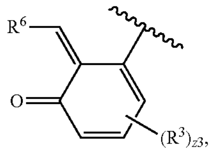

wherein $R^3$, $R^6$, and z3 are as described herein, including in embodiments. In embodiments, $R^2$ is independently

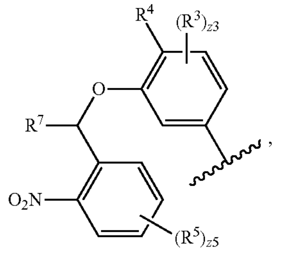

wherein $R^3$, $R^4$, $R^5$, $R^7$, z3, and z5 are as described herein, including in embodiments. In embodiments, $R^2$ is independently

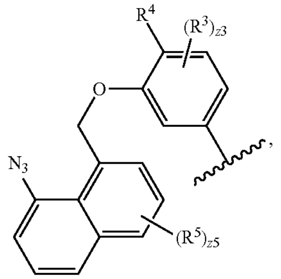

wherein $R^3$, $R^4$, $R^5$, z3, and z5 are as described herein, including in embodiments. In embodiments, $R^2$ is independently

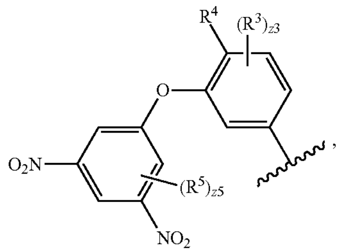

wherein $R^3$, $R^4$, $R^5$, z3, and z5 are as described herein, including in embodiments. In embodiments, $R^2$ is independently

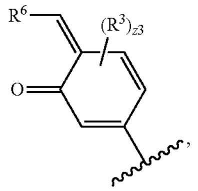

wherein $R^3$, $R^6$, and z3 are as described herein, including in embodiments. In embodiments, $R^2$ is independently

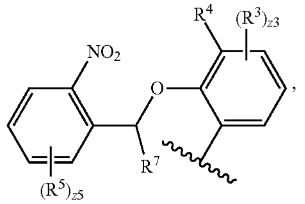

wherein $R^3$, $R^4$, $R^5$, $R^7$, z3, and z5 are as described herein, including in embodiments. In embodiments, $R^2$ is independently

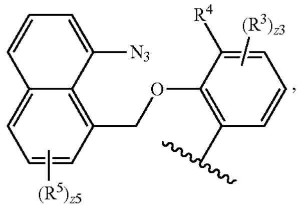

wherein $R^3$, $R^4$, $R^5$, z3, and z5 are as described herein, including in embodiments. In embodiments, $R^2$ is independently

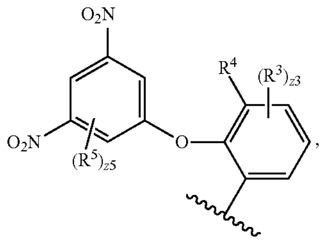

wherein $R^3$, $R^4$, $R^5$, z3, and z5 are as described herein, including in embodiments. In embodiments, $R^2$ is independently

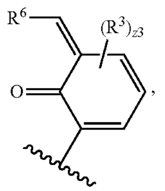

wherein $R^3$, $R^6$, and z3 are as described herein, including in embodiments.

In embodiments, $R^2$ is independently
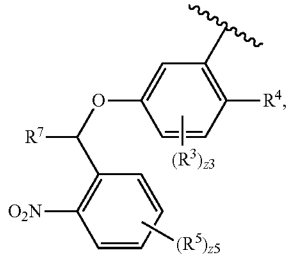
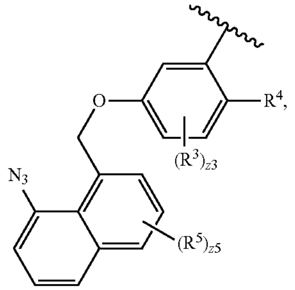
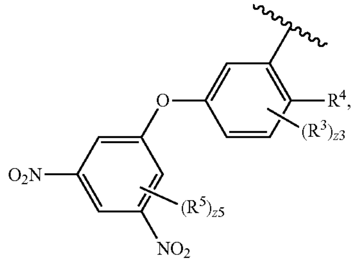
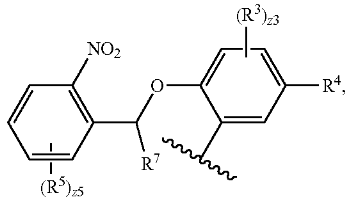
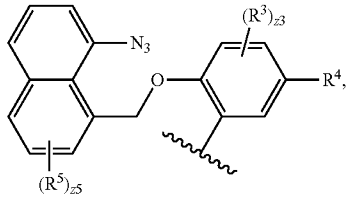
or
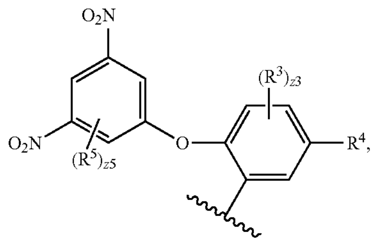
wherein $R^3$, $R^4$, $R^5$, $R^7$, z3, and z5 are as described herein, including in embodiments.
In embodiments, $R^2$ is independently
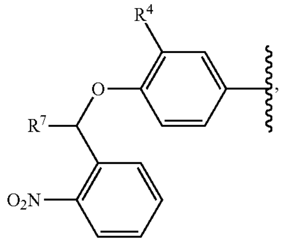
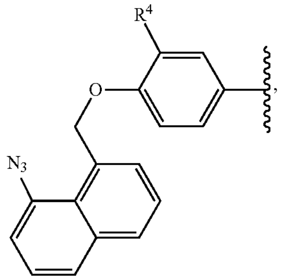
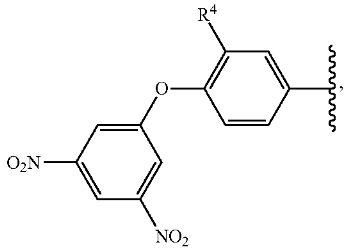
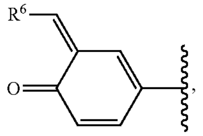
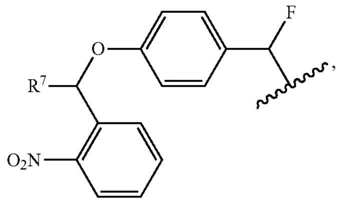
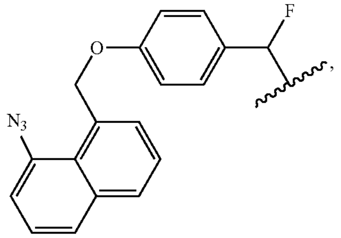
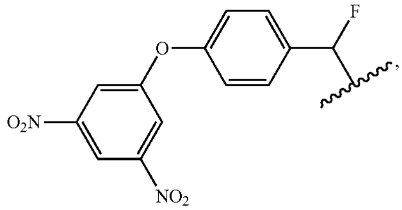
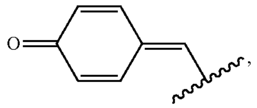

-continued
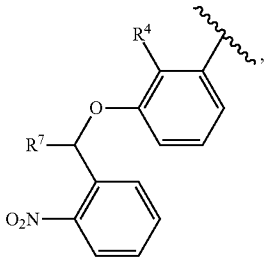
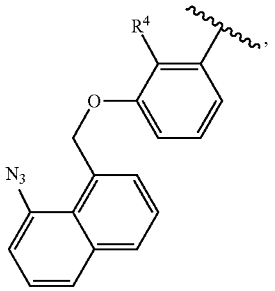
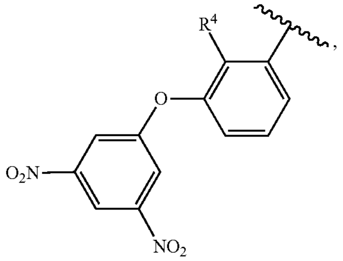
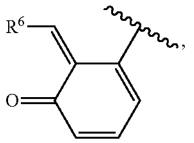
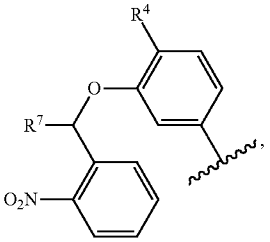
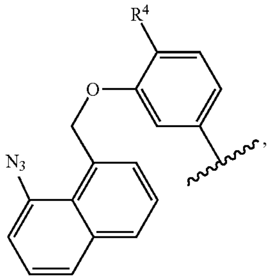
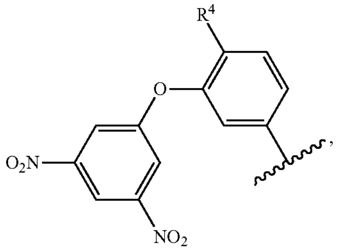
-continued
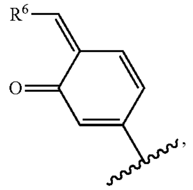
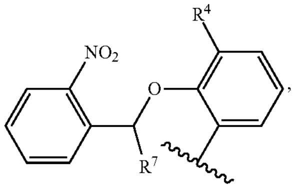
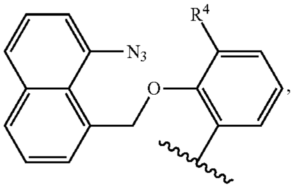
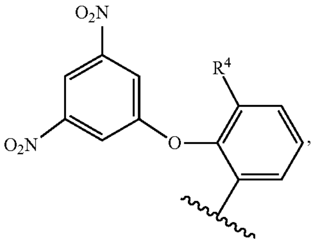
or
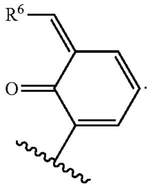
$R^4$, $R^6$, and $R^7$ are as described herein, including in embodiments.
In embodiments, $R^2$ is independently
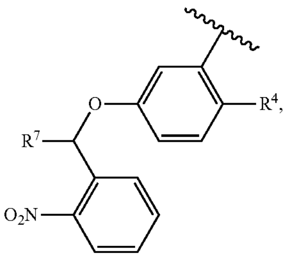
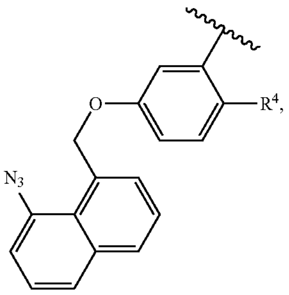
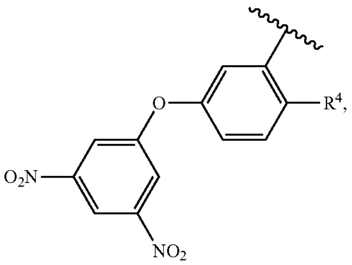

-continued

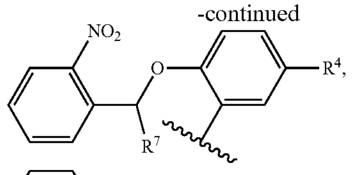

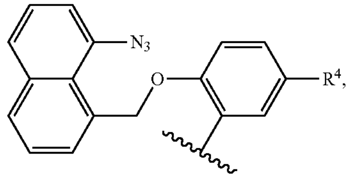

or

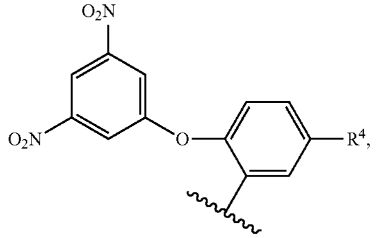

wherein $R^4$ and $R^7$ are as described herein, including in embodiments.

In embodiments, $R^3$ is independently unsubstituted methoxy. In embodiments, $R^3$ is independently —$SO_3^-$. In embodiments, $R^3$ is independently —$COO^-$.

In embodiments, $R^4$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^4$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^4$ is independently —$CH_2F$ or —$CHF_2$. In embodiments, $R^4$ is independently —$CH_2F$. In embodiments, $R^4$ is independently —$CHF_2$.

In embodiments, $R^5$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^5$ is independently halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^5$ is independently unsubstituted $C_1$-$C_4$ alkyl. In embodiments, $R^5$ is independently unsubstituted methyl. In embodiments, $R^5$ is independently unsubstituted ethyl. In embodiments, $R^5$ is independently unsubstituted n-propyl. In embodiments, $R^5$ is independently unsubstituted isopropyl. In embodiments, $R^5$ is independently unsubstituted n-butyl. In embodiments, $R^5$ is independently unsubstituted tert-butyl. In embodiments, $R^5$ is independently unsubstituted —O—($C_1$-$C_4$ alkyl). In embodiments, $R^5$ is independently unsubstituted methoxy. In embodiments, $R^5$ is independently unsubstituted ethoxy. In embodiments, $R^5$ is independently unsubstituted n-propoxy. In embodiments, $R^5$ is independently unsubstituted isopropoxy. In embodiments, $R^5$ is independently unsubstituted n-butoxy. In embodiments, $R^5$ is independently unsubstituted tert-butoxy.

In embodiments, z5 is 0. In embodiments, z5 is 1. In embodiments, z5 is 2. In embodiments, z5 is 3. In embodiments, z5 is 4. In embodiments, z5 is 5. In embodiments, z5 is 6.

In embodiments, $R^6$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^6$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, $R^6$ is independently hydrogen or halogen. In embodiments, $R^6$ is independently hydrogen or —F. In embodiments, $R^6$ is independently hydrogen. In embodiments, $R^6$ is independently hydrogen or —F.

In embodiments, $R^7$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^7$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^7$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, $R^7$ is independently hydrogen, unsubstituted $C_1$-$C_4$ alkyl, $-SO_3^-$, or $-COO^-$. In embodiments, $R^7$ is independently hydrogen, unsubstituted methyl, $-SO_3^-$, or $-COO^-$. In embodiments, $R^7$ is independently hydrogen. In embodiments, $R^7$ is independently unsubstituted $C_1$-$C_4$ alkyl. In embodiments, $R^7$ is independently unsubstituted methyl. In embodiments, $R^7$ is independently unsubstituted ethyl. In embodiments, $R^7$ is independently unsubstituted n-propyl. In embodiments, $R^7$ is independently unsubstituted isopropyl. In embodiments, $R^7$ is independently unsubstituted n-butyl. In embodiments, $R^7$ is independently unsubstituted tert-butyl. In embodiments, $R^7$ is independently $-SO_3^-$. In embodiments, $R^7$ is independently $-COO^-$.

In an aspect is provided a crosslinking agent having the formula: $R^1$-$L^1$-$R^2$ (I); wherein $R^1$ is a photo-activated bioconjugate reactive moiety; $R^2$ is a proximity enhanced bioconjugate reactive moiety; $L^1$ is a covalent linker; the bonding reactivity of $R^1$ with a first biomolecule after contact of $R^1$ with radiation is greater than the bonding reactivity of R with the first biomolecule prior to contact of $R^1$ with radiation.

In an aspect is provided a crosslinking agent having the formula: $R^1$-$L^1$-$R^2$ (I). $R^1$, $L^1$, and $R^2$ are as described herein. $R^1$ is a photo-activated bioconjugate reactive moiety. $R^2$ is a proximity enhanced bioconjugate reactive moiety. $L^1$ is a covalent linker. The bonding reactivity of $R^1$ with a first biomolecule after contact of $R^1$ with radiation is greater than the bonding reactivity of $R^1$ with the first biomolecule prior to contact of $R^1$ with radiation.

In an aspect is provided a crosslinking agent having the formula: $R^1$-$L^1$-$R^2$ (I); wherein $R^1$ is a first photo-activated bioconjugate reactive moiety; $R^2$ is a second photo-activated bioconjugate reactive moiety; $L^1$ is a covalent linker; the bonding reactivity of $R^1$ with a first biomolecule after contact of $R^1$ with radiation is greater than the bonding reactivity of $R^1$ with the first biomolecule prior to contact of $R^1$ with radiation; and the bonding reactivity of $R^2$ with a second biomolecule after contact of $R^2$ with radiation is greater than the bonding reactivity of $R^2$ with the second biomolecule prior to contact of $R^2$ with radiation.

In an aspect is provided a crosslinking agent having the formula: $R^1$-$L^1$-$R^2$ (I). $R^1$, $L^1$, and $R^2$ are as described herein. $R^1$ is a first photo-activated bioconjugate reactive moiety. $R^2$ is a second photo-activated bioconjugate reactive moiety. $L^1$ is a covalent linker. The bonding reactivity of $R^1$ with a first biomolecule after contact of $R^1$ with radiation is greater than the bonding reactivity of $R^1$ with the first biomolecule prior to contact of $R^1$ with radiation. The bonding reactivity of $R^2$ with a second biomolecule after contact of $R^2$ with radiation is greater than the bonding reactivity of $R^2$ with the second biomolecule prior to contact of $R^2$ with radiation.

In embodiments, $R^1$ is a first photo-activated bioconjugate reactive moiety capable of bonding to a first biomolecule. In embodiments, $R^2$ is a second photo-activated bioconjugate reactive moiety capable of bonding to a second biomolecule or a second location of the first biomolecule.

In embodiments, $R^1$ and $R^2$ are the same. In embodiments, $R^1$ and $R^2$ are different.

In embodiments, $R^1$ is independently

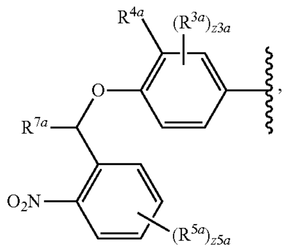
,

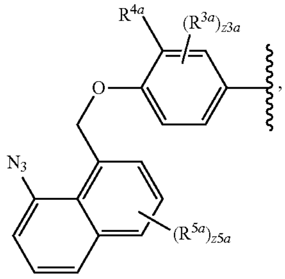
,

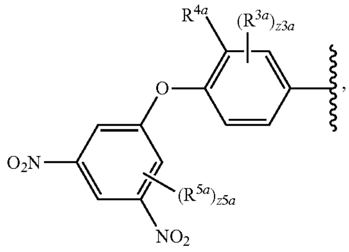
,

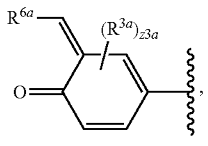
,

-continued
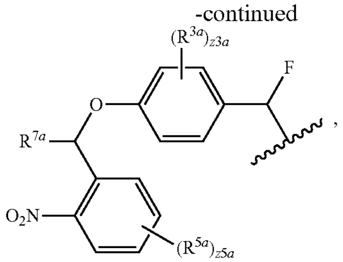
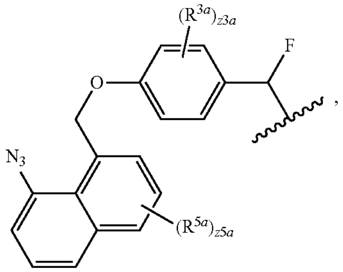
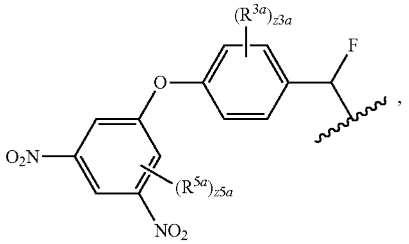
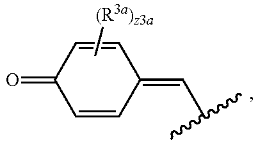
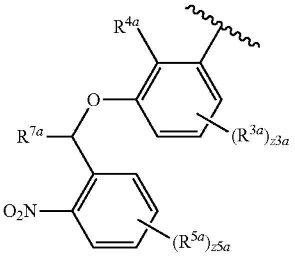
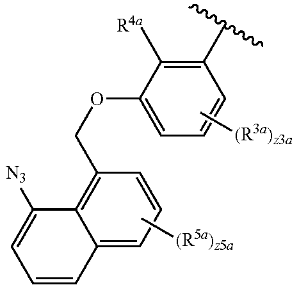
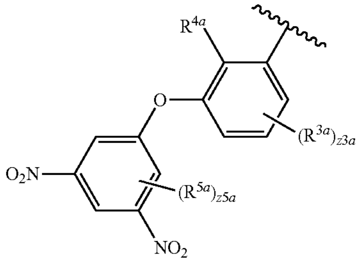
-continued
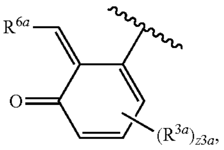
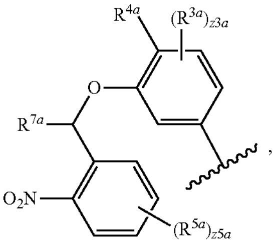
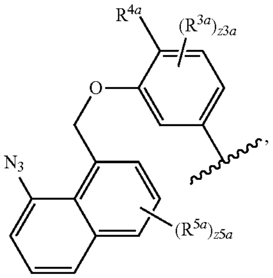
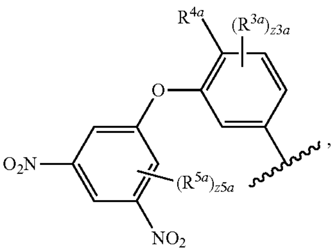
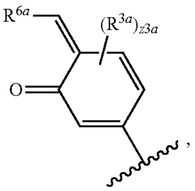
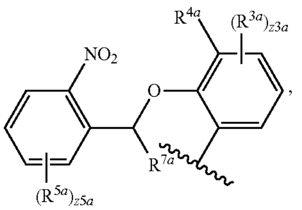
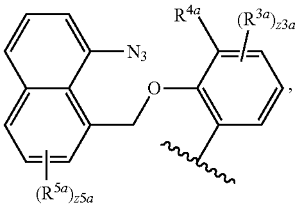

-continued

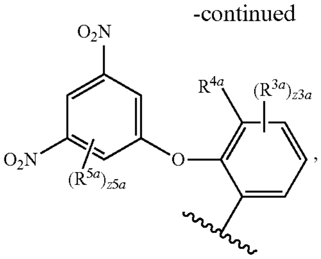

, or

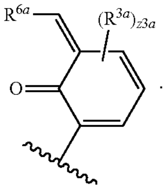

.

or $R^{4a}$, $R^{6a}$, and $R^{7a}$ are each independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety. $R^{3a}$ and $R^{5a}$ are each independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety. The symbol z3a is an integer from 0 to 4. The symbol z5a is an integer from 0 to 6.

In embodiments, $R^{4a}$, $R^{6a}$, and $R^{7a}$ are each independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryly.

In embodiments, $R^1$ is independently

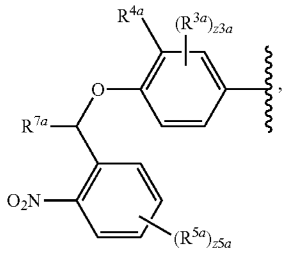

wherein $R^{3a}$, $R^{4a}$, $R^{5a}$, $R^{7a}$, z3a, and z5a are as described herein, including in embodiments. In embodiments, $R^1$ is independently

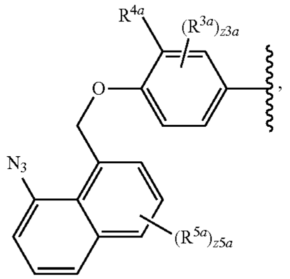

wherein $R^{3a}$, $R^{4a}$, $R^{5a}$, z3a, and z5a are as described herein, including in embodiments. In embodiments, $R^1$ is independently

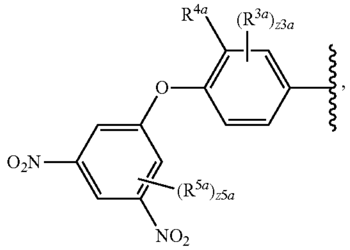

wherein $R^{3a}$, $R^{4a}$, $R^{5a}$, z3a, and z5a are as described herein, including in embodiments. In embodiments, $R^1$ is independently

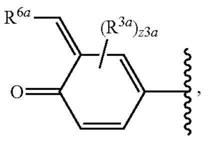

wherein $R^{3a}$, $R^{6a}$, and z3a are as described herein, including in embodiments. In embodiments, $R^1$ is independently

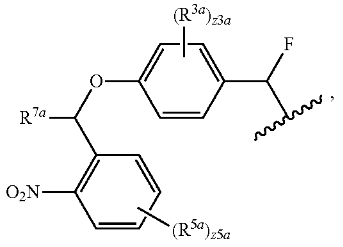

wherein $R^{3a}$, $R^{5a}$, $R^{7a}$, z3a, and z5a are as described herein, including in embodiments. In embodiments, $R^1$ is independently

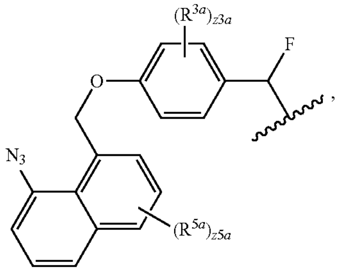

wherein $R^{3a}$, $R^{5a}$, z3a, and z5a are as described herein, including in embodiments. In embodiments, $R^1$ is independently

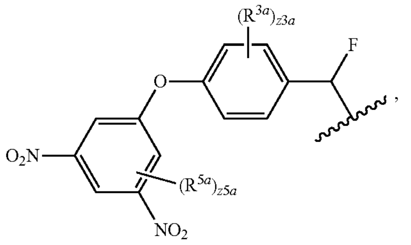

wherein $R^{3a}$, $R^{5a}$, z3a, and z5a are as described herein, including in embodiments. In embodiments, $R^1$ is independently

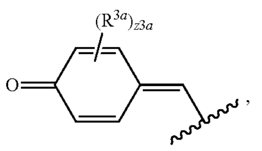

wherein $R^{3a}$ and z3a are as described herein, including in embodiments. In embodiments, $R^1$ is independently

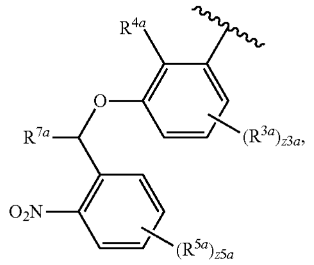

wherein $R^{3a}$, $R^{4a}$, $R^{5a}$, $R^{7a}$, z3a, and z5a are as described herein, including in embodiments. In embodiments, $R^1$ is independently

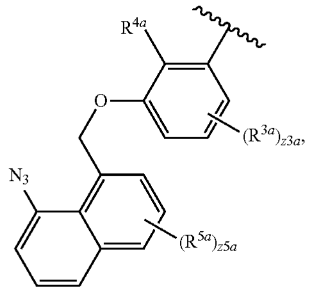

wherein $R^{3a}$, $R^{4a}$, $R^{5a}$, z3a, and z5a are as described herein, including in embodiments. In embodiments, $R^1$ is independently

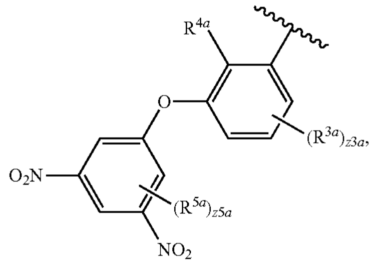

wherein $R^{3a}$, $R^{4a}$, $R^{5a}$, z3a, and z5a are as described herein, including in embodiments. In embodiments, $R^1$ is independently

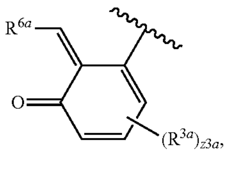

wherein $R^{3a}$, $R^{6a}$, and z3a are as described herein, including in embodiments. In embodiments, $R^1$ is independently

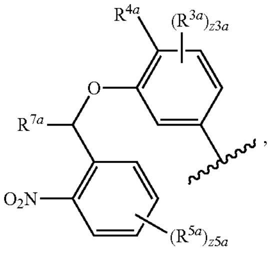

wherein $R^{3a}$, $R^{4a}$, $R^{5a}$, $R^{7a}$, z3a, and z5a are as described herein, including in embodiments. In embodiments, $R^1$ is independently

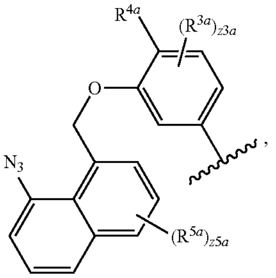

wherein $R^{3a}$, $R^{4a}$, $R^{5a}$, z3a, and z5a are as described herein, including in embodiments. In embodiments, $R^1$ is independently

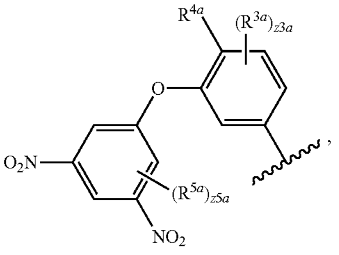

wherein $R^{3a}$, $R^{4a}$, $R^{5a}$, z3a, and z5a are as described herein, including in embodiments. In embodiments, $R^1$ is independently

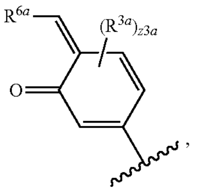

wherein $R^{3a}$, $R^{6a}$, and z3a are as described herein, including in embodiments. In embodiments, $R^1$ is independently

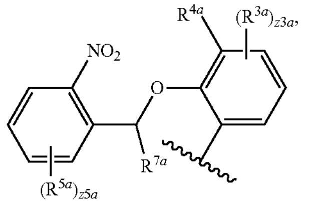

wherein $R^{3a}$, $R^{4a}$, $R^{5a}$, $R^{7a}$, z3a, and z5a are as described herein, including in embodiments. In embodiments, $R^1$ is independently

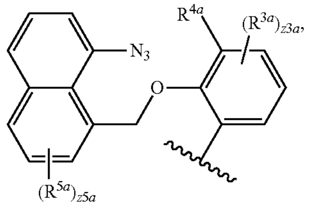

wherein $R^{3a}$, $R^{4a}$, $R^{5a}$, z3a, and z5a are as described herein, including in embodiments. In embodiments, $R^1$ is independently

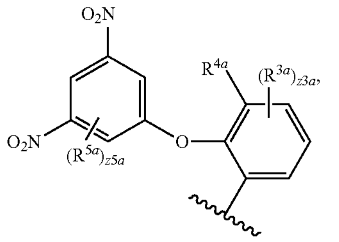

wherein $R^{3a}$, $R^{4a}$, $R^{5a}$, z3a, and z5a are as described herein, including in embodiments. In embodiments, $R^2$ is independently

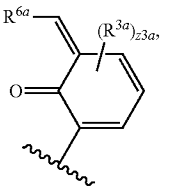

wherein $R^{3a}$, $R^{6a}$, and z3a are as described herein, including in embodiments.

In embodiments, $R^1$ is independently
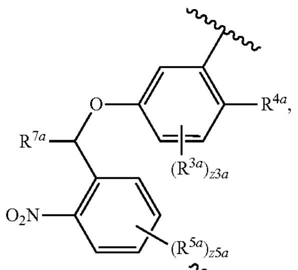
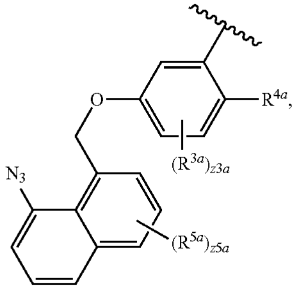
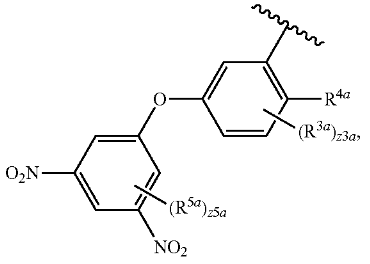
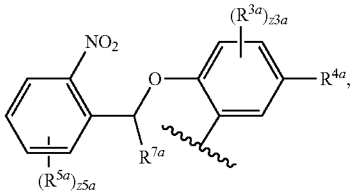
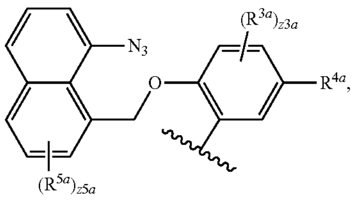
or
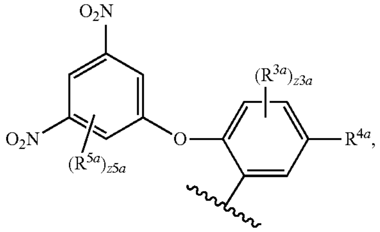
wherein $R^{3a}$, $R^{4a}$, $R^{5a}$, $R^{7a}$, z3a, and z5a are as described herein, including in embodiments.
In embodiments, $R^1$ is independently
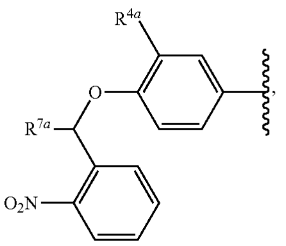
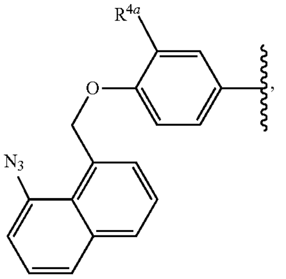
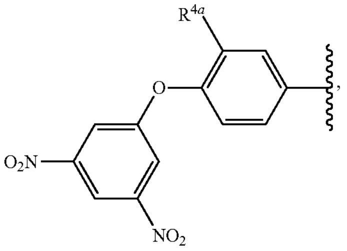
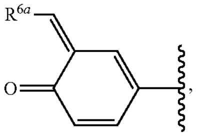
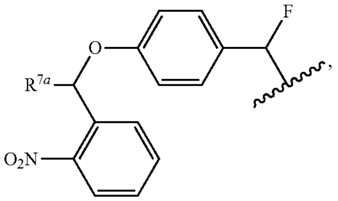
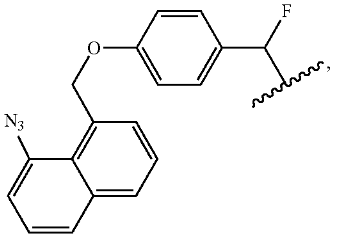
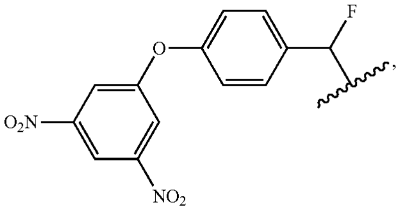
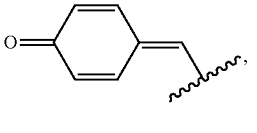

-continued
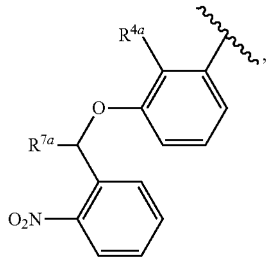
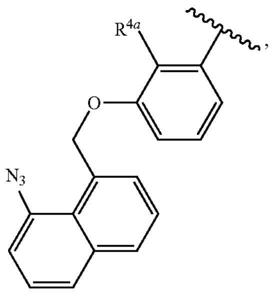
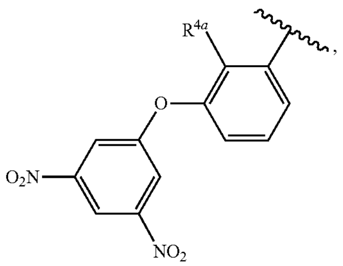
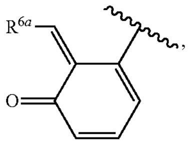
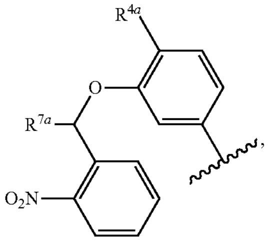
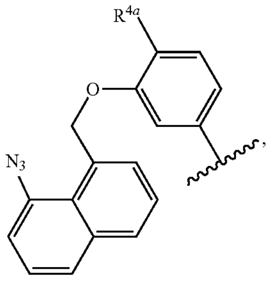
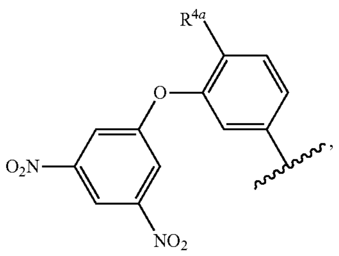
-continued
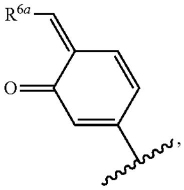
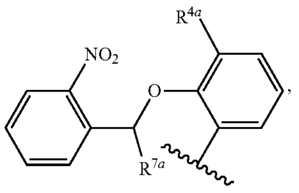
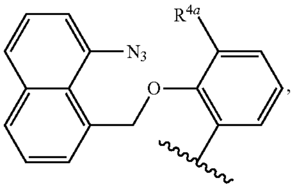
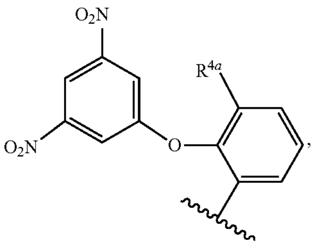
or
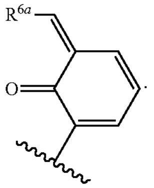
$R^{4a}$, $R^{6a}$, and $R^{7a}$ are as described herein, including in embodiments.
In embodiments, $R^1$ is independently
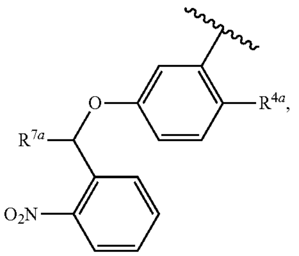
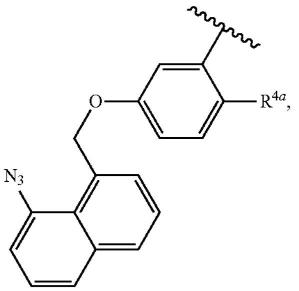
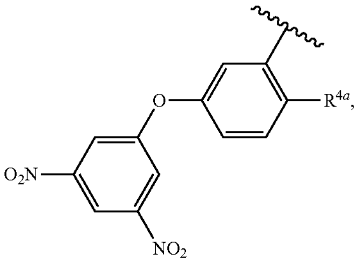

-continued

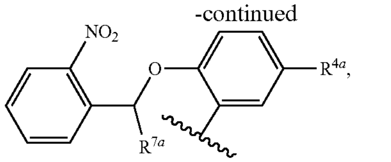

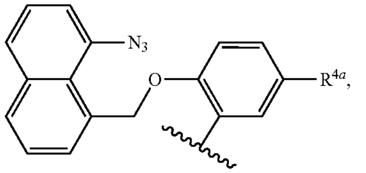

or

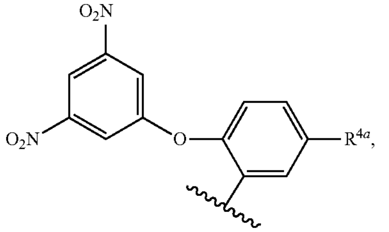

wherein $R^{4a}$ and $R^{7a}$ are as described herein, including in embodiments.

In embodiments, $R^{3a}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, a bioconjugate reactive moiety, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{3a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3a}$ is substituted with a plurality of groups selected from substituent groups, size-limited substituent groups, and lower substituent groups; each substituent group, size-limited substituent group, and/or lower substituent group may optionally be different. In embodiments, when $R^{3a}$ is substituted, it is substituted with at least one substituent group. In embodiments, when $R^{3a}$ is substituted, it is substituted with at least one size-limited substituent group. In embodiments, when $R^{3a}$ is substituted, it is substituted with at least one lower substituent group.

In embodiments, $R^{3a}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{3a}$ is independently a substituted or unsubstituted alkynyl, —$N_3$, or a bioconjugate reactive moiety. In embodiments, $R^{3a}$ is independently a substituted or unsubstituted alkynyl. In embodiments, $R^{3a}$ is independently —$N_3$. In embodiments, $R^{3a}$ is independently a bioconjugate reactive moiety.

In embodiments, $R^{3a}$ is independently substituted or unsubstituted aryl.

In embodiments, $R^{3a}$ is independently unsubstituted methoxy. In embodiments, $R^{3a}$ is independently —$SO_3^-$. In embodiments, $R^{3a}$ is independently —$COO^-$.

In embodiments, z3a is 0. In embodiments, z3a is 1. In embodiments, z3a is 2. In embodiments, z3a is 3. In embodiments, z3a is 4.

In embodiments, $R^{4a}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{4a}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, a bioconjugate reactive moiety, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{4a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{4a}$ is substituted with a plurality of groups selected from substituent groups, size-limited substituent groups, and lower substituent groups; each substituent group, size-limited substituent group, and/or lower substituent group may optionally be different. In embodiments, when $R^{4a}$ is substituted, it is substituted with at least one substituent group. In embodiments, when $R^{4a}$ is substituted, it is substituted with at least one size-limited substituent group. In embodiments, when $R^{4a}$ is substituted, it is substituted with at least one lower substituent group.

In embodiments, $R^{4a}$ is independently $-CH_2F$ or $-CHF_2$. In embodiments, $R^{4a}$ is independently $-CH_2F$. In embodiments, $R^{4a}$ is independently $-CHF_2$.

In embodiments, $R^{5a}$ is independently halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, a bioconjugate reactive moiety, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{5a}$ is independently halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, a bioconjugate reactive moiety, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{5a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5a}$ is substituted with a plurality of groups selected from substituent groups, size-limited substituent groups, and lower substituent groups; each substituent group, size-limited substituent group, and/or lower substituent group may optionally be different. In embodiments, when $R^{5a}$ is substituted, it is substituted with at least one substituent group. In embodiments, when $R^{5a}$ is substituted, it is substituted with at least one size-limited substituent group. In embodiments, when $R^{5a}$ is substituted, it is substituted with at least one lower substituent group.

In embodiments, $R^{5a}$ is independently unsubstituted $C_1$-$C_4$ alkyl. In embodiments, $R^{5a}$ is independently unsubstituted methyl. In embodiments, $R^{5a}$ is independently unsubstituted ethyl. In embodiments, $R^{5a}$ is independently unsubstituted n-propyl. In embodiments, $R^{5a}$ is independently unsubstituted isopropyl. In embodiments, $R^{5a}$ is independently unsubstituted n-butyl. In embodiments, $R^{5a}$ is independently unsubstituted tert-butyl. In embodiments, $R^{5a}$ is independently unsubstituted $-O-(C_1$-$C_4$ alkyl). In embodiments, $R^{5a}$ is independently unsubstituted methoxy. In embodiments, $R^{5a}$ is independently unsubstituted ethoxy. In embodiments, $R^{5a}$ is independently unsubstituted n-propoxy In embodiments, $R^{5a}$ is independently unsubstituted isopropoxy. In embodiments, $R^{5a}$ is independently unsubstituted n-butoxy. In embodiments, $R^{5a}$ is independently unsubstituted tert-butoxy.

In embodiments, z5a is 0. In embodiments, z5a is 1. In embodiments, z5a is 2. In embodiments, z5a is 3. In embodiments, z5a is 4. In embodiments, z5a is 5. In embodiments, z5a is 6.

In embodiments, $R^{6a}$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{6a}$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{6a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6a}$ is substituted with a plurality of groups selected from substituent groups, size-limited substituent groups, and lower substituent groups; each substituent group, size-limited substituent group, and/or lower substituent group may optionally be different. In embodiments, when $R^{6a}$ is substituted, it is substituted with at least one substituent group. In embodiments, when $R^{6a}$ is substituted, it is substituted with at least one size-limited substituent group. In embodiments, when $R^{6a}$ is substituted, it is substituted with at least one lower substituent group.

In embodiments, $R^{6a}$ is independently hydrogen or halogen. In embodiments, $R^{6a}$ is independently hydrogen or —F. In embodiments, $R^{6a}$ is independently hydrogen. In embodiments, $R^{6a}$ is independently hydrogen or —F.

In embodiments, $R^{7a}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{7a}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC (O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with at least one substituent group, size-limited substituent group, or lower substituent group) or unsubstituted alkyl, substituted (e.g., substituted with at least one substituent group, size-limited substituent group, or lower substituent group) or unsubstituted heteroalkyl, substituted (e.g., substituted with at least one substituent group, size-limited substituent group, or lower substituent group) or unsubstituted cycloalkyl, substituted (e.g., substituted with at least one substituent group, size-limited substituent group, or lower substituent group) or unsubstituted heterocycloalkyl, substituted (e.g., substituted with at least one substituent group, size-limited substituent group, or lower substituent group) or unsubstituted aryl, or substituted (e.g., substituted with at least one substituent group, size-limited substituent group, or lower substituent group) or unsubstituted heteroaryl.

In embodiments, a substituted $R^{7a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{7a}$ is substituted with a plurality of groups selected from substituent groups, size-limited substituent groups, and lower substituent groups; each substituent group, size-limited substituent group, and/or lower substituent group may optionally be different. In embodiments, when $R^{7a}$ is substituted, it is substituted with at least one substituent group. In embodiments, when $R^{7a}$ is substituted, it is substituted with at least one size-limited substituent group. In embodiments, when $R^{7a}$ is substituted, it is substituted with at least one lower substituent group.

In embodiments, $R^{7a}$ is independently hydrogen, unsubstituted $C_1$-$C_4$ alkyl, or —$COO^-$. In embodiments, $R^{7a}$ is independently hydrogen, unsubstituted methyl, or —$COO^-$. In embodiments, $R^{7a}$ is independently hydrogen. In embodiments, $R^{7a}$ is independently unsubstituted $C_1$-$C_4$ alkyl. In embodiments, $R^{7a}$ is independently unsubstituted methyl. In embodiments, $R^{7a}$ is independently unsubstituted ethyl. In embodiments, $R^{7a}$ is independently unsubstituted n-propyl. In embodiments, $R^{7a}$ is independently unsubstituted isopropyl. In embodiments, $R^{7a}$ is independently unsubstituted n-butyl. In embodiments, $R^{7a}$ is independently unsubstituted tert-butyl. In embodiments, $R^{7a}$ is independently —$COO^-$.

In embodiments, $L^1$ is —C(O)NH-$L^{1B}$-$L^{1C}$-NHC(O)—. $L^{1B}$ and $L^{1C}$ are as described herein, including in embodiments. In embodiments, $L^1$ is

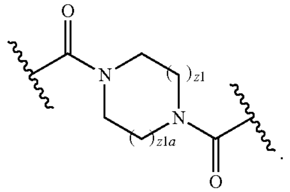

The symbol z1 is independently an integer from 0 to 2. The symbol z1a is independently an integer from 0 to 2. In embodiments, $L^1$ is

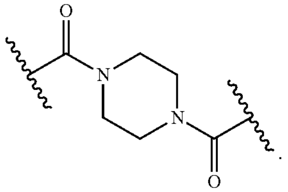 [SMILES: *C(=O)N1CCN(C(*)=O)CC1]

In embodiments, z1 is 0. In embodiments, z1 is 1. In embodiments, z1 is 2. In embodiments, z1a is 0. In embodiments, z1a is 1. In embodiments, z1a is 2.

In an aspect is provided a crosslinking agent having the formula: $R^1$-$L^1$-$R^2$ (I); wherein $R^1$ is a proximity enhanced bioconjugate reactive moiety; $R^2$ is a photo-activated bioconjugate reactive moiety; $L^1$ is a covalent linker; the bonding reactivity of $R^2$ with a second biomolecule after contact of $R^2$ with radiation is greater than the bonding reactivity of $R^2$ with the second biomolecule prior to contact of $R^2$ with radiation.

In an aspect is provided a crosslinking agent having the formula: $R^1$-$L^1$-$R^2$ (I). $R^1$, $L^1$, and $R^2$ are as described herein. $R^1$ is a proximity enhanced bioconjugate reactive moiety. $R^2$ is a photo-activated bioconjugate reactive moiety. $L^1$ is a covalent linker. The bonding reactivity of $R^2$ with a second biomolecule after contact of $R^2$ with radiation is greater than the bonding reactivity of $R^2$ with the second biomolecule prior to contact of $R^2$ with radiation.

In embodiments, $R^1$ is a proximity enhanced bioconjugate reactive moiety capable of bonding to a first biomolecule. In embodiments, $R^2$ is a photo-activated bioconjugate reactive moiety capable of bonding to a second biomolecule or a second location of the first biomolecule.

In embodiments, $R^1$ is

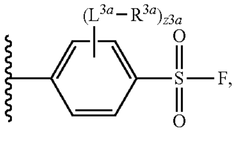
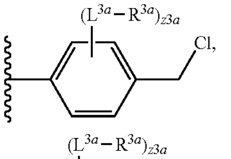
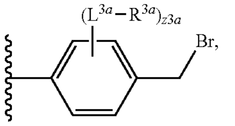
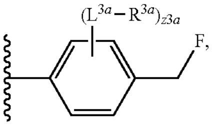
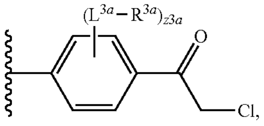
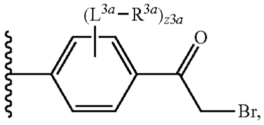
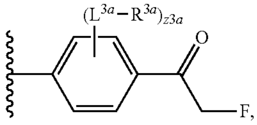
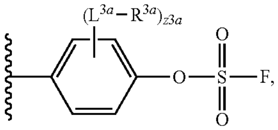
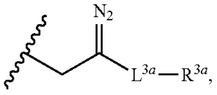

-continued

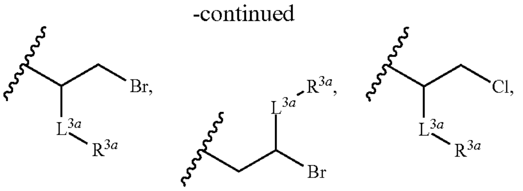
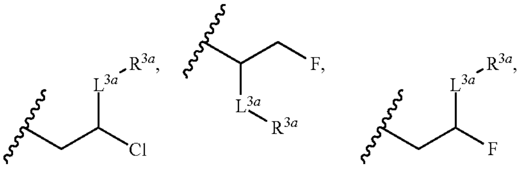
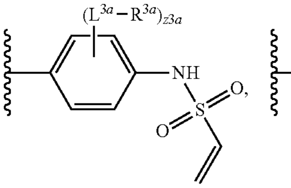
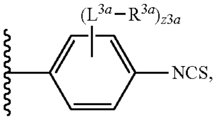
or
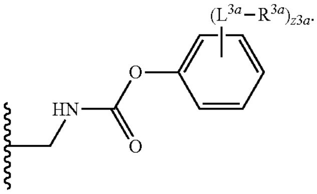

$L^{3a}$, $R^{3a}$, and z3a are as described herein, including in embodiments.

In embodiments, $R^1$ is

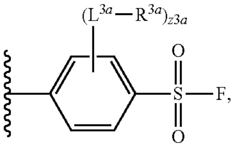
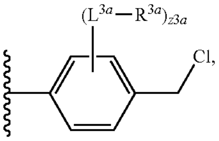
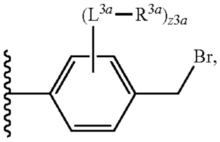
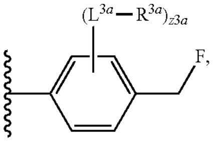
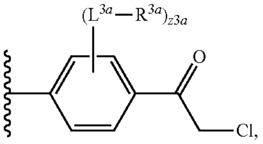
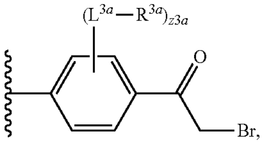
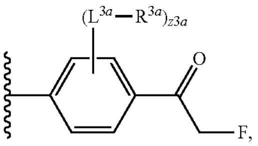
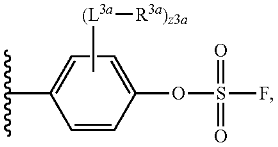
or
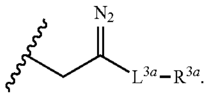

$L^{3a}$, $R^{3a}$, and z3a are as described herein, including in embodiments.

In embodiments, $R^1$ is independently

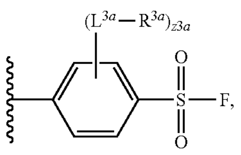

wherein $L^{3a}$, $R^{3a}$, and z3a are as described herein, including in embodiments. In embodiments, $R^1$ is independently

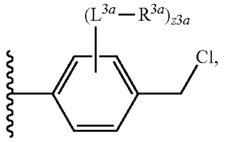

wherein $L^{3a}$, $R^{3a}$, and z3a are as described herein, including in embodiments. In embodiments, $R^1$ is independently

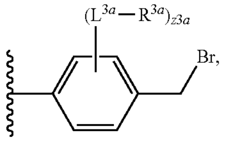

wherein $L^{3a}$, $R^{3a}$, and z3a are as described herein, including in embodiments. In embodiments, $R^1$ is independently

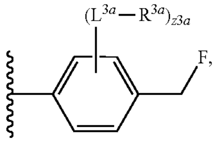

wherein $L^{3a}$, $R^{3a}$, and z3a are as described herein, including in embodiments. In embodiments, $R^1$ is independently

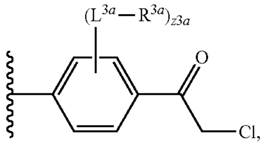

wherein $L^{3a}$, $R^{3a}$, and z3a are as described herein, including in embodiments. In embodiments, $R^1$ is independently

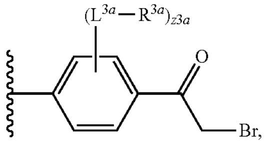

wherein $L^{3a}$, $R^{3a}$, and z3a are as described herein, including in embodiments. In embodiments, $R^1$ is independently

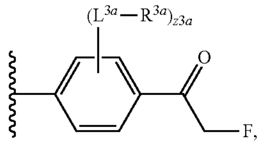

wherein $L^{3a}$, $R^{3a}$, and z3a are as described herein, including in embodiments. In embodiments, $R^1$ is independently

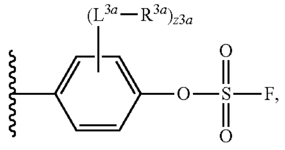

wherein $L^{3a}$, $R^{3a}$, and z3a are as described herein, including in embodiments. In embodiments, $R^1$ is independently

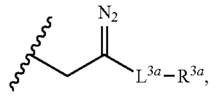

wherein $L^{3a}$ and $R^{3a}$ are as described herein, including in embodiments. In embodiments, $R^1$ is independently

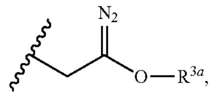

wherein $R^{3a}$ is as described herein, including in embodiments. In embodiments, $R^1$ is independently

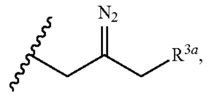

wherein $R^{3a}$ is as described herein, including in embodiments. In embodiments, $R^1$ is independently

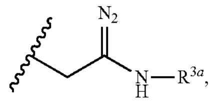

wherein $R^{3a}$ is as described herein, including in embodiments. In embodiments, $R^1$ is independently

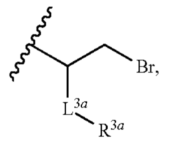

wherein $L^{3a}$ and $R^{3a}$ are as described herein, including in embodiments. In embodiments, $R^1$ is independently

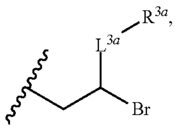

wherein $L^{3a}$ and $R^{3a}$ are as described herein, including in embodiments. In embodiments, $R^1$ is independently

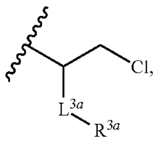

wherein $L^{3a}$ and $R^{3a}$ are as described herein, including in embodiments. In embodiments, $R^1$ is independently

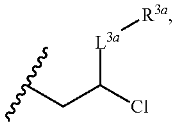

wherein $L^{3a}$ and $R^{3a}$ are as described herein, including in embodiments. In embodiments, $R^1$ is independently

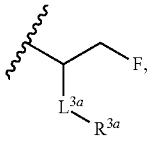

wherein $L^{3a}$ and $R^{3a}$ are as described herein, including in embodiments. In embodiments, $R^1$ is independently

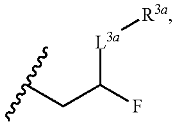

wherein $L^{3a}$ and $R^{3a}$ are as described herein, including in embodiments. In embodiments, $R^1$ is independently

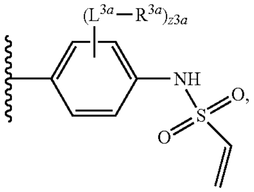

wherein $L^{3a}$ and $R^{3a}$ are as described herein, including in embodiments. In embodiments, $R^1$ is independently

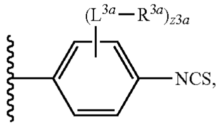

wherein $L^{3a}$ and $R^{3a}$ are as described herein, including in embodiments. In embodiments, $R^1$ is independently

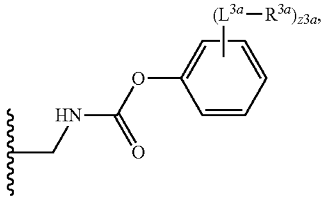

wherein $L^{3a}$ and $R^{3a}$ are as described herein, including in embodiments. In embodiments, $R^1$ is independently

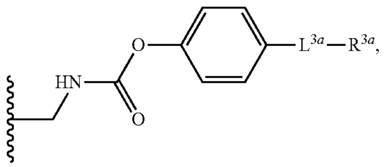

wherein $L^{3a}$ and $R^{3a}$ are as described herein, including in embodiments. In embodiments, $R^{3a}$ is independently substituted or unsubstituted alkyl. In embodiments, $R^{3a}$ is independently substituted or unsubstituted aryl.

In embodiments, $R^1$ is independently

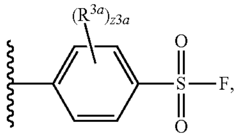 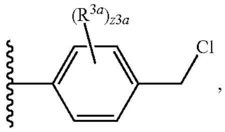 ,

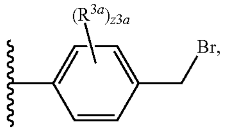 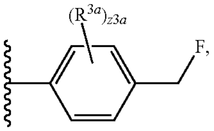

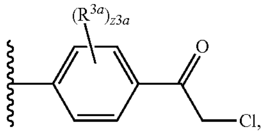

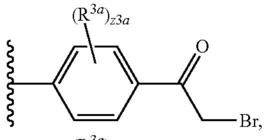 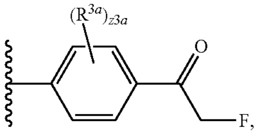

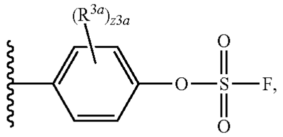 or 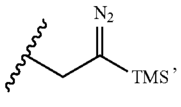

wherein $R^{3a}$ and z3a are as described herein.

In embodiments, $R^1$ is independently
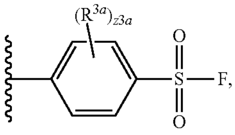
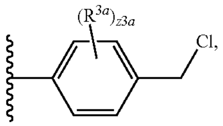
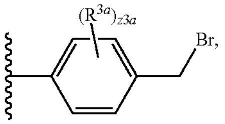
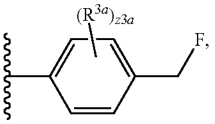
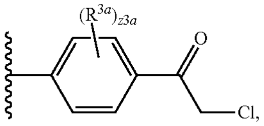
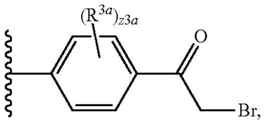
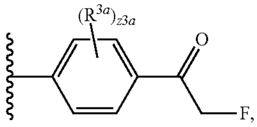
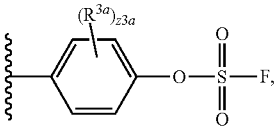
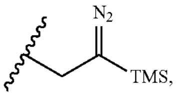
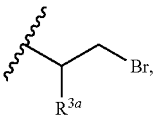
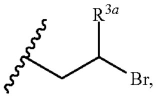
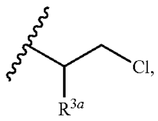
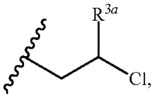
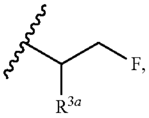
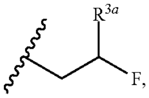
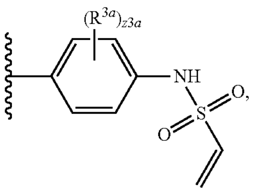
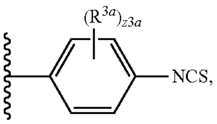
or
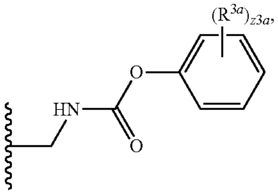
wherein $R^{3a}$ and z3a are as described herein.
In embodiments, $R^1$ is independently
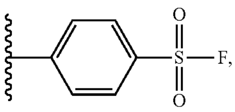
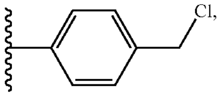
-continued
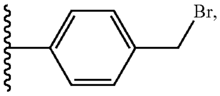
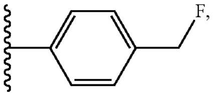
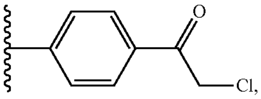
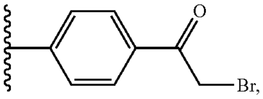
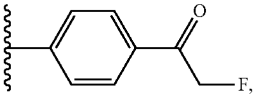
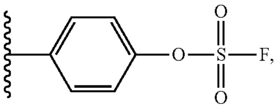
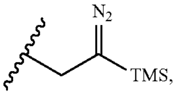
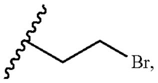
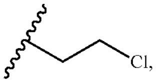
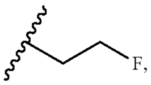
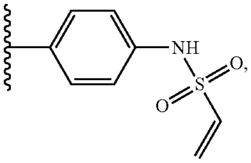
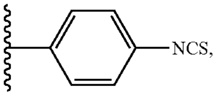
or
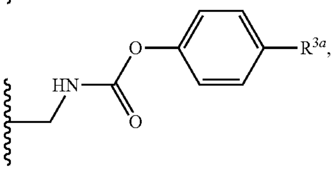
wherein $R^{3a}$ is as described herein, including in embodiments.
In embodiments, $R^1$ is independently
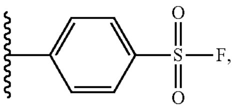
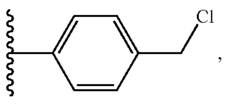
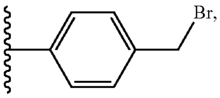
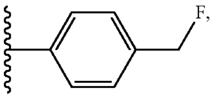

-continued

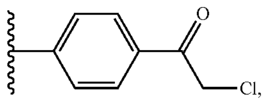

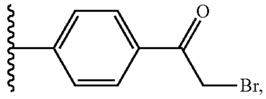

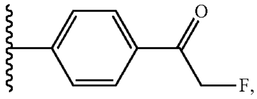

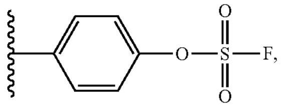

or

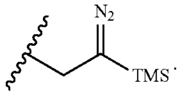

In embodiments, $R^1$ is independently

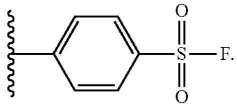 [SMILES: *c1ccc(S(=O)(=O)F)cc1]

In embodiments, $R^1$ is independently

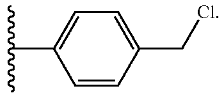 [SMILES: *c1ccc(CBr)cc1]

In embodiments, $R^1$ is independently

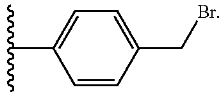

In embodiments, $R^1$ is independently

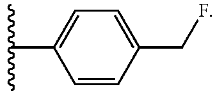 [SMILES: *c1ccc(CF)cc1]

In embodiments, $R^1$ is independently

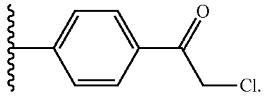 [SMILES: *c1ccc(C(=O)CCl)cc1]

In embodiments, $R^1$ is independently

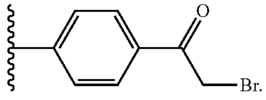 [SMILES: *c1ccc(C(=O)CBr)cc1]

In embodiments, $R^1$ is independently

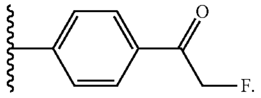 [SMILES: *c1ccc(C(=O)CF)cc1]

In embodiments, $R^1$ is independently

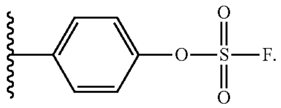 [SMILES: *c1ccc(OS(=O)(=O)F)cc1]

In embodiments, $R^1$ is independently

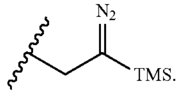

$L^{3a}$ is independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{3a}$ is independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^{3a}$ is independently a bond, —$S(O)_2$—, —NH—, —O—, —S—, —C(O)—, —C(O)NH—, —NHC(O)—, —NHC(O)NH—, —C(O)O—, —OC(O)—, substituted (e.g., substituted with at least one substituent group, size-limited substituent group, or lower substituent group) or unsubstituted alkylene, substituted (e.g., substituted with at least one substituent group, size-limited substituent group, or lower substituent group) or unsubstituted heteroalkylene, substituted (e.g., substituted with at least one substituent group, size-limited substituent group, or lower substituent group) or unsubstituted cycloalkylene, substituted (e.g., substituted with at least one substituent group, size-limited substituent group, or lower substituent group) or unsubstituted heterocycloalkylene, substituted (e.g., substituted with at least one substituent group, size-limited substituent group, or lower substituent group) or unsubstituted arylene, or substituted (e.g., substituted with at least one substituent group, size-limited substituent group, or lower substituent group) or unsubstituted heteroarylene.

In embodiments, a substituted $L^{3a}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{3a}$ is substituted with a plurality of groups selected from substituent groups, size-limited substituent groups, and lower substituent groups; each substituent group, size-limited substituent group, and/or lower substituent group may optionally be different. In embodiments, when $L^{3a}$ is substituted, it is substituted with at least one substituent group. In embodiments, when $L^{3a}$ is substituted, it is substituted with at least one size-limited substituent group. In embodiments, when $L^{3a}$ is substituted, it is substituted with at least one lower substituent group.

In embodiments, $L^{3a}$ is independently a bond, —S(O)$_2$—, —NH—, —O—, —S—, —C(O)—, —C(O)NH—, —NHC(O)—, —NHC(O)NH—, —C(O)O—, —OC(O)—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, 2 to 3 membered, or 4 to 5 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 8 membered, 3 to 6 membered, 4 to 6 membered, 4 to 5 membered, or 5 to 6 membered), unsubstituted arylene (e.g., $C_6$-$C_{10}$ or phenylene), or unsubstituted heteroarylene (e.g., 5 to 10 membered, 5 to 9 membered, or 5 to 6 membered).

In embodiments, the crosslinking agent has the formula:

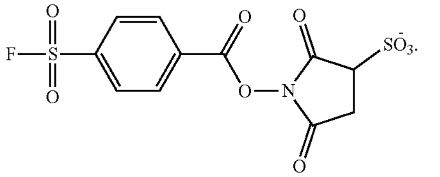

In embodiments, the crosslinking agent has the formula:

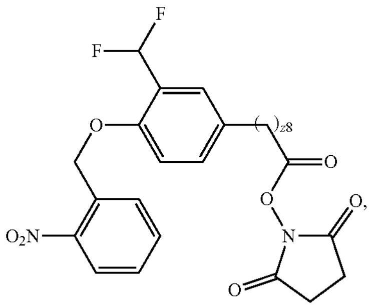

wherein z8 is an integer from 0 to 5.

In embodiments, the crosslinking agent has the formula:

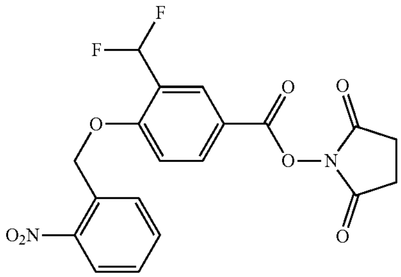

or

-continued

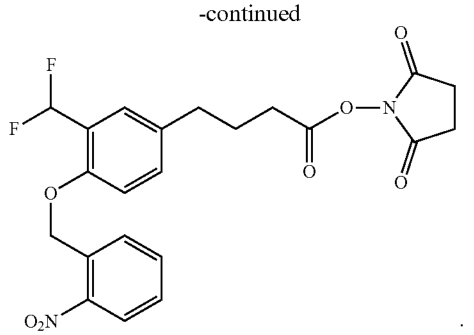

In embodiments, the crosslinking agent has the formula:

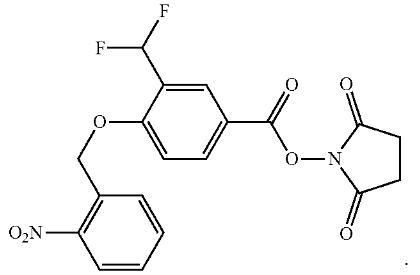 [SMILES: O=C(ON1C(=O)CCC1=O)c1ccc(OCc2ccccc2[N+](=O)[O-])c(C(F)F)c1]

In embodiments, the crosslinking agent has the formula:

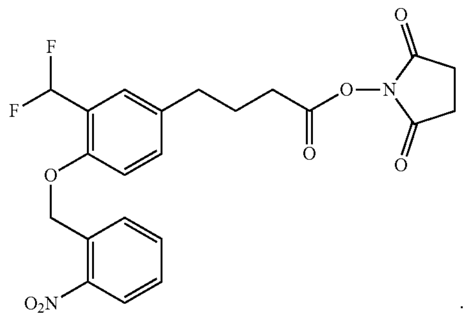 [SMILES: O=C(CCCc1ccc(OCc2ccccc2[N+](=O)[O-])c(C(F)F)c1)ON1C(=O)CCC1=O]

In embodiments, the crosslinking agent has the formula:

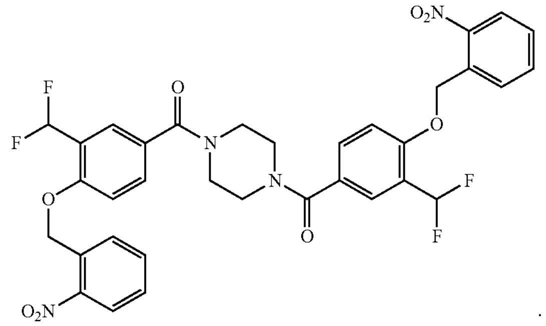 [SMILES: O=C(c1ccc(OCc2ccccc2[N+](=O)[O-])c(C(F)F)c1)N1CCN(C(=O)c2ccc(OCc3ccccc3[N+](=O)[O-])c(C(F)F)c2)CC1]

In embodiments, the crosslinking agent includes a heavy isotope. For example, the crosslinking agent may include $^{2}H$, $^{13}C$, or $^{15}N$, or a combination of one or more of the foregoing. Additional isotopic labels may be found, for example in Chavez, J. D. & Bruce, J. E. Chemical crosslinking with mass spectrometry: a tool for systems structural biology. Curr. Opin. Chem. Biol. 48, 8-18 (2018), which is incorporated herein by reference in its entirety for all purposes.

III. Methods of Use

Figure 1B:
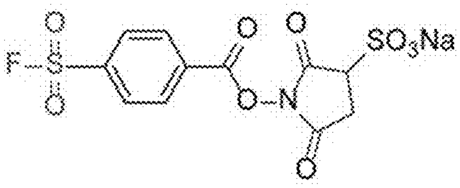
Figure 1C:
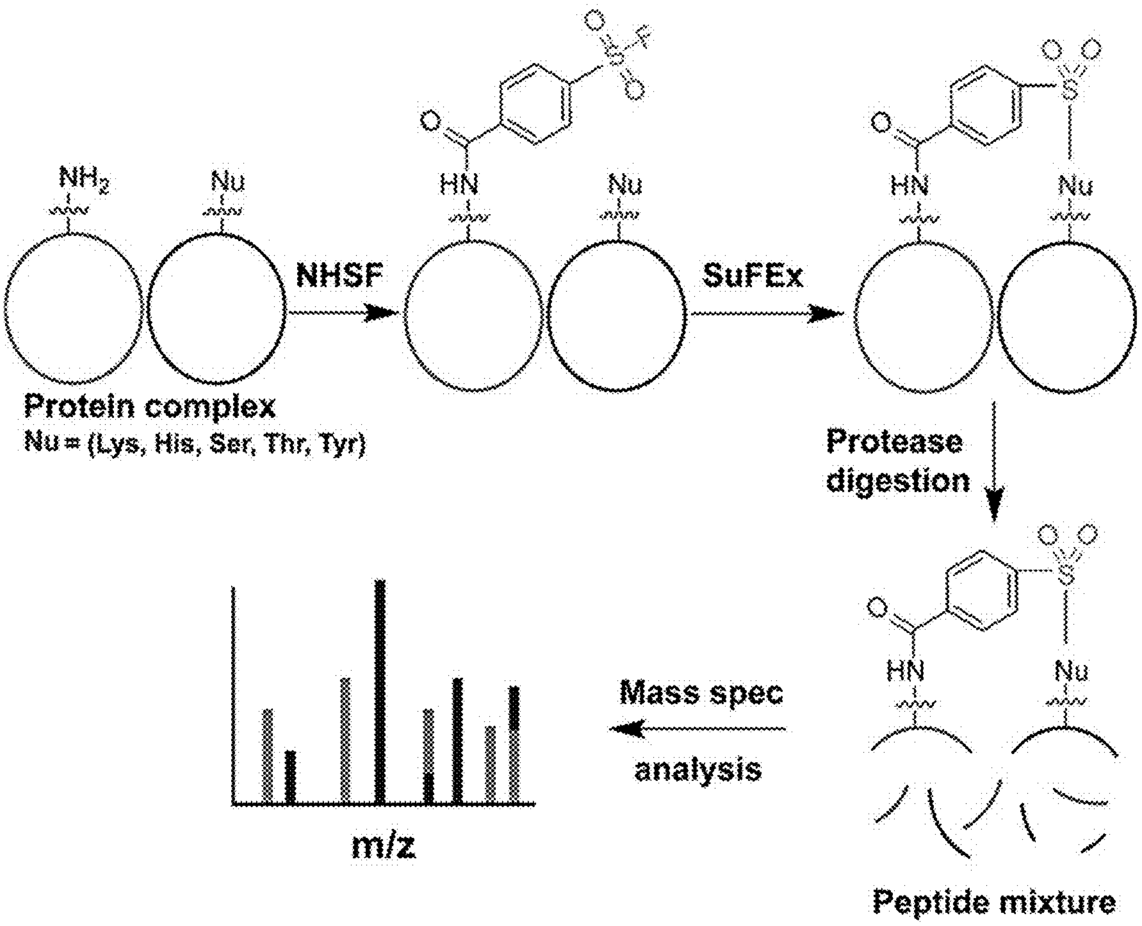

In an aspect is provided a method of detecting a covalently conjugated molecule, the method including i) contacting a first biomolecule and a second biomolecule with a crosslinking agent to form the covalently conjugated biomolecule; ii) identifying a first point of attachment of the crosslinking agent to the first biomolecule using mass spectroscopy; and iii) identifying a second point of attachment of the crosslinking agent to the second biomolecule using mass spectroscopy; thereby detecting a covalently conjugated molecule. The crosslinking agent has the formula: $R^1$-$L^4$-$R^2$ (I). $R^1$, $L^1$, and $R^2$ are as described herein. $R^1$ is a bioconjugate reactive moiety capable of bonding to the first biomolecule. $R^2$ is a proximity enhanced bioconjugate reactive moiety capable of bonding to the second biomolecule. $L^1$ is a covalent linker. The bonding reactivity of $R^1$ with the first molecule is greater than the bonding reactivity of $R^2$ with the second biomolecule. In embodiments, the method is schematically shown in FIGS. 1A-1C. In embodiments, the second order rate constant of $R^1$ with the first molecule is greater than the second order rate constant of $R^2$ with the second biomolecule.

In an aspect is provided a method of detecting a covalently conjugated biomolecule, the method including i) contacting a first biomolecule and a second biomolecule with a crosslinking agent to form the covalently conjugated biomolecule; ii) identifying a first point of attachment of the crosslinking agent to the first biomolecule; and iii) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a bioconjugate reactive moiety; $R^2$ is a proximity enhanced bioconjugate reactive moiety; $L^1$ is a covalent linker; and the bonding reactivity of $R^1$ with the first biomolecule is greater than the bonding reactivity of $R^2$ with the second biomolecule. $R^1$, $L^1$, and $R^2$ are as described herein. $R^1$ is a bioconjugate reactive moiety. $R^2$ is a proximity enhanced bioconjugate reactive moiety. $L^1$ is a covalent linker. The bonding reactivity of R with the first biomolecule is greater than the bonding reactivity of $R^2$ with the second biomolecule. In embodiments, the method is schematically shown in FIGS. 1A-1C. In embodiments, the second order rate constant of $R^1$ with the first biomolecule is greater than the second order rate constant of $R^2$ with the second biomolecule.

In embodiments, the covalently conjugated biomolecule includes a first biomolecule conjugated to a second biomolecule.

In embodiments, the first point of attachment is identified using mass spectrometry. In embodiments, the second point of attachment is identified using mass spectrometry.

In embodiments a (e.g., first or second) point of attachment is an atom (e.g., carbon, nitrogen, sulfur, or oxygen). In embodiments, a (e.g., first or second) point of attachment is an amino acid. In embodiments, a (e.g., first or second) point of attachment is an amine moiety, a carboxylate moiety, or a sulfhydryl moiety.

In embodiments, the first biomolecule is a protein, nucleic acid, or glycan; and the second biomolecule is a protein, nucleic acid, or glycan. In embodiments, the first biomolecule is a first protein; and the second biomolecule is a second protein. In embodiments, the first biomolecule is a first protein; and the second biomolecule is a second protein, wherein $R^1$ is a bioconjugate reactive moiety reactive with a first amino acid of the first protein, and $R^2$ is a proximity enhanced bioconjugate reactive moiety reactive with a second amino acid of the second protein. In embodiments, the first biomolecule is a first nucleic acid; and the second biomolecule is a second nucleic acid. In embodiments, the first biomolecule is a first glycan; and the second biomolecule is a second glycan. In embodiments, the first biomolecule is a protein; and the second biomolecule is a nucleic acid. In embodiments, the first biomolecule is a protein; and the second biomolecule is a glycan. In embodiments, the first biomolecule is a nucleic acid; and the second biomolecule is a protein. In embodiments, the first biomolecule is a nucleic acid; and the second biomolecule is a glycan. In embodiments, the first biomolecule is a glycan; and the second biomolecule is a protein. In embodiments, the first biomolecule is a glycan; and the second biomolecule is a nucleic acid.

In embodiments, the first biomolecule is a protein or nucleic acid; and the second biomolecule is a protein or nucleic acid. In embodiments, the first biomolecule is a first protein; and the second biomolecule is a second protein. In embodiments, the first biomolecule is a first protein; and the second biomolecule is a second protein, wherein $R^1$ is a bioconjugate reactive moiety reactive with a first amino acid of the first protein, and $R^2$ is a proximity enhanced bioconjugate reactive moiety reactive with the second amino acid of the second protein.

In embodiments, $R^1$ reacts with an amine moiety of the first biomolecule, carboxylate moiety of the first biomolecule, sulfhydryl moiety of the first biomolecule, or hydroxyl moiety of the first biomolecule. In embodiments, $R^1$ reacts with an amine moiety of the first biomolecule, carboxylate moiety of the first biomolecule, or sulfhydryl moiety of the first biomolecule.

In embodiments, $R^1$ reacts with an amino terminus of the first biomolecule, a lysine side chain of the biomolecule, a glutamate side chain of the first amino acid of the first biomolecule, an aspartate side chain of the first amino acid of the first biomolecule, or a cysteine side chain of the first amino acid of the first biomolecule.

In embodiments, $R^2$ reacts with an amine moiety of the second biomolecule, imidazolyl moiety of the second biomolecule, or hydroxyl moiety of the second biomolecule.

In embodiments, $R^2$ reacts with an amino terminus of the second biomolecule, a lysine side chain of the second amino acid of the second biomolecule, a histidine side chain of the second amino acid of the second biomolecule, a serine side chain of the second amino acid of the second biomolecule, a threonine side chain of the second amino acid of the second biomolecule, or a tyrosine side chain of the second amino acid of the biomolecule.

In embodiments, the first point of attachment is an amino terminus of the first biomolecule, a lysine side chain of the first biomolecule, a glutamate side chain of the first biomolecule, an aspartate side chain of the first biomolecule, or a cysteine side chain of the first biomolecule.

In embodiments, the second point of attachment is an amino terminus of the second biomolecule, a lysine side chain of the second biomolecule, a histidine side chain of the second biomolecule, a serine side chain of the second biomolecule, a threonine side chain of the second biomolecule, or a tyrosine side chain of the second biomolecule.

In an aspect is provided a method of detecting an intramolecular crosslinked protein, the method including: i)

contacting the protein with a crosslinking agent, wherein the crosslinking agent bonds to a first amino acid of the protein and a second amino acid of the protein to form the intramolecular crosslinked protein; ii) identifying a first point of attachment of the crosslinking agent to the protein using mass spectroscopy; and iii) identifying a second point of attachment of the crosslinking agent to the protein using mass spectroscopy. The crosslinking agent has the formula: $R^1$-$L^1$-$R^2$ (I). $R^1$, $L^1$, and $R^2$ are as described herein. $R^1$ is a bioconjugate reactive moiety capable of bonding with the first amino acid. $R^2$ is a proximity enhanced bioconjugate reactive moiety capable of bonding with the second amino acid. $L^1$ is a covalent linker. The bonding reactivity of $R^1$ with the first amino acid is greater than the bonding reactivity of $R^2$ with the second amino acid (e.g., under identical conditions and wherein the bonding reactivity is the second order rate constant measured in the absence of the other bioconjugate reactive moiety).

In an aspect is provided a method of detecting an intramolecular crosslinked protein, the method including: i) contacting the protein with a crosslinking agent, wherein the crosslinking agent bonds to a first amino acid of the protein and a second amino acid of the protein to form the intramolecular crosslinked protein; ii) identifying a first point of attachment of the crosslinking agent to the protein; and iii) identifying a second point of attachment of the crosslinking agent to the protein and thereby detecting the intramolecular crosslinked protein. The crosslinking agent has the formula: $R^1$-$L^1$-$R^2$ (I); wherein $R^1$ is a bioconjugate reactive moiety; $R^2$ is a proximity enhanced bioconjugate reactive moiety; $L^1$ is a covalent linker; and the bonding reactivity of $R^1$ with the first amino acid is greater than the bonding reactivity of $R^2$ with the second amino acid. $R^1$, $L^1$, and $R^2$ are as described herein. $R^1$ is a bioconjugate reactive moiety. $R^2$ is a proximity enhanced bioconjugate reactive moiety. $L^1$ is a covalent linker. The bonding reactivity of $R^1$ with the first amino acid is greater than the bonding reactivity of $R^2$ with the second amino acid (e.g., under identical conditions and wherein the bonding reactivity is the second order rate constant measured in the absence of the other bioconjugate reactive moiety).

In embodiments, the first point of attachment is identified using mass spectrometry. In embodiments, the second point of attachment is identified using mass spectrometry.

In embodiments, the bonding reactivity of $R^1$ is at least 10 fold greater than $R^2$. In embodiments, the bonding reactivity of $R^1$ is about 10 fold greater than $R^2$. In embodiments, the bonding reactivity of $R^1$ is about 10 to about 100 fold greater than $R^2$. In embodiments, all bonding reactivity comparisons are calculated, predicted, or measured under identical conditions and wherein the bonding reactivity is the second order rate constant measured in the absence of the other bioconjugate reactive moiety. In embodiments, the bonding reactivity (e.g., intrinsic reactivity) of $R^1$ towards a given moiety (e.g., an amine nucleophile) is greater (e.g., at least 10-fold greater) than the reactivity of $R^2$ towards the same moiety (e.g., an amine nucleophile), as determined by the second order rate constants in solution (e.g., water).

In embodiments, $R^1$ reacts with an amine moiety, a carboxylate moiety, or a sulfhydryl moiety. In embodiments, $R^1$ reacts with an amine moiety of a protein, carboxylate moiety of a protein, or sulfhydryl moiety of a protein.

In embodiments, $R^1$ reacts with a diol of RNA and $R^2$ reacts with a saccharide. In embodiments, $R^1$ reacts with a hydroxyl of RNA and $R^2$ reacts with a saccharide.

In embodiments, $R^1$ reacts with an amino terminus of the protein, a lysine side chain of the protein, a glutamate side chain of the first amino acid of the protein, an aspartate side chain of the first amino acid of the protein, or a cysteine side chain of the first amino acid of the protein.

In embodiments, $R^1$ reacts with the amino terminus of the first protein. In embodiments, $R^1$ reacts with the amino terminus of the intramolecular crosslinked protein. In embodiments, $R^1$ reacts with a lysine side chain of the first protein. In embodiments, $R^1$ reacts with a lysine side chain of the intramolecular crosslinked protein. In embodiments, $R^1$ reacts with a glutamate side chain of the first amino acid of the first protein. In embodiments, $R^1$ reacts with a glutamate side chain of the intramolecular crosslinked protein. In embodiments, $R^1$ reacts with an aspartate side chain of the first amino acid of the first protein. In embodiments, $R^1$ reacts with an aspartate side chain of the intramolecular crosslinked protein. In embodiments, $R^1$ reacts with a cysteine side chain of the first amino acid of the first protein. In embodiments, $R^1$ reacts with a cysteine side chain of the intramolecular crosslinked protein In embodiments, $R^1$ reacts with the amino terminus of the first protein or the intramolecular crosslinked protein, a lysine side chain of the first protein or the intramolecular crosslinked protein, a glutamate side chain of the first amino acid of the first protein or the intramolecular crosslinked protein, an aspartate side chain of the first amino acid of the first protein or the intramolecular crosslinked protein, or a cysteine side chain of the first amino acid of the first protein or the intramolecular crosslinked protein.

In embodiments, $R^2$ reacts with an amine moiety, imidazolyl moiety, or hydroxyl moiety.

In embodiments, $R^2$ reacts with a protein amine moiety, protein imidazolyl moiety, or protein hydroxyl moiety.

In embodiments, $R^2$ reacts with an amine moiety of the protein, imidazolyl moiety of the protein, or hydroxyl moiety of the protein.

In embodiments, $R^2$ reacts with an amino terminus of the protein, a lysine side chain of the second amino acid of the protein, a histidine side chain of the second amino acid of the protein, a serine side chain of the second amino acid of the protein, a threonine side chain of the second amino acid of the protein, or a tyrosine side chain of the second amino acid of the protein.

In embodiments, $R^2$ is a proximity enhanced bioconjugate reactive moiety as described in Xiang, Z. et al. Adding an unnatural covalent bond to proteins through proximity-enhanced bioreactivity. Nature methods 10, 885-888 (2013) and Wang, L. Genetically encoding new bioreactivity. New Biotechnology 38, 16-25 (2017), both of which are incorporated herein by reference in their entirety for all purposes. In embodiments, $R^2$ is a proximity enhanced bioconjugate reactive moiety as described in Mix, K. A., Aronoff, M. R. & Raines, R. T. Diazo Compounds: Versatile Tools for Chemical Biology. ACS Chem. Biol. 11, 3233-3244 (2016), which is incorporated herein by reference in its entirety for all purposes. In embodiments, $R^2$ is a proximity enhanced bioconjugate reactive moiety as described in Chen, X.-H. et al. Genetically Encoding an Electrophilic Amino Acid for Protein Stapling and Covalent Binding to Native Receptors. ACS Chem. Biol. 9, 1956-1961 (2014); Furman, J. L. et al. A Genetically Encoded aza-Michael Acceptor for Covalent Cross-Linking of Protein-Receptor Complexes. J. Am. Chem. Soc. 136, 8411-8417 (2014); Xuan, W. et al. Genetic Incorporation of a Reactive Isothiocyanate Group into Proteins. Angew. Chem. Int. Ed. 55, 10065-10068 (2016); and Xuan, W. et al. Protein Crosslinking by Genetically Encoded Noncanonical Amino Acids with Reactive Aryl Carbamate Side Chains. Angew. Chem. Int. Ed. 56, 5096-5100 (2017), all of which are incorporated herein by reference in their entirety for all purposes.

In embodiments, $R^2$ reacts with the amino terminus of the second protein. In embodiments, $R^2$ reacts with the amino terminus of the crosslinked protein. In embodiments, $R^2$ reacts with a lysine side chain of the second amino acid of the second protein. In embodiments, $R^2$ reacts with a lysine side chain of the crosslinked protein. In embodiments, $R^2$ reacts with a histidine side chain of the second amino acid of the second protein. In embodiments, $R^2$ reacts with a histidine side chain of the crosslinked protein. In embodiments, $R^2$ reacts with a serine side chain of the second amino acid of the second protein. In embodiments, $R^2$ reacts with a serine side chain of the crosslinked protein. In embodiments, $R^2$ reacts with a threonine side chain of the second amino acid of the second protein. In embodiments, $R^2$ reacts with a threonine side chain of the crosslinked protein. In embodiments, $R^2$ reacts with a tyrosine side chain of the second amino acid of the second protein. In embodiments, $R^2$ reacts with a tyrosine side chain of the crosslinked protein.

In embodiments, $R^2$ reacts with the amino terminus of the second protein. In embodiments, $R^2$ reacts with the amino terminus of the intramolecular crosslinked protein. In embodiments, $R^2$ reacts with a lysine side chain of the second amino acid of the second protein. In embodiments, $R^2$ reacts with a lysine side chain of the intramolecular crosslinked protein. In embodiments, $R^2$ reacts with a histidine side chain of the second amino acid of the second protein. In embodiments, $R^2$ reacts with a histidine side chain of the intramolecular crosslinked protein. In embodiments, $R^2$ reacts with a serine side chain of the second amino acid of the second protein. In embodiments, $R^2$ reacts with a serine side chain of the intramolecular crosslinked protein. In embodiments, $R^2$ reacts with a threonine side chain of the second amino acid of the second protein. In embodiments, $R^2$ reacts with a threonine side chain of the intramolecular crosslinked protein. In embodiments, $R^2$ reacts with a tyrosine side chain of the second amino acid of the second protein. In embodiments, $R^2$ reacts with a tyrosine side chain of the intramolecular crosslinked protein.

In embodiments, $R^2$ reacts with the amino terminus of the second protein or the intramolecular crosslinked protein, a lysine side chain of the second amino acid of the second protein or the intramolecular crosslinked protein, a histidine side chain of the second amino acid of the second protein or the intramolecular crosslinked protein, a serine side chain of the second amino acid of the second protein or the intramolecular crosslinked protein, a threonine side chain of the second amino acid of the second protein or the intramolecular crosslinked protein, or a tyrosine side chain of the second amino acid of the second protein or the intramolecular crosslinked protein. In embodiments, $R^2$ reacts with a serine side chain of the second amino acid of the second protein wherein the serine side chain hydroxyl is not activated relative to an average reactivity of a serine side chain hydroxyl (e.g., pKa about 13). In embodiments, $R^2$ reacts with a serine side chain of the intramolecular crosslinked protein wherein the serine side chain hydroxyl is not activated relative to an average reactivity of a serine side chain hydroxyl (e.g., pKa about 13). In embodiments, $R^2$ reacts with a threonine side chain of the second amino acid of the second protein wherein the threonine side chain hydroxyl is not activated relative to an average reactivity of a threonine side chain hydroxyl (e.g., pKa about 13). In embodiments, $R^2$ reacts with a threonine side chain of the intramolecular crosslinked protein wherein the threonine side chain hydroxyl is not activated relative to an average reactivity of a threonine side chain hydroxyl (e.g., pKa about 13).

In embodiments, the first point of attachment is an amino terminus of the protein, a lysine side chain of the protein, a glutamate side chain of the protein, an aspartate side chain of the protein, or a cysteine side chain of the protein.

In embodiments, the first point of attachment is an adenosine moiety of the nucleic acid, a guanosine moiety of the nucleic acid, a cytidine moiety of the nucleic acid, a thymidine moiety of the nucleic acid, or a uridine moiety of the nucleic acid.

In embodiments, the first point of attachment is a 2' hydroxyl of the glycan, a 3' hydroxyl of the glycan, a 6' hydroxyl of the glycan, a 2' moiety of the glycan, a 3'moiety of the glycan, or a 6'moiety of the glycan.

In embodiments, the second point of attachment is an amino terminus of the protein, a lysine side chain of the protein, a histidine side chain of the protein, a serine side chain of the protein, a threonine side chain of the protein, or a tyrosine side chain of the protein.

In embodiments, the second point of attachment is an adenosine moiety of the nucleic acid, a guanosine moiety of the nucleic acid, a cytidine moiety of the nucleic acid, a thymidine moiety of the nucleic acid, or a uridine moiety of the nucleic acid.

In embodiments, the second point of attachment is a 2' hydroxyl of the glycan, a 3' hydroxyl of the glycan, a 6' hydroxyl of the glycan, a 2' moiety of the glycan, a 3'moiety of the glycan, or a 6'moiety of the glycan.

In embodiments, the distance between the first point of attachment and the second point of attachment is from about 5 to about 50 Å. In embodiments, the distance between the first point of attachment and the second point of attachment is from about 5 to about 15 Å. In embodiments, the distance between the first point of attachment and the second point of attachment is from about 5 to about 20 Å. In embodiments, the distance between the first point of attachment and the second point of attachment is from about 5 to about 25 Å. In embodiments, the distance between the first point of attachment and the second point of attachment is from about 5 to about 30 Å. In embodiments, the distance between the first point of attachment and the second point of attachment is from about 5 to about 35 Å. In embodiments, the distance between the first point of attachment and the second point of attachment is from about 5 to about 40 Å. In embodiments, the distance between the first point of attachment and the second point of attachment is from about 5 to about 45 Å. In embodiments, the distance between the first point of attachment and the second point of attachment is from about 20 Å. In embodiments, the distance between the first point of attachment and the second point of attachment is about 20 Å.

In embodiments, the distance between the first point of attachment and the second point of attachment is from 5 to 50 Å. In embodiments, the distance between the first point of attachment and the second point of attachment is from 5 to 15 Å. In embodiments, the distance between the first point of attachment and the second point of attachment is from 5 to 20 Å. In embodiments, the distance between the first point of attachment and the second point of attachment is from 5 to 25 Å. In embodiments, the distance between the first point of attachment and the second point of attachment is from 5 to 30 Å. In embodiments, the distance between the first point of attachment and the second point of attachment is from 5 to 35 Å. In embodiments, the distance between the first point of attachment and the second point of attachment is from 5 to 40 Å. In embodiments, the distance between the first point of attachment and the second point of attachment is from 5 to 45 Å.

In embodiments, the first point of attachment is an amino terminus of the first protein or the intramolecular crosslinked protein, a lysine side chain of the first amino acid of the first protein or the intramolecular crosslinked protein, a glutamate side chain of the first amino acid of the first protein or the intramolecular crosslinked protein, an aspartate side chain of the first amino acid of the first protein or the intramolecular crosslinked protein, or a cysteine side chain of the first amino acid of the first protein or the intramolecular crosslinked protein.

In embodiments, the first point of attachment is an amino terminus of the first protein or the intramolecular crosslinked protein, a lysine side chain of the first amino acid of the first protein or the intramolecular crosslinked protein, a glutamate side chain of the first amino acid of the first protein or the intramolecular crosslinked protein, an aspartate side chain of the first amino acid of the first protein or the intramolecular crosslinked protein, or a cysteine side chain of the first amino acid of the first protein or the intramolecular crosslinked protein.

In embodiments, the second point of attachment is an amino terminus of the first protein or the intramolecular crosslinked protein, a lysine side chain of the second amino acid of the first protein or the intramolecular crosslinked protein, a histidine side chain of the second amino acid of the first protein or the intramolecular crosslinked protein, a serine side chain of the second amino acid of the first protein or the intramolecular crosslinked protein, a threonine side chain of the second amino acid of the first protein or the intramolecular crosslinked protein, or a tyrosine side chain of the second amino acid of the first protein or the intramolecular crosslinked protein.

In embodiments, the second point of attachment is an amino terminus of the second protein or the intramolecular crosslinked protein, a lysine side chain of the second amino acid of the second protein or the intramolecular crosslinked protein, a histidine side chain of the second amino acid of the second protein or the intramolecular crosslinked protein, a serine side chain of the second amino acid of the second protein or the intramolecular crosslinked protein, a threonine side chain of the second amino acid of the second protein or the intramolecular crosslinked protein, or a tyrosine side chain of the second amino acid of the second protein or the intramolecular crosslinked protein.

In an aspect is provided a method of detecting a covalently conjugated biomolecule including a first biomolecule conjugated to a second biomolecule, the method including i) contacting the first biomolecule with a crosslinking agent to form an activated biomolecule; ii) contacting the activated biomolecule with radiation in the presence of the second biomolecule thereby forming the covalently conjugated biomolecule; iii) identifying a first point of attachment of the crosslinking agent to the first biomolecule; and iv) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a bioconjugate reactive moiety; $R^2$ is a photo-activated bioconjugate reactive moiety; $L^1$ is a covalent linker; and the bonding reactivity of $R^2$ with the second biomolecule after contact of $R^2$ with radiation is greater than the bonding reactivity of $R^2$ with the second biomolecule prior to contact of $R^2$ with radiation. $R^1$, $L^1$, and $R^2$ are as described herein. $R^1$ is a bioconjugate reactive moiety. $R^2$ is a photo-activated bioconjugate reactive moiety. $L^1$ is a covalent linker. The bonding reactivity of $R^2$ with the second biomolecule after contact of $R^2$ with radiation is greater than the bonding reactivity of $R^2$ with the second biomolecule prior to contact of $R^2$ with radiation. In embodiments, the second order rate constant of $R^2$ with the second biomolecule after contact of $R^2$ with radiation is greater than the second order rate constant of $R^2$ with the second biomolecule prior to contact of $R^2$ with radiation.

In embodiments, the first point of attachment is identified using mass spectrometry. In embodiments, the second point of attachment is identified using mass spectrometry.

In embodiments, the radiation has a wavelength of from about 300 to about 400 nm. In embodiments, the radiation has a wavelength of from about 320 to about 380 nm. In embodiments, the radiation has a wavelength of from about 350 to about 370 nm. In embodiments, the radiation has a wavelength of about 300 nm. In embodiments, the radiation has a wavelength of about 305 nm. In embodiments, the radiation has a wavelength of about 310 nm. In embodiments, the radiation has a wavelength of about 315 nm. In embodiments, the radiation has a wavelength of about 320 nm. In embodiments, the radiation has a wavelength of about 325 nm. In embodiments, the radiation has a wavelength of about 330 nm. In embodiments, the radiation has a wavelength of about 335 nm. In embodiments, the radiation has a wavelength of about 340 nm. In embodiments, the radiation has a wavelength of about 345 nm. In embodiments, the radiation has a wavelength of about 350 nm. In embodiments, the radiation has a wavelength of about 355 nm. In embodiments, the radiation has a wavelength of about 360 nm. In embodiments, the radiation has a wavelength of about 365 nm. In embodiments, the radiation has a wavelength of about 370 nm. In embodiments, the radiation has a wavelength of about 375 nm. In embodiments, the radiation has a wavelength of about 380 nm. In embodiments, the radiation has a wavelength of about 385 nm. In embodiments, the radiation has a wavelength of about 390 nm. In embodiments, the radiation has a wavelength of about 395 nm. In embodiments, the radiation has a wavelength of about 400 nm. In embodiments, the radiation has a wavelength of about 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or about 400 nm. In embodiments, the radiation has a wavelength of 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 nm.

In embodiments, the first biomolecule is a protein, nucleic acid, or glycan; and the second biomolecule is a protein, nucleic acid, or glycan. In embodiments, the first biomolecule is a first protein; and the second biomolecule is a second protein. In embodiments, the first biomolecule is a first protein; and the second biomolecule is a second protein, wherein $R^1$ is a bioconjugate reactive moiety reactive with a first amino acid of the first protein, and $R^2$ is a photoactivated bioconjugate reactive moiety reactive with the second amino acid of the second protein. In embodiments, the first biomolecule is a first nucleic acid; and the second biomolecule is a second nucleic acid. In embodiments, the first biomolecule is a first glycan; and the second biomolecule is a second glycan.

In embodiments, $R^1$ reacts with an amine moiety of the first biomolecule, carboxylate moiety of the first biomolecule, or sulfhydryl moiety of the first biomolecule.

In embodiments, $R^1$ reacts with an amino terminus of the first biomolecule, a lysine side chain of the first biomolecule, a glutamate side chain of the first amino acid of the first biomolecule, an aspartate side chain of the first amino acid of the first biomolecule, or a cysteine side chain of the first amino acid of the first biomolecule.

In embodiments, $R^2$ reacts with an amine moiety of the second biomolecule, a carboxyl moiety of the second biomolecule, a hydroxyl moiety of the second biomolecule, an amido moiety of the second biomolecule, a guanidinyl moiety of the second biomolecule, or a thioether moiety of the second biomolecule.

In embodiments, $R^2$ reacts with an amino terminus of the second biomolecule, a carboxyl terminus of the second biomolecule, an aspartic acid side chain of the second amino acid of the second biomolecule, a glutamic acid side chain of the second amino acid of the second biomolecule, a lysine side chain of the second amino acid of the second biomolecule, a serine side chain of the second amino acid of the second biomolecule, a threonine side chain of the second amino acid of the second biomolecule, a tyrosine side chain of the second amino acid of the second biomolecule, a glutamine side chain of the second amino acid of the second biomolecule, an arginine side chain of the second amino acid of the second biomolecule, an asparagine side chain of the second amino acid of the second biomolecule, or a methionine side chain of the second amino acid of the second biomolecule.

In embodiments, the first point of attachment is an amino terminus of the first biomolecule, a lysine side chain of the first amino acid of the first biomolecule, a glutamate side chain of the first amino acid of the first biomolecule, an aspartate side chain of the first amino acid of the first biomolecule, or a cysteine side chain of the first amino acid of the first biomolecule.

In embodiments, the second point of attachment is an amino terminus of the second biomolecule, carboxyl terminus of the second biomolecule, an aspartic acid side chain of the second amino acid of the second biomolecule, a glutamic acid side chain of the second amino acid of the second biomolecule, a lysine side chain of the second amino acid of the second biomolecule, a serine side chain of the second amino acid of the second biomolecule, a threonine side chain of the second amino acid of the second biomolecule, a tyrosine side chain of the second amino acid of the second biomolecule, a glutamine side chain of the second amino acid of the second biomolecule, an arginine side chain of the second amino acid of the second biomolecule, an asparagine side chain of the second amino acid of the second biomolecule, or a methionine side chain of the second amino acid of the second biomolecule.

In an aspect is provided a method of detecting an intramolecular crosslinked protein, the method including: i) combining a protein with a crosslinking agent in a reaction vessel and contacting the crosslinking agent with radiation thereby forming the intramolecular crosslinked protein; ii) identifying a first point of attachment of the crosslinking agent to the protein; and iii) identifying a second point of attachment of the crosslinking agent to the protein and thereby detecting the intramolecular crosslinked protein. The crosslinking agent has the formula: $R^1$-$L^1$-$R^2$ (I); wherein $R^1$ is a bioconjugate reactive moiety; $R^2$ is a photo-activated bioconjugate reactive moiety; $L^1$ is a covalent linker; and the bonding reactivity of $R^2$ with the second amino acid of the protein after contact of $R^2$ with radiation is greater than the bonding reactivity of $R^2$ with the second amino acid of the protein prior to contact of $R^2$ with radiation. $R^1$, $L^1$, and $R^2$ are as described herein. $R^1$ is a bioconjugate reactive moiety. $R^2$ is a photo-activated bioconjugate reactive moiety. $L^1$ is a covalent linker. The bonding reactivity of $R^2$ with the second amino acid of the protein after contact of $R^2$ with radiation is greater than the bonding reactivity of $R^2$ with the second amino acid of the protein prior to contact of $R^2$ with radiation.

In embodiments, the first point of attachment is identified using mass spectrometry. In embodiments, the second point of attachment is identified using mass spectrometry.

In embodiments, $R^1$ reacts with an amine moiety, a carboxylate moiety, or a sulfhydryl moiety. In embodiments, $R^1$ reacts with an amine moiety of the protein, a carboxylate moiety of the protein, or a sulfhydryl moiety of the protein.

In embodiments, $R^1$ reacts with a diol of RNA and $R^2$ reacts with a saccharide. In embodiments, $R^1$ reacts with a hydroxyl of RNA and $R^2$ reacts with a saccharide.

In embodiments, $R^1$ reacts with an amino terminus of the protein, a lysine side chain of the protein, a glutamate side chain of the first amino acid of the protein, an aspartate side chain of the first amino acid of the protein, or a cysteine side chain of the first amino acid of the protein. In embodiments, $R^1$ reacts with an amino terminus of the protein. In embodiments, $R^1$ reacts with a lysine side chain of the protein. In embodiments, $R^1$ reacts with a glutamate side chain of the first amino acid of the protein. In embodiments, $R^1$ reacts with an aspartate side chain of the first amino acid of the protein. In embodiments, $R^1$ reacts with a cysteine side chain of the first amino acid of the protein.

In embodiments, $R^2$ reacts with an amine moiety, carboxyl moiety, hydroxyl moiety, amido moiety, guanidinyl moiety, or thiol moiety. In embodiments, $R^2$ reacts with an amine moiety of the protein, a carboxyl moiety of the protein, a hydroxyl moiety of the protein, an amido moiety of the protein, a guanidinyl moiety of the protein, or a thioether moiety of the protein. In embodiments, $R^2$ reacts with an amine moiety of the protein. In embodiments, $R^2$ reacts with a carboxyl moiety of the protein. In embodiments, $R^2$ reacts with a hydroxyl moiety of the protein. In embodiments, $R^2$ reacts with an amido moiety of the protein. In embodiments, $R^2$ reacts with a guanidinyl moiety of the protein. In embodiments, $R^2$ reacts with a thioether moiety of the protein.

In embodiments, $R^2$ reacts with an amino terminus of the protein, a carboxyl terminus of the protein, an aspartic acid side chain of the second amino acid of the protein, a glutamic acid side chain of the second amino acid of the protein, a lysine side chain of the second amino acid of the protein, a serine side chain of the second amino acid of the protein, a threonine side chain of the second amino acid of the protein, a tyrosine side chain of the second amino acid of the protein, a glutamine side chain of the second amino acid of the protein, an arginine side chain of the second amino acid of the protein, an asparagine side chain of the second amino acid of the protein, or a methionine side chain of the second amino acid of the protein.

In embodiments, $R^2$ reacts with an amino terminus of the protein. In embodiments, $R^2$ reacts with a carboxyl terminus of the protein. In embodiments, $R^2$ reacts with an aspartic acid side chain of the second amino acid of the protein. In embodiments, $R^2$ reacts with a glutamic acid side chain of the second amino acid of the protein. In embodiments, $R^2$ reacts with a lysine side chain of the second amino acid of the protein. In embodiments, $R^2$ reacts with a serine side chain of the second amino acid of the protein. In embodiments, $R^2$ reacts with a threonine side chain of the second amino acid of the protein. In embodiments, $R^2$ reacts with a tyrosine side chain of the second amino acid of the protein. In embodiments, $R^2$ reacts with a glutamine side chain of the second amino acid of the protein. In embodiments, $R^2$ reacts with an arginine side chain of the second amino acid of the protein. In embodiments, $R^2$ reacts with an asparagine side chain of the second amino acid of the protein. In embodiments, $R^2$ reacts with a methionine side chain of the second amino acid of the protein.

In embodiments, the first point of attachment is an amino terminus of the protein, a lysine side chain of the protein, a glutamate side chain of the protein, an aspartate side chain of the protein, or a cysteine side chain of the protein.

In embodiments, the second point of attachment is an amino terminus of the protein, a carboxyl terminus of the protein, an aspartic acid side chain of the protein, a glutamic acid side chain of the protein, a lysine side chain of the protein, a serine side chain of the protein, a threonine side chain of the protein, a tyrosine side chain of the protein, a glutamine side chain of the protein, an arginine side chain of the protein, an asparagine side chain of the protein, or a methionine side chain of the protein.

In embodiments, the first point of attachment is an amino terminus of the protein, a lysine side chain of the protein, a glutamate side chain of the protein, an aspartate side chain of the protein, or a cysteine side chain of the protein.

In embodiments, the first point of attachment is an adenosine moiety of the nucleic acid, a guanosine moiety of the nucleic acid, a cytidine moiety of the nucleic acid, a thymidine moiety of the nucleic acid, or a uridine moiety of the nucleic acid.

In embodiments, the first point of attachment is a 2' hydroxyl of the glycan, a 3' hydroxyl of the glycan, a 6' hydroxyl of the glycan, a 2' moiety of the glycan, a 3'moiety of the glycan, or a 6'moiety of the glycan.

In embodiments, the second point of attachment is an amino terminus of the protein, a lysine side chain of the protein, a histidine side chain of the protein, a serine side chain of the protein, a threonine side chain of the protein, or a tyrosine side chain of the protein.

In embodiments, the second point of attachment is an adenosine moiety of the nucleic acid, a guanosine moiety of the nucleic acid, a cytidine moiety of the nucleic acid, a thymidine moiety of the nucleic acid, or a uridine moiety of the nucleic acid.

In embodiments, the second point of attachment is a 2' hydroxyl of the glycan, a 3' hydroxyl of the glycan, a 6' hydroxyl of the glycan, a 2' moiety of the glycan, a 3'moiety of the glycan, or a 6'moiety of the glycan.

In embodiments, the distance between the first point of attachment and the second point of attachment is from about 5 to about 50 Å. In embodiments, the distance between the first point of attachment and the second point of attachment is from about 5 to about 15 Å. In embodiments, the distance between the first point of attachment and the second point of attachment is from about 5 to about 20 Å. In embodiments, the distance between the first point of attachment and the second point of attachment is from about 5 to about 25 Å. In embodiments, the distance between the first point of attachment and the second point of attachment is from about 5 to about 30 Å. In embodiments, the distance between the first point of attachment and the second point of attachment is from about 5 to about 35 Å. In embodiments, the distance between the first point of attachment and the second point of attachment is from about 5 to about 40 Å. In embodiments, the distance between the first point of attachment and the second point of attachment is from about 5 to about 45 Å. In embodiments, the distance between the first point of attachment and the second point of attachment is from about 20 Å. In embodiments, the distance between the first point of attachment and the second point of attachment is about 20 Å. In embodiments, the distance between the first point of attachment and the second point of attachment is from about 22 Å. In embodiments, the distance between the first point of attachment and the second point of attachment is about 22 Å. In embodiments, the distance between the first point of attachment and the second point of attachment is from about 24 Å. In embodiments, the distance between the first point of attachment and the second point of attachment is about 24 Å.

In embodiments, the distance between the first point of attachment and the second point of attachment is from 5 to 50 Å. In embodiments, the distance between the first point of attachment and the second point of attachment is from 5 to 15 Å. In embodiments, the distance between the first point of attachment and the second point of attachment is from 5 to 20 Å. In embodiments, the distance between the first point of attachment and the second point of attachment is from 5 to 25 Å. In embodiments, the distance between the first point of attachment and the second point of attachment is from 5 to 30 Å. In embodiments, the distance between the first point of attachment and the second point of attachment is from 5 to 35 Å. In embodiments, the distance between the first point of attachment and the second point of attachment is from 5 to 40 Å. In embodiments, the distance between the first point of attachment and the second point of attachment is from 5 to 45 Å.

In an aspect is provided a method of detecting a covalently conjugated biomolecule including a first biomolecule conjugated to a second biomolecule, the method including i) contacting a crosslinking agent with a first radiation in the presence of the first biomolecule, thereby forming an activated biomolecule; ii) contacting the activated biomolecule with an optionally different second radiation in the presence of the second biomolecule thereby forming a covalently conjugated biomolecule; (iii) identifying a first point of attachment of the crosslinking agent to the first biomolecule; and iv) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a first photo-activated bioconjugate reactive moiety; $R^2$ is a second photo-activated bioconjugate reactive moiety; $L^1$ is a covalent linker; the bonding reactivity of $R^1$ with the first biomolecule after contact of $R^1$ with the first radiation is greater than the bonding reactivity of $R^1$ with the first biomolecule prior to contact of $R^1$ with the first radiation; and the bonding reactivity of $R^2$ with the second biomolecule after contact of $R^2$ with the second radiation is greater than the bonding reactivity of $R^2$ with the second biomolecule prior to contact of $R^2$ with the second radiation. $R^1$, $L^1$, and $R^2$ are as described herein. $R^1$ is a first photo-activated bioconjugate reactive moiety. $R^2$ is a second photo-activated bioconjugate reactive moiety. $L^1$ is a covalent linker. The bonding reactivity of $R^1$ with the first biomolecule after contact of $R^1$ with the first radiation is greater than the bonding reactivity of $R^1$ with the first biomolecule prior to contact of $R^1$ with the first radiation. The bonding reactivity of $R^2$ with the second biomolecule after contact of $R^2$ with the second radiation is greater than the bonding reactivity of $R^2$ with the second biomolecule prior to contact of $R^2$ with the second radiation. In embodiments, the second order rate constant of $R^1$ with the first biomolecule after contact of $R^1$ with the first radiation is greater than the second order rate constant of $R^1$ with the first biomolecule prior to contact of $R^1$ with the first radiation. In embodiments, the second order rate constant of $R^2$ with the second biomolecule after contact of $R^2$ with the second radiation is greater than the second order rate constant of $R^2$ with the second biomolecule prior to contact of $R^2$ with the second radiation.

In embodiments, the first point of attachment is identified using mass spectrometry. In embodiments, the second point of attachment is identified using mass spectrometry.

In embodiments, the first radiation has a wavelength of from about 300 to about 400 nm. In embodiments, the first radiation has a wavelength of from about 320 to about 380 nm. In embodiments, the first radiation has a wavelength of from about 350 to about 370 nm. In embodiments, the first radiation has a wavelength of about 300 nm. In embodiments, the first radiation has a wavelength of about 305 nm. In embodiments, the first radiation has a wavelength of about 310 nm. In embodiments, the first radiation has a wavelength of about 315 nm. In embodiments, the first radiation has a wavelength of about 320 nm. In embodiments, the first radiation has a wavelength of about 325 nm. In embodiments, the first radiation has a wavelength of about 330 nm. In embodiments, the first radiation has a wavelength of about 335 nm. In embodiments, the first radiation has a wavelength of about 340 nm. In embodiments, the first radiation has a wavelength of about 345 nm. In embodiments, the first radiation has a wavelength of about 350 nm. In embodiments, the first radiation has a wavelength of about 355 nm. In embodiments, the first radiation has a wavelength of about 360 nm. In embodiments, the first radiation has a wavelength of about 365 nm. In embodiments, the first radiation has a wavelength of about 370 nm. In embodiments, the first radiation has a wavelength of about 375 nm. In embodiments, the first radiation has a wavelength of about 380 nm. In embodiments, the first radiation has a wavelength of about 385 nm. In embodiments, the first radiation has a wavelength of about 390 nm. In embodiments, the first radiation has a wavelength of about 395 nm. In embodiments, the first radiation has a wavelength of about 400 nm. In embodiments, the first radiation has a wavelength of about 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or about 400 nm. In embodiments, the first radiation has a wavelength of 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 nm.

In embodiments, the second radiation has a wavelength of from about 300 to about 400 nm. In embodiments, the second radiation has a wavelength of from about 320 to about 380 nm. In embodiments, the second radiation has a wavelength of from about 350 to about 370 nm. In embodiments, the second radiation has a wavelength of about 300 nm. In embodiments, the second radiation has a wavelength of about 305 nm. In embodiments, the second radiation has a wavelength of about 310 nm. In embodiments, the second radiation has a wavelength of about 315 nm. In embodiments, the second radiation has a wavelength of about 320 nm. In embodiments, the second radiation has a wavelength of about 325 nm. In embodiments, the second radiation has a wavelength of about 330 nm. In embodiments, the second radiation has a wavelength of about 335 nm. In embodiments, the second radiation has a wavelength of about 340 nm. In embodiments, the second radiation has a wavelength of about 345 nm. In embodiments, the second radiation has a wavelength of about 350 nm. In embodiments, the second radiation has a wavelength of about 355 nm. In embodiments, the second radiation has a wavelength of about 360 nm. In embodiments, the second radiation has a wavelength of about 365 nm. In embodiments, the second radiation has a wavelength of about 370 nm. In embodiments, the second radiation has a wavelength of about 375 nm. In embodiments, the second radiation has a wavelength of about 380 nm. In embodiments, the second radiation has a wavelength of about 385 nm. In embodiments, the second radiation has a wavelength of about 390 nm. In embodiments, the second radiation has a wavelength of about 395 nm. In embodiments, the second radiation has a wavelength of about 400 nm. In embodiments, the second radiation has a wavelength of about 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or about 400 nm. In embodiments, the second radiation has a wavelength of 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 nm.

In an aspect is provided a method of detecting a covalently conjugated biomolecule including a first biomolecule conjugated to a second biomolecule, the method including i) contacting a crosslinking agent with radiation in the presence of the first biomolecule and the second biomolecule, thereby forming the covalently conjugated biomolecule; ii) identifying a first point of attachment of the crosslinking agent to the first biomolecule; and iii) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a first photo-activated bioconjugate reactive moiety; $R^2$ is a second photo-activated bioconjugate reactive moiety; $L^1$ is a covalent linker; the bonding reactivity of $R^1$ with the first biomolecule after contact of $R^1$ with radiation is greater than the bonding reactivity of $R^1$ with the first biomolecule prior to contact of $R^1$ with radiation; and the bonding reactivity of $R^2$ with the second biomolecule after contact of $R^2$ with radiation is greater than the bonding reactivity of $R^2$ with the second biomolecule prior to contact of $R^2$ with radiation. $R^1$, $L^1$, and $R^2$ are as described herein. $R^1$ is a first photo-activated bioconjugate reactive moiety. $R^2$ is a second photo-activated bioconjugate reactive moiety. $L^1$ is a covalent linker. The bonding reactivity of $R^1$ with the first biomolecule after contact of $R^1$ with radiation is greater than the bonding reactivity of $R^1$ with the first biomolecule prior to contact of $R^1$ with radiation. The bonding reactivity of $R^2$ with the second biomolecule after contact of $R^2$ with radiation is greater than the bonding reactivity of $R^2$ with the second biomolecule prior to contact of $R^2$ with radiation. In embodiments, the second order rate constant of $R^1$ with the first biomolecule after contact of $R^1$ with radiation is greater than the second order rate constant of $R^1$ with the first biomolecule prior to contact of $R^1$ with radiation. In embodiments, the second order rate constant of $R^2$ with the second biomolecule after contact of $R^2$ with radiation is greater than the second order rate constant of $R^2$ with the second biomolecule prior to contact of $R^2$ with radiation.

In embodiments, the first point of attachment is identified using mass spectrometry. In embodiments, the second point of attachment is identified using mass spectrometry.

In embodiments, the radiation has a wavelength of from about 300 to about 400 nm. In embodiments, the radiation has a wavelength of from about 320 to about 380 nm. In embodiments, the radiation has a wavelength of from about 350 to about 370 nm. In embodiments, the radiation has a wavelength of about 300 nm. In embodiments, the radiation has a wavelength of about 305 nm. In embodiments, the radiation has a wavelength of about 310 nm. In embodiments, the radiation has a wavelength of about 315 nm. In embodiments, the radiation has a wavelength of about 320 nm. In embodiments, the radiation has a wavelength of about 325 nm. In embodiments, the radiation has a wavelength of about 330 nm. In embodiments, the radiation has a wavelength of about 335 nm. In embodiments, the radiation has a wavelength of about 340 nm. In embodiments, the radiation has a wavelength of about 345 nm. In embodiments, the radiation has a wavelength of about 350 nm. In embodiments, the radiation has a wavelength of about 355 nm. In embodiments, the radiation has a wavelength of about 360 nm. In embodiments, the radiation has a wavelength of about 365 nm. In embodiments, the radiation has a wavelength of about 370 nm. In embodiments, the radiation has a wavelength of about 375 nm. In embodiments, the radiation has a wavelength of about 380 nm. In embodiments, the radiation has a wavelength of about 385 nm. In embodiments, the radiation has a wavelength of about 390 nm. In embodiments, the radiation has a wavelength of about 395 nm. In embodiments, the radiation has a wavelength of about 400 nm. In embodiments, the radiation has a wavelength of about 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or about 400 nm. In embodiments, the radiation has a wavelength of 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 nm.

In embodiments, the first biomolecule is a protein, nucleic acid, or glycan; and the second biomolecule is a protein, nucleic acid, or glycan. In embodiments, the first biomolecule is a first protein; and the second biomolecule is a second protein. In embodiments, the first biomolecule is a first protein; and the second biomolecule is a second protein, wherein $R^1$ is a bioconjugate reactive moiety reactive with a first amino acid of the first protein, and $R^2$ is a proximity enhanced bioconjugate reactive moiety reactive with a second amino acid of the second protein. In embodiments, the first biomolecule is a first nucleic acid; and the second biomolecule is a second nucleic acid. In embodiments, the first biomolecule is a first glycan; and the second biomolecule is a second glycan. In embodiments, the first biomolecule is a protein; and the second biomolecule is a nucleic acid. In embodiments, the first biomolecule is a protein; and the second biomolecule is a glycan. In embodiments, the first biomolecule is a nucleic acid; and the second biomolecule is a protein. In embodiments, the first biomolecule is a nucleic acid; and the second biomolecule is a glycan. In embodiments, the first biomolecule is a glycan; and the second biomolecule is a protein. In embodiments, the first biomolecule is a glycan; and the second biomolecule is a nucleic acid.

In embodiments, $R^1$ reacts with an amine moiety of the first biomolecule, a carboxyl moiety of the first biomolecule, a hydroxyl moiety of the first biomolecule, an amido moiety of the first biomolecule, a guanidinyl moiety of the first biomolecule, or a thioether moiety of the first biomolecule.

In embodiments, $R^1$ reacts with an amino terminus of the first biomolecule, a carboxyl terminus of the first biomolecule, an aspartic acid side chain of the first amino acid of the first biomolecule, a glutamic acid side chain of the first amino acid of the first biomolecule, a lysine side chain of the first amino acid of the first biomolecule, a serine side chain of the first amino acid of the first biomolecule, a threonine side chain of the first amino acid of the first biomolecule, a tyrosine side chain of the first amino acid of the first biomolecule, a glutamine side chain of the first amino acid of the first biomolecule, an arginine side chain of the first amino acid of the first biomolecule, an asparagine side chain of the first amino acid of the first biomolecule, or a methionine side chain of the first amino acid of the first biomolecule.

In embodiments, $R^2$ reacts with an amine moiety of the second biomolecule, a carboxyl moiety of the second biomolecule, a hydroxyl moiety of the second biomolecule, an amido moiety of the second biomolecule, a guanidinyl moiety of the second biomolecule, or a thioether moiety of the second biomolecule.

In embodiments, $R^2$ reacts with an amino terminus of the second biomolecule, a carboxyl terminus of the second biomolecule, an aspartic acid side chain of the second amino acid of the second biomolecule, a glutamic acid side chain of the second amino acid of the second biomolecule, a lysine side chain of the second amino acid of the second biomolecule, a serine side chain of the second amino acid of the second biomolecule, a threonine side chain of the second amino acid of the second biomolecule, a tyrosine side chain of the second amino acid of the second biomolecule, a glutamine side chain of the second amino acid of the second biomolecule, an arginine side chain of the second amino acid of the second biomolecule, an asparagine side chain of the second amino acid of the second biomolecule, or a methionine side chain of the second amino acid of the second biomolecule.

In embodiments, the first point of attachment is an amino terminus of the first biomolecule, a carboxyl terminus of the first biomolecule, an aspartic acid side chain of the first biomolecule, a glutamic acid side chain of the first biomolecule, a lysine side chain of the first biomolecule, a serine side chain of the first biomolecule, a threonine side chain of the first biomolecule, a tyrosine side chain of the first biomolecule, a glutamine side chain of the first biomolecule, an arginine side chain of the first biomolecule, an asparagine side chain of the first biomolecule, or a methionine side chain of the first biomolecule.

In embodiments, the second point of attachment is an amino terminus of the second biomolecule, a carboxyl terminus of the second biomolecule, an aspartic acid side chain of the second biomolecule, a glutamic acid side chain of the second biomolecule, a lysine side chain of the second biomolecule, a serine side chain of the second biomolecule, a threonine side chain of the second biomolecule, a tyrosine side chain of the second biomolecule, a glutamine side chain of the second biomolecule, an arginine side chain of the second biomolecule, an asparagine side chain of the second biomolecule, or a methionine side chain of the second biomolecule.

In an aspect is provided a method of detecting an intramolecular crosslinked protein, the method including: i) combining a protein with a crosslinking agent in a reaction vessel and contacting the crosslinking agent with radiation thereby forming the intramolecular crosslinked protein; ii) identifying a first point of attachment of the crosslinking agent to the protein; and iii) identifying a second point of attachment of the crosslinking agent to the protein and thereby detecting the intramolecular crosslinked protein. The crosslinking agent has the formula: $R^1$-$L^1$-$R^2$ (I); $R^1$ is a first photo-activated bioconjugate reactive moiety; $R^2$ is a second photo-activated bioconjugate reactive moiety; $L^1$ is a covalent linker; the bonding reactivity of $R^1$ with a first amino acid of the protein after contact of $R^1$ with radiation is greater than the bonding reactivity of $R^1$ with the first amino acid of the protein prior to contact of $R^1$ with radiation; and the bonding reactivity of $R^2$ with the second biomolecule after contact of $R^2$ with radiation is greater than the bonding reactivity of $R^2$ with the second amino acid of the protein prior to contact of $R^2$ with radiation. $R^1$, $L^1$, and $R^2$ are as described herein. $R^1$ is a first photo-activated bioconjugate reactive moiety. $R^2$ is a second photo-activated bioconjugate reactive moiety. $L^1$ is a covalent linker. The bonding reactivity of $R^1$ with a first amino acid of the protein after contact of $R^1$ with radiation is greater than the bonding reactivity of $R^1$ with the first amino acid of the protein prior to contact of $R^1$ with radiation. The bonding reactivity of $R^2$ with the second amino acid of the protein after contact of $R^2$ with radiation is greater than the bonding reactivity of $R^2$ with the second amino acid of the protein prior to contact of $R^2$ with radiation.

In embodiments, the first point of attachment is identified using mass spectrometry. In embodiments, the second point of attachment is identified using mass spectrometry.

In embodiments, the radiation has a wavelength of from about 300 to about 400 nm. In embodiments, the radiation has a wavelength of from about 320 to about 380 nm. In embodiments, the radiation has a wavelength of from about 350 to about 370 nm. In embodiments, the radiation has a wavelength of about 300 nm. In embodiments, the radiation has a wavelength of about 305 nm. In embodiments, the radiation has a wavelength of about 310 nm. In embodiments, the radiation has a wavelength of about 315 nm. In embodiments, the radiation has a wavelength of about 320 nm. In embodiments, the radiation has a wavelength of about 325 nm. In embodiments, the radiation has a wavelength of about 330 nm. In embodiments, the radiation has a wavelength of about 335 nm. In embodiments, the radiation has a wavelength of about 340 nm. In embodiments, the radiation has a wavelength of about 345 nm. In embodiments, the radiation has a wavelength of about 350 nm. In embodiments, the radiation has a wavelength of about 355 nm. In embodiments, the radiation has a wavelength of about 360 nm. In embodiments, the radiation has a wavelength of about 365 nm. In embodiments, the radiation has a wavelength of about 370 nm. In embodiments, the radiation has a wavelength of about 375 nm. In embodiments, the radiation has a wavelength of about 380 nm. In embodiments, the radiation has a wavelength of about 385 nm. In embodiments, the radiation has a wavelength of about 390 nm. In embodiments, the radiation has a wavelength of about 395 nm. In embodiments, the radiation has a wavelength of about 400 nm. In embodiments, the radiation has a wavelength of about 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or about 400 nm. In embodiments, the radiation has a wavelength of 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 nm.

In embodiments, $R^1$ reacts with an amine moiety, carboxyl moiety, hydroxyl moiety, amido moiety, guanidinyl moiety, or thiol moiety. In embodiments, $R^1$ reacts with an amine moiety of the protein, a carboxyl moiety of the protein, a hydroxyl moiety of the protein, an amido moiety of the protein, a guanidinyl moiety of the protein, or a thioether moiety of the protein. In embodiments, $R^1$ reacts with an amine moiety of the protein. In embodiments, $R^1$ reacts with a carboxyl moiety of the protein. In embodiments, $R^1$ reacts with a hydroxyl moiety of the protein. In embodiments, $R^1$ reacts with an amido moiety of the protein. In embodiments, $R^1$ reacts with a guanidinyl moiety of the protein. In embodiments, $R^1$ reacts with a thioether moiety of the protein.

In embodiments, $R^1$ reacts with an amino terminus of the protein, a carboxyl terminus of the protein, an aspartic acid side chain of the first amino acid of the protein, a glutamic acid side chain of the first amino acid of the protein, a lysine side chain of the first amino acid of the protein, a serine side chain of the first amino acid of the protein, a threonine side chain of the first amino acid of the protein, a tyrosine side chain of the first amino acid of the protein, a glutamine side chain of the first amino acid of the protein, an arginine side chain of the first amino acid of the protein, an asparagine side chain of the first amino acid of the protein, or a methionine side chain of the first amino acid of the protein.

In embodiments, $R^2$ reacts with an amine moiety, carboxyl moiety, hydroxyl moiety, amido moiety, guanidinyl moiety, or thiol moiety. In embodiments, $R^2$ reacts with an amine moiety of the protein, a carboxyl moiety of the protein, a hydroxyl moiety of the protein, an amido moiety of the protein, a guanidinyl moiety of the protein, or a thioether moiety of the protein. In embodiments, $R^2$ reacts with an amine moiety of the protein. In embodiments, $R^2$ reacts with a carboxyl moiety of the protein. In embodiments, $R^2$ reacts with a hydroxyl moiety of the protein. In embodiments, $R^2$ reacts with an amido moiety of the protein. In embodiments, $R^2$ reacts with a guanidinyl moiety of the protein. In embodiments, $R^2$ reacts with a thioether moiety of the protein.

In embodiments, $R^2$ reacts with an amino terminus of the protein, a carboxyl terminus of the protein, an aspartic acid side chain of the second amino acid of the protein, a glutamic acid side chain of the second amino acid of the protein, a lysine side chain of the second amino acid of the protein, a serine side chain of the second amino acid of the protein, a threonine side chain of the second amino acid of the protein, a tyrosine side chain of the second amino acid of the protein, a glutamine side chain of the second amino acid of the protein, an arginine side chain of the second amino acid of the protein, an asparagine side chain of the second amino acid of the protein, or a methionine side chain of the second amino acid of the protein.

In embodiments, $R^2$ reacts with an amino terminus of the protein. In embodiments, $R^2$ reacts with a carboxyl terminus of the protein. In embodiments, $R^2$ reacts with an aspartic acid side chain of the second amino acid of the protein. In embodiments, $R^2$ reacts with a glutamic acid side chain of the second amino acid of the protein. In embodiments, $R^2$ reacts with a lysine side chain of the second amino acid of the protein. In embodiments, $R^2$ reacts with a serine side chain of the second amino acid of the protein. In embodiments, $R^2$ reacts with a threonine side chain of the second amino acid of the protein. In embodiments, $R^2$ reacts with a tyrosine side chain of the second amino acid of the protein. In embodiments, $R^2$ reacts with a glutamine side chain of the second amino acid of the protein. In embodiments, $R^2$ reacts with an arginine side chain of the second amino acid of the protein. In embodiments, $R^2$ reacts with an asparagine side chain of the second amino acid of the protein. In embodiments, $R^2$ reacts with a methionine side chain of the second amino acid of the protein.

In embodiments, the first point of attachment is an amino terminus of the protein, a carboxyl terminus of the protein, an aspartic acid side chain of the protein, a glutamic acid side chain of the protein, a lysine side chain of the protein, a serine side chain of the protein, a threonine side chain of the protein, a tyrosine side chain of the protein, a glutamine side chain of the protein, an arginine side chain of the protein, an asparagine side chain of the protein, or a methionine side chain of the protein.

In embodiments, the first point of attachment is an amino terminus of the protein, a lysine side chain of the protein, a glutamate side chain of the protein, an aspartate side chain of the protein, or a cysteine side chain of the protein.

In embodiments, the first point of attachment is an adenosine moiety of the nucleic acid, a guanosine moiety of the nucleic acid, a cytidine moiety of the nucleic acid, a thymidine moiety of the nucleic acid, or a uridine moiety of the nucleic acid.

In embodiments, the first point of attachment is a 2' hydroxyl of the glycan, a 3' hydroxyl of the glycan, a 6' hydroxyl of the glycan, a 2' moiety of the glycan, a 3'moiety of the glycan, or a 6'moiety of the glycan.

In embodiments, the second point of attachment is an amino terminus of the protein, a carboxyl terminus of the protein, an aspartic acid side chain of the protein, a glutamic acid side chain of the protein, a lysine side chain of the protein, a serine side chain of the protein, a threonine side chain of the protein, a tyrosine side chain of the protein, a glutamine side chain of the protein, an arginine side chain of the protein, an asparagine side chain of the protein, or a methionine side chain of the protein.

In embodiments, the second point of attachment is an amino terminus of the protein, a lysine side chain of the protein, a histidine side chain of the protein, a serine side chain of the protein, a threonine side chain of the protein, or a tyrosine side chain of the protein.

In embodiments, the second point of attachment is an adenosine moiety of the nucleic acid, a guanosine moiety of the nucleic acid, a cytidine moiety of the nucleic acid, a thymidine moiety of the nucleic acid, or a uridine moiety of the nucleic acid.

In embodiments, the second point of attachment is a 2' hydroxyl of the glycan, a 3' hydroxyl of the glycan, a 6' hydroxyl of the glycan, a 2' moiety of the glycan, a 3'moiety of the glycan, or a 6'moiety of the glycan.

In embodiments, the distance between the first point of attachment and the second point of attachment is from about 5 to about 50 Å. In embodiments, the distance between the first point of attachment and the second point of attachment is from about 5 to about 15 Å. In embodiments, the distance between the first point of attachment and the second point of attachment is from about 5 to about 20 Å. In embodiments, the distance between the first point of attachment and the second point of attachment is from about 5 to about 25 Å. In embodiments, the distance between the first point of attachment and the second point of attachment is from about 5 to about 30 Å. In embodiments, the distance between the first point of attachment and the second point of attachment is from about 5 to about 35 Å. In embodiments, the distance between the first point of attachment and the second point of attachment is from about 5 to about 40 Å. In embodiments, the distance between the first point of attachment and the second point of attachment is from about 5 to about 45 Å. In embodiments, the distance between the first point of attachment and the second point of attachment is from about 20 Å. In embodiments, the distance between the first point of attachment and the second point of attachment is about 20 Å. In embodiments, the distance between the first point of attachment and the second point of attachment is from about 22 Å. In embodiments, the distance between the first point of attachment and the second point of attachment is about 22 Å. In embodiments, the distance between the first point of attachment and the second point of attachment is from about 24 Å. In embodiments, the distance between the first point of attachment and the second point of attachment is about 24 Å.

In embodiments, the distance between the first point of attachment and the second point of attachment is from 5 to 50 Å. In embodiments, the distance between the first point of attachment and the second point of attachment is from 5 to 15 Å. In embodiments, the distance between the first point of attachment and the second point of attachment is from 5 to 20 Å. In embodiments, the distance between the first point of attachment and the second point of attachment is from 5 to 25 Å. In embodiments, the distance between the first point of attachment and the second point of attachment is from 5 to 30 Å. In embodiments, the distance between the first point of attachment and the second point of attachment is from 5 to 35 Å. In embodiments, the distance between the first point of attachment and the second point of attachment is from 5 to 40 Å. In embodiments, the distance between the first point of attachment and the second point of attachment is from 5 to 45 Å.

In an aspect is provided a method of detecting a covalently conjugated biomolecule including a first biomolecule conjugated to a second biomolecule, the method including i) contacting the first biomolecule with a crosslinking agent to form an activated biomolecule; ii) contacting the activated biomolecule with radiation in the presence of the second biomolecule thereby forming the covalently conjugated biomolecule; iii) identifying a first point of attachment of the crosslinking agent to the first biomolecule; and iv) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a proximity enhanced bioconjugate reactive moiety; $R^2$ is a photo-activated bioconjugate reactive moiety; $L^1$ is a covalent linker; and the bonding reactivity of $R^2$ with the second biomolecule after contact of $R^2$ with radiation is greater than the bonding reactivity of $R^2$ with the second biomolecule prior to contact of $R^2$ with radiation. $R^1$, $L^1$, and $R^2$ are as described herein. $R^1$ is a proximity enhanced bioconjugate reactive moiety. $R^2$ is a photo-activated bioconjugate reactive moiety. $L^1$ is a covalent linker. The bonding reactivity of $R^2$ with the second biomolecule after contact of $R^2$ with radiation is greater than the bonding reactivity of $R^2$ with the second biomolecule prior to contact of $R^2$ with radiation. In embodiments, the second order rate constant of $R^2$ with the second biomolecule after contact of $R^2$ with radiation is greater than the second order rate constant of $R^2$ with the second biomolecule prior to contact of $R^2$ with radiation.

In embodiments, the first point of attachment is identified using mass spectrometry. In embodiments, the second point of attachment is identified using mass spectrometry.

In embodiments, $R^1$ is a proximity enhanced bioconjugate reactive moiety as described in Xiang, Z. et al. Adding an unnatural covalent bond to proteins through proximity-enhanced bioreactivity. Nature methods 10, 885-888 (2013) and Wang, L. Genetically encoding new bioreactivity. New Biotechnology 38, 16-25 (2017), both of which are incorporated herein by reference in their entirety for all purposes. In embodiments, $R^1$ is a proximity enhanced bioconjugate reactive moiety as described in Mix, K. A., Aronoff, M. R. & Raines, R. T. Diazo Compounds: Versatile Tools for Chemical Biology. ACS Chem. Biol. 11, 3233-3244 (2016), which is incorporated herein by reference in its entirety for all purposes. In embodiments, $R^1$ is a proximity enhanced bioconjugate reactive moiety as described in Chen, X.-H. et al. Genetically Encoding an Electrophilic Amino Acid for Protein Stapling and Covalent Binding to Native Receptors. ACS Chem. Biol. 9, 1956-1961 (2014); Furman, J. L. et al. A Genetically Encoded aza-Michael Acceptor for Covalent Cross-Linking of Protein-Receptor Complexes. J. Am. Chem. Soc. 136, 8411-8417 (2014); Xuan, W. et al. Genetic Incorporation of a Reactive Isothiocyanate Group into Proteins. Angew. Chem. Int. Ed. 55, 10065-10068 (2016); and Xuan, W. et al. Protein Crosslinking by Genetically Encoded Noncanonical Amino Acids with Reactive Aryl Carbamate Side Chains. Angew. Chem. Int. Ed. 56, 5096-5100 (2017), all of which are incorporated herein by reference in their entirety for all purposes.

In an aspect is provided a method of detecting an intramolecular crosslinked protein, the method including: i) combining a protein with a crosslinking agent in a reaction vessel and contacting the crosslinking agent with radiation thereby forming the intramolecular crosslinked protein; ii) identifying a first point of attachment of the crosslinking agent to the protein; and iii) identifying a second point of attachment of the crosslinking agent to the protein and thereby detecting the intramolecular crosslinked protein. The crosslinking agent has the formula: $R^1$-$L^1$-$R^2$ (I); wherein $R^1$ is a proximity enhanced bioconjugate reactive moiety; $R^2$ is a photo-activated bioconjugate reactive moiety; $L^1$ is a covalent linker; and the bonding reactivity of $R^2$ with the second amino acid of the protein after contact of $R^2$ with radiation is greater than the bonding reactivity of $R^2$ with the second amino acid of the protein prior to contact of $R^2$ with radiation. $R^1$, $L^1$, and $R^2$ are as described herein. $R^1$ is a proximity enhanced bioconjugate reactive moiety. $R^2$ is a photo-activated bioconjugate reactive moiety. $L^1$ is a covalent linker. The bonding reactivity of $R^2$ with the second amino acid of the protein after contact of $R^2$ with radiation is greater than the bonding reactivity of $R^2$ with the second amino acid of the protein prior to contact of $R^2$ with radiation.

In embodiments, the first point of attachment is identified using mass spectrometry. In embodiments, the second point of attachment is identified using mass spectrometry.

In an aspect is provided a method of detecting a covalently conjugated biomolecule including a first biomolecule conjugated to a second biomolecule, the method including i) contacting the first biomolecule with a crosslinking agent to form an activated biomolecule; ii) contacting the activated biomolecule with radiation in the presence of the second biomolecule thereby forming the covalently conjugated biomolecule; iii) identifying a first point of attachment of the crosslinking agent to the first biomolecule; and iv) identifying a second point of attachment of the crosslinking agent to the second biomolecule; thereby detecting the covalently conjugated biomolecule. The crosslinking agent has the formula: $R^1$-$L^1$-$R^2$ (I); wherein $R^1$ is a photo-activated bioconjugate reactive moiety; $R^2$ is a proximity enhanced bioconjugate reactive moiety; $L^1$ is a covalent linker; and the bonding reactivity of $R^1$ with the first biomolecule after contact of $R^1$ with radiation is greater than the bonding reactivity of $R^1$ with the first biomolecule prior to contact of $R^1$ with radiation. $R^1$, $L^1$, and $R^2$ are as described herein. $R^1$ is a photo-activated bioconjugate reactive moiety. $R^2$ is a proximity enhanced bioconjugate reactive moiety. $L^1$ is a covalent linker. The bonding reactivity of $R^1$ with the first biomolecule after contact of $R^1$ with radiation is greater than the bonding reactivity of $R^1$ with the first biomolecule prior to contact of $R^1$ with radiation. In embodiments, the second order rate constant of $R^1$ with the first biomolecule after contact of $R^1$ with radiation is greater than the second order rate constant of $R^1$ with the first biomolecule prior to contact of $R^1$ with radiation.

In an aspect is provided a method of detecting an intramolecular crosslinked protein, the method including: i) combining a protein with a crosslinking agent in a reaction vessel and contacting the crosslinking agent with radiation thereby forming the intramolecular crosslinked protein; ii) identifying a first point of attachment of the crosslinking agent to the protein; and iii) identifying a second point of attachment of the crosslinking agent to the protein and thereby detecting the intramolecular crosslinked protein. The crosslinking agent has the formula: $R^1$-$L^1$-$R^2$ (I); wherein $R^1$ is a photo-activated bioconjugate reactive moiety; $R^2$ is a proximity enhanced bioconjugate reactive moiety; $L^1$ is a covalent linker; and the bonding reactivity of $R^1$ with the first amino acid of the protein after contact of $R^1$ with radiation is greater than the bonding reactivity of $R^1$ with the first amino acid of the protein prior to contact of $R^1$ with radiation. $R^1$, $L^1$, and $R^2$ are as described herein. $R^1$ is a photo-activated bioconjugate reactive moiety. $R^2$ is a proximity enhanced bioconjugate reactive moiety. $L^1$ is a covalent linker. The bonding reactivity of $R^1$ with the first amino acid of the protein after contact of $R^1$ with radiation is greater than the bonding reactivity of $R^1$ with the first amino acid of the protein prior to contact of $R^1$ with radiation.

In embodiments, the first point of attachment is identified using mass spectrometry. In embodiments, the second point of attachment is identified using mass spectrometry.

In embodiments, the method is used to identify protein-protein interactions. In embodiments, the method is used to identify protein-protein interactions in a cell. In embodiments, the method is used to identify protein-protein interactions in a mammalian cell. In embodiments, the method is used to identify protein-protein interactions in a human cell. In embodiments, the method is used to identify protein-protein interactions in a bacterial cell. In embodiments, the method is used to identify protein-protein interactions in an *E. coli* cell. In embodiments, the method is used to identify protein-protein interactions between cells. In embodiments, the method is used to identify protein-protein interactions in a disease cell. In embodiments, the method is used to identify protein-protein interactions in a cancer cell. In embodiments, the method is used to identify protein-protein interactions in cell lysates. In embodiments, the method is used to identify protein-protein interactions in blood. In embodiments, the method is used to identify protein-protein interactions in plasma. In embodiments, the method is used to identify protein-protein interactions in an extracellular matrix. In embodiments, the method is used to identify protein-protein interactions in a tissue. In embodiments, the method is used to identify protein-protein interactions in vitro. In embodiments, the method is used to identify protein-protein interactions in a culture. In embodiments, the method is used to identify protein-protein interactions in a cell culture. In embodiments, the method is used to identify protein-protein interactions in a tissue culture. In embodiments, the method is used to identify protein-protein interactions in an isolated protein.

In embodiments, the method is used to identify protein-nucleic acid interactions. In embodiments, the method is used to identify protein-nucleic acid interactions in a cell. In embodiments, the method is used to identify protein-nucleic acid interactions in a mammalian cell. In embodiments, the method is used to identify protein-nucleic acid interactions in a human cell. In embodiments, the method is used to identify protein-nucleic acid interactions in a bacterial cell. In embodiments, the method is used to identify protein-nucleic acid interactions in an *E. coli* cell. In embodiments, the method is used to identify protein-nucleic acid interactions between cells. In embodiments, the method is used to identify protein-nucleic acid interactions in a disease cell. In embodiments, the method is used to identify protein-nucleic acid interactions in a cancer cell. In embodiments, the method is used to identify protein-nucleic acid interactions in cell lysates. In embodiments, the method is used to identify protein-nucleic acid interactions in blood. In embodiments, the method is used to identify protein-nucleic acid interactions in plasma. In embodiments, the method is used to identify protein-nucleic acid interactions in an extracellular matrix. In embodiments, the method is used to identify protein-nucleic acid interactions in a tissue. In embodiments, the method is used to identify protein-nucleic acid interactions in vitro. In embodiments, the method is used to identify protein-nucleic acid interactions in a culture. In embodiments, the method is used to identify protein-nucleic acid interactions in a cell culture. In embodiments, the method is used to identify protein-nucleic acid interactions in a tissue culture. In embodiments, the method is used to identify protein-nucleic acid interactions in an isolated protein/nucleic acid complex.

In embodiments, the method is used to identify protein-glycan interactions. In embodiments, the method is used to identify protein-glycan interactions in a cell. In embodiments, the method is used to identify protein-glycan interactions in a mammalian cell. In embodiments, the method is used to identify protein-glycan interactions in a human cell. In embodiments, the method is used to identify protein-glycan interactions in a bacterial cell. In embodiments, the method is used to identify protein-glycan interactions in an *E. coli* cell. In embodiments, the method is used to identify protein-glycan interactions between cells. In embodiments, the method is used to identify protein-glycan interactions in a disease cell. In embodiments, the method is used to identify protein-glycan interactions in a cancer cell. In embodiments, the method is used to identify protein-glycan interactions in cell lysates. In embodiments, the method is used to identify protein-glycan interactions in blood. In embodiments, the method is used to identify protein-glycan interactions in plasma. In embodiments, the method is used to identify protein-glycan interactions in an extracellular matrix. In embodiments, the method is used to identify protein-glycan interactions in a tissue. In embodiments, the method is used to identify protein-glycan interactions in vitro. In embodiments, the method is used to identify protein-glycan interactions in a culture. In embodiments, the method is used to identify protein-glycan interactions in a cell culture. In embodiments, the method is used to identify protein-glycan interactions in a tissue culture. In embodiments, the method is used to identify protein-glycan interactions in an isolated protein/glycan complex.

In embodiments, the method is used to identify nucleic acid-nucleic acid interactions. In embodiments, the method is used to identify nucleic acid-nucleic acid interactions in a cell. In embodiments, the method is used to identify nucleic acid-nucleic acid interactions in a mammalian cell. In embodiments, the method is used to identify nucleic acid-nucleic acid interactions in a human cell. In embodiments, the method is used to identify nucleic acid-nucleic acid interactions in a bacterial cell. In embodiments, the method is used to identify nucleic acid-nucleic acid interactions in an *E. coli* cell. In embodiments, the method is used to identify nucleic acid-nucleic acid interactions between cells. In embodiments, the method is used to identify nucleic acid-nucleic acid interactions in a disease cell. In embodiments, the method is used to identify nucleic acid-nucleic acid interactions in a cancer cell. In embodiments, the method is used to identify nucleic acid-nucleic acid interactions in cell lysates. In embodiments, the method is used to identify nucleic acid-nucleic acid interactions in blood. In embodiments, the method is used to identify nucleic acid-nucleic acid interactions in plasma. In embodiments, the method is used to identify nucleic acid-nucleic acid interactions in an extracellular matrix. In embodiments, the method is used to identify nucleic acid-nucleic acid interactions in a tissue. In embodiments, the method is used to identify nucleic acid-nucleic acid interactions in vitro. In embodiments, the method is used to identify nucleic acid-nucleic acid interactions in a culture. In embodiments, the method is used to identify nucleic acid-nucleic acid interactions in a cell culture. In embodiments, the method is used to identify nucleic acid-nucleic acid interactions in a tissue culture. In embodiments, the method is used to identify nucleic acid-nucleic acid interactions in an isolated nucleic acid.

In embodiments, the method is used to identify glycan-glycan interactions. In embodiments, the method is used to identify glycan-glycan interactions in a cell. In embodiments, the method is used to identify glycan-glycan interactions in a mammalian cell. In embodiments, the method is used to identify glycan-glycan interactions in a human cell. In embodiments, the method is used to identify glycan-glycan interactions in a bacterial cell. In embodiments, the method is used to identify glycan-glycan interactions in an *E. coli* cell. In embodiments, the method is used to identify glycan-glycan interactions between cells. In embodiments, the method is used to identify glycan-glycan interactions in a disease cell. In embodiments, the method is used to identify glycan-glycan interactions in a cancer cell. In embodiments, the method is used to identify glycan-glycan interactions in cell lysates. In embodiments, the method is used to identify glycan-glycan interactions in blood. In embodiments, the method is used to identify glycan-glycan interactions in plasma. In embodiments, the method is used to identify glycan-glycan interactions in an extracellular matrix. In embodiments, the method is used to identify glycan-glycan interactions in a tissue. In embodiments, the method is used to identify glycan-glycan interactions in vitro. In embodiments, the method is used to identify glycan-glycan interactions in a culture. In embodiments, the method is used to identify glycan-glycan interactions in a cell culture. In embodiments, the method is used to identify glycan-glycan interactions in a tissue culture. In embodiments, the method is used to identify glycan-glycan interactions in an isolated glycan.

In embodiments, the method is used to identify nucleic acid-glycan interactions. In embodiments, the method is used to identify nucleic acid-glycan interactions in a cell. In embodiments, the method is used to identify nucleic acid-glycan interactions in a mammalian cell. In embodiments, the method is used to identify nucleic acid-glycan interactions in a human cell. In embodiments, the method is used to identify nucleic acid-glycan interactions in a bacterial cell. In embodiments, the method is used to identify nucleic acid-glycan interactions in an *E. coli* cell. In embodiments, the method is used to identify nucleic acid-glycan interactions between cells. In embodiments, the method is used to identify nucleic acid-glycan interactions in a disease cell. In embodiments, the method is used to identify nucleic acid-glycan interactions in a cancer cell. In embodiments, the method is used to identify nucleic acid-glycan interactions in cell lysates. In embodiments, the method is used to identify nucleic acid-glycan interactions in blood. In embodiments, the method is used to identify nucleic acid-glycan interactions in plasma. In embodiments, the method is used to identify nucleic acid-glycan interactions in an extracellular matrix. In embodiments, the method is used to identify nucleic acid-glycan interactions in a tissue. In embodiments, the method is used to identify nucleic acid-glycan interactions in vitro. In embodiments, the method is used to identify nucleic acid-glycan interactions in a culture. In embodiments, the method is used to identify nucleic acid-glycan interactions in a cell culture. In embodiments, the method is used to identify nucleic acid-glycan interactions in a tissue culture. In embodiments, the method is used to identify nucleic acid-glycan interactions in an isolated nucleic acid/glycan complex.

In an aspect is provided a method of identifying contacts between biomolecules (e.g., proteins, nucleic acids, and/or glycans) including a method of detecting a covalently conjugated biomolecule as described herein, including in embodiments.

In an aspect is provided a method of detecting an intramolecular contacts in a biomolecule (e.g., protein, nucleic acid, or glycan) including a method of detecting an intramolecular crosslinked biomolecule (e.g., protein, nucleic acid, or glycan) as described herein, including in embodiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

IV. Embodiments

Embodiment P1. A method of detecting a covalently conjugated molecule, said method comprising i) contacting a first biomolecule and a second biomolecule with a crosslinking agent to form the covalently conjugated biomolecule;

ii) identifying a first point of attachment of the crosslinking agent to the first biomolecule using mass spectroscopy; and iii) identifying a second point of attachment of the crosslinking agent to the second biomolecule using mass spectroscopy;

thereby detecting a covalently conjugated molecule;

wherein the crosslinking agent has the formula:

$$R^1\text{-}L^1\text{-}R^2 \quad \text{(I);}$$

wherein $R^1$ is a bioconjugate reactive moiety capable of bonding to said first biomolecule;

$R^2$ is a proximity enhanced bioconjugate reactive moiety capable of bonding to said second biomolecule;

$L^1$ is a covalent linker; and wherein the bonding reactivity of $R^1$ with said first molecule is greater than the bonding reactivity of $R^2$ with said second biomolecule.

Embodiment P2. The method of embodiment P1, wherein the first biomolecule is a protein or nucleic acid; and the second biomolecule is a protein or nucleic acid.

Embodiment P3. The method of embodiment P1, wherein the first biomolecule is a first protein; and the second biomolecule is a second protein, $R^1$ is a bioconjugate reactive moiety reactive with a first amino acid of said first protein, and $R^2$ is a proximity enhanced bioconjugate reactive moiety reactive with said second amino acid of said second protein.

Embodiment P4. A method of detecting an intramolecular crosslinked protein, said method comprising:

i) contacting the protein with a crosslinking agent, wherein said crosslinking agent bonds to a first amino acid of said protein and a second amino acid of said protein to form a crosslinked protein;

ii) identifying a first point of attachment of said crosslinking agent to said protein using mass spectroscopy; and iii) identifying a second point of attachment of said crosslinking agent to said protein using mass spectroscopy;

wherein the crosslinking agent has the formula:

$$R^1\text{-}L^1\text{-}R^2 \quad (I);$$

wherein $R^1$ is a bioconjugate reactive moiety capable of bonding with said first amino acid;

$R^2$ is a proximity enhanced bioconjugate reactive moiety capable of bonding with said second amino acid;

$L^1$ is a covalent linker; and wherein the bonding reactivity of $R^1$ with said first amino acid is greater than the bonding reactivity of $R^2$ with said second amino acid.

Embodiment P5. The method of any one of embodiments P1 to P4, wherein the bonding reactivity of $R^1$ is at least 10 fold greater than $R^2$.

Embodiment P6. The method of any one of embodiments P1 to P4, wherein the bonding reactivity of $R^1$ is about 10 to about 100 fold greater than $R^2$.

Embodiment P7. The method of any one of embodiments P1 to P6, wherein $R^1$ reacts with an amine moiety, a carboxylate moiety, or a sulfhydryl moiety.

Embodiment P8. The method of any one of embodiments P1 or P3 to P6, wherein $R^1$ reacts with an amine moiety of a protein, carboxylate moiety of a protein, or sulfhydryl moiety of a protein.

Embodiment P9. The method of any one of embodiments P1 or P3 to P6, wherein $R^1$ reacts with the amino terminus of said first protein or said intramolecular crosslinked protein, a lysine side chain of said first protein or said intramolecular crosslinked protein, a glutamate side chain of said first amino acid of said first protein or said intramolecular crosslinked protein, an aspartate side chain of said first amino acid of said first protein or said intramolecular crosslinked protein, or a cysteine side chain of said first amino acid of said first protein or said intramolecular crosslinked protein.

Embodiment P10. The method of any one of embodiments P1 to P9, wherein $R^1$ is

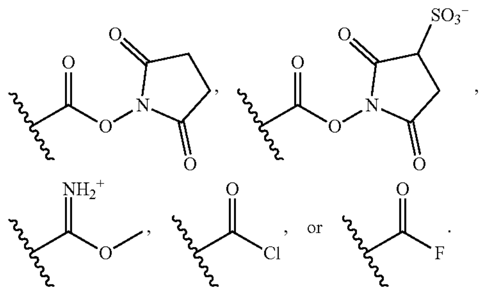

Embodiment P11. The method of any one of embodiments P1 to P10, wherein $R^2$ reacts with an amine moiety, imidazolyl moiety, or hydroxyl moiety.

Embodiment P12. The method of any one of embodiments P1 to P10, wherein $R^2$ reacts with a protein amine moiety, protein imidazolyl moiety, or protein hydroxyl moiety.

Embodiment P13. The method of any one of embodiments P1 or P3 to P10, wherein $R^2$ reacts with the amino terminus of said second protein or said crosslinked protein, a lysine side chain of said second amino acid of said second protein or said intramolecular crosslinked protein, a histidine side chain of said second amino acid of said second protein or said intramolecular crosslinked protein, a serine side chain of said second amino acid of said second protein or said intramolecular crosslinked protein, a threonine side chain of said second amino acid of said second protein or said intramolecular crosslinked protein, or a tyrosine side chain of said second amino acid of said second protein or said intramolecular crosslinked protein.

Embodiment P14. The method of any one of embodiments P1 to P13, wherein $R^2$ is

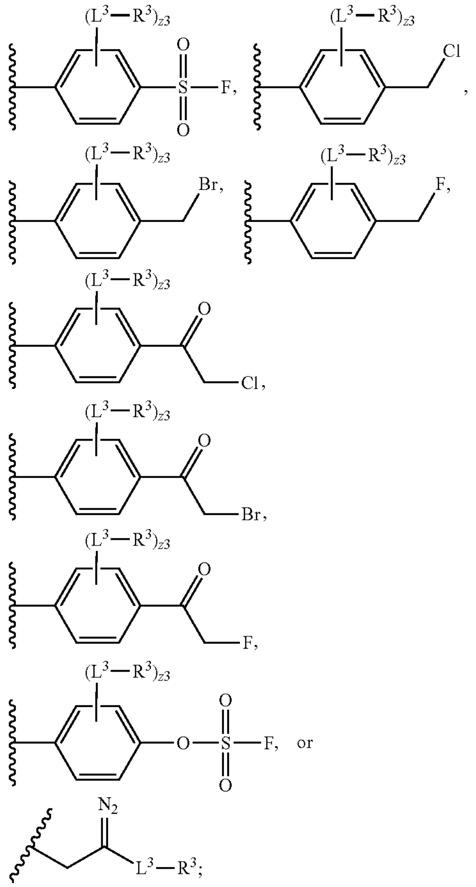

wherein $L^3$ is a bond, $-S(O)_2-$, $-NH-$, $-O-$, $-S-$, $-C(O)-$, $-C(O)NH-$, $-NHC(O)-$, $-NHC(O)NH-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCl_3$, $-OCH_2Cl$, $-OCH_2Br$, $-OCH_2F$, $-OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety; and z3 is an integer from 0 to 4.

Embodiment P15. The method of embodiment P14, wherein $R^3$ is a substituted or unsubstituted alkynyl, —$N_3$, or a bioconjugate reactive moiety.

Embodiment P16. The method of embodiment P14, wherein z3 is 0.

Embodiment P17. The method of any one of embodiments P1 to P16, wherein $L^1$ has the formula: -$L^{1A}$-$L^{1B}$-$L^{1C}$-$L^{1D}$-, wherein $L^{1A}$ is connected directly to $R^1$;

$L^{1A}$, $L^{1B}$, $L^{1C}$, and $L^{1D}$ are each independently a bond, —$N(R^{10})$—, —C(O)—, —$C(O)N(R^{10})$—, —$N(R^{10})C(O)$—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconugate linker; and $R^{10}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P18. The method of any one of embodiments P1 to P16, wherein $L^1$ is a bond, —$N(R^{10})$—, —C(O)—, —$C(O)N(R^{10})$—, —$N(R^{10})C(O)$—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconugate linker.

Embodiment P19. The method of any one of embodiments P1 to P16, wherein $L^1$ is cleavable by mass spectroscopy.

Embodiment P20. The method of embodiment P19, wherein $L^1$ is

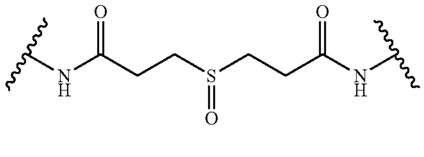

or

-continued

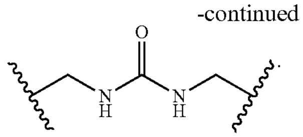

Embodiment P21. The method of any one of embodiments P1 to P16, wherein $L^1$ is a bond or substituted or unsubstituted $C_1$-$C_4$ alkylene.

Embodiment P22. The method of any one of embodiments P1 to P16, wherein $L^1$ is an unsubstituted $C_1$-$C_4$ alkylene.

Embodiment P23. The method of any one of embodiments P1 to P16, wherein $L^1$ is

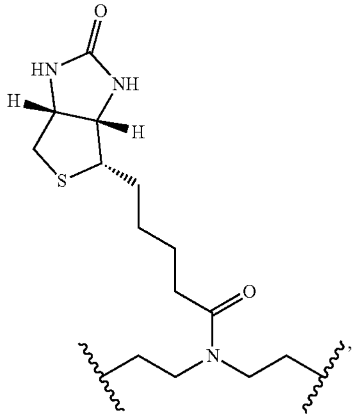

,

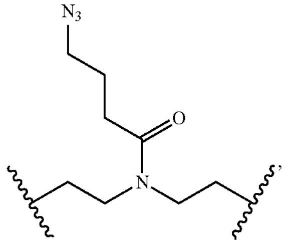

, or

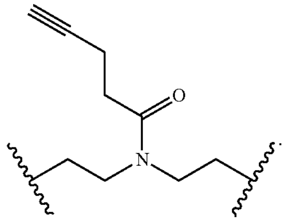

.

Embodiment P24. The method of any one of embodiments P1 to P23, wherein the distance between the first point of attachment and the second point of attachment is from about 5 to about 50 Å.

Embodiment P25. The method of any one of embodiments P1 to P23, wherein the distance between the first point of attachment and the second point of attachment is from about 20 Å.

Embodiment P26. The method of any one of embodiments P1 to P25, wherein the first point of attachment is an amino terminus of said first protein or said intramolecular crosslinked protein, a lysine side chain of said first amino acid of said first protein or said intramolecular crosslinked protein, a glutamate side chain of said first amino acid of said first protein or said intramolecular crosslinked protein, an aspartate side chain of said first amino acid of said first protein or said intramolecular crosslinked protein, or a cysteine side chain of said first amino acid of said first protein or said intramolecular crosslinked protein.

Embodiment P27. The method of any one of embodiments P1 to P25, wherein the second point of attachment is an amino terminus of said first protein or said intramolecular crosslinked protein, a lysine side chain of said second amino acid of said first protein or said intramolecular crosslinked protein, a histidine side chain of said second amino acid of said first protein or said intramolecular crosslinked protein, a serine side chain of said second amino acid of said first protein or said intramolecular crosslinked protein, a threonine side chain of said second amino acid of said first protein or said intramolecular crosslinked protein, or a tyrosine side chain of said second amino acid of said first protein or said intramolecular crosslinked protein.

Embodiment P28. The method of embodiment P1 or embodiment P4, wherein the crosslinking agent has the formula:

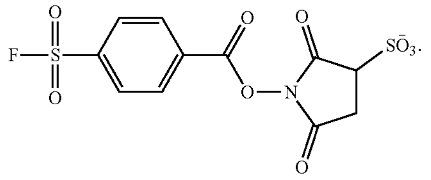

Embodiment P29. The method of any one of embodiments P1 to P28 wherein the crosslinking agent comprises a heavy isotope.

V. Additional Embodiments

Embodiment 1. A method of detecting a covalently conjugated biomolecule comprising a first biomolecule conjugated to a second biomolecule, said method comprising i) contacting the first biomolecule and the second biomolecule with a crosslinking agent to form the covalently conjugated biomolecule;

ii) identifying a first point of attachment of the crosslinking agent to the first biomolecule using mass spectroscopy; and iii) identifying a second point of attachment of the crosslinking agent to the second biomolecule using mass spectroscopy;

thereby detecting the covalently conjugated biomolecule; wherein the crosslinking agent has the formula:

$$R^1\text{-}L^1\text{-}R^2 \quad (I);$$

wherein $R^1$ is a bioconjugate reactive moiety;

$R^2$ is a proximity enhanced bioconjugate reactive moiety;

$L^1$ is a covalent linker; and wherein the bonding reactivity of $R^1$ with said first biomolecule is greater than the bonding reactivity of $R^2$ with said second biomolecule.

Embodiment 2. The method of embodiment 1, wherein the first biomolecule is a protein, nucleic acid, or glycan; and the second biomolecule is a protein, nucleic acid, or glycan.

Embodiment 3. The method of embodiment 1, wherein the first biomolecule is a first protein; and the second biomolecule is a second protein, $R^1$ is a bioconjugate reactive moiety reactive with a first amino acid of said first protein, and $R^2$ is a proximity enhanced bioconjugate reactive moiety reactive with said second amino acid of said second protein.

Embodiment 4. The method of any one of embodiments 1 to 3, wherein $R^1$ reacts with an amine moiety of said first biomolecule, carboxylate moiety of said first biomolecule, or sulfhydryl moiety of said first biomolecule.

Embodiment 5. The method of any one of embodiments 1 to 3, wherein $R^1$ reacts with an amino terminus of said first biomolecule, a lysine side chain of said first biomolecule, a glutamate side chain of said first amino acid of said first biomolecule, an aspartate side chain of said first amino acid of said first biomolecule, or a cysteine side chain of said first amino acid of said first biomolecule.

Embodiment 6. The method of any one of embodiments 1 to 5, wherein $R^2$ reacts with an amine moiety of said second biomolecule, imidazolyl moiety of said second biomolecule, or hydroxyl moiety of said second biomolecule.

Embodiment 7. The method of any one of embodiments 1 to 5, wherein $R^2$ reacts with an amino terminus of said second biomolecule, a lysine side chain of said second amino acid of said second biomolecule, a histidine side chain of said second amino acid of said second biomolecule, a serine side chain of said second amino acid of said second biomolecule, a threonine side chain of said second amino acid of said second biomolecule, or a tyrosine side chain of said second amino acid of said biomolecule.

Embodiment 8. The method of any one of embodiments 1 to 7, wherein the first point of attachment is an amino terminus of said first biomolecule, a lysine side chain of said first biomolecule, a glutamate side chain of said first biomolecule, an aspartate side chain of said first biomolecule, or a cysteine side chain of said first biomolecule.

Embodiment 9. The method of any one of embodiments 1 to 8, wherein the second point of attachment is an amino terminus of said second biomolecule, a lysine side chain of said second biomolecule, a histidine side chain of said second biomolecule, a serine side chain of said second biomolecule, a threonine side chain of said second biomolecule, or a tyrosine side chain of said second biomolecule.

Embodiment 10. A method of detecting an intramolecular crosslinked protein, said method comprising:

i) contacting the protein with a crosslinking agent, wherein said crosslinking agent bonds to a first amino acid of said protein and a second amino acid of said protein to form the intramolecular crosslinked protein;

ii) identifying a first point of attachment of said crosslinking agent to said protein using mass spectroscopy; and iii) identifying a second point of attachment of said crosslinking agent to said protein using mass spectroscopy;

wherein the crosslinking agent has the formula:

$$R^1\text{-}L^1\text{-}R^2 \quad (I);$$

wherein $R^1$ is a bioconjugate reactive moiety;

$R^2$ is a proximity enhanced bioconjugate reactive moiety;

$L^1$ is a covalent linker; and wherein the bonding reactivity of $R^1$ with said first amino acid is greater than the bonding reactivity of $R^2$ with said second amino acid.

Embodiment 11. The method of embodiment 10, wherein $R^1$ reacts with an amine moiety of said protein, a carboxylate moiety of said protein, or a sulfhydryl moiety of said protein.

Embodiment 12. The method of embodiment 10, wherein $R^1$ reacts with an amino terminus of said protein, a lysine side chain of said protein, a glutamate side chain of said first amino acid of said protein, an aspartate side chain of said first amino acid of said protein, or a cysteine side chain of said first amino acid of said protein.

Embodiment 13. The method of any one of embodiments 10 to 12, wherein $R^2$ reacts with an amine moiety of said protein, imidazolyl moiety of said protein, or hydroxyl moiety of said protein.

Embodiment 14. The method of any one of embodiments 10 to 12, wherein $R^2$ reacts with an amino terminus of said protein, a lysine side chain of said second amino acid of said protein, a histidine side chain of said second amino acid of said protein, a serine side chain of said second amino acid of said protein, a threonine side chain of said second amino acid of said protein, or a tyrosine side chain of said second amino acid of said protein.

Embodiment 15. The method of any one of embodiments 10 to 14, wherein the first point of attachment is an amino terminus of said protein, a lysine side chain of said protein, a glutamate side chain of said protein, an aspartate side chain of said protein, or a cysteine side chain of said protein.

Embodiment 16. The method of any one of embodiments 10 to 14, wherein the second point of attachment is an amino terminus of said protein, a lysine side chain of said protein, a histidine side chain of said protein, a serine side chain of said protein, a threonine side chain of said protein, or a tyrosine side chain of said protein.

Embodiment 17. The method of any one of embodiments 1 to 16, wherein the bonding reactivity of $R^1$ is at least 10 fold greater than $R^2$.

Embodiment 18. The method of any one of embodiments 1 to 16, wherein the bonding reactivity of $R^1$ is about 10 to about 100 fold greater than $R^2$.

Embodiment 19. The method of any one of embodiments 1 to 18, wherein $R^1$ is

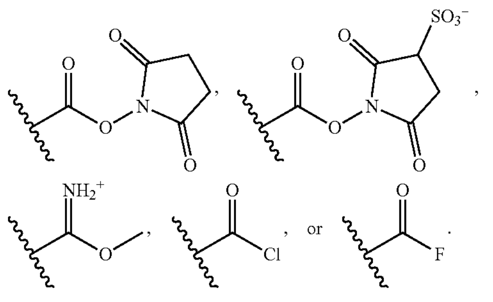

Embodiment 20. The method of any one of embodiments 1 to 19, wherein $R^2$ is

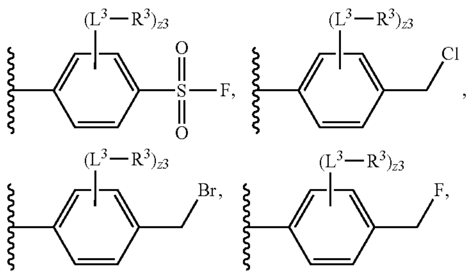

-continued

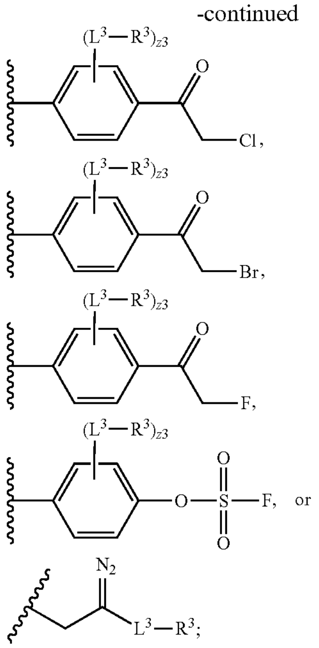

wherein $L^3$ is a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety; and z3 is an integer from 0 to 4.

Embodiment 21. The method of embodiment 20, wherein $R^3$ is a substituted or unsubstituted alkynyl, —$N_3$, or a bioconjugate reactive moiety.

Embodiment 22. The method of embodiment 20, wherein z3 is 0.

Embodiment 23. The method of any one of embodiments 1 to 22, wherein $L^1$ has the formula: -$L^{1A}$-$L^{1B}$-$L^{1C}$-$L^{1D}$-; wherein $L^{1A}$ is connected directly to $R^1$;

$L^{1A}$, $L^{1B}$, $L^{1C}$, and $L^{1D}$ are each independently a bond, —$N(R^{10})$—, —C(O)—, —$C(O)N(R^{10})$—, —$N(R^{10})C(O)$—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker; and $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 24. The method of any one of embodiments 1 to 22, wherein $L^1$ is a bond, —$N(R^{10})$—, —C(O)—, —C(O)$N(R^{10})$—, —$N(R^{10})$C(O)—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

Embodiment 25. The method of any one of embodiments 1 to 22, wherein $L^1$ is cleavable by mass spectroscopy.

Embodiment 26. The method of embodiment 25, wherein $L^1$ is

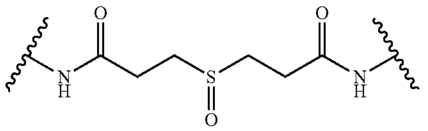

or

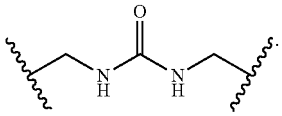

Embodiment 27. The method of any one of embodiments 1 to 22, wherein $L^1$ is a bond or substituted or unsubstituted $C_1$-$C_4$ alkylene.

Embodiment 28. The method of any one of embodiments 1 to 22, wherein $L^1$ is an unsubstituted $C_1$-$C_4$ alkylene.

Embodiment 29. The method of any one of embodiments 1 to 22, wherein $L^1$ is

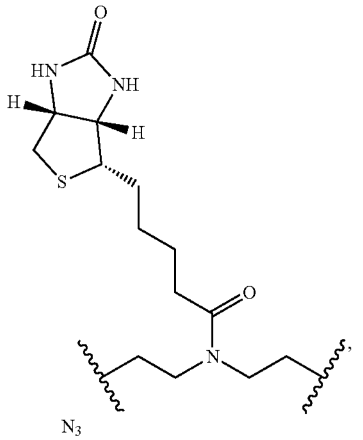

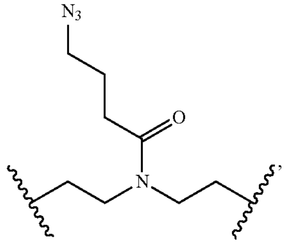

or

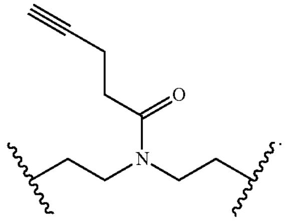

Embodiment 30. The method of any one of embodiments 1 to 29, wherein the distance between the first point of attachment and the second point of attachment is from about 5 to about 50 Å.

Embodiment 31. The method of any one of embodiments 1 to 29, wherein the distance between the first point of attachment and the second point of attachment is from about 20 Å.

Embodiment 32. The method of any one of embodiments 1 to 24, wherein the crosslinking agent has the formula:

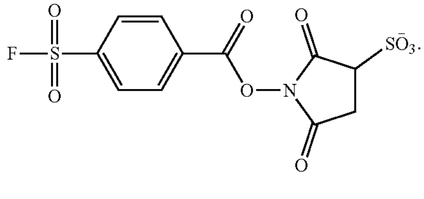

Embodiment 33. A method of detecting a covalently conjugated biomolecule comprising a first biomolecule conjugated to a second biomolecule, said method comprising i) contacting said first biomolecule with a crosslinking agent to form an activated biomolecule, wherein the crosslinking agent has the formula:

$$R^1\text{-}L^1\text{-}R^2 \quad (I);$$

wherein $R^1$ is a bioconjugate reactive moiety; $R^2$ is a photo-activated bioconjugate reactive moiety; and $L^1$ is a covalent linker;

wherein the bioconjugate reactive moiety reacts with said first biomolecule thereby forming said activated biomolecule;

ii) contacting the activated biomolecule with radiation in the presence of said second biomolecule thereby forming the covalently conjugated biomolecule;

iii) identifying a first point of attachment of the crosslinking agent to the first biomolecule using mass spectroscopy; and iv) identifying a second point of attachment of the crosslinking agent to the second biomolecule using mass spectroscopy;

thereby detecting the covalently conjugated biomolecule;

wherein the bonding reactivity of $R^2$ with said second biomolecule after contact of $R^2$ with radiation is greater than the bonding reactivity of $R^2$ with said second biomolecule prior to contact of $R^2$ with radiation.

Embodiment 34. The method of embodiment 33, wherein the first biomolecule is a protein, nucleic acid, or glycan; and the second biomolecule is a protein, nucleic acid, or glycan.

Embodiment 35. The method of embodiment 33, wherein the first biomolecule is a first protein; and the second biomolecule is a second protein, $R^1$ is a bioconjugate reactive moiety reactive with a first amino acid of said first protein, and $R^2$ is a photo-activated bioconjugate reactive moiety reactive with a second amino acid of said second protein.

Embodiment 36. The method of any one of embodiments 33 to 35, wherein $R^1$ reacts with an amine moiety of said first biomolecule, carboxylate moiety of said first biomolecule, or sulfhydryl moiety of said first biomolecule.

Embodiment 37. The method of any one of embodiments 33 to 36, wherein $R^1$ reacts with an amino terminus of said first biomolecule, a lysine side chain of said first biomolecule, a glutamate side chain of said first amino acid of said first biomolecule, an aspartate side chain of said first amino acid of said first biomolecule, or a cysteine side chain of said first amino acid of said first biomolecule.

Embodiment 38. The method of any one of embodiments 33 to 37, wherein $R^2$ reacts with an amine moiety of said second biomolecule, a carboxyl moiety of said second biomolecule, a hydroxyl moiety of said second biomolecule, an amido moiety of said second biomolecule, a guanidinyl moiety of said second biomolecule, or a thioether moiety of said second biomolecule.

Embodiment 39. The method of any one of embodiments 33 to 37, wherein $R^2$ reacts with an amino terminus of said second biomolecule, a carboxyl terminus of said second biomolecule, an aspartic acid side chain of said second amino acid of said second biomolecule, a glutamic acid side chain of said second amino acid of said second biomolecule, a lysine side chain of said second amino acid of said second biomolecule, a serine side chain of said second amino acid of said second biomolecule, a threonine side chain of said second amino acid of said second biomolecule, a tyrosine side chain of said second amino acid of said second biomolecule, a glutamine side chain of said second amino acid of said second biomolecule, an arginine side chain of said second amino acid of said second biomolecule, an asparagine side chain of said second amino acid of said second biomolecule, or a methionine side chain of said second amino acid of said second biomolecule.

Embodiment 40. The method of any one of embodiments 33 to 39, wherein the first point of attachment is an amino terminus of said first biomolecule, a lysine side chain of said first amino acid of said first biomolecule, a glutamate side chain of said first amino acid of said first biomolecule, an aspartate side chain of said first amino acid of said first biomolecule, or a cysteine side chain of said first amino acid of said first biomolecule.

Embodiment 41. The method of any one of embodiments 33 to 40, wherein the second point of attachment is an amino terminus of said second biomolecule, carboxyl terminus of said second biomolecule, an aspartic acid side chain of said second amino acid of said second biomolecule, a glutamic acid side chain of said second amino acid of said second biomolecule, a lysine side chain of said second amino acid of said second biomolecule, a serine side chain of said second amino acid of said second biomolecule, a threonine side chain of said second amino acid of said second biomolecule, a tyrosine side chain of said second amino acid of said second biomolecule, a glutamine side chain of said second amino acid of said second biomolecule, an arginine side chain of said second amino acid of said second biomolecule, an asparagine side chain of said second amino acid of said second biomolecule, or a methionine side chain of said second amino acid of said second biomolecule.

Embodiment 42. A method of detecting an intramolecular crosslinked protein, said method comprising:

i) combining a protein with a crosslinking agent in a reaction vessel and contacting said crosslinking agent with radiation thereby forming the intramolecular crosslinked protein, wherein said crosslinking agent has the formula:

$$R^1\text{-}L^1\text{-}R^2 \qquad (I);$$

wherein $R^1$ is a bioconjugate reactive moiety; $R^2$ is a photo-activated bioconjugate reactive moiety; and $L^1$ is a covalent linker;

wherein said bioconjugate reactive moiety bonds to a first amino acid of said protein; and said photo-activated bioconjugate reactive moiety bonds to a second amino acid of said protein thereby forming said intramolecular crosslinked protein;

ii) identifying a first point of attachment of said crosslinking agent to said protein using mass spectroscopy; and iii) identifying a second point of attachment of said crosslinking agent to said protein using mass spectroscopy and thereby detecting the intramolecular crosslinked protein;

wherein the bonding reactivity of $R^2$ with said second amino acid after said contacting of said crosslinking agent with radiation is greater than the bonding reactivity of $R^2$ with said second amino acid prior to said contacting of said crosslinking agent with radiation.

Embodiment 43. The method of embodiment 42, wherein $R^1$ reacts with an amine moiety of said protein, a carboxylate moiety of said protein, or a sulfhydryl moiety of said protein.

Embodiment 44. The method of any one of embodiments 42 to 43, wherein $R^1$ reacts with an amino terminus of said protein, a lysine side chain of said protein, a glutamate side chain of said first amino acid of said protein, an aspartate side chain of said first amino acid of said protein, or a cysteine side chain of said first amino acid of said protein.

Embodiment 45. The method of any one of embodiments 42 to 44, wherein $R^2$ reacts with an amine moiety of said protein, a carboxyl moiety of said protein, a hydroxyl moiety of said protein, an amido moiety of said protein, a guanidinyl moiety of said protein, or a thioether moiety of said protein.

Embodiment 46. The method of any one of embodiments 42 to 44, wherein $R^2$ reacts with an amino terminus of said protein, a carboxyl terminus of said protein, an aspartic acid side chain of said second amino acid of said protein, a glutamic acid side chain of said second amino acid of said protein, a lysine side chain of said second amino acid of said protein, a serine side chain of said second amino acid of said protein, a threonine side chain of said second amino acid of said protein, a tyrosine side chain of said second amino acid of said protein, a glutamine side chain of said second amino acid of said protein, an arginine side chain of said second amino acid of said protein, an asparagine side chain of said second amino acid of said protein, or a methionine side chain of said second amino acid of said protein.

Embodiment 47. The method of any one of embodiments 42 to 46, wherein the first point of attachment is an amino terminus of said protein, a lysine side chain of said protein, a glutamate side chain of said protein, an aspartate side chain of said protein, or a cysteine side chain of said protein.

Embodiment 48. The method of any one of embodiments 42 to 47, wherein the second point of attachment is an amino terminus of said protein, a carboxyl terminus of said protein, an aspartic acid side chain of said protein, a glutamic acid side chain of said protein, a lysine side chain of said protein, a serine side chain of said protein, a threonine side chain of said protein, a tyrosine side chain of said protein, a glutamine side chain of said protein, an arginine side chain of said protein, an asparagine side chain of said protein, or a methionine side chain of said protein.

Embodiment 49. The method of any one of embodiments 33 to 48, wherein the distance between the first point of attachment and the second point of attachment is from about 5 to about 50 Å.

Embodiment 50. The method of any one of embodiments 33 to 48, wherein the distance between the first point of attachment and the second point of attachment is about 20 Å.

Embodiment 51. The method of any one of embodiments 33 to 50, wherein the bonding reactivity of $R^1$ is at least 10 fold greater than $R^2$.

Embodiment 52. The method of any one of embodiments 33 to 51, wherein $R^1$ is

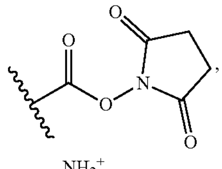,
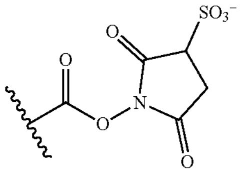,
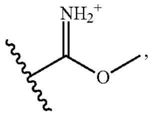,
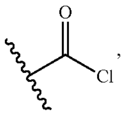, or
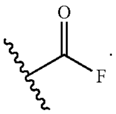.

Embodiment 53. The method of any one of embodiments 33 to 52, wherein $R^2$ is

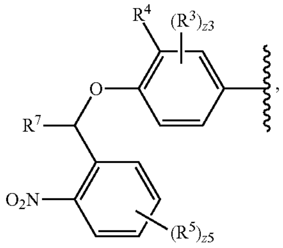,

-continued

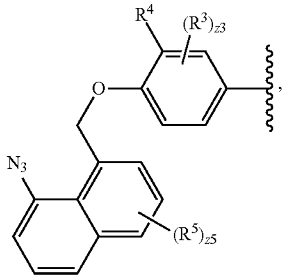,

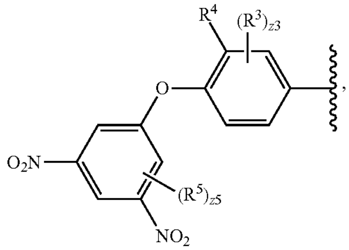,

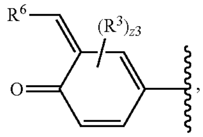,

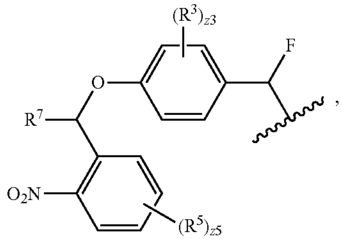,

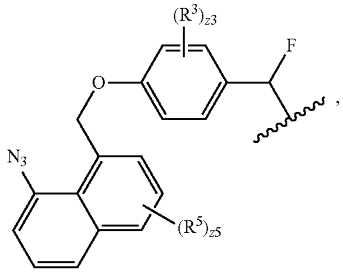,

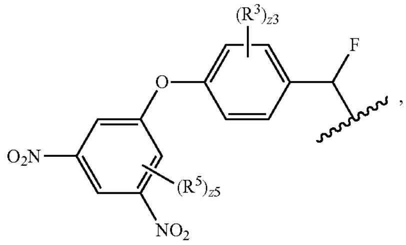,

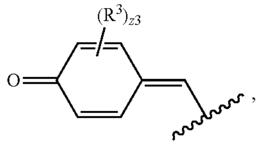,

-continued

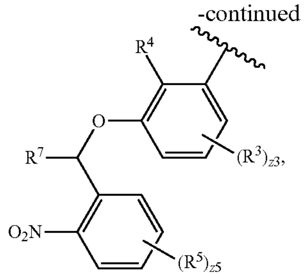

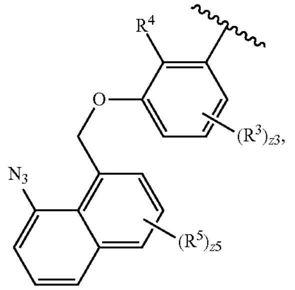

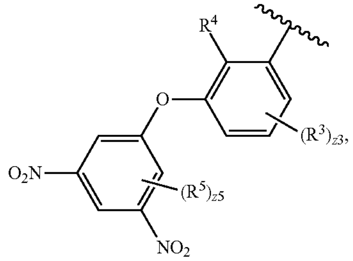

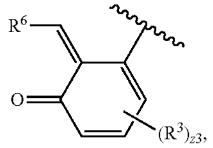

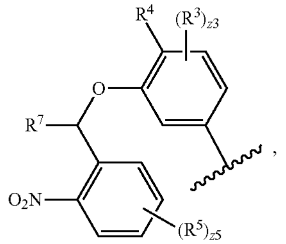

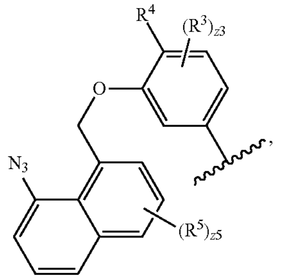

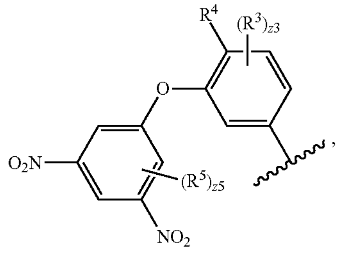

-continued

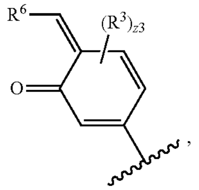

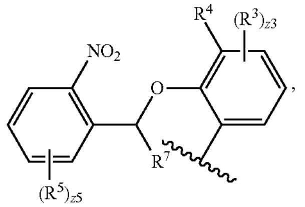

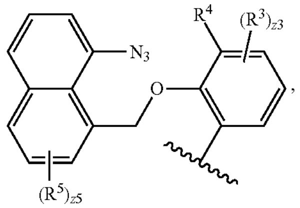

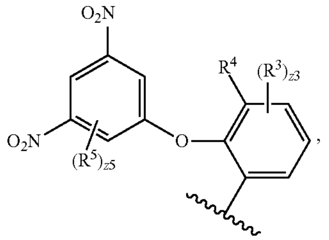

or

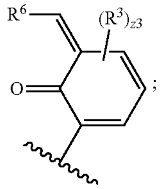

wherein $R^3$ and $R^5$ are independently halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and z3 is an integer from 0 to 3.

z5 is an integer from 0 to 6;

$R^4$ is independently $-CH_2F$ or $-CHF_2$;

$R^6$ is independently hydrogen or $-F$; and $R^7$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)$ H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$COO^-$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 54. The method of embodiment 53, wherein z3 is 0.

Embodiment 55. The method of embodiment 53, wherein $R^5$ is independently unsubstituted methoxy.

Embodiment 56. The method of embodiment 53, wherein z5 is 0 to 2.

Embodiment 57. The method of embodiment 53, wherein $R^7$ is independently hydrogen, unsubstituted methyl, or —$COO^-$.

Embodiment 58. The method of any one of embodiments 33 to 57, wherein $L^1$ has the formula: -$L^{1A}$-$L^{1B}$-$L^{1C}$-$L^{1D}$-; wherein $L^{1A}$ is connected directly to $R^1$;

$L^{1A}$, $L^{1B}$, $L^{1C}$, and $L^{1D}$ are each independently a bond, —$N(R^{10})$—, —C(O)—, —$C(O)N(R^{10})$—, —$N(R^{10})C(O)$—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker; and $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 59. The method of any one of embodiments 33 to 57, wherein $L^1$ is a bond, —$N(R^{10})$—, —C(O)—, —$C(O)N(R^{10})$—, —$N(R^{10})C(O)$—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

Embodiment 60. The method of any one of embodiments 33 to 57, wherein $L^1$ is cleavable by mass spectroscopy.

Embodiment 61. The method of any one of embodiments 33 to 57, wherein $L^1$ is a bond or substituted or unsubstituted $C_1$-$C_4$ alkylene.

Embodiment 62. The method of any one of embodiments 33 to 57, wherein $L^1$ is an unsubstituted $C_1$-$C_4$ alkylene.

Embodiment 63. The method of any one of embodiments 33 to 59, wherein the crosslinking agent has the formula:

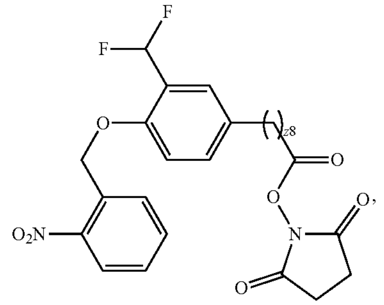

wherein z8 is an integer from 0 to 5.

Embodiment 64. The method of any one of embodiments 33 to 59, wherein the crosslinking agent has the formula:

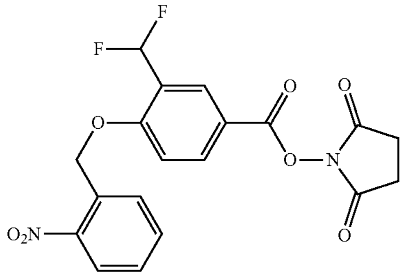

or

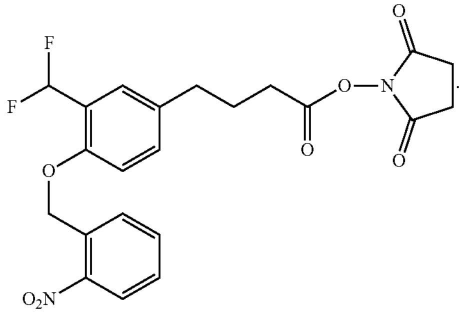

Embodiment 65. A method of detecting a covalently conjugated biomolecule comprising a first biomolecule conjugated to a second biomolecule, said method comprising i) contacting a crosslinking agent with radiation in the presence of said first biomolecule, thereby forming an activated biomolecule, wherein the crosslinking agent has the formula:

$$R^1\text{-}L^1\text{-}R^2 \qquad (I);$$

wherein $R^1$ is a first photo-activated bioconjugate reactive moiety; $R^2$ is a second photo-activated bioconjugate reactive moiety; and $L^1$ is a covalent linker;

wherein $R^1$ reacts with said first biomolecule thereby forming said activated biomolecule;

ii) contacting the activated biomolecule with radiation in the presence of said second biomolecule thereby forming a covalently conjugated biomolecule;

iii) identifying a first point of attachment of the crosslinking agent to the first biomolecule using mass spectroscopy; and iv) identifying a second point of attachment of the crosslinking agent to the second biomolecule using mass spectroscopy;

thereby detecting the covalently conjugated biomolecule;

wherein the bonding reactivity of $R^1$ with said first biomolecule after contact of $R^1$ with radiation is greater than the bonding reactivity of $R^1$ with said first biomolecule prior to contact of $R^1$ with radiation; and wherein the bonding reactivity of $R^2$ with said second biomolecule after contact of $R^2$ with radiation is greater than the bonding reactivity of $R^2$ with said second biomolecule prior to contact of $R^2$ with radiation.

Embodiment 66. A method of detecting a covalently conjugated biomolecule comprising a first biomolecule conjugated to a second biomolecule, said method comprising i) contacting a crosslinking agent with radiation in the presence of the first biomolecule and the second biomolecule, thereby forming the covalently conjugated biomolecule, wherein the crosslinking agent has the formula:

$$R^1\text{-}L^1\text{-}R^2 \quad (I);$$

wherein $R^1$ is a first photo-activated bioconjugate reactive moiety; $R^2$ is a second photo-activated bioconjugate reactive moiety; and $L^1$ is a covalent linker;

ii) identifying a first point of attachment of the crosslinking agent to the first biomolecule using mass spectroscopy; and iii) identifying a second point of attachment of the crosslinking agent to the second biomolecule using mass spectroscopy;

thereby detecting the covalently conjugated biomolecule;

wherein the bonding reactivity of $R^1$ with said first biomolecule after contact of $R^1$ with radiation is greater than the bonding reactivity of $R^1$ with said first biomolecule prior to contact of $R^1$ with radiation; and wherein the bonding reactivity of $R^2$ with said second biomolecule after contact of $R^2$ with radiation is greater than the bonding reactivity of $R^2$ with said second biomolecule prior to contact of $R^2$ with radiation.

Embodiment 67. The method of any one of embodiments 65 to 66, wherein the first biomolecule is a protein, nucleic acid, or glycan; and the second biomolecule is a protein, nucleic acid, or glycan.

Embodiment 68. The method of any one of embodiments 65 to 66, wherein the first biomolecule is a first protein; and the second biomolecule is an optionally different second protein, $R^1$ is a first photo-activated bioconjugate reactive moiety that is reactive with a first amino acid of said first protein, and $R^2$ is an optionally different second photo-activated bioconjugate reactive moiety that is reactive with a second amino acid of said second protein.

Embodiment 69. The method of any one of embodiments 65 to 68, wherein $R^1$ reacts with an amine moiety of said first biomolecule, a carboxyl moiety of said first biomolecule, a hydroxyl moiety of said first biomolecule, an amido moiety of said first biomolecule, a guanidinyl moiety of said first biomolecule, or a thioether moiety of said first biomolecule.

Embodiment 70. The method of any one of embodiments 65 to 68, wherein $R^1$ reacts with an amino terminus of said first biomolecule, a carboxyl terminus of said first biomolecule, an aspartic acid side chain of said first amino acid of said first biomolecule, a glutamic acid side chain of said first amino acid of said first biomolecule, a lysine side chain of said first amino acid of said first biomolecule, a serine side chain of said first amino acid of said first biomolecule, a threonine side chain of said first amino acid of said first biomolecule, a tyrosine side chain of said first amino acid of said first biomolecule, a glutamine side chain of said first amino acid of said first biomolecule, an arginine side chain of said first amino acid of said first biomolecule, an asparagine side chain of said first amino acid of said first biomolecule, or a methionine side chain of said first amino acid of said first biomolecule.

Embodiment 71. The method of any one of embodiments 67 to 72, wherein $R^2$ reacts with an amine moiety of said second biomolecule, a carboxyl moiety of said second biomolecule, a hydroxyl moiety of said second biomolecule, an amido moiety of said second biomolecule, a guanidinyl moiety of said second biomolecule, or a thioether moiety of said second biomolecule.

Embodiment 72. The method of any one of embodiments 65 to 70, wherein $R^2$ reacts with an amino terminus of said second biomolecule, a carboxyl terminus of said second biomolecule, an aspartic acid side chain of said second amino acid of said second biomolecule, a glutamic acid side chain of said second amino acid of said second biomolecule, a lysine side chain of said second amino acid of said second biomolecule, a serine side chain of said second amino acid of said second biomolecule, a threonine side chain of said second amino acid of said second biomolecule, a tyrosine side chain of said second amino acid of said second biomolecule, a glutamine side chain of said second amino acid of said second biomolecule, an arginine side chain of said second amino acid of said second biomolecule, an asparagine side chain of said second amino acid of said second biomolecule, or a methionine side chain of said second amino acid of said second biomolecule.

Embodiment 73. The method of any one of embodiments 65 to 72, wherein the first point of attachment is an amino terminus of said first biomolecule, a carboxyl terminus of said first biomolecule, an aspartic acid side chain of said first biomolecule, a glutamic acid side chain of said first biomolecule, a lysine side chain of said first biomolecule, a serine side chain of said first biomolecule, a threonine side chain of said first biomolecule, a tyrosine side chain of said first biomolecule, a glutamine side chain of said first biomolecule, an arginine side chain of said first biomolecule, an asparagine side chain of said first biomolecule, or a methionine side chain of said first biomolecule.

Embodiment 74. The method of any one of embodiments 65 to 73, wherein the second point of attachment is an amino terminus of said second biomolecule, a carboxyl terminus of said second biomolecule, an aspartic acid side chain of said second biomolecule, a glutamic acid side chain of said second biomolecule, a lysine side chain of said second biomolecule, a serine side chain of said second biomolecule, a threonine side chain of said second biomolecule, a tyrosine side chain of said second biomolecule, a glutamine side chain of said second biomolecule, an arginine side chain of said second biomolecule, an asparagine side chain of said second biomolecule, or a methionine side chain of said second biomolecule.

Embodiment 75. A method of detecting an intramolecular crosslinked protein, said method comprising:

i) combining a protein with a crosslinking agent in a reaction vessel and contacting said crosslinking agent with radiation thereby forming the intramolecular crosslinked protein, wherein the crosslinking agent has the formula:

$R^1$-$L^1$-$R^2$ (I); wherein $R^1$ is a first photo-activated bioconjugate reactive moiety; $R^2$ is a second photo-activated bioconjugate reactive moiety; and $L^1$ is a covalent linker;

ii) identifying a first point of attachment of said crosslinking agent to said protein using mass spectroscopy; and iii) identifying a second point of attachment of said crosslinking agent to said protein using mass spectroscopy and thereby detecting said intramolecular crosslinked protein;

wherein the bonding reactivity of $R^1$ with a first amino acid of the protein after contact of R' with radiation is greater than the bonding reactivity of $R^1$ with the first amino acid of the protein prior to contact of $R^1$ with radiation; and wherein the bonding reactivity of $R^2$ with a second amino acid of the protein after contact of $R^2$ with radiation is greater than the bonding reactivity of $R^2$ with the second amino acid of the protein prior to contact of $R^2$ with radiation.

Embodiment 76. The method of embodiments 75, wherein $R^1$ reacts with an amine moiety of said protein, a carboxyl moiety of said protein, a hydroxyl moiety of said protein, an amido moiety of said protein, a guanidinyl moiety of said protein, or a thioether moiety of said protein.

Embodiment 77. The method of embodiment 75, wherein $R^1$ reacts with an amino terminus of said protein, a carboxyl terminus of said protein, an aspartic acid side chain of said first amino acid of said protein, a glutamic acid side chain of said first amino acid of said protein, a lysine side chain of said first amino acid of said protein, a serine side chain of said first amino acid of said protein, a threonine side chain of said first amino acid of said protein, a tyrosine side chain of said first amino acid of said protein, a glutamine side chain of said first amino acid of said protein, an arginine side chain of said first amino acid of said protein, an asparagine side chain of said first amino acid of said protein, or a methionine side chain of said first amino acid of said protein.

Embodiment 78. The method of any one of embodiments 75 to 77, wherein $R^2$ reacts with an amine moiety of said protein, a carboxyl moiety of said protein, a hydroxyl moiety of said protein, an amido moiety of said protein, a guanidinyl moiety of said protein, or a thioether moiety of said protein.

Embodiment 79. The method of any one of embodiments 75 to 77, wherein $R^2$ reacts with an amino terminus of said protein, a carboxyl terminus of said protein, an aspartic acid side chain of said second amino acid of said protein, a glutamic acid side chain of said second amino acid of said protein, a lysine side chain of said second amino acid of said protein, a serine side chain of said second amino acid of said protein, a threonine side chain of said second amino acid of said protein, a tyrosine side chain of said second amino acid of said protein, a glutamine side chain of said second amino acid of said protein, an arginine side chain of said second amino acid of said protein, an asparagine side chain of said second amino acid of said protein, or a methionine side chain of said second amino acid of said protein.

Embodiment 80. The method of any one of embodiments 75 to 79, wherein the first point of attachment is an amino terminus of said protein, a carboxyl terminus of said protein, an aspartic acid side chain of said protein, a glutamic acid side chain of said protein, a lysine side chain of said protein, a serine side chain of said protein, a threonine side chain of said protein, a tyrosine side chain of said protein, a glutamine side chain of said protein, an arginine side chain of said protein, an asparagine side chain of said protein, or a methionine side chain of said protein.

Embodiment 81. The method of any one of embodiments 65 to 80, wherein the second point of attachment is an amino terminus of said protein, a carboxyl terminus of said protein, an aspartic acid side chain of said protein, a glutamic acid side chain of said protein, a lysine side chain of said protein, a serine side chain of said protein, a threonine side chain of said protein, a tyrosine side chain of said protein, a glutamine side chain of said protein, an arginine side chain of said protein, an asparagine side chain of said protein, or a methionine side chain of said protein.

Embodiment 82. The method of any one of embodiments 65 to 81, wherein the distance between the first point of attachment and the second point of attachment is from about 5 to about 50 Å.

Embodiment 83. The method of any one of embodiments 65 to 81, wherein the distance between the first point of attachment and the second point of attachment is about 20 Å.

Embodiment 84. The method of any one of embodiments 65 to 83, wherein $R^1$ is

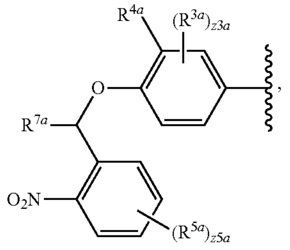

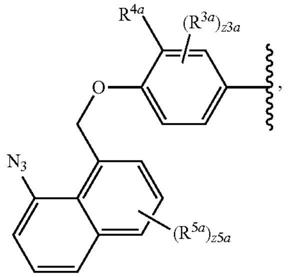

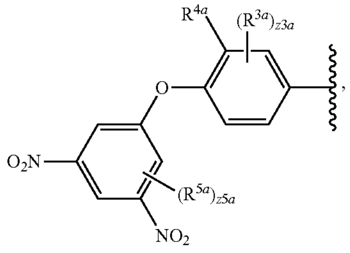

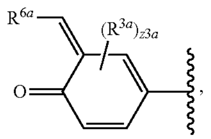

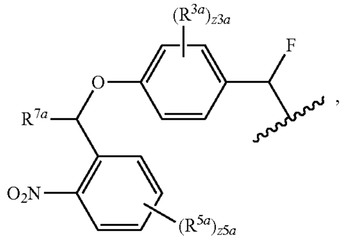

-continued
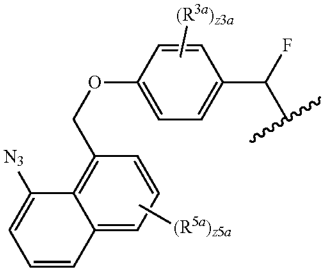
,
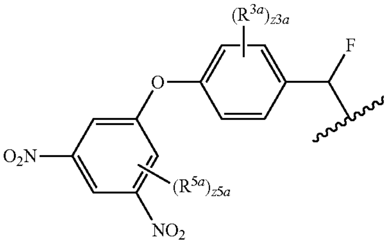
,
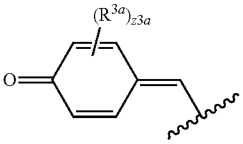
,
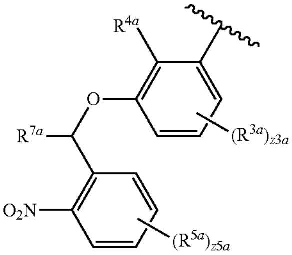
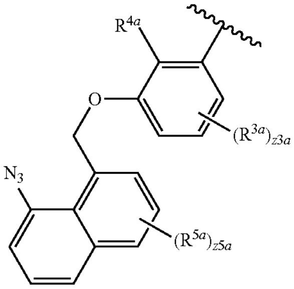
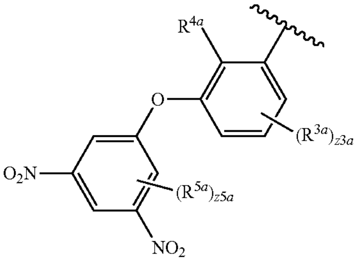
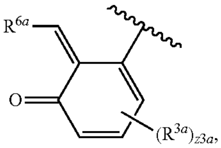
,
-continued
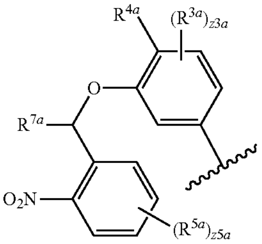
,
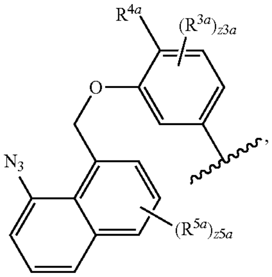
,
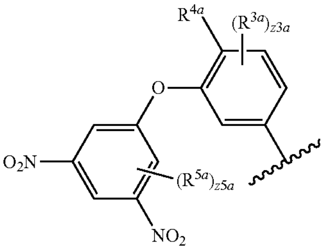
,
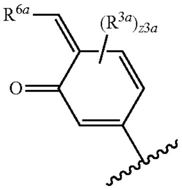
,
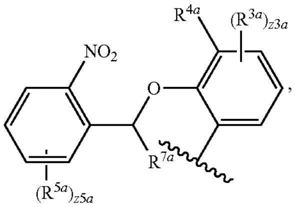
,
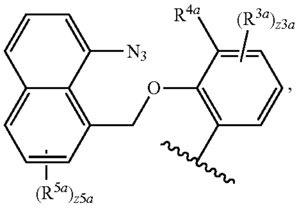
,
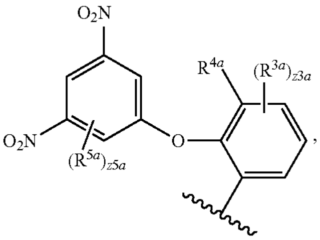
, or -continued

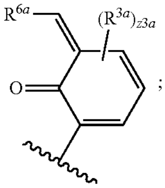

;

wherein $R^{3a}$ and $R^{5a}$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and z3a is an integer from 0 to 3.

z5a is an integer from 0 to 6;

$R^{4a}$ is independently —$CH_2F$ or —$CHF_2$;

$R^{6a}$ is independently hydrogen or —F; and $R^{7a}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$COO^-$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 85. The method of embodiment 84, wherein z3a is 0.

Embodiment 86. The method of any one of embodiments 84 to 85, wherein $R^{5a}$ is independently unsubstituted methoxy.

Embodiment 87. The method of any one of embodiments 84 to 86, wherein z5a is 0 to 2.

Embodiment 88. The method of any one of embodiments 84 to 87, wherein $R^{7a}$ is independently hydrogen, unsubstituted methyl, or —$COO^-$.

Embodiment 89. The method of any one of embodiments 65 to 88, wherein $R^2$ is

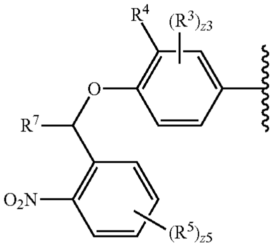

,

-continued

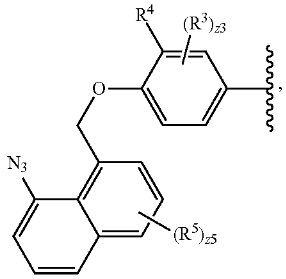

,

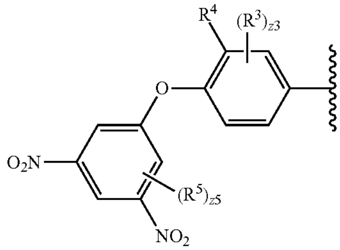

,

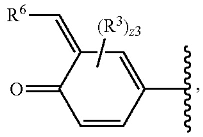

,

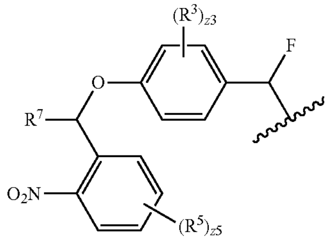

,

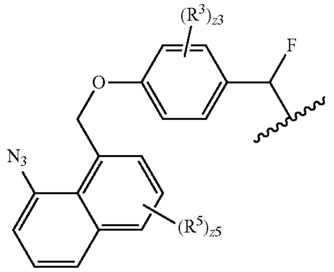

,

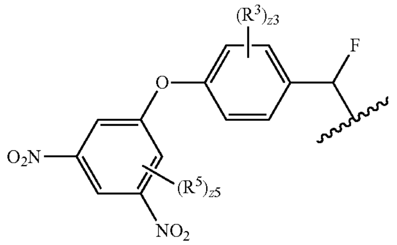

,

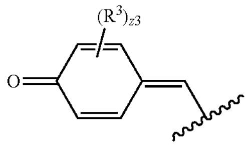

,

-continued

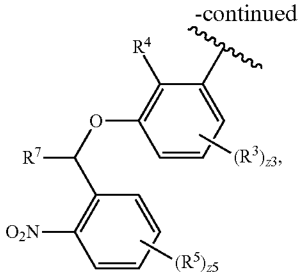

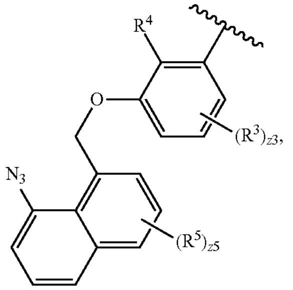

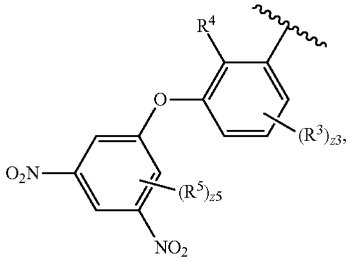

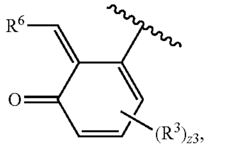

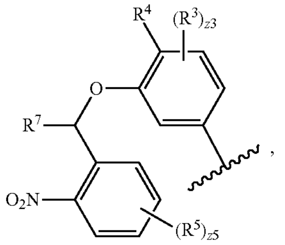

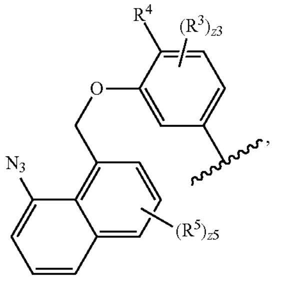

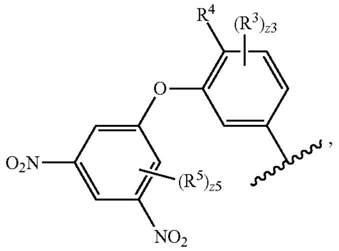

-continued

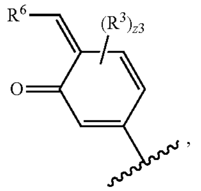

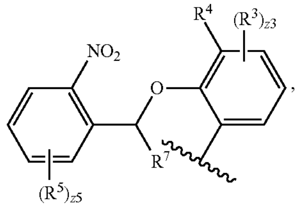

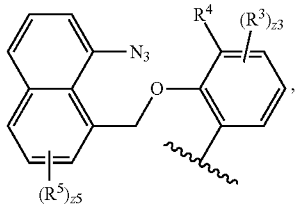

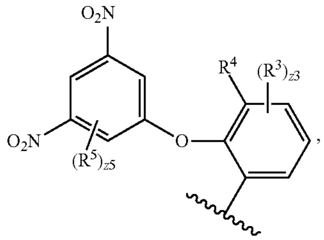

or

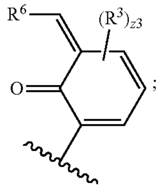

wherein $R^3$ and $R^5$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and z3 is an integer from 0 to 3.

z5 is an integer from 0 to 6;

$R^4$ is independently —$CH_2F$ or —$CHF_2$;

$R^6$ is independently hydrogen or —F; and $R^7$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)

H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$COO^-$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 90. The method of embodiment 89, wherein z3 is 0.

Embodiment 91. The method of any one of embodiments 89 to 90, wherein $R^5$ is independently unsubstituted methoxy.

Embodiment 92. The method of any one of embodiments 89 to 91, wherein z5 is 0 to 2.

Embodiment 93. The method of any one of embodiments 89 to 92, wherein $R^7$ is independently hydrogen, unsubstituted methyl, or —$COO^-$.

Embodiment 94. The method of any one of embodiments 65 to 93, wherein $L^1$ has the formula: -$L^{1A}$-$L^{1B}$-$L^{1C}$-$L^{1D}$-;

wherein $L^{1A}$ is connected directly to $R^1$;

$L^{1A}$, $L^{1B}$, $L^{1C}$, and $L^{1D}$ are each independently a bond, —N($R^{10}$)—, —C(O)—, —C(O)N($R^{10}$)—, —N($R^{10}$)C(O)—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker; and $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 95. The method of any one of embodiments 65 to 93, wherein $L^1$ is a bond, —N($R^{10}$)—, —C(O)—, —C(O)N($R^{10}$)—, —N($R^{10}$)C(O)—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

Embodiment 96. The method of any one of embodiments 65 to 93, wherein $L^1$ is cleavable by mass spectroscopy.

Embodiment 97. The method of any one of embodiments 65 to 93, wherein $L^1$ is

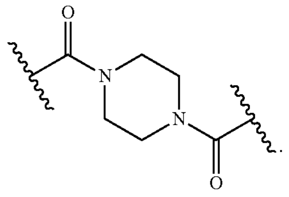 [SMILES: *C(=O)N1CCN(C(*)=O)CC1]

Embodiment 98. The method of any one of embodiments 65 to 93, wherein $L^1$ is a bond or substituted or unsubstituted $C_1$-$C_4$ alkylene.

Embodiment 99. The method of any one of embodiments 65 to 93, wherein $L^1$ is an unsubstituted $C_1$-$C_4$ alkylene.

Embodiment 100. The method of any one of embodiments 65 to 99, wherein $R^1$ and $R^2$ are the same.

Embodiment 101. The method of any one of embodiments 65 to 99, wherein $R^1$ and $R^2$ are different.

Embodiment 102. The method of any one of embodiments 65 to 95, wherein the crosslinking agent has the formula:

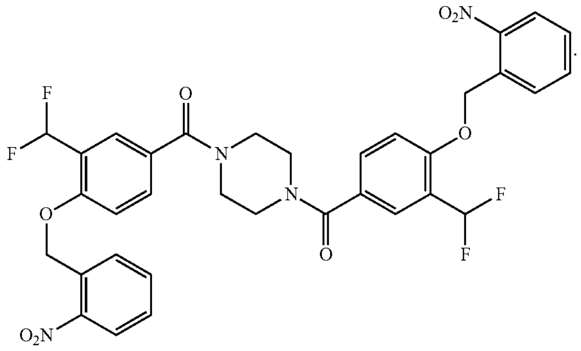 [SMILES: O=C(c1ccc(OCc2ccccc2[N+](=O)[O-])c(C(F)F)c1)N1CCN(C(=O)c2ccc(OCc3ccccc3[N+](=O)[O-])c(C(F)F)c2)CC1]

Embodiment 103. The method of any one of embodiments 1 to 102, wherein the crosslinking agent comprises a heavy isotope.

Embodiment 104. A crosslinking agent having the formula $$R^1\text{-}L^1\text{-}R^2 \quad (I);$$

wherein $R^1$ is a bioconjugate reactive moiety;

$R^2$ is a proximity enhanced bioconjugate reactive moiety;

$L^1$ is a covalent linker; and wherein the bonding reactivity of $R^1$ with a first biomolecule is greater than the bonding reactivity of $R^2$ with a second biomolecule.

Embodiment 105. The crosslinking agent of embodiment 104, wherein R is

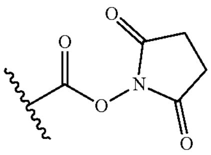
,
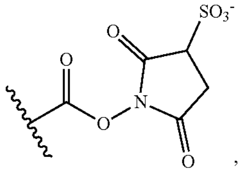
,
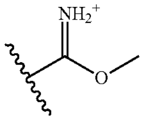
,
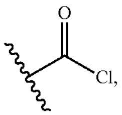
or
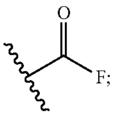

$R^2$ is

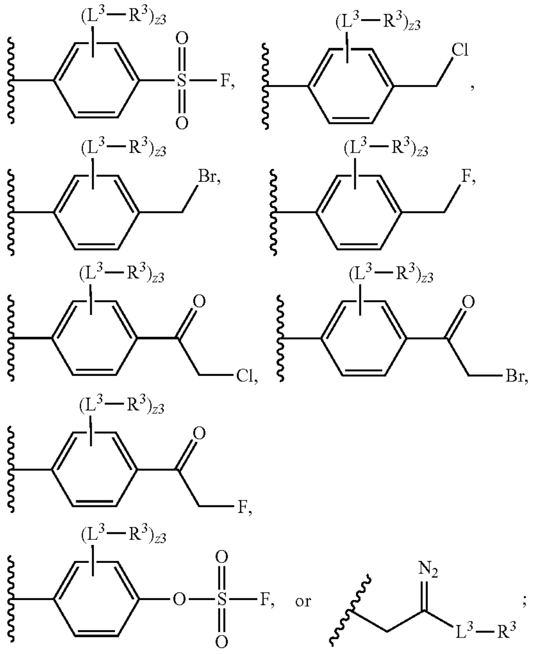

$L^3$ is a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety;

z3 is an integer from 0 to 4;

$L^1$ has the formula: -$L^{1A}$-$L^{1B}$-$L^{1C}$-$L^{1D}$-;

$L^{1A}$ is connected directly to $R^1$;

$L^{1A}$, $L^{1B}$, $L^{1C}$, and $L^{1D}$ are each independently a bond, —$N(R^{10})$—, —C(O)—, —$C(O)N(R^{10})$—, —$N(R^{10})C(O)$—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconugate linker; and $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 106. The crosslinking agent of embodiment 105, wherein $R^1$ is

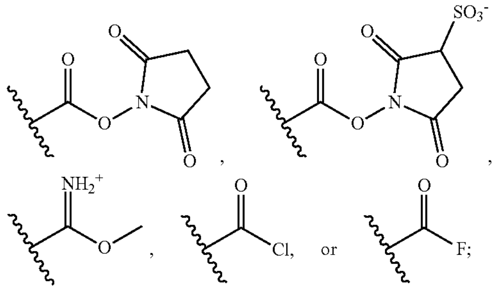

$R^2$ is

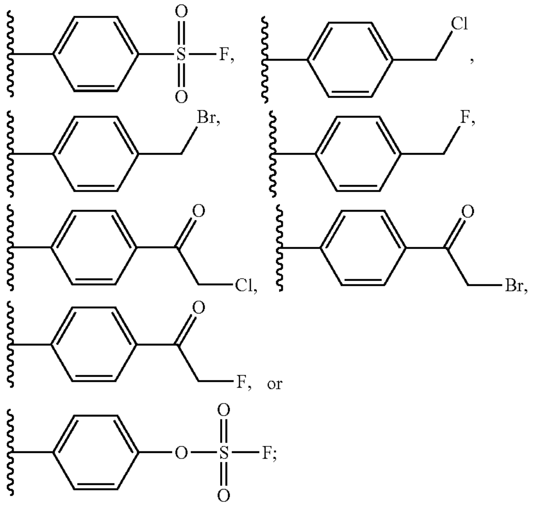

and $L^1$ is a bond or substituted or unsubstituted $C_1$-$C_4$ alkylene.

Embodiment 107. The crosslinking agent of embodiment 105, having the formula

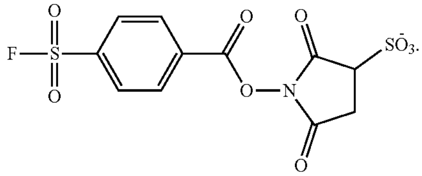

Embodiment 108. A crosslinking agent having the formula $R^1$-$L^1$-$R^2$ (I);

wherein $R^1$ is a bioconjugate reactive moiety;

$R^2$ is a photo-activated bioconjugate reactive moiety;

$L^1$ is a covalent linker; and wherein the bonding reactivity of $R^2$ with a second biomolecule after contact of $R^2$ with radiation is greater than the bonding reactivity of $R^2$ with said second biomolecule prior to contact of $R^2$ with radiation.

Embodiment 109. The crosslinking agent of embodiment 108, wherein $R^1$ is

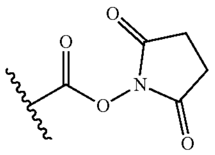
,
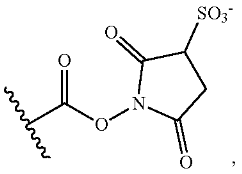
,
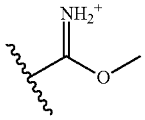
,
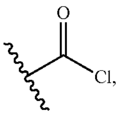
or
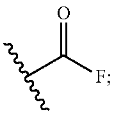

$R^2$ is

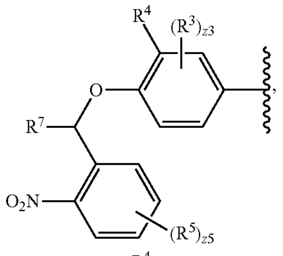

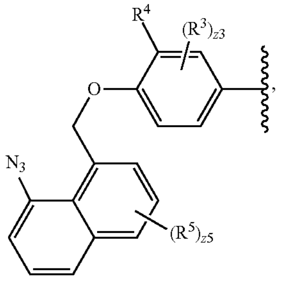

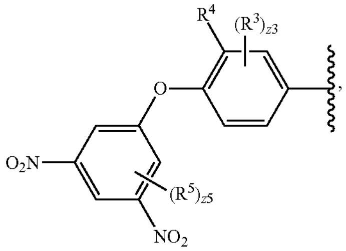

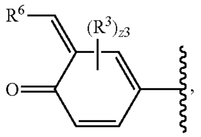

-continued

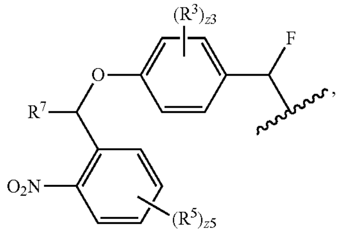

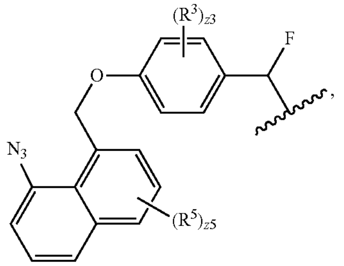

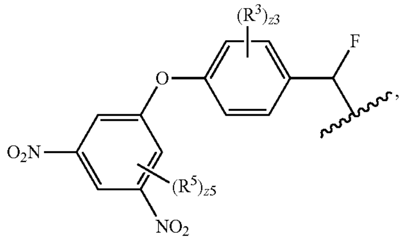

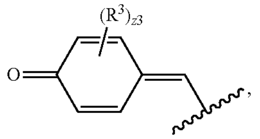

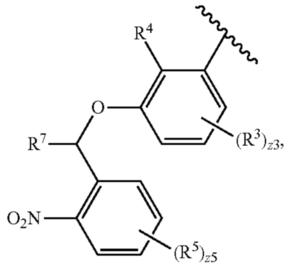

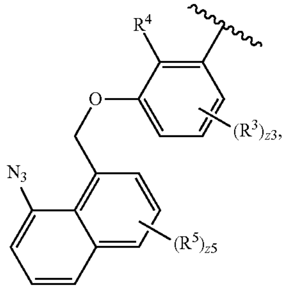

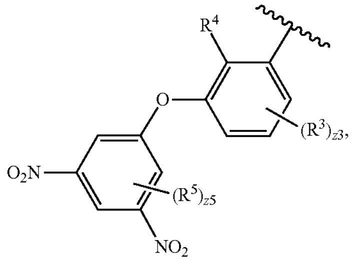

-continued

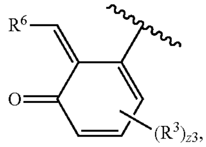,

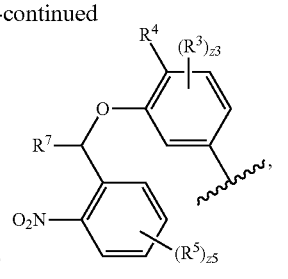,

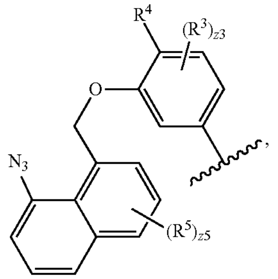,

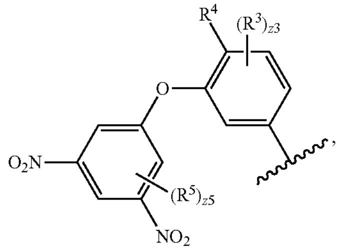,

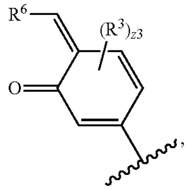,

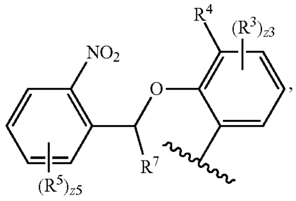,

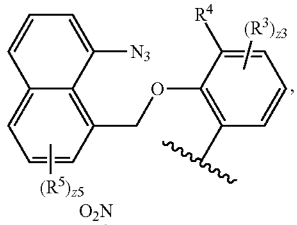,

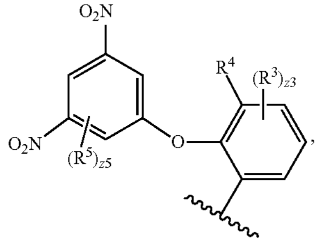, or

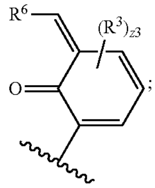;

$R^3$ and $R^5$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and z3 is an integer from 0 to 3.

z5 is an integer from 0 to 6;

$R^4$ is independently —$CH_2F$ or —$CHF_2$;

$R^6$ is independently hydrogen or —F; and $R^7$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$COO^-$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ has the formula: -$L^{1A}$-$L^{1B}$-$L^{1C}$-$L^{1D}$-;

$L^{1A}$ is connected directly to $R^1$;

$L^{1A}$, $L^{1B}$, $L^{1C}$, and $L^{1D}$ are each independently a bond, —N($R^{10}$)—, —C(O)—, —C(O)N($R^{10}$)—, —N($R^{10}$)C(O)—, —N(H)—, —C(O)N(H)—, —N(H)C(O)—, —C(O)O—, —OC(O)—, —S(O)$_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker; and $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 110. The crosslinking agent of embodiment 109, wherein $R^1$ is

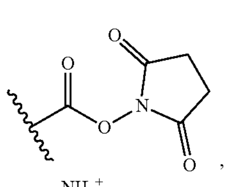,

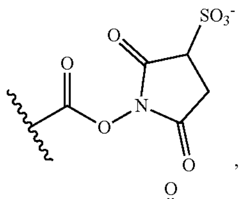,

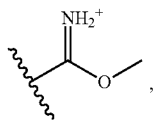,

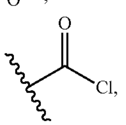, or

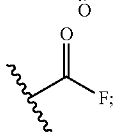;

$R^2$ is
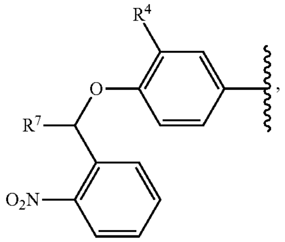
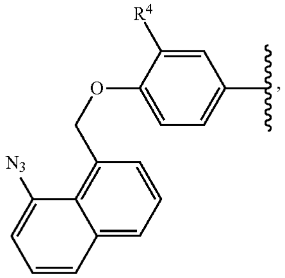
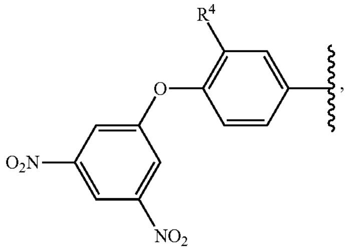
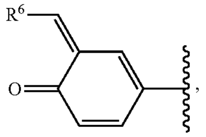
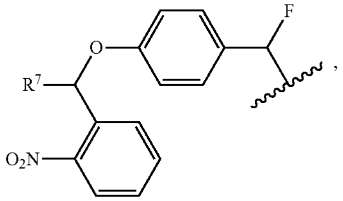
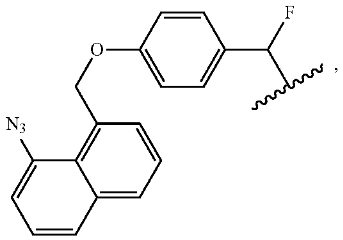
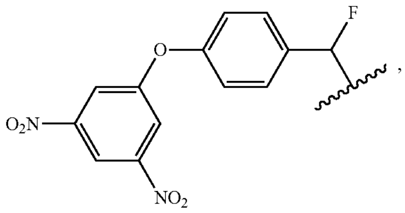
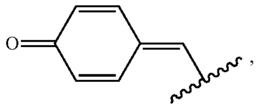
-continued
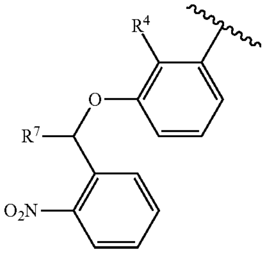
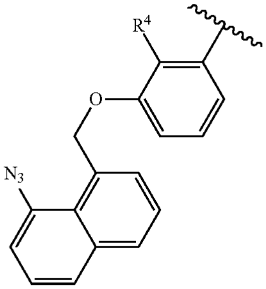
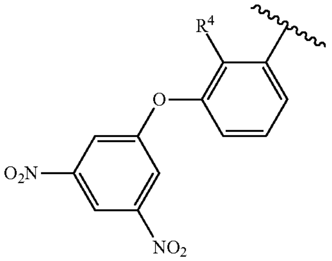
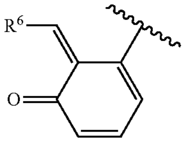
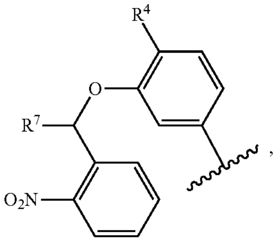
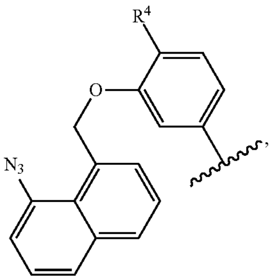
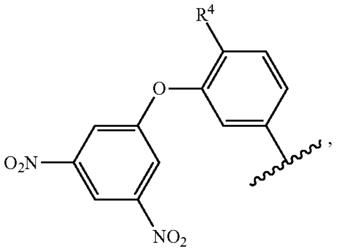

-continued

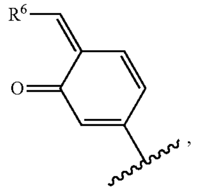

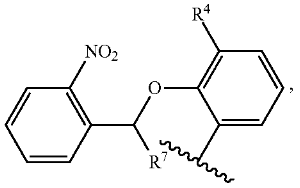

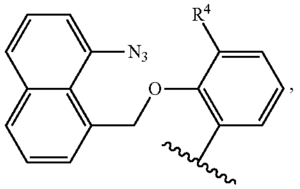

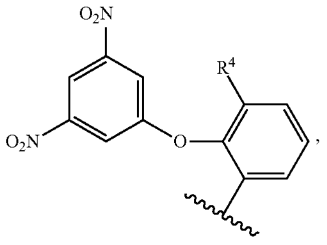

or

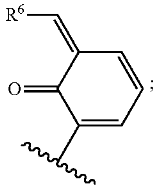

and $L^1$ is a bond or substituted or unsubstituted $C_1$-$C_4$ alkylene.

Embodiment 111. The crosslinking agent of embodiment 109, having the formula

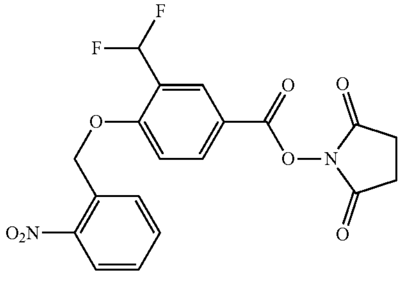

or

-continued

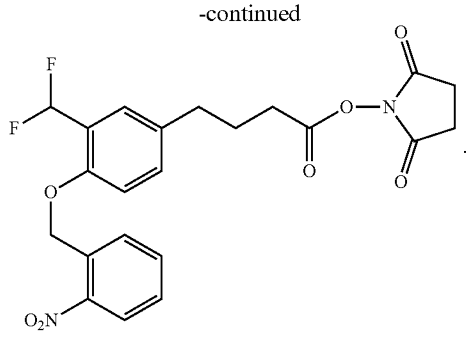

Embodiment 112. A crosslinking agent having the formula $$R^1\text{-}L^1\text{-}R^2 \qquad (I);$$

wherein $R^1$ is a first photo-activated bioconjugate reactive moiety;

$R^2$ is an optionally different second photo-activated bioconjugate reactive moiety;

$L^1$ is a covalent linker;

wherein the bonding reactivity of $R^1$ with a first biomolecule after contact of $R^1$ with radiation is greater than the bonding reactivity of $R^1$ with said first biomolecule prior to contact of $R^1$ with radiation; and wherein the bonding reactivity of $R^2$ with a second biomolecule after contact of $R^2$ with radiation is greater than the bonding reactivity of $R^2$ with said second biomolecule prior to contact of $R^2$ with radiation.

Embodiment 113. The crosslinking agent of embodiment 112, wherein $R^1$ is

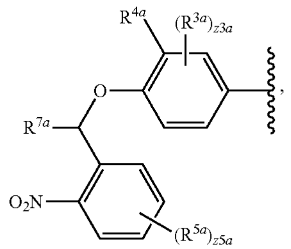

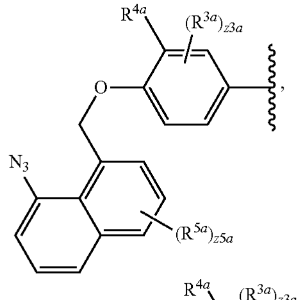

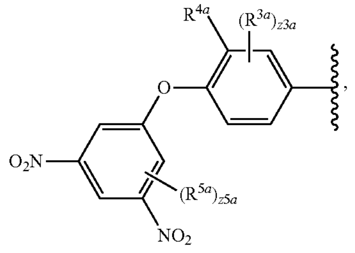

-continued
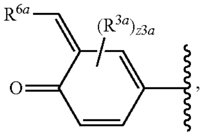
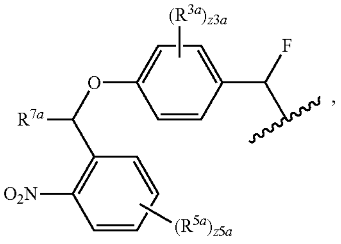
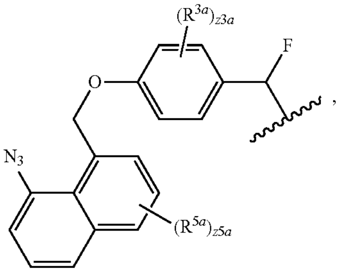
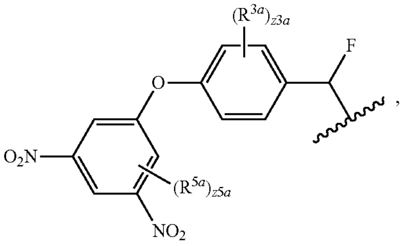
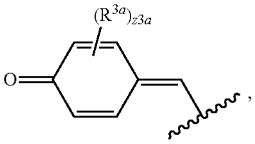
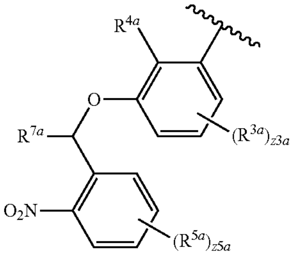
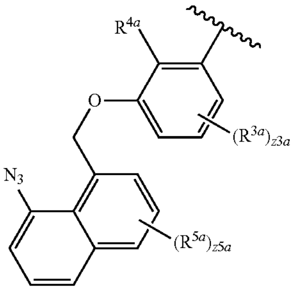
-continued
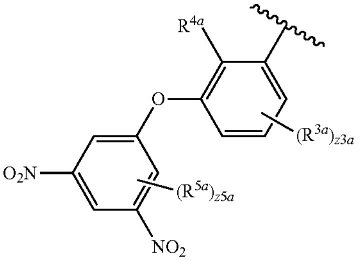
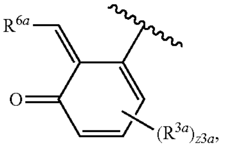
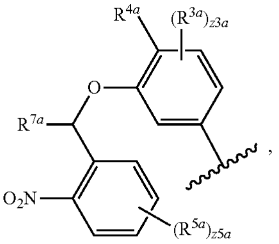
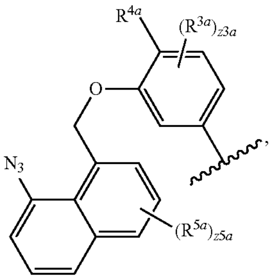
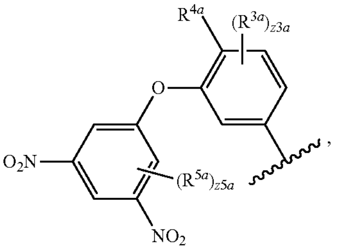
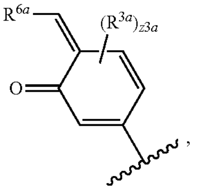
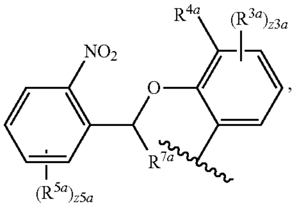

-continued

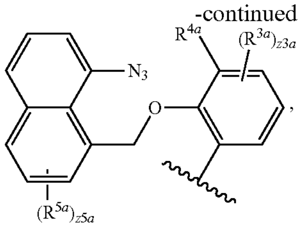

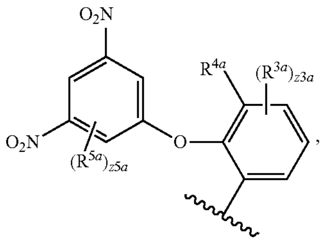

or

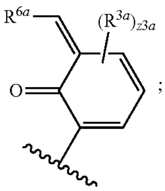

;

$R^{3a}$ and $R^{5a}$ are independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{4a}$ is independently $—CH_2F$ or $—CHF_2$;

$R^{6a}$ is independently hydrogen or —F; and $R^{7a}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, $—COO^-$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is

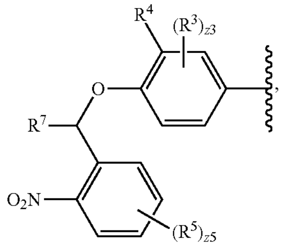

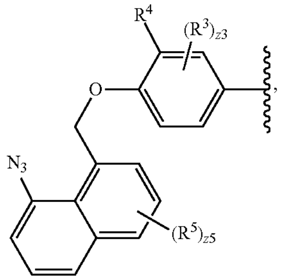

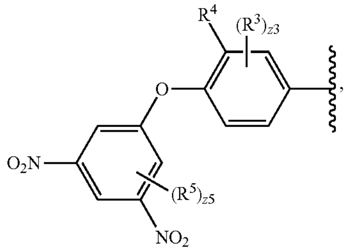

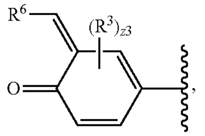

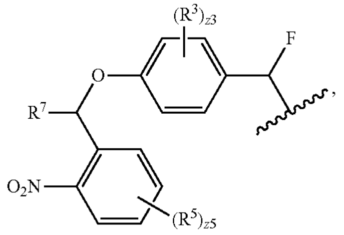

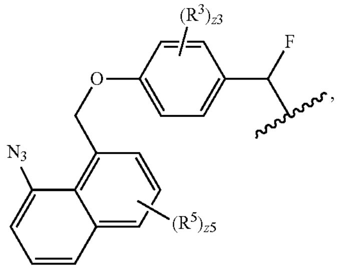

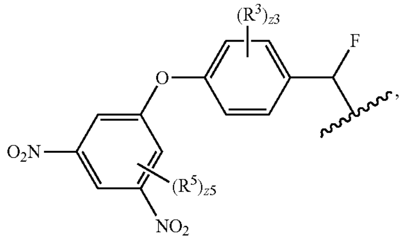

-continued

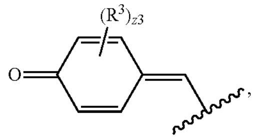

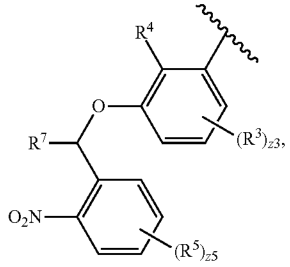

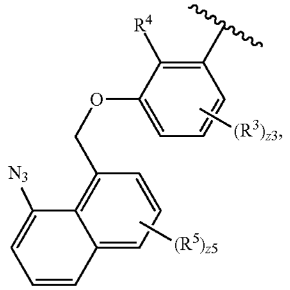

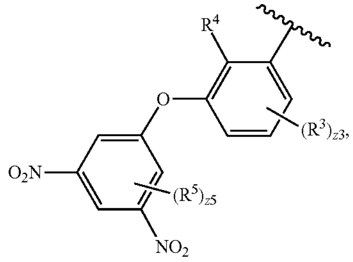

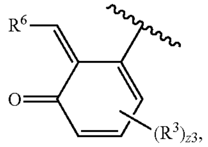

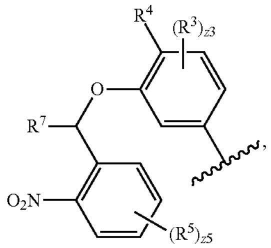

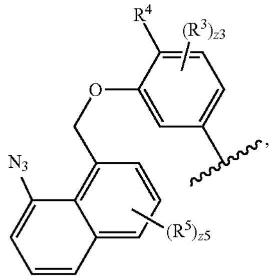

-continued

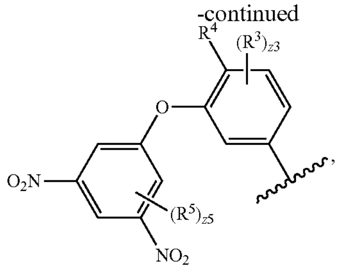

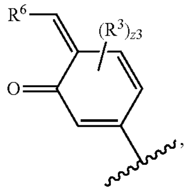

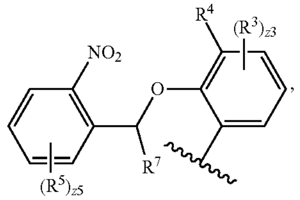

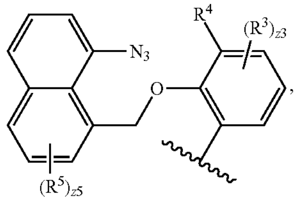

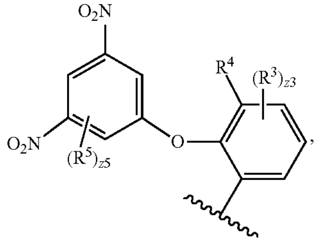

or

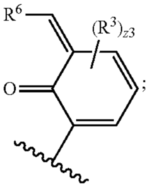

$R^3$ and $R^5$ are independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is independently $—CH_2F$ or $—CHF_2$;

$R^6$ is independently hydrogen or —F; and $R^7$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, $—COO^-$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z3 and z3a are each independently an integer from 0 to 3.

z5 and z5a are each independently an integer from 0 to 6;

$L^1$ has the formula: $-L^{1A}-L^{1B}-L^{1C}-L^{1D}-$;

$L^{1A}$ is connected directly to $R^1$;

$L^{1A}$, $L^{1B}$, $L^{1C}$, and $L^{1D}$ are each independently a bond, $—N(R^{10})—$, —C(O)—, $—C(O)N(R^{10})—$, $—N(R^{10})C(O)—$, —N(H)—, —C(O)N(H)—, —N(H)C(O)—, —C(O)O—, —OC(O)—, $—S(O)_2—$, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker; and $R^{10}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 114. The crosslinking agent of embodiment 113, wherein $R^1$ is

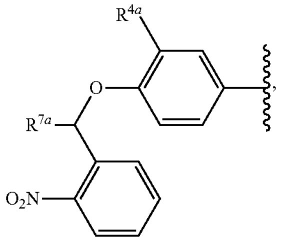

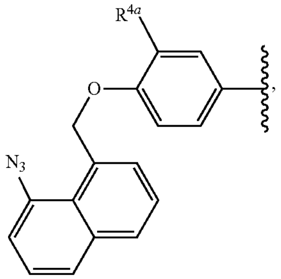

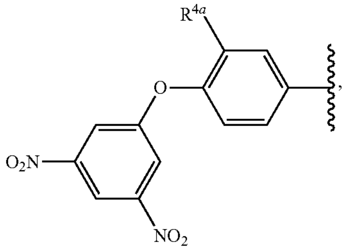

-continued

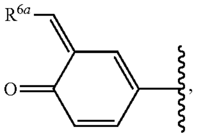

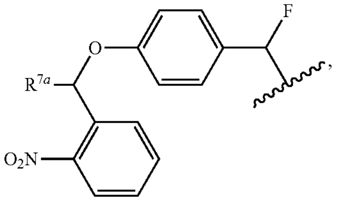

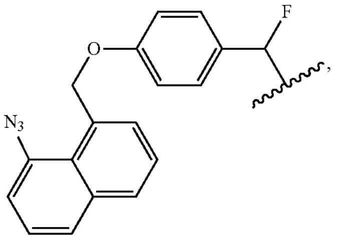

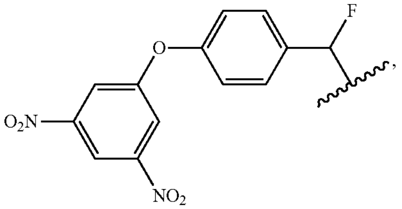

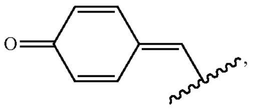

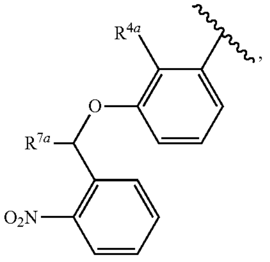

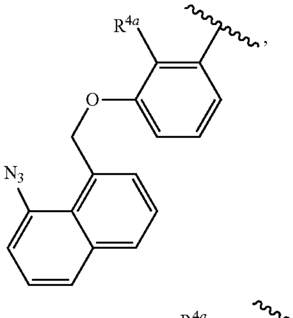

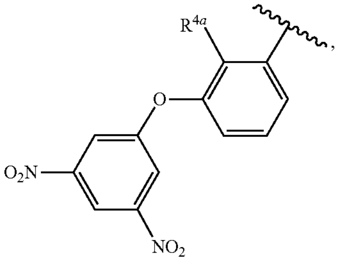

-continued
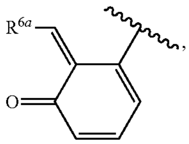
,
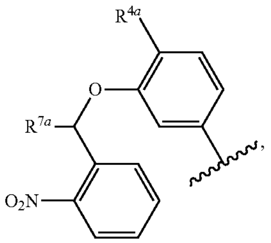
,
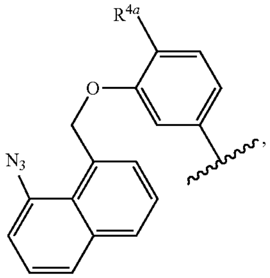
,
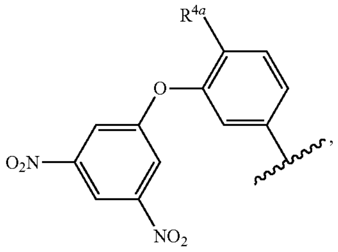
,
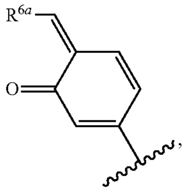
,
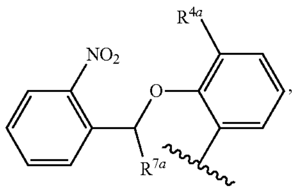
,
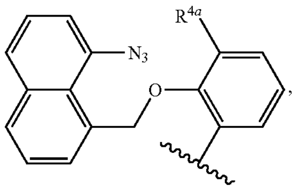
,
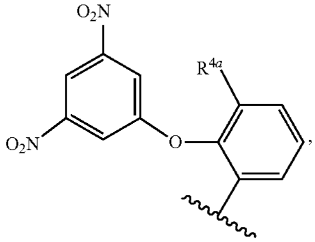
, or
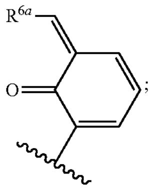
;
$R^2$ is
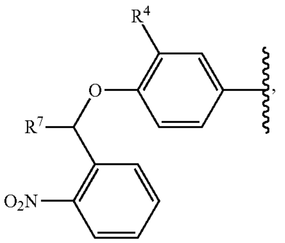
,
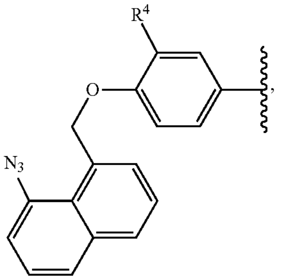
,
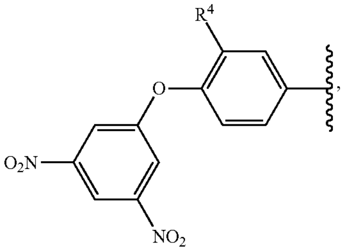
,
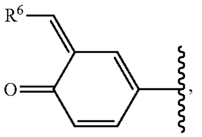
,
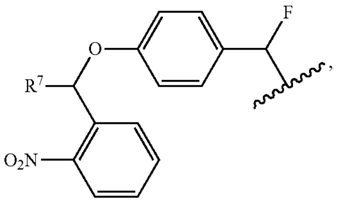
,
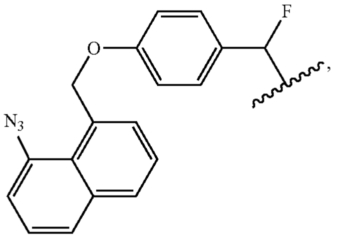
,
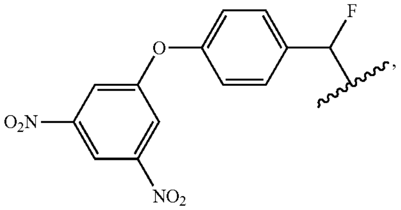
,
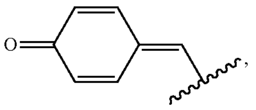
, -continued

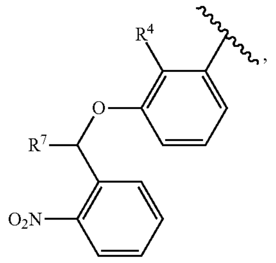

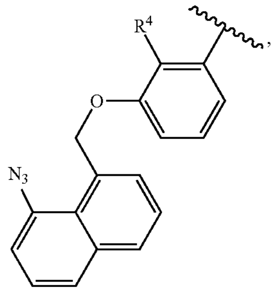

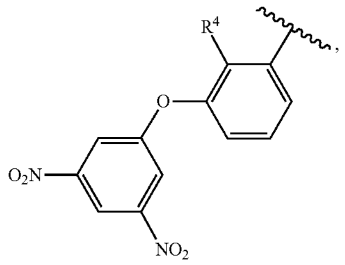

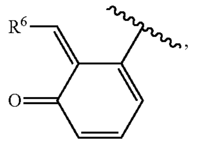

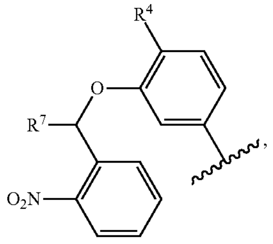

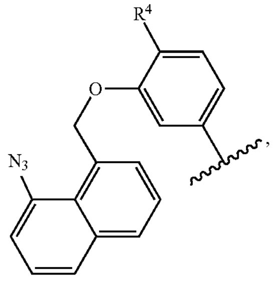

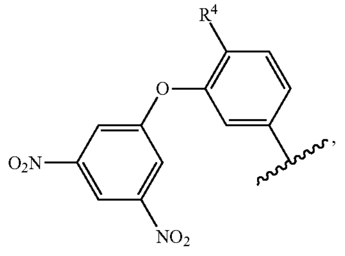

-continued

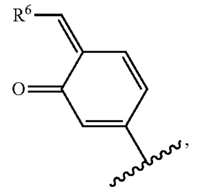

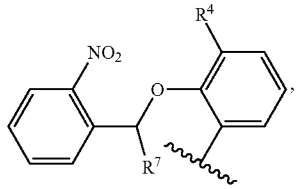

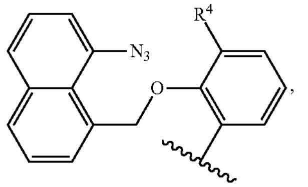

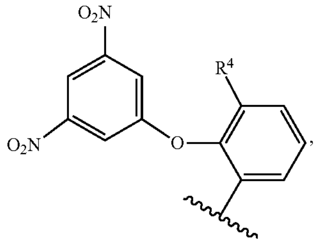

or

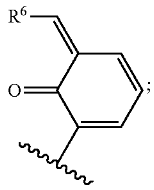

and $L^1$ is

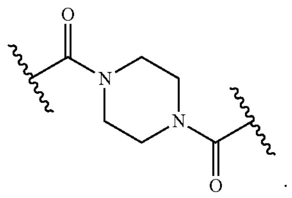 [SMILES: *C(=O)N1CCN(C(*)=O)CC1]

Embodiment 115. The crosslinking agent of embodiment 113, having the formula

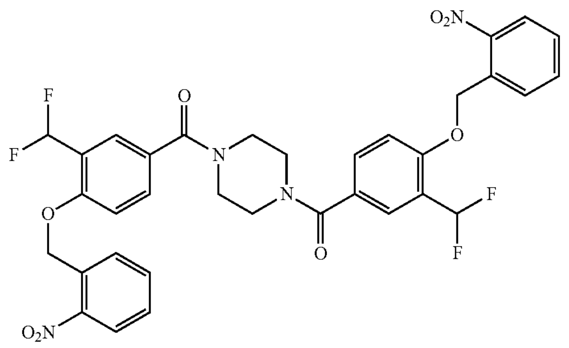 [SMILES: O=C(c1ccc(OCc2ccccc2[N+](=O)[O-])c(C(F)F)c1)N1CCN(C(=O)c2ccc(OCc3ccccc3[N+](=O)[O-])c(C(F)F)c2)CC1]

EXAMPLES

Here we report a new "plant-and-cast" cross-linking strategy that employs a hetero-bifunctional crosslinker that contains a highly reactive succinimide ester as well as a less reactive sulfonyl-fluoride. The succinimide ester reacts rapidly with surface Lys residues "planting" the reagent at fixed locations on protein. The pendant aryl sulfonyl fluoride is then "cast" across a limited range of the protein surface, where it can react with multiple amino acids weakly nucleophilic sidechains in a proximity-enhanced reaction. Using proteins of known structures, we demonstrated that the hetero-bifunctional agent formed cross-links between Lys residues and His, Ser, Thr, Tyr and Lys sidechains. This geometric specificity contrasts with current bis-succinimide esters, which often generates non-specific cross-links between lysines brought into proximity by rare thermal fluctuations. Thus, the current method can provide diverse and robust distance restraints to guide integrative modeling. This work also provides the first example of targeting unactivated Ser and Thr residues using sulfonyl-fluorides. In addition, this methodology yielded a variety of novel cross-links when applied to the complex *E. coli* cell lysate. Finally, in combination with genetically encoded chemical cross-linking, cross-linking using this reagent markedly increased the identification of weak and transient enzyme-substrate interactions in live cells. Proximity-dependent crosslinking will dramatically expand the scope and power of CXMS for defining the identities and structures of protein complexes. We developed a "Plant-and-Cast" strategy, in which a hetero-bifunctional crosslinker is "planted" onto surface Lys residues using a highly reactive succinimide ester. The half-reacted cross-linker then "casts" a much less reactive sulfonyl-fluoride across the proximal surface resulting in cross-links to neighboring Ser, Thr, Tyr, His, or Lys sidechains in a proximity-enhanced reaction.

Chemical cross-linking mass spectrometry (CXMS) offers the unique ability to decipher protein interaction networks and to derive tertiary structural information of proteins, and thus is increasingly used to study large and transient protein assemblies and intrinsically disordered proteins that are challenging for classic protein structural analysis techniques (1-5). In CXMS, a bifunctional chemical reagent is applied to proteins to cross-link pairs of amino acid residues, which are identified by tandem MS. The identity and distance constraints obtained for amino acids then afford information of protein interactions and tertiary structures. The versatility and throughput of CXMS in combination with X-ray crystallography, NMR, or cryo-electron microscopy are advancing structural biology and interactomics in great strides.

The chemistry of the crosslinker is critical for acquiring abundant and accurate information in CXMS. Currently the most widely used crosslinkers consist of homobifunctional N-hydroxysuccinimidyl (NHS) esters to react with Lys (4, 5). Crosslinkers targeting Glu and Asp have also been developed (6-8), yet they require the carboxylic acid residue to be activated prior to cross-linking under reaction conditions that can distort protein structure (5). Alternatively, disulfides can be formed between Cys residues after treatment with reagents such as $I_2$, which create highly reactive intermediates (9). However, these methods have limitations that have kept CXMS from reaching its full potential. The restricted repertoire of residues, Lys, Glu, Asp, Cys, limits the number and types of restraints that can be obtained. Moreover, the high reactivity of the intermediates often leads to spurious cross-links between residues that are far apart in the native structures of proteins, but brought into proximity by rare thermal fluctuations that are then trapped due to the high reactivity of the cross-linking chemistry. Thus, the $C\alpha$-$C\alpha$ distances between cross-linked residues are often far greater than the combined distance of the sidechains plus the cross-linking moiety (10). This ambiguity decreases the precision with which inter-residue distances can be specified, complicating their use as structural restraints for molecular modeling of complexes.

Besides these residue-specific chemistries, photoactivated crosslinkers such as diazirines target virtually all amino acids non-selectively (11). However, the possibility of excessive cross-linking dramatically complicates the data analysis, which remains a daunting challenge for CXMS, and high-density cross-linking may artificially distort protein tertiary structure as well (4, 5). In addition, photo-crosslinkers generally have short half-lives and thus limited use in studying weak and transient protein-protein interactions (PPIs) (12). Clearly, new chemical cross-linking strategies that are able to target a wide range of amino acid residues specifically with defined cross-linking sites could have a large impact on CXMS.

To address this need, we introduce here a new "plant-and-cast" strategy in which highly reactive and weakly reactive electrophiles are combined into a single crosslinker (FIG. 1A). The stronger electrophile, in this case a succinimide ester, reacts rapidly with Lys sidechains, placing the weakly reactive electrophile on the surface of the protein. The flexibility of the Lys sidechain allows the half-reacted crosslinker to cast about along the protein surface, where its proximity and very high local concentration will facilitate reaction with a variety of sidechains that are generally not accessed by traditional cross-linking agents.

We report a proximity-enhanced chemical crosslinker that is able to target multiple amino acid residues with high specificity and efficiency for CXMS. A heterobifunctional crosslinker containing N-hydroxysulfosuccinimide and aryl sulfonyl fluoride moieties (NHSF, FIG. 1B) was designed and shown to form cross-links between Lys and neighboring nucleophilic residues including His, Lys, Ser, Thr, and Tyr on proteins. Importantly, we found high structural compatibility of the identified cross-linking sites by NHSF, highlighting the potential of NHSF for accurate structural studies of proteins. We further showed that NHSF could cross-link complex *E. coli* whole cell lysate revealing new cross-linked peptides undetectable with existing reagents. Finally, we showed that this approach can enhance the identification of weak and transient protein interactions when combined with genetically encoded chemical cross-linking (GECX) (12).

In summary, we develop a new "plant-and-cast" approach to chemical cross-linking that relies the use of a crosslinker with two groups of graded reactivity towards nucleophilic sidechains. In this approach, the more reactive residue plants the reagent in place, leaving the less reactive group free to cast over the protein surface, ultimately forming cross-links via proximity-enhanced reactivity. This work represents our first attempt to reduce this concept to practice; given the success described herein, we expect that it should be broadly applicable. We report a heterobifunctional chemical cross-linker NHSF capable of targeting multiple amino acid residues including Lys, His, Ser, Thr, and Tyr for CXMS via proximity-enhanced SuFEx reactivity. Existing CXMS chemical crosslinkers target Lys, Cys, Asp, and Glu only; the ability to cross-link His, Ser, Thr, and Tyr has not been feasible before and thus will dramatically expand the diversity of proteins amenable to CXMS with increasing multiplicity of cross-links. In particular, Tyr residues are often enriched at protein-protein interfaces (24). In addition, we demonstrated that NHSF shows no nonspecific cross-linking and provides distance constraints highly compatible with crystal structures, which will afford more accurate structural information to simplify the complexity and to improve the accuracy of structural modeling of large protein assemblies. This feature of NHSF should also be invaluable for the validation of structures obtained with cryo-electron microscopy. Moreover, CXMS is unable to address weak and transient protein interactions. Here we further demonstrated that GECX in combination with NHSF cross-linking markedly increased the identification of weak and transient enzyme-substrate interactions in live cells, which will find broad applications in the identification of unknown protein interactions. Future developments of NHSF will include MS-cleavable modification to advance simplified MS workflows and isotopic labeling to enable quantitative cross-linking MS. Lastly, aryl sulfonyl fluoride has been reported to react with catalytic Ser residues but is inactive toward unactivated Ser residues under physiological conditions (21, 25). Results described herein of NHSF cross-linking firstly show that aryl sulfonyl fluoride is able to react with non-catalytic Ser and Thr via proximity-enhanced reactivity, which will be valuable for designing reactive probes and covalent inhibitors in chemical biology and molecular pharmacology.

In addition to NHSF's application in structural biology and in identification of individual protein-protein interactions, this method may further be developed into a drug target discovery engine which works on the protein level. Current methods for drug target discovery include deep sequencing and CRISPR-based gene editing technologies, which all work on the gene expression or transcription level (i.e., on the nucleic acid level). We can apply NHSF to crosslink cell lysate samples, for example, one sample of healthy cells and the other cancer cells, to compare differences in protein-protein interactions on the global proteomic scale. Using this method we can identify novel protein-protein interactions that occur specifically in cancer cells when compared to normal samples or are increased in cancer cells when compared to normal cells. This same technique can be applied to compare protein-protein interaction states in other disease cells compared to normal. Alternatively, specific protein-protein interactions in healthy cells can be reduced or lost when compared to cancer or disease cells. The changes in protein-protein interactions identify novel drug targets which can be used in drug discovery.

Further optimization of the NHSF-based crosslinker will be carried out to achieve the above goals. To increase the signal over noise of identification of crosslinked peptides, an bioorthogonal functional group (e.g., a bioconjugate reactive moiety) will be introduced into the crosslinker to enable enrichment of the crosslinked peptides during sample preparation, so that more crosslinked peptides can be identified by tandem MS from the overwhelming amount of peptides generated from complex cell lysates. To quantitatively compare two samples in parallel, the crosslinker will be isotopically labeled for quantitative MS analysis.

Example 1: A "Plant-and-Cast" Strategy for Developing Specific, Multi-Targeting Crosslinker Reactivity and selectivity are two opposing demands, which are difficult to achieve simultaneously when designing chemical crosslinkers—especially when the reaction needs to be compatible with proteins and their milieu. Recently, we developed proximity-enabled bioreactivity (13-16), which allows unnatural amino acids (Uaas) bearing biocompatible functional groups to react with specific natural residues of proteins selectively by bringing the two residues into proximity (17). The terms "non-naturally occurring amino acid" and "unnatural amino acid" refer to amino acid analogs, synthetic amino acids, and amino acid mimetics, which are not found in nature. This methodology has enabled us to capture weak PPIs and transient enzyme-substrate interactions (12). In particular, a sulfonyl fluoride-containing Uaa is able to react with Lys and His (18), and a fluorosulfate-containing Uaa FSY reacts with Lys, His, and Tyr, both via sulfur-fluoride exchange (SuFEx) reactions (19). Proximity enhanced reactivity is a recently appreciated approach to direct and control reactivity, with wide-ranging applications in chemical biology (20). Also, sulfonyl fluorides have gained much attention recently in chemical proteomics and covalent drug discovery (21, 22), in which sulfonyl fluorides form non-covalent complex with target proteins and subsequently modify the protein covalently with high specificity toward multiple nucleophilic residues.

Since aryl sulfonyl fluorides have low intrinsic reactivity with nucleophilic residues at physiological conditions (21), we reasoned that a heterobifunctional crosslinker containing NHS and aryl sulfonyl fluoride groups (NHSF, FIG. 1B) would enhance the cross-linking efficiency over a homobifunctional crosslinker containing aryl sulfonyl fluoride group only. An initial rapid second order reaction of the highly reactive NHS moiety with exposed Lys residues will plant the aryl sulfonyl fluoride in close proximity to nucleophilic residues, and the resultant proximity would enhance a subsequent first-order SuFEx reaction between aryl sulfonyl fluoride and a range of nucleophilic residues to achieve efficient cross-linking (FIG. 1C). The high effective concentration of the sulfonyl-fluoride would assure reaction with weakly nucleophilic sidechains (e.g., Ser, Thr) that ordinarily would be un-reactive. Although this type of heterobifunctional crosslinker has been previously attempted for step-wise cross-linking of two proteins with known interactions (23), no single cross-linked residue was identified and its application for the powerful CXMS had not yet been explored to our knowledge.

Figure 2A:
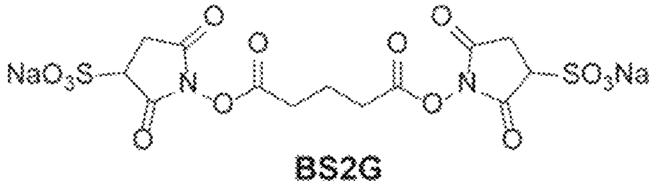
FIGS. 2A-2D. Reaction of NHSF with peptide 7KR.
Figure 2A:
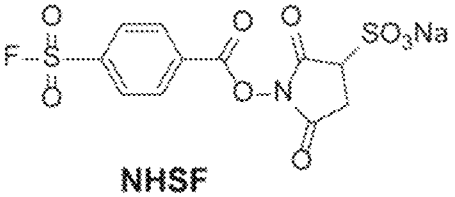
Figure 2B:
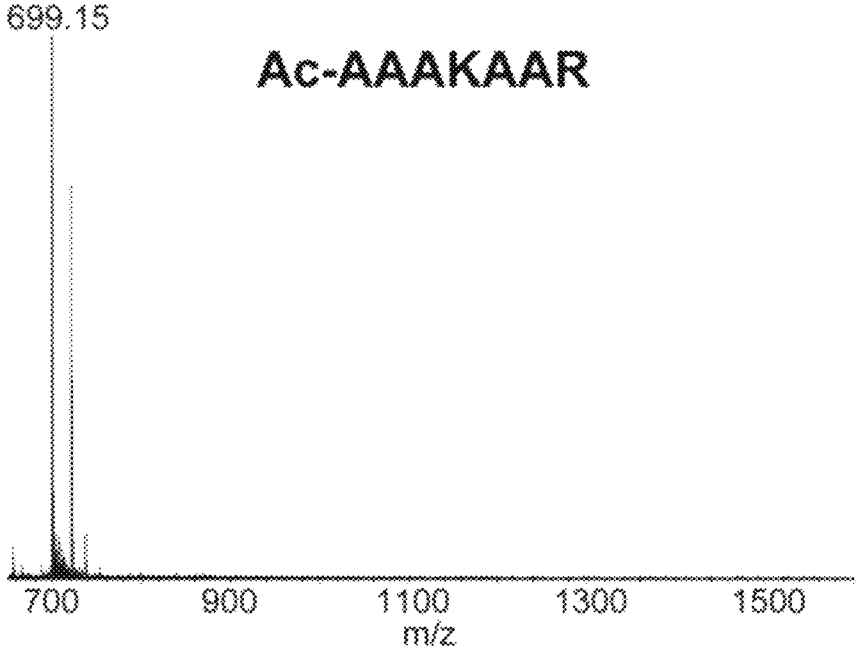
Figure 2C:
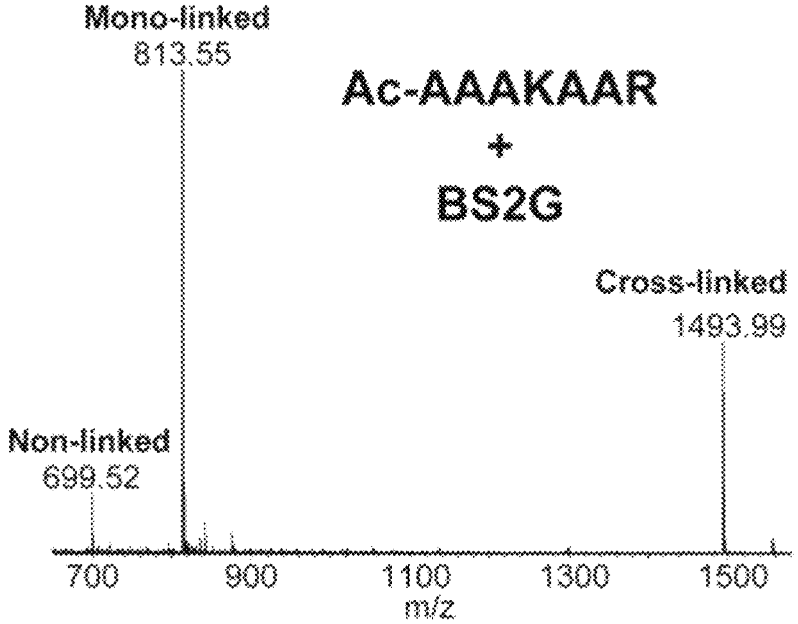
Figure 2D:
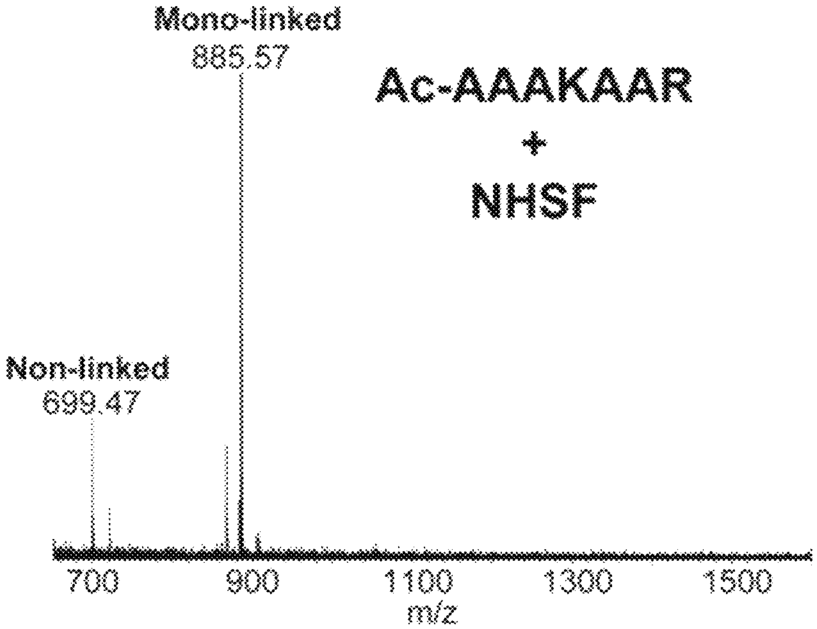

Reaction of NHSF with Model Peptide. We first tested the reactivity of NHSF with a model peptide (Ac-AAAKAAR (SEQ ID NO:1), 7KR) with a single Lys as a reactive group, and compared its reactivity towards BS2G (bis(sulfosuccinimidyl) 2,2,4,4-glutarate-d4, FIG. 2A), a commercial NHS-based homo-bifunctional crosslinker of similar length. With the peptide in the same molar ratio of BS2G, we detected both a mono-linked peptide as well as the cross-linked dimer (FIG. 2C). In contrast, when NHSF was used, the reaction stops at the mono-adduct created by reaction of the succinimide ester group with the Lys sidechain. Only trace amounts of the corresponding sulfonamide was formed (FIG. 2D), consistent with the much lower reactivity of SF compared with the succinimide ester. Owing to the low reactivity of sulfonyl-fluorides and the lack of reactive groups in 7KR, additional reaction was not observed with the Arg sidechain. Also the tethered sulfonyl-fluoride in the mono-adduct was resistant to spontaneous hydrolysis. This experiment suggests the ability to plant and stably cast the sulfonyl-fluoride group across a protein surface.

Figure 3A:
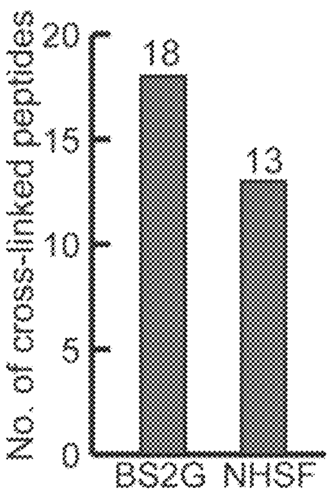
FIGS. 3A-3D. CXMS analyses of BSA protein cross-linked with NHSF or BS2G.
Figure 3B:
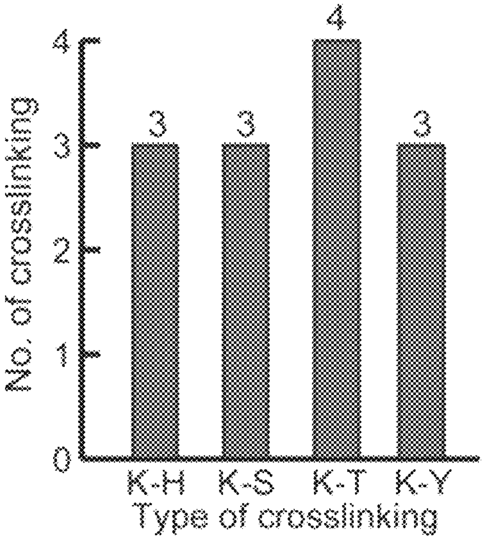
Figure 3C:
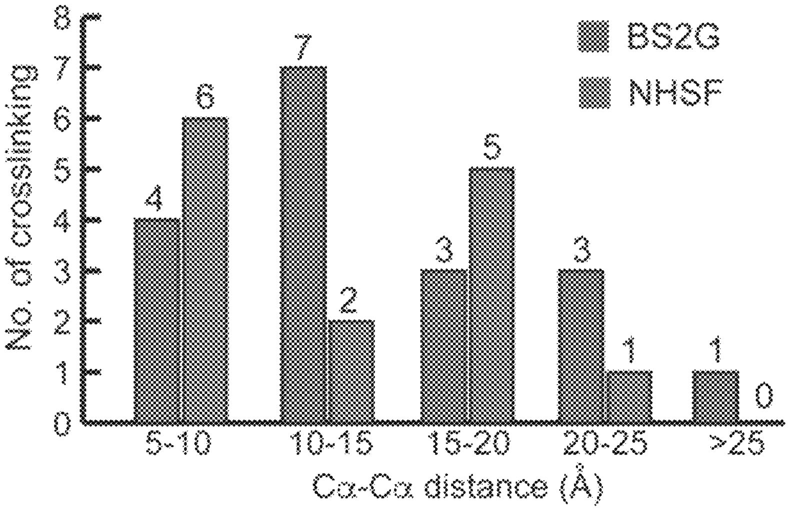
Figure 3D:
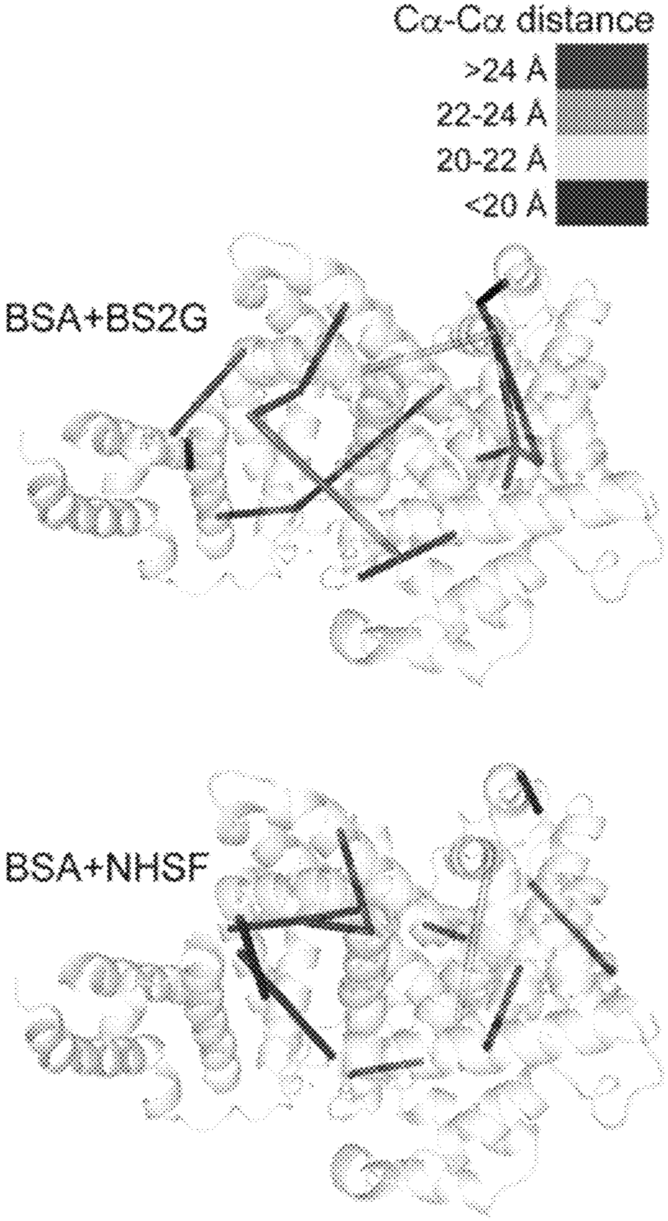

NHSF Cross-links Bovine Serum Albumin. To determine the ability of NHSF to cross-link proteins, Bovine Serum Albumin (BSA) was cross-linked by BS2G and NHSF, separately. A total of 18 inter-peptide cross-links of BS2G sample and 13 inter-peptide cross-links of NHSF sample were identified by MS (FIG. 3A, Tables 1, 2). While only Lys-Lys or N-terminal $NH_2$-Lys cross-linking sites were identified in the BS2G sample, multiple new cross-linking sites of Lys-His, Lys-Ser, Lys-Thr and Lys-Tyr were detected in the NHSF sample (FIG. 3B), confirming the ability of NHSF to cross-link Lys with multiple weakly nucleophilic residues via proximity-enhanced SuFEx reaction as designed. Interestingly, no Lys-Lys cross-links were observed when NHSF was used. Thus, the information obtained from NHSF cross-linking was complementary to that of BS2G. The maximum Cα-Cα distance of Lys-Lys cross-linking site is ~20 Å for BS2G, and 17-22 Å for NHSF cross-linking based on the combined structures of the amino acid sidechains plus the covalently connected cross-linking agent. We therefore use a limit of 20 Å for reasonable cross-linking distances, and evaluated the Cα-Cα distances for all cross-linked residues in the BSA structure (FIG. 3C and FIG. 3D): There was only one cross-linked peptide slightly exceeding this limit for the NHSF sample, which measured a distance of 21.2 Å. In contrast, there were four cross-linked peptides exceeding the distance limit for the BS2G sample.

Figure 4A:
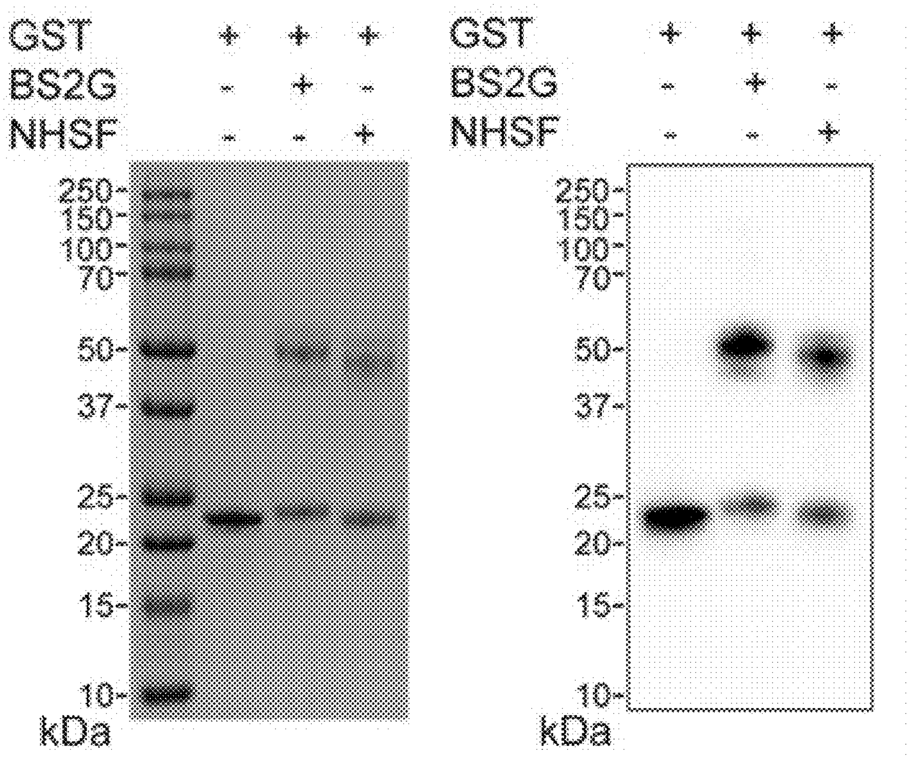
FIGS. 4A-4E. CXMS analyses of GST protein cross-linked with NHSF or BS2G.
Figure 4B:
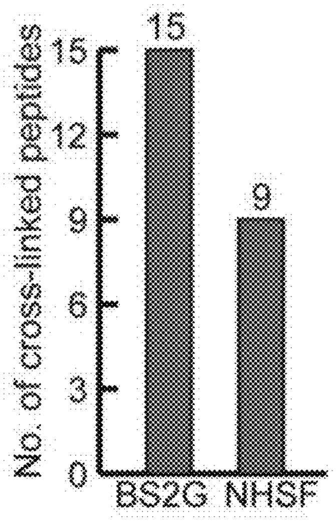
Figure 4C:
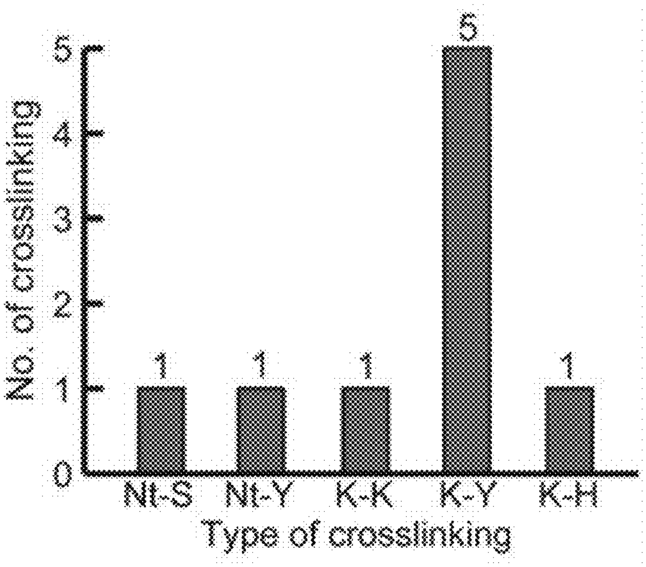
Figure 4D:
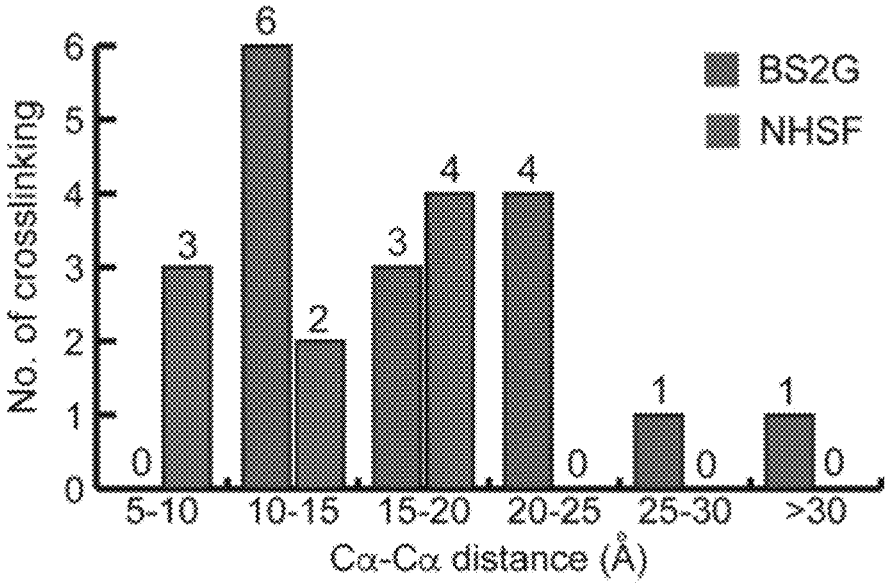
Figure 4E:
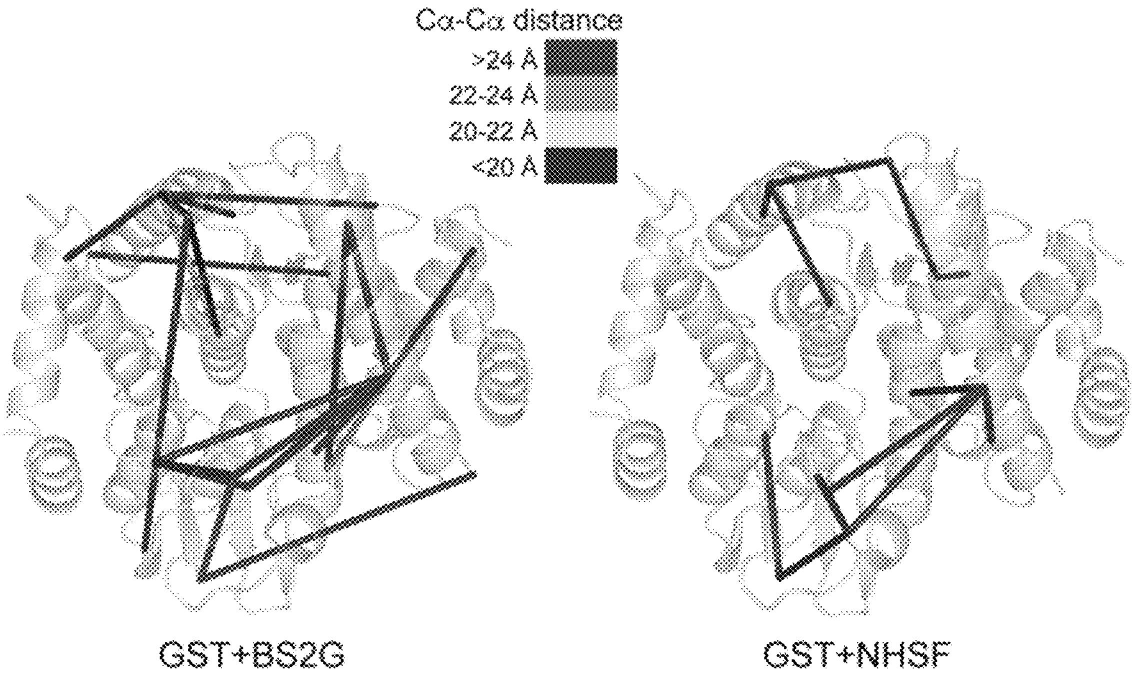

NHSF Cross-links Glutathione S-Transferase. To further validate the cross-linking specificity of NHSF, the homodimeric Glutathione S-Transferase (GST) was cross-linked by NHSF or BS2G. As shown by SDS-PAGE and Western blot run under reducing and denatured conditions, GST was successful cross-linked in the dimeric form by both cross-linkers (FIG. 4A). MS identified 15 cross-linked peptides in the BS2G sample and 9 cross-linked peptides in the NHSF sample (FIG. 4B, Table 3, Table 4). Again, only N-terminal $NH_2$-Lys or Lys-Lys cross-links were identified for BS2G-treated GST, but multiple new types of cross-linked sites were identified in the NHSF cross-linked GST sample, including 1 N-terminal $NH_2$—Ser, 1 N-terminal $NH_2$-Tyr, 5 Lys-Tyr, and 1 Lys-His (FIG. 4C), further confirming NHSF's unique ability to cross-link these residues that are infeasible to target with existing chemical crosslinkers. The one Lys-Lys cross-link observed for the NHSF sample was also observed with the BS2G as a crosslinker at a reasonable inter-residue distance (Cα-Cα distance=16.7 Å). All other Cα-Cα distances of cross-linked sites of NHSF cross-linking were highly compatible with the crystal structure of GST. By contrast, 6 out of 15 cross-links of BS2G cross-linking were incompatible with the GST structure (FIG. 4D and FIG. 4E). In summary, the NHSF crosslinker primarily identifies cross-links that are orthogonal to the set identified by BS2G, showing the complementarity of the two approaches. Moreover, the distance information obtained with NHSF are more compatible with the native structures of BSA and GST.

Figure 5A:
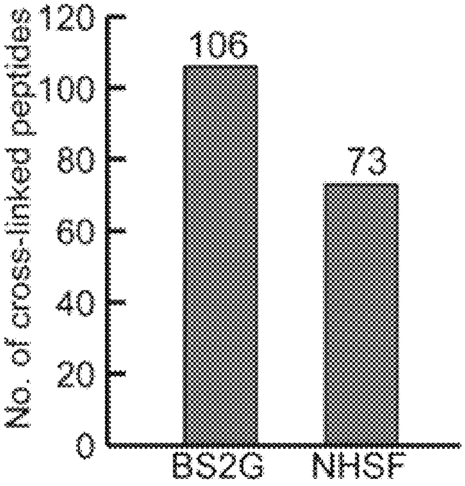
FIGS. 5A-5G. CXMS analysis of *E. coli* cell lysate with NHSF or BS2G.
Figure 5B:
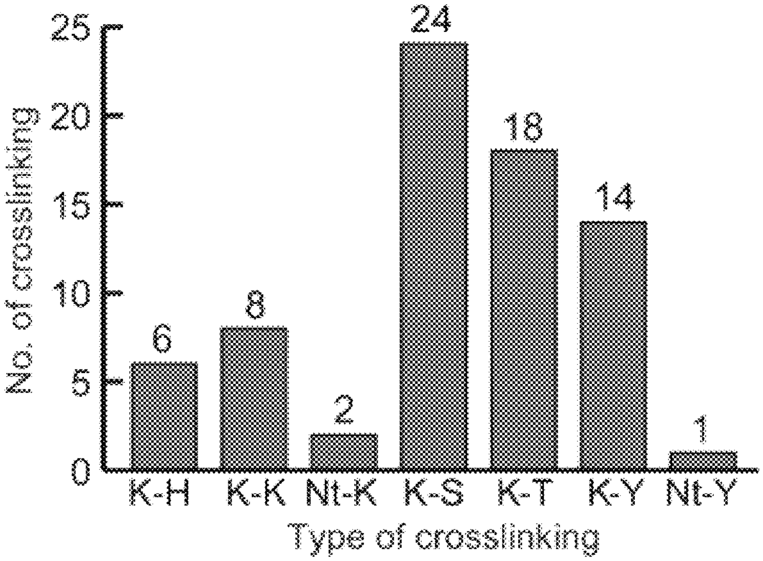
Figure 5C:
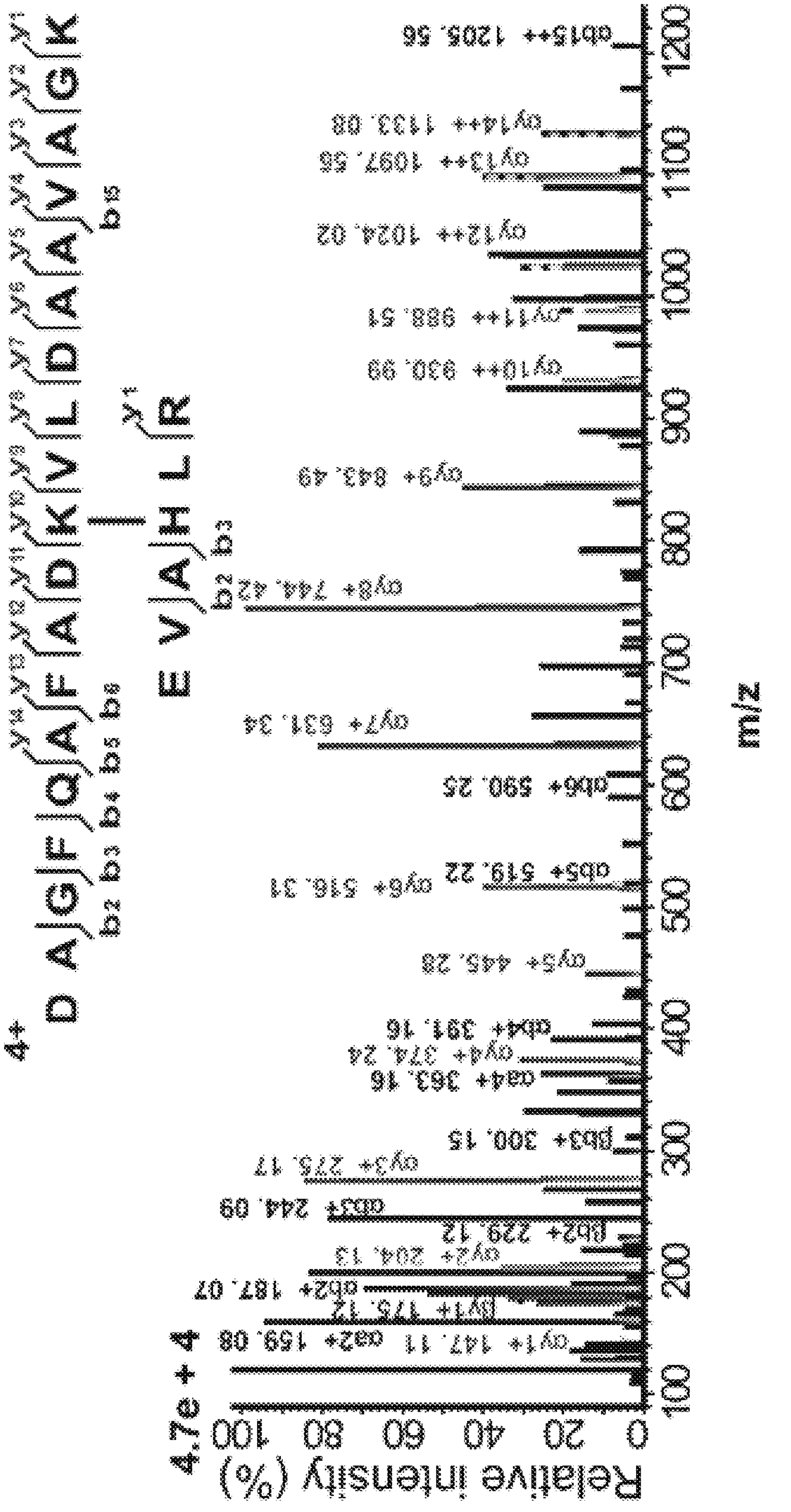
Figure 5D:
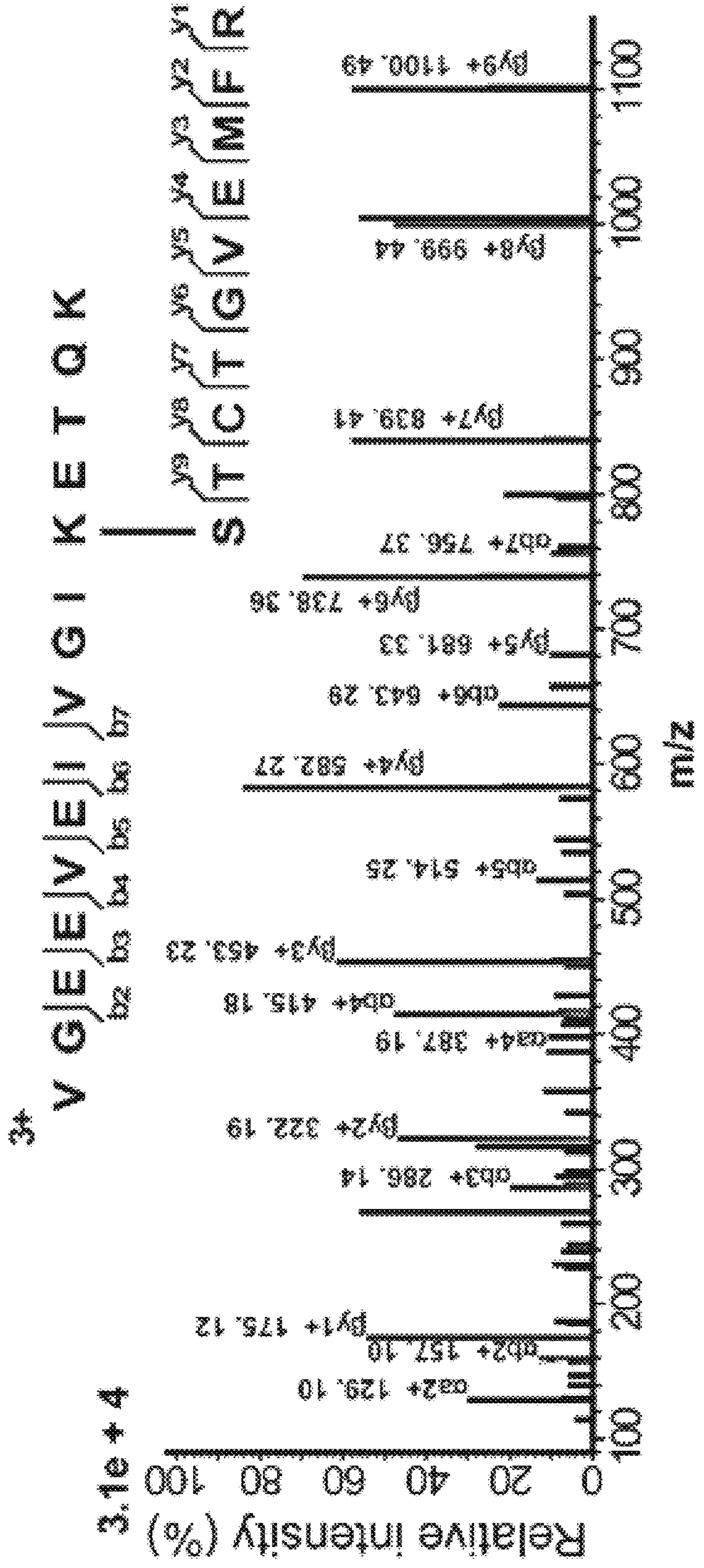
Figure 5E:
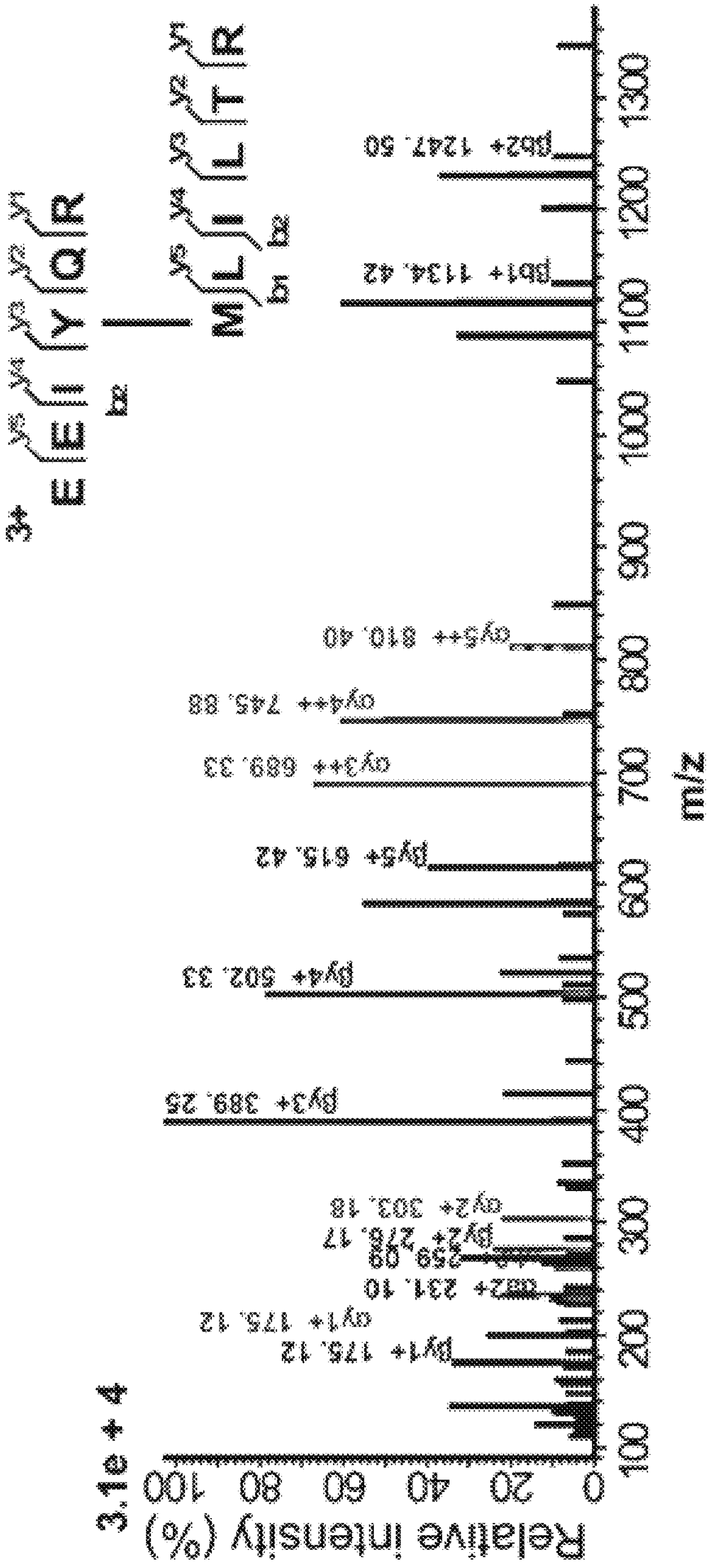
Figure 5F:
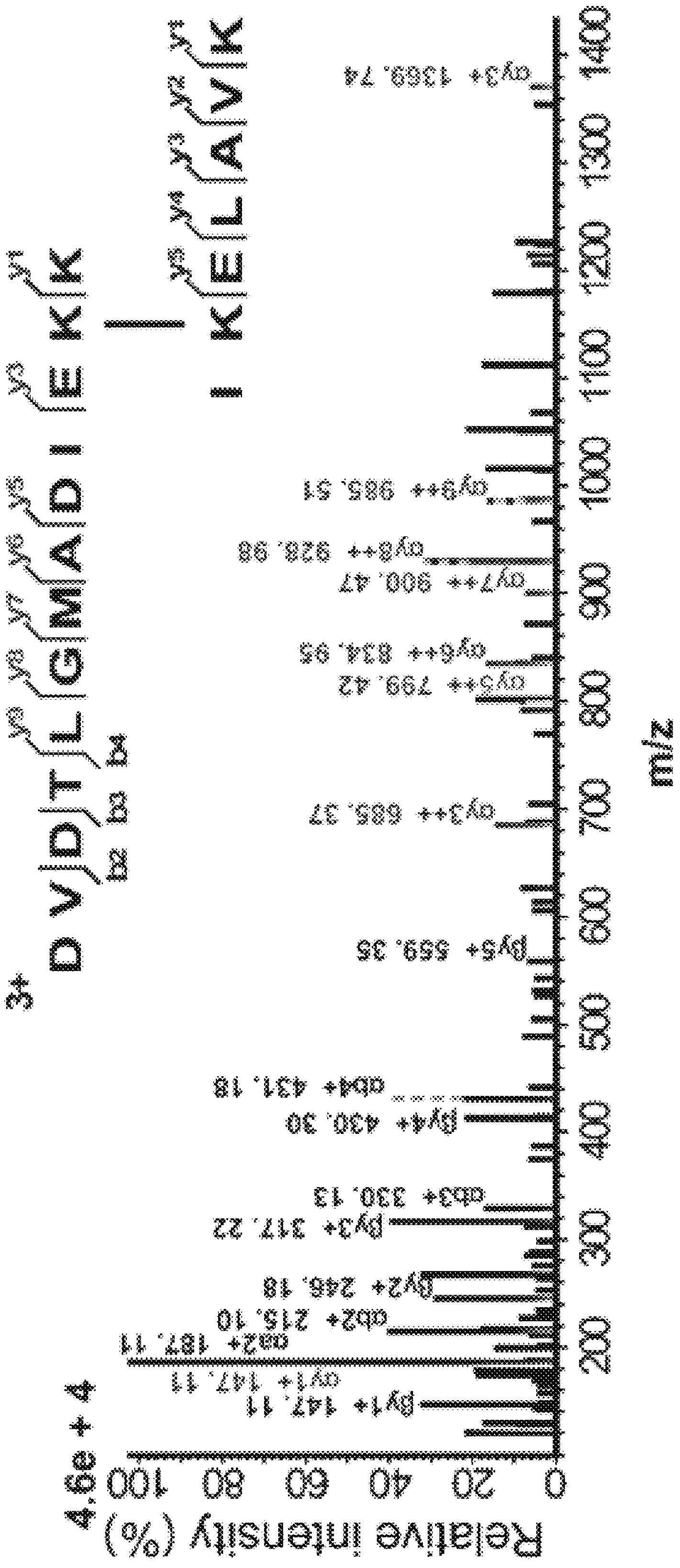
Figure 5G:
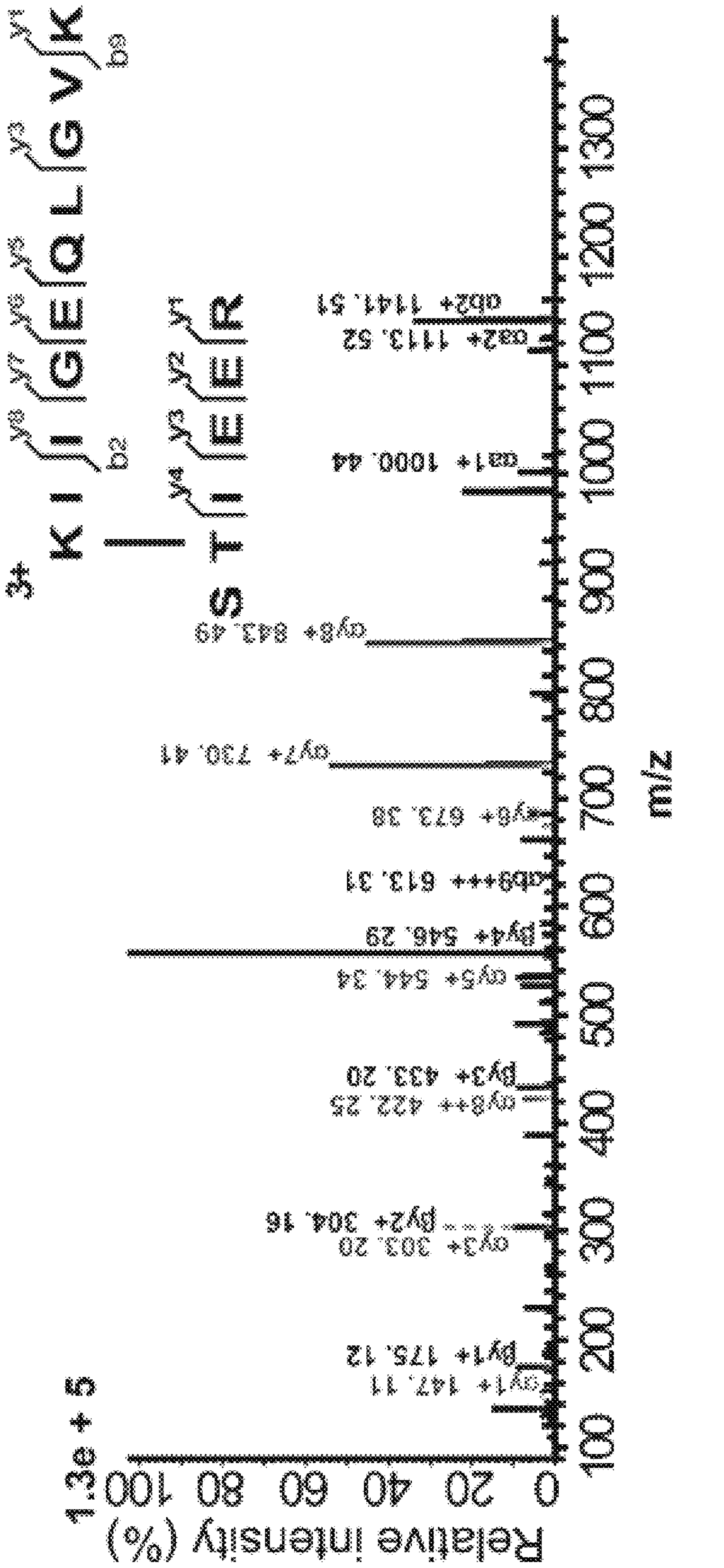

Example 2: NHSF Cross-Links *E. coli* Whole Cell Lysate Demonstrates the Applicability to Complex Mixtures and Defines the Chemo-Selectivity of the Cross-Linking Reaction To determine whether NHSF could be used in complex biological samples to generate novel cross-links for MS identification, we applied BS2G and NHSF on *E. coli* whole cell lysate. Consistent with the results from model proteins, we obtained large and comparable number of inter-linked peptides by BS2G (106) and NHSF (73) (FIG. 5A, Table 5 and Table 6). Six types of cross-links were identified by MS (FIG. 5B). Each type of cross-link was unambiguously supported by high-quality mass spectra (FIGS. 5C-5G).

Remarkably, 86% of the cross-links involved the sidechains of Ser, Thr, Tyr and His, which are inaccessible using other commonly employed chemical cross-linking reagents. Thus, NHSF is first-in-class in the chemical cross-linking field, and its chemoselectivity and distance-dependent reactivity bodes well for its use as a complement to existing technologies. We attribute the relatively low abundance of Lys-Lys cross-links to the relatively low reactivity of the sulfonyl-fluoride group. It is possible the dearth of Lys-Lys cross-links with NHSF reflects the high intrinsic reactivity of the succinimide ester, which effectively blocks the Lys sidechains towards further reaction, as seen in the above work with the model peptide. Once planted, the remaining sulfonyl-fluoride group is free to react with the remaining sidechains at a slower rate. The discovery of high-frequency cross-linking at Ser and Thr sidechains was rather unexpected, and speaks to the large rate acceleration that can be achieved from proximity-enhanced reactions. Finally, we note that the relative rates of the initial reaction with the succinimide ester is second order (first order in NHSF and first order in deprotonated Lys sidechains), while the second step is first order. Thus, the relative rates of the two reactions can be easily manipulated by changing the pH and the concentration of NHSF, which can be used in future applications to effect different product distributions. NHSF in Combination with GECX to Identify Enzyme-substrate Interaction.

Figure 6A:
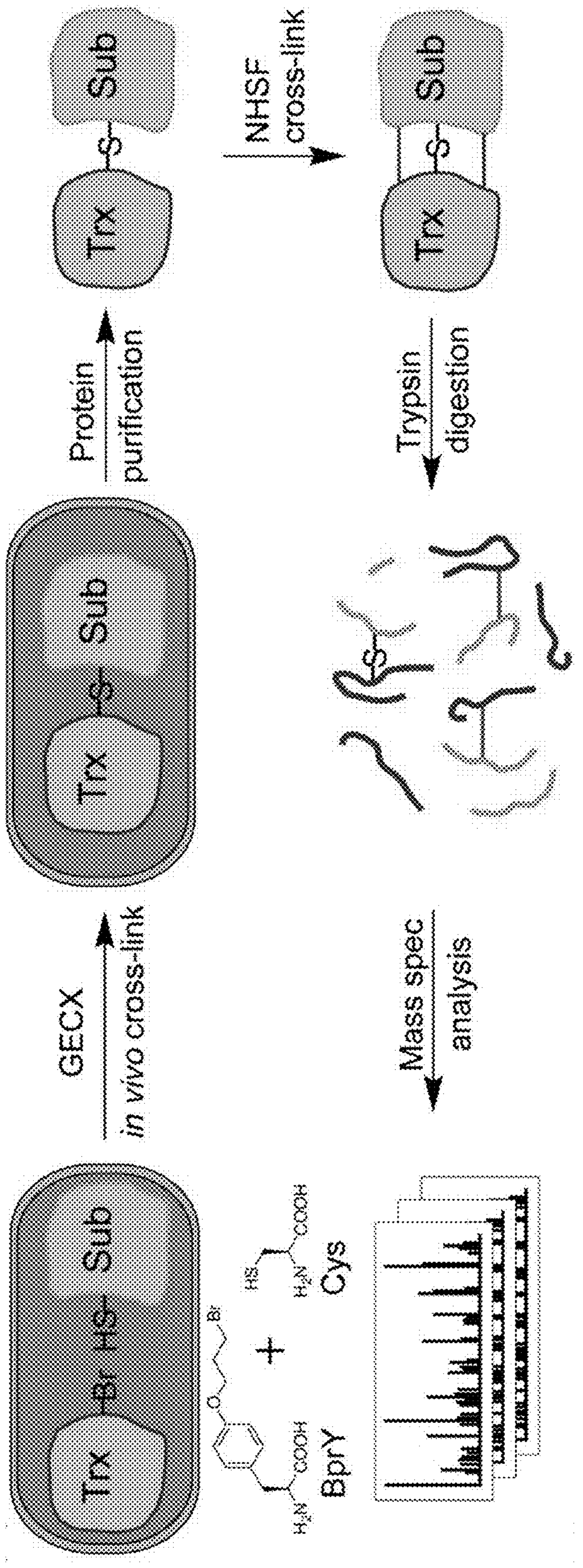

An outstanding challenge for studying PPIs and their networks is to identify weak and transient protein interactions. We previously developed GECX, which uses a bioreactive Uaa to capture such interactions in situ for subsequent MS identification (12). However, as a single cross-linked peptide is generated for each interacting protein in GECX, which may or may not be identifiable by tandem MS, the number of identified proteins with direct cross-linked peptides remains low. Since NHSF targets multiple residues, we reasoned it could be combined with GECX to increase the identifiable cross-linked peptides (FIG. 6A).

Using GECX, we genetically incorporated Uaa O-(3-bromopropyl)-L-tyrosine (BprY, FIG. 6A) into thioredoxin (Trx) to capture Trx-interacting proteins in *E. coli* cells (12, 15). Whenever a substrate protein of Trx interacts with Trx, BprY reacts with the Cys residue of the substrate protein via proximity-enhanced reactivity, thus covalently cross-linking the substrate protein with Trx in vivo. The cross-linked Trx complex was purified via the His6 tag appended at the C-terminus of Trx, further treated with or without NHSF, and then subjected to MS analysis. In the absence of NHSF treatment, 7 cross-linked peptides of Trx and interacting proteins were identified in tandem mass spectra (12). With NHSF treatment, an additional 7 new pairs of peptides of Trx and interacting proteins cross-linked by NHSF were identified (FIG. 6B). These results suggest that GECX followed by NHSF cross-linking indeed increased the number of identifiable cross-linked proteins that interact with thioredoxin.

Example 3: Synthesis and Characterization of Compounds

Chemical synthesis of NHSF. The synthesis of NHSF follows a previously published method with slight modifications (23). Briefly, a mixture of 4-(fluorosulfonyl)benzoic acid (0.6 g, 2.8 mmol), N-hydroxysulfosuccinimide (0.44 g, 2.0 mmol), and dicyclohexylcarbodiimide (DCC, 0.6 g, 2.8 mmol) in 10 mL dry DMF was stirred under $N_2$. The mixture was allowed to react on ice for 2 h and then overnight at room temperature (RT). After reaction, the dicyclohexylurea (DCU) precipitate was remove by filtration. The filtrate was then added to 25 mL ethyl acetate and diethyl ether mixture (v/v, 3:2) to afford white precipitates. The crude material was further purified by HPLC and lyophilized to give final product as a white solid. NMR: 1H NMR ($D_2O$, 800 MHz): δ 8.493 (d, J=9.2 Hz, 2H), 8.255 (d, J=9.2 Hz, 2H), 4.507 (m, 1H), 3.4 (m, 1H), 3.229 (dd, J=2.9, 19.0 Hz, 1H). $^{13}C$ NMR (DMSO-d6, 200 MHz): δ 169.1, 165.5, 132.3, 130.0, 56.9, 31.6. HRMS (ESI-MRMS): Calcd. for $C_{11}H_7FNO_9S_2$ $[M-H]^-$ m/z 379.9541, found 379.9544.

Solid phase peptide synthesis (SPPS). Ac-AAAKAAR (SEQ ID NO:1) peptide was synthesized with Rink amide resins on a 0.1 mmol scale using a Biotage Initiator+ Alstra peptide synthesizer. A typical SPPS reaction cycle includes Fmoc deprotection, washing, and coupling steps. The deprotection was carried out for 5 min at 70° C. with 4.5 mL 20% 4-methylpiperidine in DMF. A standard coupling step was done for 5 min at 75° C. with 5 equivalents Fmoc-protected amino acids, 4.98 equivalents HCTU, and 10 equivalents DIPEA (relative to the amino groups on resin) in DMF at a final concentration of 0.125 M amino acids. Peptide cleavage was carried out in the presence of TFA/$H_2O$/TIS (95:2.5:2.5, v/v) for 2 h at RT. The crude peptide was obtained after precipitation in cold diethyl ether. Peptide purification was carried out on a Varian Prostar 210 HPLC system with a C4 prep column using solvent A (0.1% TFA in water) and B (0.1% TFA in acetonitrile). After 5 min equilibration with 5% B at a flow rate of 5 mL/min, a linear gradient of 5-35% B in 30 min was used. The mass and purity of synthesized peptides were verified by a Shimazu AXIMA MALDI-TOF mass spectrometer and an HP 1100 analytical HPLC system, respectively.

Molecular cloning of pBAD-GST. *E. coli* wild type glutathione S-transferase gene (Gene ID: 945758) was PCR amplified from genomic DNA extracted from DH10β bacterial cells, and cloned into pBAD vector with forward primer containing Nde I (GTTGTTCATATGAAATTGTTCTACAAACCGGGTGCCTGC (SEQ ID NO:2)) and reverse primer containing Hind III restriction site (GTTGTTAAGCTTTTAATGGTGATGGTGATGGTGC TTTAAGCCTTCCGCTGACAG (SEQ ID NO:3)). The sequence was verified with DNA sequencing by GENEWIZ.

Expression and purification of GST. Plasmid pBAD-GST was transformed into BL21(DE3) cells and plated on LB argar plate supplemented with 100 μg/mL ampicillin. Several colonies were picked from the plate and inoculated to 100 mL 2×YT (5 g/L NaCl, 16 g/L Tryptone, 10 g/L Yeast extract). The cells were grown at 37° C., 220 rpm to an OD 0.5, with good aeration and the relevant antibiotic selection. Then the medium was added with 0.2% L-arabinose and the expression were carried out at 18° C., 220 rpm for 18-22 h. The cells were harvested at 3000 g, 4° C. for 10 min. The cell pellet was washed with cold IMAC buffer (25 mM sodium phosphate, 20 mM imidazole, 500 mM NaCl, pH 7.5), centrifuged again at 3000 g, 4° C. for 10 min, and resuspended in 15 mL IMAC buffer. The tube was then frozen on dry ice and stored at −20° C. For protein purification, the frozen cells were thawed quickly and resuspended well, and supplemented with EDTA free protease inhibitor cocktail, 0.5 mg/mL lysozyme, 1 μg/mL DNase by vortexing for 2 min. The cells were opened by sonication, after which the cell lysis solution was centrifuged at 25,000 g at 4° C. for 40 min. The supernatant was collected and incubated with 100 μL TALON® Metal Affinity resin at 4° C. for 1 h. The resin was washed with equal volume of IMAC buffer for 2 times at 4° C., and then transferred into a Pierce™ Centrifuge Columns (ThermoFisher Scientific). After 2 times wash with 500 μL IMAC buffer, the protein was eluted four times with 120 μL 25 mM sodium phosphate, 500 mM imidazole, 500 mM NaCl, pH 7.5. The fractions containing the target protein were analyzed by running 12% Tris-glycine sodium dodecyl sulfate-polyacrylamide gel electrophoresis (SDS-PAGE) gel.

Preparation of *E. coli* cell lysate. DH10β bacterial cells were cultured overnight. After cells were harvested by centrifugation, cell pellets were washed twice with PBS. Cells were resuspended with lysis buffer (50 mM Hepes, pH 8.3, 150 mM NaCl, 1×EDTA-free Complete Protease Inhibitor Cocktail) and incubate with lysozyme (1 mg/mL), DNase I (0.5 mg/mL) and RNase A (0.1 mg/mL) at 4° C. for 30 min. Cell lysates were sonicated for 3 min with 30% energy and filtrated with Amicon-0.5 ml 10K unit for 3 times.

Peptide and protein cross-linking. 7KR peptide: In a 20 μL reaction, 10 μM 7KR peptide (in PBS buffer, pH 7.5) was cross-linked at RT for 1 h with 10 μM BS2G or 10 μM NHSF. Reactions were acidified by formic acid at final concentration of 5% and desalted with Stagetip. BSA: In a 20 μL reaction, 10 μM BSA (69 kDa, in PBS buffer, pH 7.5) was cross-linked at RT for 1 h with 1 mM BS2G or 1 mM NHSF, which corresponded to a 1:100 protein:cross-linker molar ratio. BS2G cross-linking reaction was terminated at RT by adding 20 mM ammonium bicarbonate and incubating for 20 min. NHSF cross-linking reaction was terminated at RT by adding 10 mM Dithiothreitol (DTT) and incubating for 20 min. GST: In a 20 μL reaction, 10 μM GST (23 kDa, in PBS buffer, pH 7.5) was cross-linked at RT for 1 h with 0.5 mM BS2G or 0.5 mM NHSF, which corresponded to a 1:50 protein:cross-linker molar ratio. The cross-linking reactions were similarly terminated as described in the BSA section above. *E. coli* cell lysate: 20 uL lysate (10 mg/mL protein, 50 mM Hepes, pH 8.3, 150 mM NaCl) was incubate with 40 mM BS2G or 40 mM NHSF at RT for 2 h. BS2G cross-linking reaction was terminated at RT by adding 100 mM ammonium bicarbonate and incubating for 20 min. NHSF cross-linking reaction was terminated at RT by adding 100 mM DTT and incubating for 20 min. Thioredoxin sample: The cloning of thioredoxin, in vivo cross-linking via GECX, and purification were carried out as described before (12). The His-tag pull-down sample of thioredoxin (20 uL, 3.45 mg/mL protein, 50 mM Hepes, pH 8.3, 150 mM NaCl) was incubate with 20 mM NHSF at RT for 1 h. NHSF cross-linking reaction was terminated at RT by adding 100 mM DTT and incubating for 20 min.

Protein digestion. All protein samples were precipitated by six volumes of acetone at −20° C. for 30 min. Precipitated proteins were dried in air and resuspended in 8 M urea, 100 mM Tris, pH 8.5. After reduction with 2 mM DTT for 20 min and alkylation with 10 mM iodoacetamide for 15 min in the dark, samples were diluted to 2 M urea with 100 mM Tris, pH 8.5, and digested with trypsin (at 50:1 protein:enzyme ratio) at 37° C. for 16 h. Digestion was stopped by adding formic acid to 5% final concentration, and digested peptides were desalted with stagetip.

Tandem mass spectrometric analysis. Mass spectrometry experiments were performed using an Orbitrap Fusion Lumos™ instrument (ThermoFisher, San Jose, CA) coupled with an UltiMate™ 3000 nano LC. Mobile phase A and B were water and acetonitrile, respectively, with 0.1% formic acid. Protein digests were loaded directly onto a C18 PepMap EASYspray column (ThermoFisher Scientific, part number ES803) at a flow rate of 300 nL/min. *E. coli* whole cell lysate digests were separated at 300 nL/min using a linear gradient of 2% to 35% B over 115 min. All other samples (except thioredoxin pull-down samples) were separated using a linear gradient of 2% to 40% B over 38 min. Survey scans of peptide precursors were performed from 375 to 1500 m/z at 60,000 FWHM resolution with a $4\times10^5$ ion count target and a maximum injection time of 50 ms. The instrument was set to run in top speed mode with 3 second cycles for the survey and the MS/MS scans. After a survey scan, tandem MS was then performed on the most abundant precursors exhibiting a charge state from 2 to 7 (3 to 8 for

*E. coli* samples) of greater than $5\times10^4$ intensity by isolating them in the quadrupole at 1.6 Da. Higher energy collisional dissociation (HCD) fragmentation was applied with 30% collision energy and resulting fragments detected in the Orbitrap detector at a resolution of 30,000. The maximum injection time limited was 50 ms and dynamic exclusion was set to 60 seconds with a 10 ppm mass tolerance around the precursor.

Measurement of thioredoxin His-tag pull down samples were performed using an Orbitrap Fusion Lumos™ instrument (ThermoFisher, San Jose, CA) coupled with an EasyLC1200 (ThermoFisher). Mobile phase A and B were water and 80% acetonitrile, respectively, with 0.1% formic acid. Protein digests were loaded directly onto a PicoFrit emitter (New Objective) self-packed to a 20 cm C18 column with 1.9 μm Reprosil PUR beads (Dr. Maisch GmbH HPLC) running at a flow rate of 300 nL/min. Digested peptides were separated at 300 nL/min using a linear gradient of 5% to 37% B over 120 min. Survey scans of peptide precursors were performed from 350 to 1650 m/z at 120,000 FWHM resolution with a $2\times10^5$ ion count target and a maximum injection time of 100 ms. The instrument was set to run in top speed mode with 3 second cycles for the survey and the MS/MS scans. After a survey scan, tandem MS was then performed on the most abundant precursors exhibiting a charge state from 2 to 7 of greater than $5\times10^4$ intensity by isolating them in the quadrupole at 1.2 m/z. HCD fragmentation was applied with 28% collision energy and resulting fragments detected in the Orbitrap detector at a resolution of 30,000. AGC target was set at $8\times10^4$ and the maximum injection time limited was 50 ms (the AGC target is allowed to be exceeded if there is available parallelizable time). Both MS1 and MS2 data are recorded at Profile mode. The dynamic exclusion was set to 30 seconds with a 10-ppm mass tolerance around the precursor from reselection.

Data analysis. Cross-linked peptides were identified using pLink 2 software. pLink search parameters: precursor mass tolerance 20 p.p.m., fragment mass tolerance 20 p.p.m., peptide length minimum 6 amino acids and maximum 60 amino acids per chain, peptide mass minimum 600 and maximum 6,000 Da per chain, fixed modification C 57.02146, enzyme trypsin, three missed cleavage sites per chain. The *E. coli* protein sequences were downloaded from Uniprot. Other protein sequences (such as GST, BSA) were also downloaded from Uniprot. Data of thioredoxin sample was searched with slightly modified parameters set (peptide mass minimum 300 and maximum 2,500 Da per chain, peptide length minimum 3 amino acids and maximum 25 amino acids per chain).

TABLE 1

CXMS analysis of BS2G cross-linked BSA

| No. | Cross-linking site | Cross-linked peptides (cross-linked residues underlined) | Cα Cα Distance (Å) |
|---|---|---|---|
| 1 | BSA$^{211}$-BSA$^{245}$ | EKVLASSAR-LSQKFPK | 20.3 |
| 2 | BSA$^{235}$-BSA$^{263}$ | LVTDLTKVHK-ALKAWSVAR | 9.6 |
| 3 | BSA$^{228}$-BSA$^{489}$ | LCVLHEKTPVSEK-CASIQKFGER | 13.5 |

TABLE 1-continued

CXMS analysis of BS2G cross-linked BSA

| No. | Cross-linking site | Cross-linked peptides (cross-linked residues underlined) | Cα Cα Distance (Å) |
|---|---|---|---|
| 4 | BSA$^{245}$-BSA$^{263}$ | LVTDLTKVHK-LSQKFPK | 19.4 |
| 5 | BSA$^{245}$-BSA$^{318}$ | SHCIAEVEKDAIPEN LPPLTADFAEDKDVCKNY QEAK-LSQKFPK | 4.2 |
| 6 | BSA$^{130}$-BSA$^{140}$ | LKPDPNTLCDEFKADEK-NECFLSHKDDSPDLPK | 24 |
| 7 | BSA$^{401}$-BSA$^{437}$ | KVPQVSTPTLVEVSR-LKHLVDEPQNLIK | 28.3 |
| 8 | BSA$^{28}$-BSA$^{36}$ | FKDLGEEHFK-DTHKSEIAHR | 12.7 |
| 9 | BSA$^{544}$-BSA$^{548}$ | LFTFHADICTLPDTEKQIK-KQTALVELLK | 6.5 |
| 10 | BSA$^{235}$-BSA$^{374}$ | LAKEYEATLEECCAK-ALKAWSVAR | 13.6 |
| 11 | BSA$^{420}$-BSA$^{568}$ | QNCDQFEKLGEYGFQNALIVR-ATEEQLKTVMENFVAFVDK | 14.5 |
| 12 | BSA$^{455}$-BSA$^{463}$ | CCTKPESER-SLGKVGTR | 13.5 |
| 13 | BSA$^{235}$-BSA$^{266}$ | VHKECCHGDLLECADDRADLAK-ALKAWSVAR | 10.5 |
| 14 | BSA$^{140}$-BSA$^{455}$ | LKPDPNTLCDEFKADEK-SLGKVGFR | 21.2 |
| 15 | BSA$^{437}$-BSA$^{561}$ | KVPQVSTPTLVEVSR-HKPKATEEQLK | 11.7 |
| 16 | BSA$^{235}$-BSA$^{245}$ | ALKAWSVAR-LSQKFPK | 15.1 |
| 17 | BSA$^{304}$-BSA$^{318}$ | SHCIAEVEKDAIPEN LPPLTADFAEDKDVCK-LKECCDKPLLEK | 18.5 |
| 18 | BSA$^{245}$-BSA$^{318}$ | SHCIAEVEKDAIPENLP PLTADFAEDKDVCK-LSQKFPK | 4.2 |

TABLE 2

CXMS analysis of NHSF cross-linked BSA

| No. | Cross-linking site | Cross-linked Peptides (cross-linked residues underlined) | Cα Cα Distance (Å) |
|---|---|---|---|
| 1 | BSA$^{455}$-BSA$^{475}$ | MPCTEDYLSLILNR-SLGKVGTR | 9.5 |
| 2 | BSA$^{399}$-BSA$^{402}$ | DDPHACYSTVFDKLK-HLVDEPQNLIK | 5.8 |
| 3 | BSA$^{235}$-BSA$^{270}$ | VHKECCHGDLLECADDR ADLAK-ALKAWSVAR | 16.4 |
| 4 | BSA$^{295}$-BSA$^{299}$ | LKECCDKPLLEK-YICDNQDTISSK | 8.9 |

TABLE 2-continued

CXMS analysis of NHSF cross-linked BSA

| No. | Cross-linking site | Cross-linked Peptides (cross-linked residues underlined) | Cα Cα Distance (Å) |
|---|---|---|---|
| 5 | BSA329-BSA340 | SHCIAEVEKDAIPENLPPLTADFAEDK-DVCKNYQEAK | 16.4 |
| 6 | BSA455-BSA472 | MPCTEDYLSLILNR-SLGKVGTR | 10 |
| 7 | BSA495-BSA501 | CCTESLVNR-TPVSEKVTK | 9.8 |
| 8 | BSA463-BSA475 | MPCTEDYLSLILNR-CCTKPESER | 13.8 |
| 9 | BSA487-BSA495 | TPVSEKVTK-LCVLHEK | 10.8 |
| 10 | BSA138-BSA145 | PDPNTLCDEFKADEK-DDSPDLPKLK | 16.2 |
| 11 | BSA225-BSA245 | LRCASIQK-LSQKFPK | 21.2 |
| 12 | BSA133-BSA140 | NECFLSHKDDSPDLPK-LKPDPNTLCDEFK | 18.2 |
| 13 | BSA424-BSA455 | LGEYGFQNALIVR-SLGKVGTR | 8.7 |

TABLE 3

CXMS analysis of BS2G cross-linked GST

| No. | Cross-linking site | Cross-linked Peptides (cross-linked residues underlined) | Cα Cα Distance (Å) |
|---|---|---|---|
| 1 | GST49-GST131 | LENGDDYFAVNPKGQVPALLLDDGTLLTEGVAIMQYLADSVPDR-AQLEKK | 11.3 |
| 2 | GST6-GST34 | LFYKPGACSLASHITLR-ESGKDFTLVSVDLMKK | 12.5 |
| 3 | GST131-GST169 | WAYAVKLNLEGLEHIAAFMQR-AQLEKK | 14.4 |
| 4 | GST93-GST131 | YKTIEWLNYIATELHK-AQLEKK | 21.8 |
| 5 | GST35-GST131 | KRLENGDDYFAVNPK-AQLEKK | 16.7 |
| 6 | GST6-GST35 | LFYKPGACSLASHITLR-KRLENGDDYFAVNPK | 11.0 |
| 7 | GST1-GST141 | LQYVNEALKDEHWICGQR-MKLFYK | 29.1 |
| 8 | GST93-GST122 | GFTPLFRPDTPEEYKPTVR-YKTIEWLNYIATELHK | 30.8 |
| 9 | GST122-GST131 | GFTPLFRPDTPEEYKPTVR-AQLEKK | 14.6 |
| 10 | GST23-GST122 | GFTPLFRPDTPEEYKPTVR-ESGKDFTLVSVDLMK | 39.1 |

TABLE 3-continued

CXMS analysis of BS2G cross-linked GST

| No. | Cross-linking site | Cross-linked Peptides (cross-linked residues underlined) | Cα Cα Distance (Å) |
|---|---|---|---|
| 11 | GST49-GST131 | RLENGDDYFAVNPKGQVPALLLDDGTLLTEGVAIMQYLADSVPDR-AQLEKK | 11.3 |
| 12 | GST34-GST131 | ESGKDFTLVSVDLMKK-AQLEKK | 18.0 |
| 13 | GST35-GST132 | KLQYVNEALKDEHWICGQR-KRLENGDDYFAVNPK | 17.1 |
| 14 | GST1-GST34 | ESGKDFTLVSVDLMKKR-MKLFYK | 23.8 |
| 15 | GST6-GST131 | LFYKPGACSLASHITLR-AQLEKK | 24.2 |

TABLE 4

CXMS analysis of NHSF cross-linked GST

| No. | Cross-linking site | Cross-linked Peptides (cross-linked residues underlined) | Cα Cα Distance (Å) |
|---|---|---|---|
| 1 | GST1-GST43 | MKLFYKPGACSLASHITLR-LENGDDYFAVNPK | 16.5 |
| 2 | GST13I-GST135 | LQYVNEALK-AQLEKK | 6.7 |
| 3 | GST43-GST131 | KRLENGDDYFAVNPK-AQLEKK | 17.8 |
| 4 | GST43-GST131 | LENGDDYFAVNPK-AQLEKK | 17.8 |
| 5 | GST34-GST43 | ESGKDFTLVSVDLMKKR-LENGDDYFAVNPK | 8.9 |
| 6 | GST35-GST131 | KRLENGDDYFAVNPK-AQLEKK | 16.7 |
| 7 | GST100-gst131 | TIEWLNYIATELHK-AQLEKK | 13.4 |
| 8 | GST1-GST1 | PGACSLASHITLR-MKLFYK | 14.9 |
| 9 | GST131-GST135 | LQYVNEALKDEHWICGQR-AQLEKK | 6.7 |

TABLE 5

CXMS analysis of BS2G cross-linked *E. coli* cell lysate

| No. | Cross-linking site | Cross-linked peptides (Numbers in parentheses indicate cross-linked residues) |
|---|---|---|
| 1 | sp\|C4ZUF6\|RL15_ECOBW (141)-sp\|C4ZUF6\|RL15_ECOBW (129) | AAIEAAGGKIEE(9)-VTKGAR(3) |
| 2 | sp\|P048251AMPN_ECOLI (852)-sp\|P04825\|AMPN_ECOLI (1) | AALEQLKGLENLSGDLYEK(7)-MTQQPQAK(1) |
| 3 | sp\|P0A799\|PGK_ECOLI (30)-sp\|P0A799\|PGK_ECOLI (84) | ADLNVPVKDGKVTSDAR(11)-DKLSNPVR(2) |
| 4 | sp\|P0AEH5\|ELAB_ECOLI (45)-sp\|P0AEH5\|ELAB_ECOLI (2) | AEKALDDVK(3)-SNQFGDTR(1) |
| 5 | sp\|P0CE48\|EFTU2_ECOLI (57)-sp\|P0CE48\|EFTU2_ECOLI (264) | AFDQDDNAPEEKAR(12)-KLLDEGR(1) |
| 6 | sp\|C4ZUJ5\|EFG_ECOBW (389)-sp\|C4ZUJ5\|EFG_ECOBW (440) | AGDIAAAIGLKDVTTGDTLCDPDAPIILER(11)-LAKEDPSFR(3) |
| 7 | sp\|P07813\|SYL_ECOLI (813)-sp\|P07813\|SYL_ECOLI (738) | AKITVPVDATEEQVR(2)-LAKAPTDGEQDR(3) |
| 8 | sp\|P0A6Y8\|DNAK_ECOLI (304)-sp\|P0A6Y8\|DNAK_ECOLI (246) | AKLESLVEDLVNR(2)-KDQGIDLR(1) |
| 9 | sp\|B1X953\|HLDD_ECODH (22)-sp\|B1X953\|HLDD_ECODH (290) | ALNDKGITDILVVDNLK(5)-AAGYDKPFK(6) |
| 10 | sp\|P0AB71\|ALF_ECOLI (319)-sp\|P0AB71\|ALF_ECOLI (327) | ANEAYLQGQLGNPKGEDQPNK(14)-KYYDPR(1) |
| 11 | sp\|B1XB26\|GLYA_ECODH (346)-sp\|B1XB26\|GLYA_ECODH (331) | ANITVNKNSVPNDPK(7)-NLTGKEADAALGR(5) |
| 12 | sp\|P00582\|DP01_ECOLI (810)-sp\|P00582\|DP01_ECOLI (829) | AQAKEQGYVETLDGR(4)-LYLPDIKSSNGAR(7) |
| 13 | sp\|P00490\|PHSM_ECOLI (54)-sp\|P00490\|PHSM_ECOLI (2) | AQPFAKPVANQR(6)-SQPIFNDK(1) |
| 14 | sp\|P0ACF8\|HNS_ECOLI (96)-sp\|P0ACF8\|HNS_ECOLI (136) | AQRPAKYSYVDENGETK(6)-SLDDFLIKQ(8) |
| 15 | sp\|P0A799\|PGK_ECOLI (49)-sp\|P0A799\|PGK_ECOLI (84) | ASLPTIELALKQGAK(11)-DKLSNPVR(2) |
| 16 | sp\|P0A7W1\|RS5_ECOLI (156)-sp\|P0A7W1\|RS5_ECOLI (159) | ATIDGLENMNSPEMVAAKR(18)-GKSVEEILGK(2) |
| 17 | sp\|P0A6F5\|CH60_ECOLI (117)-sp\|P0A6F5\|CH60_ECOLI (34) | AVAAGMNPMDLKR(12)-VTLGPKGR(6) |
| 18 | sp\|P0AEE5\|DGAL_ECOLI (136)-sp\|P0AEE5\|DGAL_ECOLI (187) | AYYVGTDSKESGIIQGDLIAK(9)-TTYVIKELNDK(6) |
| 19 | sp\|C4ZRR4\|RRF_ECOBW (138)-sp\|C4ZRR4\|RRF_ECOBW (1) | DANDKVK(5)-MISDIR(1) |
| 20 | sp\|P0A799\|PGK_ECOLI (30)-sp\|P0A799\|PGK_ECOLI (84) | DGKVTSDAR(3)-DKLSNPVR(2) |
| 21 | sp\|P0A9B2\|G3P1_ECOLI (132)-sp\|P0A9B2\|G3P1_ECOLI (331) | DNTPMFVKGANFDK(8)-VLDLIAHISK(IO) |
| 22 | sp\|B1XBY9\|RPOB_ECODH (844)-sp\|B1XBY9\|RPOB_ECODH (914) | DTKLGPEEITADIPNVGEAALSK(3)-ASDVKDSSLR(5) |
| 23 | sp\|P0A853\|TNAA_ECOLI (246)-sp\|P0A853 \|TNAA_ECOLI (239) | EAEYKDWTIEQITR(5)-FAENAYFIKQR(9) |
| 24 | sp\|B1XBY8\|RL7 ECODH (85)-sp\|B1XBY8\|RL7_ECODH (71) | EAKDLVESAPAALK(3)-VAVIKAVR(5) |

TABLE 5-continued

CXMS analysis of BS2G cross-linked *E. coli* cell lysate

| No. | Cross-linking site | Cross-linked peptides (Numbers in parentheses indicate cross-linked residues) |
|---|---|---|
| 25 | sp\|B1X905\|YFBU_ECODH (55)- sp\|B1X905\|YFBU_ECODH (1) | EFGELKEETCR(6)-MEMTNAQR(1) |
| 26 | sp\|P0A6Z3\|HTPG_ECOLI (398)- sp\|P0AEY5\|MDAB_ECOLI (106) | EGPAEDFANQEAIAKLLR(15)- KDPSKK(5) |
| 27 | sp\|P0A6Z3\|HTPG_ECOLI (398)- sp\|P0A6Z3\|HTPG_ECOLI (354) | EGPAEDFANQEAIAKLLR(15)- NALTKR(5) |
| 28 | sp\|B1XFM4\|TIG_ECODH (83)- sp\|B1XFM4\|TIG_ECODH (146) | EKINPAGAPTYVPGEYK(2)- KQQATWK(1) |
| 29 | sp\|P0A8N5\|SYK2_ECOLI (25)- sp\|P0A8N5\|SYK2_ECOLI (2) | EKLAALR(2)-SEQETR(1) |
| 30 | sp\|B1X905\|YFBU_ECODH (55)- sp\|B1X905\|YFBU_ECODH (1) | ELDREFGELKEETCR(10)- MEMTNAQR(1) |
| 31 | sp\|P0CE48\|EFTU2_ECOLI (253)- sp\|P0CE48\|EFTU2_ECOLI (264) | ETQKSTCTGVEMFR(4)-KLLDEGR(1) |
| 32 | sp\|P0CE48\|EFTU2_ECOLI (253)- sp\|P0CE48\|EFTU2_ECOLI (300) | ETQKSTCTGVEMFR(4)- PGTDCPHTK(5) |
| 33 | sp\|P0A6F5\|CH60_ECOLI (80)- sp\|P0A6F5\|CH60_ECOLI (327) | EVASKANDAAGDGTTTATVLAQAII TEGLK(5)- VVINXDTTTIIDGVGEEAAIQGR(5) |
| 34 | sp\|P0A6P1\|EFTS_ECOLI (207)- sp\|P0A6P1\|EFTS_ECOLI (214) | EYQVQLDIAMQSGKPK(14)- EIAEKMVEGR(5) |
| 35 | sp\|C4ZZT2\|ENO_ECOBW (62)- sp\|C4ZZT2\|ENO_ECOBW (56) | FLGKGVTK(4)-DGDKSR(4) |
| 36 | sp\|P62707\|GPMA_ECOLI (33)- sp\|P62707\|GPMA_ECOLI (18) | FTGWYDVDLSEKGVSEAK(12)- HGESQWNKENR(8) |
| 37 | sp\|P0AC69\|GLRX4_ECOLI (101)- sp\|P0AC69\|GLRX4_ECOLI (108) | GELQQLIKETAAK(8)- YKSEEPDAE(2) |
| 38 | sp\|P0CE48\|EFTU2_ECOLI (238)- sp\|P0ACM5\|YEGW_ECOLI (110) | GIIKVGEEVEIVGIK(4)- GFSQQVVLRGKK(11) |
| 39 | sp\|P0CE48\|EFTU2_ECOLI (238)- sp\|P0CE48\|EFTU2_ECOLI (295) | GIIKVGEEVEIVGIK(4)- GQVLAKPGTIKPHTK(6) |
| 40 | sp\|P39325\|YTFQ_ECOLI (57)- sp\|P39325\|YTFQ_ECOLI (70) | GITLKIADGQQK(5)- QENQIKAVR(6) |
| 41 | sp\|C4ZYI1\|SYT_ECOBW (614)- sp\|C4ZYI1\|SYT_ECOBW (638) | GKDLGSMDVNEVIEK(2)- SLKQLEE(3) |
| 42 | sp\|P0CE48\|EFTU2_ECOLI (177)- spIP0CE48IEFTU2_ECOLI (264) | GSALKALEGDAEWEAK(5)- KLLDEGR(1) |
| 43 | sp\|P02925\|RBSB_ECOLI (275)- sp\|P02925\|RBSB_ECOLI (281) | GVETADKVLK(7)-GEKVQAK(3) |
| 44 | sp\|P02924\|ARAF_ECOLI (156)- sp\|P02924\|ARAF_ECOLI (190) | GWDVKESAVMAITANELDTAR(5)- AAGFPEKQIYQVPTK(7) |
| 45 | sp\|P0AEX9\|MALE_ECOLI (51)- sp\|P0AEX9\|MALE_ECOLI (55) | GYNGLAEVGKK(10)-FEKDTGIK(3) |
| 46 | sp\|P62707\|GPMA_ECOLI (100)- sp\|P62707\|GPMA_ECOLI (113) | HYGALQGLNKAETAEK(10)- YGDEQVKQWR(7) |
| 47 | sp\|P0A6Y8\|DNAK_ECOLI (166)- sp\|P0A6Y8\|DNAK_ECOLI (155) | IAGLEVKR(7)-QATKDAGR(4) |
| 48 | sp\|P07118\|SYV_ECOLI (909)- sp\|P07118\|SYV_ECOLI (926) | IENKLANEGFVAR(4)- APEAVIAKER(8) |

TABLE 5-continued

CXMS analysis of BS2G cross-linked *E. coli* cell lysate

| No. | Cross-linking site | Cross-linked peptides (Numbers in parentheses indicate cross-linked residues) |
|---|---|---|
| 49 | sp\|P0AES2\|GUDD_ECOLI (250)- sp\|P0AEW6\|INGK_ECOLI (1) | IGKYLK(3)-MKFPGK(1) |
| 50 | sp\|C4ZYU1\|CSRA_ECOBW (38)- sp\|P0AAE5\|ARCD_ECOLI (57) | IGVNAPKEVSVHR(7)-MLILTR(1) |
| 51 | sp\|P24186\|FOLD_ECOLI (9)- sp\|P24186\|FOLD_ECOLI (56) | IIDGKTIAQQVR(5)- KACEEVGFVSR(1) |
| 52 | sp\|P02925\|RBSB_ECOLI (101)- sp\|P02925\|RB SB_ECOLI (119) | ILLINPTDSDAVGNAVKMANQANIP VITLDR(17)- QATKGEVVSHIASDNVLGGK(4) |
| 53 | sp\|P0A6P1\|EFTS_ECOLI (52)- sp\|P21514\|YAHA_ECOLI (60) | KAGNVAADGVIK(1)-TISHQKK(6) |
| 54 | sp\|B1XBY8\|RL7_ECODH (109)- sp\|B1XBY8 RL7_ECODH (101) | KALEEAGAEVEVK(1)- EGVSKDDAEALK(5) |
| 55 | sp\|P0A799\|PGK_ECOLI (120)- sp\|P0ADW8\|YHEV_ECOLI (47) | KDDETLSK(1)-EADKEAR(4) |
| 56 | sp\|P46142\|YGGM_ECOLI (323)- sp\|P02925\|RBSB_ECOLI (144) | KDTEQLR(1)-KAGEGAK(1) |
| 57 | sp\|P0AG67\|RS1_ECOLI (411)- sp\|P0AG67\|RS1_ECOLI (370) | KGDEIAAVVLQVDAER(1)- VEGKIK(4) |
| 58 | sp\|P0A6A8\|ACP_ECOLI (10)- sp\|P0A6A8\|ACP_ECOLI (1) | KIIGEQLGVK(1)-MSTIEER(1) |
| 59 | sp\|P0A6A8\|ACP_ECOLI (10)- sp\|P0A6A8\|ACP_ECOLI (2) | KIIGEQLGVK(1)-STIEER(1) |
| 60 | sp\|C4ZZA4\|ASTC_ECOBW (89)- sp\|C4ZZA4\|ASTC_ECOBW (2) | KLIDATFADR(1)-SQPITR(1) |
| 61 | sp\|P09373\|PFLB_ECOLI (17)- sp\|P09373\|PFLB_ECOLI (2) | LATAWEGFTKGDWQNEVNVR(10)- SELNEK(1) |
| 62 | sp\|P36683\|ACNB_ECOLI (2)- sp\|P37127\|AEGA_ECOLI (514) | LEEYRK(1)-EVKNAR(3) |
| 63 | sp\|P0A6L9\|HSCB_ECOLI (119)- sp\|P0A6L9\|HSCB_ECOLI (123) | LESFIKR(6)-KMFDTR(1) |
| 64 | sp\|P095511ARGT_ECOLI (120)- sp\|P09551\|ARGT_ECOLI (198) | LIAAKGSPIQPTLDSLK(5)- QPAGKDFAFAGSSVK(5) |
| 65 | sp\|P62707\|GPMA_ECOLI (146)- sp\|P62707\|GPMA_ECOLI (86) | LSEKELPLTESLALTIDR(4)- SWKLNER(3) |
| 66 | sp\|C4ZRL2\|YACL_ECOBW (1)- sp\|P42592\|YGJK_ECOLI (169) | MDYEFLR(1)-LEAKEGK(4) |
| 67 | sp\|C4ZZT2\|ENO_ECOBW (195)- sp\|C4ZZT2\|ENO_ECOBW (56) | MGSEVFHHLAKVLK(11)- DGDKSR(4) |
| 68 | sp\|B1XGX6\|PNP_ECODH (1)- sp\|B1XGX6\|PNP_ECODH (228) | MLNPIVR(1)-EAGKPR(4) |
| 69 | sp\|P06610\|BTUE_ECOLI (1)- sp\|P06610\|BTUE_ECOLI (157) | MQDSILTTVVK(1)-DGKVIQR(3) |
| 70 | sp\|B1XFM4\|TIG_ECODH (1)- sp\|B1XFM4\|TIG_ECODH (81) | MQVSVETTQGLGR(1)- NFIDAIIKEK(8) |
| 71 | sp\|C4ZYA1\|PDXH_ECOBW (1)- sp\|C4ZYA1\|PDXH_ECOBW (2) | MSDNDELQQIAHLR(1)- SDNDELQQIAHLR(1) |
| 72 | sp\|P18200\|PGPA_ECOLI (1)- sp\|P10100\|RLPA_ECOLI (66) | MTILPR(1)-DGKSYK(3) |

TABLE 5-continued

CXMS analysis of BS2G cross-linked *E. coli* cell lysate

| No. | Cross-linking site | Cross-linked peptides (Numbers in parentheses indicate cross-linked residues) |
|---|---|---|
| 73 | sp\|P64467\|CNU_ECOLI (9)- sp\|P64467\|CNU_ECOLI (12) | MTVQDYLLKFR(9)- KISSLESLEK(1) |
| 74 | sp\|B1X833\|SYS_ECODH (17)- sp\|B1X833\|SYS_ECODH (1) | NEPDAVAEKLAR(9)- MLDPNLLR(1) |
| 75 | sp\|P0AE08\|AHPC_ECOLI (27)- sp\|P0AE08\|AHPC_ECOLI (12) | NGEFIEITEKDTEGR(10)- IKPFKNQAFK(5) |
| 76 | sp\|B1XD64\|SYP_ECODH (547)- sp\|B1XD64\|SYP_ECODH (554) | NLDNDDIEYKYR(10)- NGEKQLIK(4) |
| 77 | sp\|B1XB26\|GLYA_ECODH (331)- sp\|B1XB26\|GLYA_ECODH (62) | NLTGKEADAALGR(5)- YAEGYPGKR(8) |
| 78 | sp\|B1XHK9\|MDH_ECODH (107)- sp\|B1XHK9\|MDH_ECODH (134) | NLVQQVAKTCPK(8)- KAGVYDK(1) |
| 79 | sp\|P0AFG6\|ODO2_ECOLI (211)- sp\|P0AFG6\|ODO2_ECOLI (218) | NSTAMLTTFNEVNMKPIMDLR(15)- KQYGEAFEK(1) |
| 80 | sp\|P0ACF8\|HNS_ECOLI (96)- sp\|P0ACF8\|HNS_ECOLI (136) | PAKYSYVDENGETK(3)- SLDDFLKQ(8) |
| 81 | sp\|P00957\|SYA_ECOLI (232)- sp\|P00957\|SYA_ECOLI (56) | QADGTMEPLPKPSVDTGMGLER(11)- DVFLGLDKR(8) |
| 82 | sp\|C4ZUS8\|KAD_ECOBW (50)- sp\|C4ZUS8\|KAD_ECOBW (40) | QAKDIMDAGK(3)- AAVKSGSELGK(4) |
| 83 | sp\|P0AFG3\|ODO1_ECOLI (589)- sp\|P0AFG3\|ODO1_ECOLI (576) | QAMAAGEKLFDWGGAENLAYATL VDEGIPVR(8)-VAKIYGDR(3) |
| 84 | sp\|B1X6Q8\|SUCC_ECODH (215)- sp\|B1X6Q8\|SUCC_ECODH (1) | QGDLICLDGKLGADGNALFR(10)- MNLHEYQAK(1) |
| 85 | sp\|P02924\|ARAF_ECOLI (45)- sp\|P02924\|ARAF_ECOLI (52) | QPEEPWFQTEWKFADK(12)- AGKDLGFEVIK(3) |
| 86 | sp\|P0A6F5\|CH60_ECOLI (364)- sp\|P0A6F5\|CH60_ECOLI (371) | QQIEEATSDYDREKLQER(14)- VAKLAGGVAVIK(3) |
| 87 | sp\|C4ZSQ9\|IF2_ECOBW (42)- sp\|C4ZSQ9\|IF2_ECOBW (2) | SADDSVSAQEKQTLIDHLNQK(11)- TDVTIK(1) |
| 88 | sp\|B1XBC1\|CAPP_ECODH (693)- sp\|B1XBC1\|CAPP_ECODH (855) | SATPEQELGKLPLGSR(10)- QAEKEGQEPDPR(4) |
| 89 | sp\|B1XHK9\|MDH_ECODH (99)- sp\|B1XHK9MDH_ECODH (134) | SDLFNVNAGIVKNLVQQVAK(12)- KAGVYDK(1) |
| 90 | sp\|P0A6F5\|CH60_ECOLI (51)- sp\|P0A6F5\|CH60_ECOLI (117) | SFGAPTITKDGVSVAR(9)- AVAAGMNPMDLKR(12) |
| 91 | sp\|P39325\|YTFQ_ECOLI (98)- sp\|P39325\|YTFQ_ECOLI (117) | SFVAQGVDAIFIAPVVATGWEPVLK EAK(25)-SIDVKDK(5) |
| 92 | sp\|P0AEH5\|ELAB_ECOLI (2)- sp\|P0AEH5\|ELAB_ECOLI (66) | SNQFGDTR(1)-AKQAVYR(2) |
| 93 | sp\|P0AEE5\|DGAL_ECOLI (269)- sp\|P0AEE5\|DGAL_ECOLI (323) | SSIPVFGVDALPEALALVKSGALAGT VLNDANNQAK(19)- VPYVGVDKDNLAEFSK(8) |
| 94 | sp\|P0AFG6\|ODO2_ECOLI (2)- sp\|P0AFG6\|ODO2_ECOLI (85) | SSVDILVPDLPESVADATVATWHK(1)- EGNSAGKETSAK(7) |
| 95 | sp\|P69503\|APT_ECOLI (2)- sp\|P69503\|APT_ECOLI (53) | TATAQQLEYLK(1)-YKNAGITK(2) |
| 96 | sp\|P0AES6\|GYRB_ECOLI (299)- sp\|P37766\|YDIF_ECOLI (159) | TLNAYMDKEGYSKK(8)- LNEVTKEDLIK(6) |

TABLE 5-continued

CXMS analysis of BS2G cross-linked *E. coli* cell lysate

| No. | Cross-linking site | Cross-linked peptides (Numbers in parentheses indicate cross-linked residues) |
|---|---|---|
| 97 | sp\|C4ZUG0\|RL6 ECOBW (44)-sp\|C4ZUG0\|RL6_ECOBW (6) | TLNDAVEVKHADNTLTFGPR(9)-VAKAPVVVPAGVDVK(3) |
| 98 | sp\|P42632\|TDCE_ECOLI (356)-sp\|P0ADY1\|PPID_ECOLI (511) | TLVTKNSFR(5)-DLKAGK(3) |
| 99 | sp\|P0A6Y8\|DNAK_ECOLI (55)-sp\|P0A6Y8\|DNAK_ECOLI (263) | TTPSIIAYTQDGETLVGQPAKR(21)-LKEAAEK(2) |
| 100 | sp\|P0A6F5\|CH60_ECOLI (277)-sp\|P0A6F5\|CH60_ECOLI (226) | VAAVKAPGFGDR(5)-KISNIR(1) |
| 101 | sp\|C4ZVL3\|PDXB_ECOBW (338)-sp\|C4ZVL3\|PDXB_ECOBW (341) | VAGIPGEFDKLR(10)-KNYLER(1) |
| 102 | sp\|P0A6F5\|CH60_ECOLI (371)-sp\|P0A6F5\|CH60_ECOLI (364) | VAKLAGGVAVIK(3)-EKLQER(2) |
| 103 | sp\|P0A6F5\|CH60_ECOLI (390)-sp\|P0A6F5\|CH60_ECOLI (277) | VGAATEVEMKEK(10)-VAAVKAPGFGDR(5) |
| 104 | sp\|B1XBY9\|RPOB_ECODH (890)-sp\|B1XBY9\|RPOB_ECODH (914) | VTPKGETQLTPEEK(4)-ASDVKDSSLR(5) |
| 105 | sp\|P0A9B2\|G3P1_ECOLI (124)-sp\|P0A9B2\|G3P1_ECOLI (192) | VVMTGPSKDNTPMFVK(8)-TVDGPSHKDWR(8) |
| 106 | sp\|C4ZSJ8\|SYM_ECOBW (466)-sp\|C4ZSJ8\|SYM_ECOBW (403) | YVDEQAPWVVAKQEGR(12)-NAGFINKR(7) |

TABLE 6

CXMS analysis of NHSF cross-linked E. coli cell lysate

| No. | Cross-linking site | Cross-linked peptides (Numbers indicates cross-linked residues) |
|---|---|---|
| 1 | sp\|P0A9B2\|G3P1_ECOLI (139)-sp\|P0A9B2\|G3P1_ECOLI (132) | YAGQDIVSNASCTTNCLAPLAK(1)-DNTPMFVKGANFDK(8) |
| 2 | sp\|P04395\|3MG2_ECOLI (261)-sp\|P0A858\|TPIS_ECOLI (177) | YAERWKPWR(6)-SATPAOAOAVHK(1) |
| 3 | sp\|P27302\|TKT1_ECOLI (596)-sp\|P27302\|TKT1_ECOLI (603) | VVSMPSTDAFDKQDAAYR(17)-ESVLPKAVTAR(6) |
| 4 | sp\|P27302\|TKT1_ECOLI (591)-sp\|P27302\|TKT1_ECOLI (599) | VVSMPSTDAFDKQDAAYR(12)-ESVLPKAVTAR(2) |
| 5 | sp\|P0A9B2\|G3P1_ECOLI (120)-sp\|P0A9B2\|G3P1_ECOLI (192) | VVMTGPSKDNTPMFVK(4)-TVDGPSHKDWR(8) |
| 6 | sp\|P0A9B2\|G3P1_ECOLI (127)-sp\|P0A9B2\|G3P1_ECOLI (192) | VVMTGPSKDNTPMFVK(11)-TVDGPSHKDWR(8) |
| 7 | sp\|B1X750\|PCKA _ECODH (340)-sp\|B1X750\|PCKA _ECODH (350) | VSYPIYHIDNIVK(7)-PVSKAGHATK(4) |
| 8 | sp\|P0AAT9\|YBEL_ECOLI (39)-sp\|P0AAT9\|YBEL_ECOLI (46) | VIKTGELTR(3)-TEVDELTR(1) |
| 9 | sp\|P0CE48\|EFTU2_ECOLI (249)-sp\|P0CE48\|EFTU2_ECOLI (254) | VGEEVEIVGIKETQK(11)-STCTGVEMFR(1) |
| 10 | sp\|C4ZXM9\|RL28_ECOBW (10)-sp\|C4ZXM9\|RL28_ECOBW (14) | VCQVTGKR(7)-PVTGNNR(3) |

TABLE 6-continued

CXMS analysis of NHSF cross-linked E. coli cell lysate

| No. | Cross-linking site | Cross-linked peptides (Numbers indicates cross-linked residues) |
|---|---|---|
| 11 | sp\|P09373\|PFLB_ECOLI (195)- sp\|P09373\|PFLB_ECOLI (2) | VALYGIDYLMKDK(11)- SELNEK(1) |
| 12 | sp\|P09373\|PFLB_ECOLI (195)- sp\|P09373\|PFLB_ECOLI (235) | VALYGIDYLMKDK(11)- ALGQMKEMAAK(6) |
| 13 | sp\|B1XA37\|PEPT _ECODH (177)- sp\|B1XA37\|PEPT _ECODH (181) | VAFTPDEEVGKGAK(11)- HFDVDAFDAR(1) |
| 14 | sp\|P0A6F5\|CH60_ECOLI (277)- sp\|P0A6F5\|CH60_ECOLI (226) | VAAVKAPGFGDR(5)-KISNIR(1) |
| 15 | sp\|B1XBY9\|RPOB _ECODH (159)- sp\|B1XBY9 RPOB _ECODH (163) | SPGVFFDSDK(8)-GKTHSSGK(2) |
| 16 | sp\|P32132\|TYPA_ECOLI (383)- sp\|P32132\|TYPA_ECOLI (386) | REGFELAVSR(9)-PKVIFR(2) |
| 17 | sp\|P0CE48\|EFTU2_ECOLI (137)- sp\|P0CE48\|EFTU2_ECOLI (159) | QVGVPYIIVFLNKCDMVD DEELLELVEMEVR(13)- ELLSQYDFPGDDTPIVR(4) |
| 18 | sp\|P0A6F5\|CH60_ECOLI (364)- sp\|P0A6F5\|CH60_ECOLI (371) | QQEEEATSDYDREKLQER(14)- VAKLAGGVAVIK(3) |
| 19 | sp\|P0A6F5\|CH60_ECOLI (358)- sp\|P0A6F5\|CH60_ECOLI (364) | QQIEEATSDYDR(8)- EKLQER(2) |
| 20 | sp\|P0A6F5\|CH60_ECOLI (360)- sp\|P0A6F5\|CH60_ECOLI (364) | QQIEEATSDYDR(10)- EKLQER(2) |
| 21 | sp\|P37902\|GLTI_ECOLI (122)- sp\|P37902\|GLTI_ECOLI (240) | QKQAAFSDTIFVVGTR(2)- KDDPQFK(1) |
| 22 | sp\|P27302\|TKT1_ECOLI (603)- sp\|P27302\|TKT1_ECOLI (585) | QDAAYRESVLPKAVTAR(12)- VVSMPSTDAFDK(6) |
| 23 | sp\|P28635\|METQ_ECOLI (97)- sp\|P28635\|METQ_ECOLI (88) | PYLDQQLKDR(8)- GDIDANAFQHK(10) |
| 24 | sp\|C4ZTI3\|YAJQ_ECOBW (2)- sp\|C4ZTI3\|YAJQ_ECOBW (135) | PSFDIVSEVDLQEAR(1)- VTGKSR(4) |
| 25 | sp\|P0A6F5\|CH60_ECOLI (261)- sp\|P0A6F5\|CH60_ECOLI (242) | PLLIIAEDVEGEALATLVVNT MR(16)-EMLPVLEAVAKAGK(11) |
| 26 | sp\|C4ZPV2\|SYI_ECOBW (116)- sp\|C4ZPV2\|SYI_ECOBW (110) | PGEKFTAAEFR(4)- VEQEYGK(5) |
| 27 | sp\|P75823\|LTAE_ECOLI (126)- sp\|P75823\|LTAE_ECOLI (119) | PDDIHFAR(5)-VAMKIK(4) |
| 28 | sp\|P0AE08\|AHPC_ECOLI (25)- sp\|P0AE08\|AHPC_ECOLI (12) | NGEFIEITEKDTEGR(8)- IKPFKNQAFK(5) |
| 29 | sp\|P0ADT8\|YGIM_ECOLI (153)- sp\|P0A9P0\|DLDH_ECOLI (239) | NELIVAQKK(8)-VTAVEAK(2) |
| 30 | sp\|P0AFG0\|NUSG_ECOLI (121)- sp\|P0AFG0\|NUSG_ECOLI (126) | LQQVGDKPRPK(7)- TLFEPGEMVR(1) |
| 31 | sp\|P0A6Y8\|DNAK_ECOLI (239)- sp\|P0A6Y8\|DNAK_ECOLI (246) | LINYLVEEFK(4)-KDQGIDLR(1) |
| 32 | sp\|P02925\|RBSB_ECOLI (57)- sp\|P02925\|RBSB_ECOLI (50) | LGYNLVVLDSQNNPAK(3)- DGAQKEADK(5) |
| 33 | sp\|P77434\|ALAC_ECOLI (349)- sp\|P0AD37\|YFEC_ECOLI (13) | KLLNEAK(1)-LTGYSR(5) |
| 34 | sp\|P0A6A8\|ACP_ECOLI (10)- sp\|P0A6A8\|ACP_ECOLI (3) | KIIGEQLGVK(1)-STIEER(2) |

TABLE 6-continued

CXMS analysis of NHSF cross-linked E. coli cell lysate

| No. | Cross-linking site | Cross-linked peptides (Numbers indicates cross-linked residues) |
|---|---|---|
| 35 | sp\|P0A6A8\|ACP_ECOLI (10)- sp\|P0A6A8\|ACP_ECOLI (2) | KIIGEQLGVK(1)-STIEER(1) |
| 36 | sp\|P23847\|DPPA_ECOLI (517)- sp\|P23847\|DPPA_ECOLI (533) | KEVKGYVVDPLGK(4)- HHFENVSIE(7) |
| 37 | sp\|P0ABT2\|DPS_ECOLI (27)- sp\|P0ABT2\|DPS_ECOLI (24) | KATVELLNR(1)-NDVSDSEK(6) |
| 38 | sp\|P0ABT2\|DPS_ECOLI (27)- sp\|P0ABT2\|DPS_ECOLI (22) | KATVELLNR(1)-NDVSDSEK(4) |
| 39 | sp\|B1XBY8\|RL7 _ECODH (109)- sp\|B1XBY8 RL7 _ECODH (100) | KALEEAGAEVEVK(1)- EGVSKDDAEALK(4) |
| 40 | sp\|C4ZYU1\|CSRA_ECOBW (38)- sp\|C4ZYU1\|CSRA_ECOBW (48) | IGVNAPKEVSVHR(7)- EEIYQR(4) |
| 41 | sp\|P07118\|SYV_ECOLI (909)- sp\|P07118\|SYV_ECOLI (926) | IENKLANEGFVAR(4)- APEAVIAKER(8) |
| 42 | sp\|P0ADN2\|YIFE_ECOLI (49)- sp\|P0ADN2\|YIFE_ECOLI (54) | HGYAFNELDLGKR(12)- EPVTEEEK(4) |
| 43 | sp\|P02925\|RBSB_ECOLI (275)- sp\|P02925\|RBSB_ECOLI (281) | GVETADKVLK(7)-GEKVQAK(3) |
| 44 | sp\|P02925\|RBSB_ECOLI (272)- sp\|P02925\|RBSB_ECOLI (281) | GVETADKVLK(4)-GEKVQAK(3) |
| 45 | sp\|P0AEP3\|GALU_ECOLI (193)- sp\|P0AEP3\|GALU_ECOLI (204) | GVELAPGESVPMVGVVEK(9)- PKADVAPSNLAIVGR(2) |
| 46 | sp\|P0CE48\|EFTU2_ECOLI (174)- sp\|P0CE48\|EFTU2_ECOLI (264) | GSALKALEGDAEWEAK(2)- KLLDEGR(1) |
| 47 | sp\|Q46942\|YQEI_ECOLI (91)- sp\|Q46942\|YQEI_ECOLI (184) | GFRAVGDTTHSLIATVPR(11)- PFFKDYK(4) |
| 48 | sp\|P02925\|RBSB_ECOLI (281)- sp\|P02925\|RBSB_ECOLI (272) | GEKVQAKYPVDLK(3)- GVETADKVLK(4) |
| 49 | sp\|P0A6P1\|EFTS_ECOLI (168)- sp P0A6P1 EFTS_ECOLI (182) | GADEELVKHIAMHVAASK(9)- PEFIKPEDVSAEVVEK(5) |
| 50 | sp\|P0A6P 1\|EFTS_ECOLI (176)- sp\|P0A6P1\|EFTS_ECOLI (182) | GADEELVKHIAMHVAASK(17)- PEFIKPEDVSAEVVEK(5) |
| 51 | sp\|C4ZZT2\|ENO_ECOBW (62)- sp\|C4ZZT2\|ENO_ECOBW (56) | FLGKGVTK(4)-DGDKSR(4) |
| 52 | sp\|B1XFM4\|TIG _ECODH (239)- sp\|B1XFM4\|TIG _ECODH (183) | FAINLKKVEER(7)- ASDFVLAMGQGR(2) |
| 53 | sp\|B1XFM4\|TIG _ECODH (238)- sp\|B1XFM4\|TIG _ECODH (183) | FAINLKKVEER(6)- ASDFVLAMGQGR(2) |
| 54 | sp\|P37095\|PEPB_ECOLI (157)- sp\|P37095\|PEPB_ECOLI (148) | EQGYMGLHTVGR(4)- ITKGEDLR(3) |
| 55 | sp\|P391731YEAD_ECOLI (197)- sp\|P39173\|YEAD_ECOLI (187) | ENVLTDGIQTFPDR(5)- FIDKVNDAK(4) |
| 56 | sp\|P0CE48\|EFTU2_ECOLI (161)- sp\|P0CE48\|EFTU2_ECOLI (264) | ELLSQYDFPGDDTPIVR(6)- KLLDEGR(1) |
| 57 | sp\|P0CE48\|EFTU2_ECOLI (159)- sp\|P0CE48\|EFTU2_ECOLI (264) | ELLSQYDFPGDDTPIVR(4)- KLLDEGR(1) |
| 58 | sp\|P32132\|TYPA_ECOLI (383)- sp\|P32132\|TYPA_ECOLI (386) | EGFELAVSR(8)-PKVIFR(2) |

TABLE 6-continued

CXMS analysis of NHSF cross-linked E. coli cell lysate

| No. | Cross-linking site | Cross-linked peptides (Numbers indicates cross-linked residues) |
|---|---|---|
| 59 | sp\|B!X905\|YFBU _ECODH (55)- sp\|B1X905\|YFBU _ECODH (103) | EFGELKEETCR(6)-YLGYVR(1) |
| 60 | sp\|C4ZYU1\|CSRA_ECOBW (48)- sp\|P0AAE5\|ARCD_ECOLI (57) | EEIYQR(4)-MLILTR(1) |
| 61 | sp\|P0ACF8\|HNS_ECOLI (22)- sp\|P0ACF8\|HNS_ECOLI (6) | ECTLETLEEMLEK(3)- SEALKILNNIR(5) |
| 62 | sp\|B1XFC2\|FETP _ECODH (28)- sp\|B1XFC2\|FETP _ECODH (31) | EAEGQDFQLYPGELGKR(16)- IYNEISK(2) |
| 63 | sp\|P0AFG6\|ODO2_ECOLI (297)- sp\|P0AFG6\|ODO2_ECOLI (300) | DVDTLGMADIEKK(12)- IKELAVK(2) |
| 64 | sp\|P0AFG6\|ODO2_ECOLI (289)- sp\|P0AFG6\|ODO2_ECOLI (298) | DVDTLGMADIEK(4)- KIKELAVK(1) |
| 65 | sp\|B1X9G2\|OPGG _ECODH (144)- sp\|B1X9G2\|OPGG _ECODH (141) | DKNDEIVSMLGASYFR(2)- VLYPINSK(7) |
| 66 | sp\|C4ZZT2\|ENO_ECOBW (254)- sp\|C4ZZT2\|ENO_ECOBW (258) | DITLAMDCAASEFYKDGK(15)- YVLAGEGNK(1) |
| 67 | sp\|P39325\|YTFQ_ECOLI (244)- sp\|P39325\|YTFQ_ECOLI (237) | DILTGSIDGVPDIYK(4)- EAGLKPGK(5) |
| 68 | sp\|P37689\|GPMI_ECOLI (237)- sp\|P37689\|GPMI_ECOLI (189) | DENDEFVKATVIR(8)- YYAMDR(2) |
| 69 | sp\|C4ZRR4\|RRF_ECOBW (138)- sp\|C4ZRR4\|RRF_ECOBW (1) | DANDKVK(5)-MISDIR(1) |
| 70 | sp\|P0A6P1\|EFTS_ECOLI (95)- sp\|P0A8M0\|SYN_ECOLI (126) | DAGFQAFADKVLDAAVAGK(10)- EVAHLR(4) |
| 71 | sp\|P0AE52\|BCP_ECOLI (72)- sp\|P0AE52\|BCP_ECOLI (77) | AGVDVLGISTDK(10)- PEKLSR(3) |
| 72 | sp\|P0A799\|PGK_ECOLI (27)- sp\|P77485\|CUSS_ECOLI (466) | ADLNVPVKDGK(8)- VTSDAR(2) |
| 73 | sp\|P76177\|YDGH_ECOLI (95)- sp\|P76177\|YDGH_ECOLI (89) | ADAEKAEETSNR(5)- VVADLYK(6) |

REFERENCES FOR EXAMPLES 1-3

1. Young M M, et al. (2000) High throughput protein fold identification by using experimental constraints derived from intramolecular cross-links and mass spectrometry. Proc. Natl. Acad. Sci. U.S.A. 97(11):5802-5806. 2. Herzog F, et al. (2012) Structural probing of a protein phosphatase 2A network by chemical cross-linking and mass spectrometry. Science 337(6100):1348-1352. 3. Shi Y, et al. (2015) A strategy for dissecting the architectures of native macromolecular assemblies. Nat Methods 12(12):1135-1138. 4. Yu C & Huang L (2018) Cross-Linking Mass Spectrometry: An Emerging Technology for Interactomics and Structural Biology. Anal. Chem. 90(1):144-165. 5. Sinz A (2018) Cross-Linking/Mass Spectrometry for Studying Protein Structures and Protein-Protein Interactions: Where Are We Now and Where Should We Go from Here? Angew. Chem. Int. Ed. Engl. 57(22):6390-6396. 6. Novak P & Kruppa G H (2008) Intra-molecular cross-linking of acidic residues for protein structure studies. Eur J Mass Spectrom (Chichester) 14(6):355-365. 7. Leitner A, et al. (2014) Chemical cross-linking/mass spectrometry targeting acidic residues in proteins and protein complexes. Proc. Natl. Acad. Sci. U.S.A. 111(26):9455-9460. 8. Gutierrez C B, et al. (2016) Developing an Acidic Residue Reactive and Sulfoxide-Containing MS-Cleavable Homobifunctional Cross-Linker for Probing Protein-Protein Interactions. Anal. Chem. 88(16):8315-8322. 9. Bass R B, Butler S L, Chervitz S A, Gloor S L, & Falke J J (2007) Use of site-directed cysteine and disulfide chemistry to probe protein structure and dynamics: applications to soluble and transmembrane receptors of bacterial chemotaxis. Methods Enzymol. 423:25-51. 10. Merkley E D, et al. (2014) Distance restraints from crosslinking mass spectrometry: mining a molecular dynamics simulation database to evaluate lysine-lysine distances. Protein Sci. 23(6):747-759. 11. Suchanek M, Radzikowska A, & Thiele C (2005) Photo-leucine and photo-methionine allow identification of protein-protein interactions in living cells. Nat Methods 2(4):261-267. 12. Yang B, et al. (2017) Spontaneous and specific chemical cross-linking in live cells to capture and identify protein interactions. Nature communications 8(1):2240. 13. Xiang Z, et al. (2013) Adding an unnatural covalent bond to proteins through proximity-enhanced bioreactivity. Nat. Methods 10(9):885-888. 14. Chen X H, et al. (2014) Genetically encoding an electrophilic amino Acid for protein stapling and covalent binding to native receptors. ACS Chem. Biol. 9(9):1956-1961. 15. Xiang Z, et al. (2014) Proximity-enabled protein crosslinking through genetically encoding haloalkane unnatural amino acids. Angew. Chem. Int. Ed. Engl. 53:2190-2193. 16. Hoppmann C, Maslennikov I, Choe S, & Wang L (2015) In Situ Formation of an Azo Bridge on Proteins Controllable by Visible Light. J. Am. Chem. Soc. 137(35):11218-11221. 17. Wang L (2017) Genetically encoding new bioreactivity. N Biotechnol 38(Pt A):16-25. 18. Hoppmann C & Wang L (2016) Proximity-enabled bioreactivity to generate covalent peptide inhibitors of p53-Mdm4. Chem Commun (Camb) 52(29):5140-5143. 19. Wang N, et al. (2018) Genetically encoding fluorosulfate-L-tyrosine to react with lysine, histidine, and tyrosine via SuFEx in proteins in vivo. J. Am. Chem. Soc. 140:4995-4999. 20. Tsukiji S, Miyagawa M, Takaoka Y, Tamura T, & Hamachi I (2009) Ligand-directed tosyl chemistry for protein labeling in vivo. Nat. Chem. Biol. 5(5):341-343. 21. Narayanan A & Jones L H (2015) Sulfonyl fluorides as privileged warheads in chemical biology. Chem Sci 6(5):2650-2659. 22. Dong J, Krasnova L, Finn M G, & Sharpless K B (2014) Sulfur(VI) fluoride exchange (SuFEx): another good reaction for click chemistry. Angew. Chem. Int. Ed. Engl. 53(36):9430-9448. 23. Woltjer R L, Weclas-Henderson L, Papayannopoulos I A, & Staros J V (1992) High-yield covalent attachment of epidermal growth factor to its receptor by kinetically controlled, stepwise affinity cross-linking. Biochemistry 31(32):7341-7346. 24. Bogan A A & Thorn K S (1998) Anatomy of hot spots in protein interfaces. J. Mol. Biol. 280(1):1-9. 25. Mukherjee H, et al. (2017) A study of the reactivity of S((VI))-F containing warheads with nucleophilic amino-acid side chains under physiological conditions. Org. Biomol. Chem. 15(45): 9685-9695.

Example 4: Photocaged Quinone Methide Crosslinkers for Light-Controlled Chemical Crosslinking of Protein-Protein and Protein-DNA Complexes Small molecule crosslinkers have been invaluable for probing biomolecular interactions and critical for the emerging cross-linking mass spectrometry (CXMS) in addressing the challenging large protein complexes and intrinsically disordered proteins. Existing chemical crosslinkers target only a small selection of amino acid residues, limiting the number and type of crosslinks, while conventional photocrosslinkers target virtually all residues non-selectively, dramatically complicating data analysis. Here we report a series of photocaged quinone methide (PQM)-based crosslinkers that are able to multitarget ten nucleophilic amino acid residues through specific Michael addition. In addition to Asp, Glu, Lys, Ser, Thr and Tyr, PQM crosslinkers notably crosslinked Gln, Arg, Asn, and Met hitherto untargetable by existing chemical crosslinkers, markedly increasing the number of residues targetable with a single crosslinker. Such multiplicity of crosslinks will significantly expand the diversity of proteins amenable to CXMS and afford abundant restraints to facilitate structural deciphering. We demonstrated the use of PQM crosslinkers in vitro, in *E. coli*, and in mammalian cells to crosslink dimeric proteins and endogenous membrane receptors. We also showed that crosslinker NHQM could directly crosslink proteins to DNA, for which few crosslinkers exist. The photoactivatable and multitargeting reactivity of these PQM crosslinkers will substantially enhance chemical crosslinking based technologies for studies of protein-protein and protein-DNA networks and for structural biology.

Small molecule crosslinkers have been invaluable for studying biomolecular interactions. An emerging technology for protein interaction and structural biology is the cross-linking mass spectrometry (CXMS), which analyzes proteins crosslinked by small molecule crosslinkers with tandem mass spectrometry, affording identities and distance restraints of crosslinked residues.[1] [2] It has been increasingly used to probe protein interaction networks and to derive tertiary structural information of large protein complexes and intrinsically disordered proteins, uniquely complementing X-ray crystallography, NMR spectroscopy, and cryo-electron microscopy. Small molecule crosslinkers are also developed for crosslinking DNA to proteins, which is a critical step for chromatin immunoprecipitation (ChIP), a method widely used for mapping DNA-protein interactions across eukaryotic genomes in cells, tissues, and whole organisms.[3] Chemical crosslinkers react with target residues specifically. For instance, the most commonly used cross-linkers contain homobifunctional N-hydroxysuccinimidyl (NHS) esters to react with Lys side chain or N-terminal amine group. Cross-linkers targeting Cys, Glu, Asp, and His have also been developed.[4] [5] [6] [7] Expanding the repertoire of residues targetable by chemical crosslinkers would increase the number and types of restraints obtainable from CXMS. Recently, we reported a plant-and-cast strategy enabling small molecule crosslinkers to crosslink Lys residues with His, Ser, Thr, Tyr, and Lys side chains through sulfur-fluoride exchange (SuFEx) reaction, showcasing the feasibility of targeting multiple amino acid residues via new chemistry.[8] However, a variety of amino acid residues remain untargetable. On the other hand, conventional photocrosslinkers (such as diazirines, azides, and benzophenones) target virtually all residues non-selectively.[9] [10] Unfortunately, such nonspecific chemistry often results in highly complex crosslinked products, dramatically complicating MS data analysis. In addition, excessive crosslinking may artificially distort protein tertiary structures.[1] [2] For DNA-protein crosslinking, formaldehyde remains the primary reagent despite its short crosslink distance (~2 Å) and limited reactivity with few amino acid residues.[3] Therefore, new small molecule crosslinkers able to multi-target different amino acid residues, especially those inaccessible to date, with specific chemistry would be invaluable for realizing the full potential of cross-linking based technologies.

We report here a new series of photocaged quinone methide (PQM)-based small molecule crosslinkers, which integrate the advantages of chemical crosslinkers (i.e., specific chemical reactivity) and conventional photocrosslinkers (i.e., photo-controllability and thus potential for spatiotemporal resolution) for crosslinking biomolecules. In protein-protein crosslinking these PQM crosslinkers were able to multitarget ten different amino acid residues through Michael addition, among which Gln, Arg, Asn, and Met were crosslinked for the first time by a chemical crosslinker. We demonstrated their use for crosslinking proteins in vitro, in *E. coli* cells and in mammalian cells, and the ability to crosslink proteins with DNA as well.

Quinone methides are efficient Michael acceptors for nucleophiles and have been versatile for chemical synthesis and chemical biology.[11] [12] [13] [14] We recently genetically encoded an unnatural amino acid (Uaa) FnbY containing a photocagedpara-quinone methide into proteins and showed its specific reactivity toward multiple nucleophilic amino acid residues placed in proximity.[15] We therefore reasoned that integration of photocaged QM into small molecule crosslinkers would enable the desired multi-targeting ability through specific Michael additional chemistry, as well as photocontrolled reactivity for potential spatiotemporal resolution.

Figure 7A:
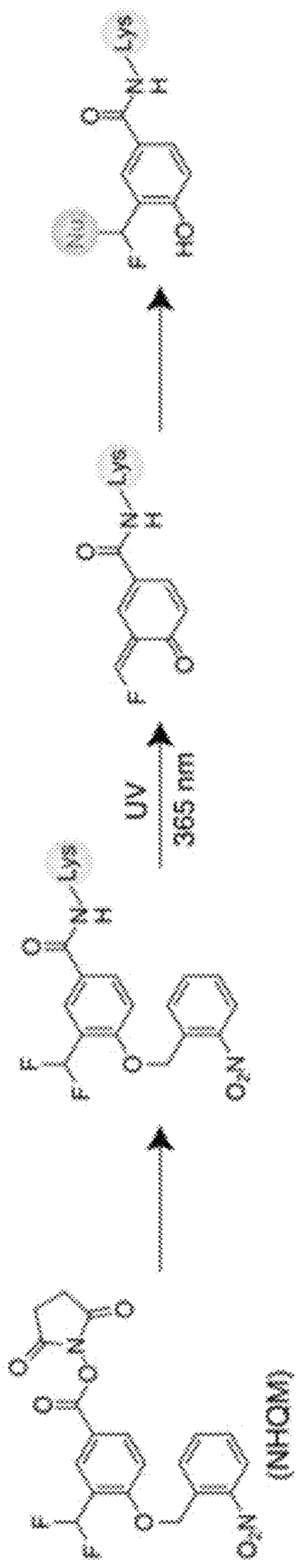
FIGS. 7A-7D. NHQM mediated protein crosslinking in vitro.
Figure 7B:
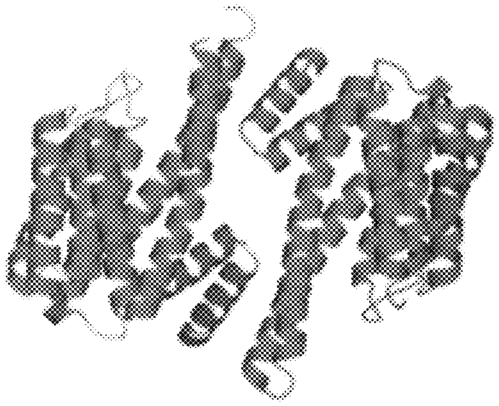
Figure 7C:
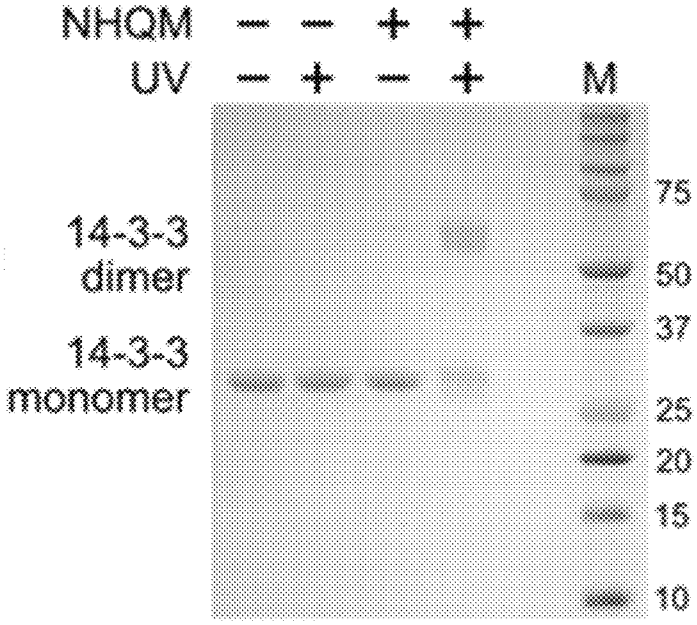
Figure 7D:
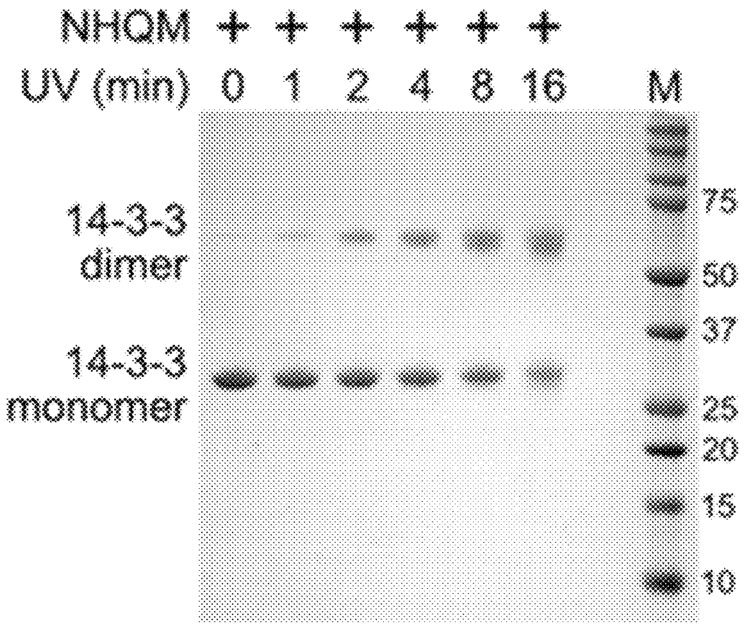
Figure 8:
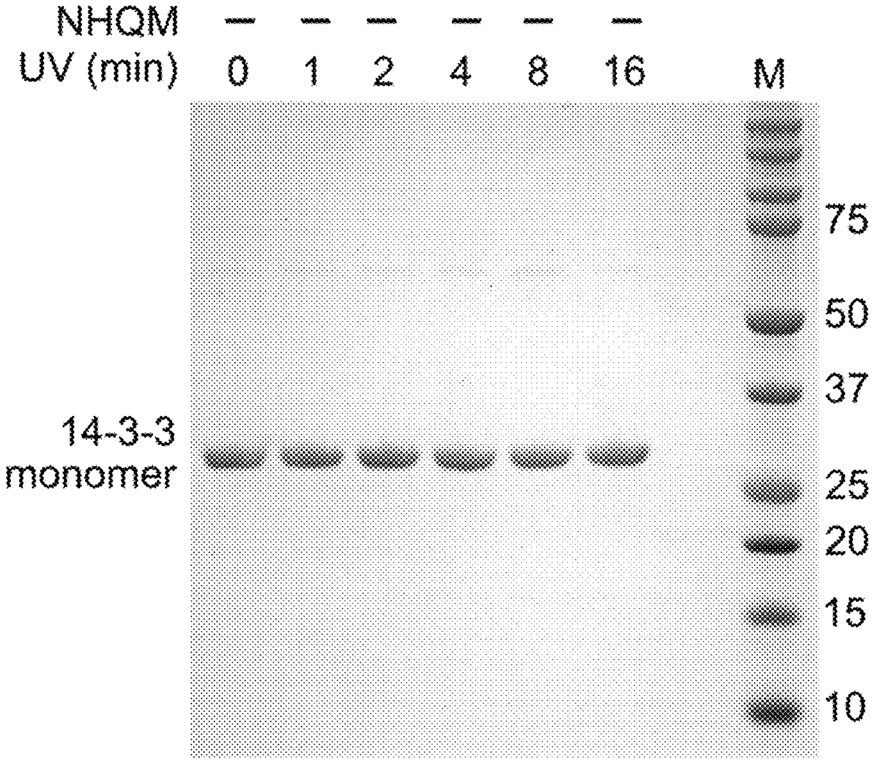
FIG. 8. SDS-PAGE analysis of NHQM-mediated dimeric crosslinking of 14-3-3 with different time duration of UV exposure. 0.25 mg/mL 14-3-3 WT was incubated without 1 mM NHQM, followed UV illumination at 365 nm for 0, 1, 2, 4, 8, 16 min. At each time point, the reaction was treated by adding 100 mM Tris-HCI, pH 7.5 and incubated at RT for 15 min. The samples were then prepared with SDS loading dye containing 100 mM DTT, boiled at 95° C. for 5 min, and run in 10% Tris-tricine SDS-PAGE gel. Results for NHQM treated samples are shown in FIG. 1D. This figure shows the negative control without adding NHQM.

We initially designed and synthesized a heterobifunctional crosslinker NHQM containing an NHS ester and a photocaged ortho-quinone methide (o-QM) (FIG. 7A). Two fluorines were installed at the methyl group ortho to the phenolic hydroxyl group, which was photocaged by an o-nitrobenzyl group. When in proximity to proteins, the reactive NHS ester will react with exposed Lys residues, planting the photocaged o-QM next to residues on interaction partners. UV release of o-nitrobenzyl induces elimination of a fluoride ion to generate o-QM spontaneously, which will subsequently crosslink with nearby nucleophilic side chains (FIG. 7A). To test the crosslinking ability of NHQM in response to light, we incubated the 14-3-3 protein, a homodimeric eukaryotic regulatory protein (FIG. 7B),[16] as a model protein with or without 1 mM NHQM in the presence or absence of UV illumination (λ=365 nm). As resolved by SDS-PAGE, crosslinked dimer of 14-3-3 was detected only with addition of NHQM crosslinker and UV illumination (FIG. 7C), suggesting that the dimeric crosslinking was through the photo-released QM. We further studied the crosslinking rate by varying the duration of UV treatment immediately after addition of NHQM. The crosslinking of 14-3-3 could be observed on SDS-PAGE as short as 1 min of UV exposure, and the intensity of the crosslinked band increased with UV exposure time (FIG. 7D, FIG. 8), indicating that NHQM-mediated crosslinking could be controlled by light with temporal resolution.

Figure 9A:
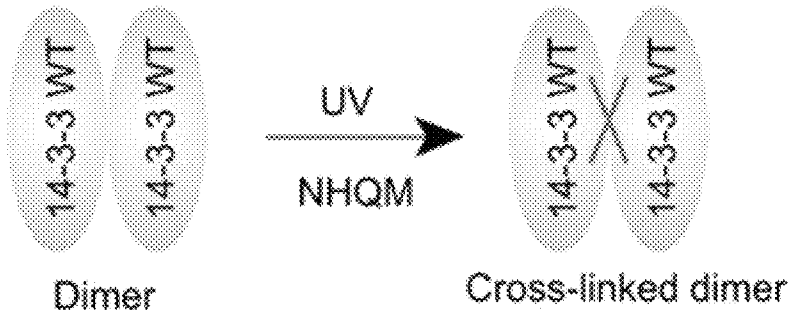
FIGS. 9A-9F. Facile differentiation of dimer and monomer via NHQM crosslinking in vitro and in cell lysate.
Figure 9B:
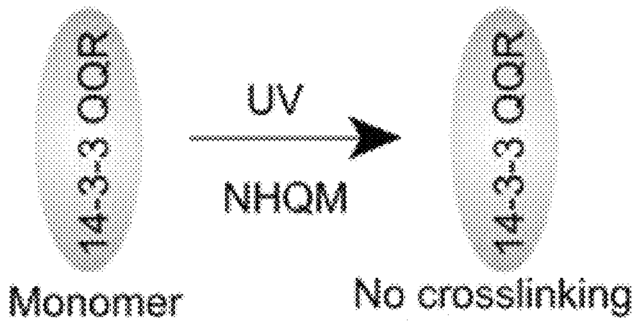
Figure 9C:
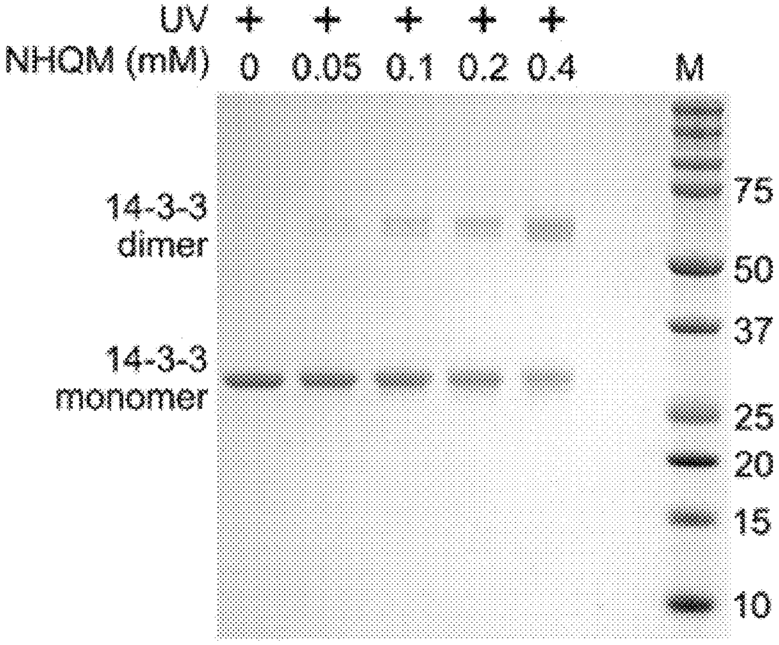
Figure 9D:
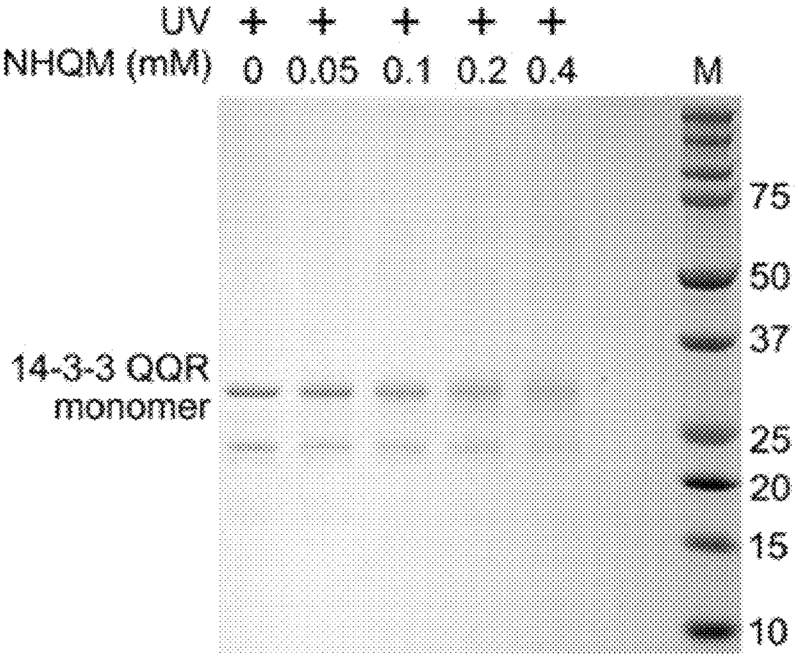
Figure 9E:
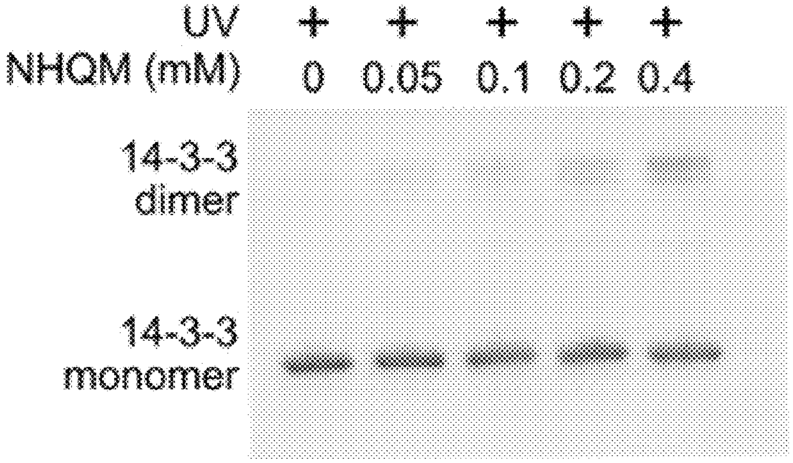
Figure 9F:
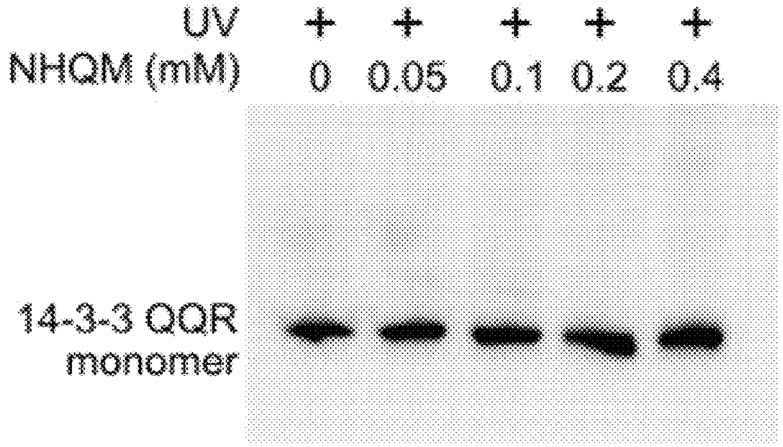

Following crosslinking, NHQM results in a short and rigid linkage, which requires close contact of target residue pairs for effective crosslinking. We therefore tested whether this feature of NHQM could be used to readily determine protein dimerization in vitro and in cell lysates. It has been reported that three mutations ($^{12}LAE^{14} \rightarrow {}^{12}QQR^{14}$) of 14-3-3 disrupt the dimer interface to form a monomer, leading to a distinct function from WT 14-3-3, such as chaperone activity.[17] [18] However, previously the 14-3-3 (QQR) mutant was isolated from cells and then characterized as a monomer using size exclusion chromatography. This in vitro process is tedious, and the results may not represent what occur in the cellular environment. We first treated purified 14-3-3 WT and QQR mutant with various amounts of NHQM and illuminated with UV light of 365 nm (FIGS. 9A-9B). Analysis by SDS-PAGE demonstrated that crosslinked dimer of 14-3-3 WT increased with higher NHQM concentration. In contrast, 14-3-3 QQR remained a monomer even at NHQM concentration up to 0.4 mM (FIGS. 9C-9D). We then applied NHQM directly to cell lysates of *E. coli* cells expressing either 14-3-3 WT or its QQR mutant, without isolating the 14-3-3 proteins. Again, western blot of 14-3-3 protein clearly showed that 14-3-3 WT protein was crosslinked as dimer but not the QQR mutant (FIGS. 9E-9F). These results show that NHQM-mediated crosslinking could be a facile method for determining protein interactions.

Figure 10B:
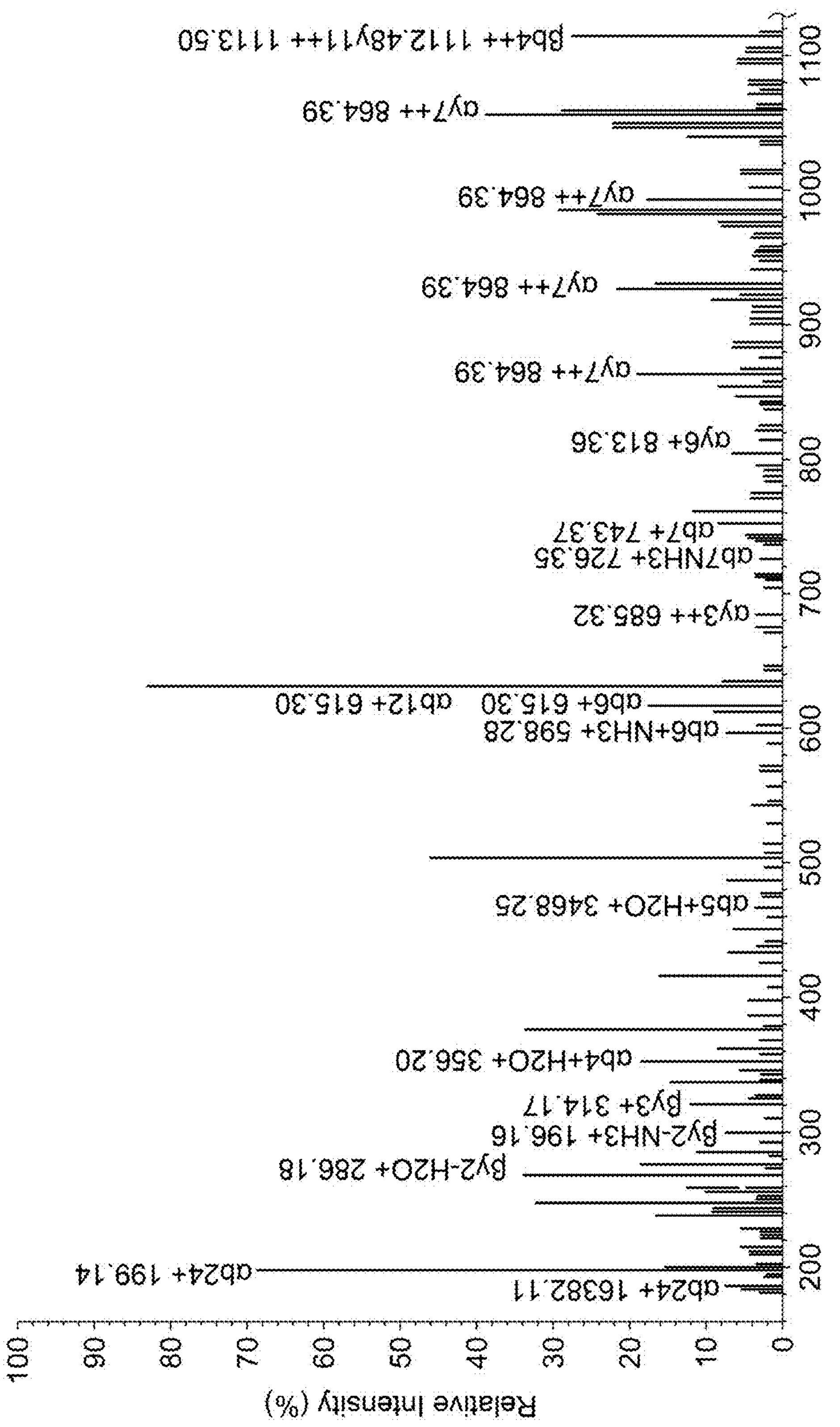
Figure 10B:
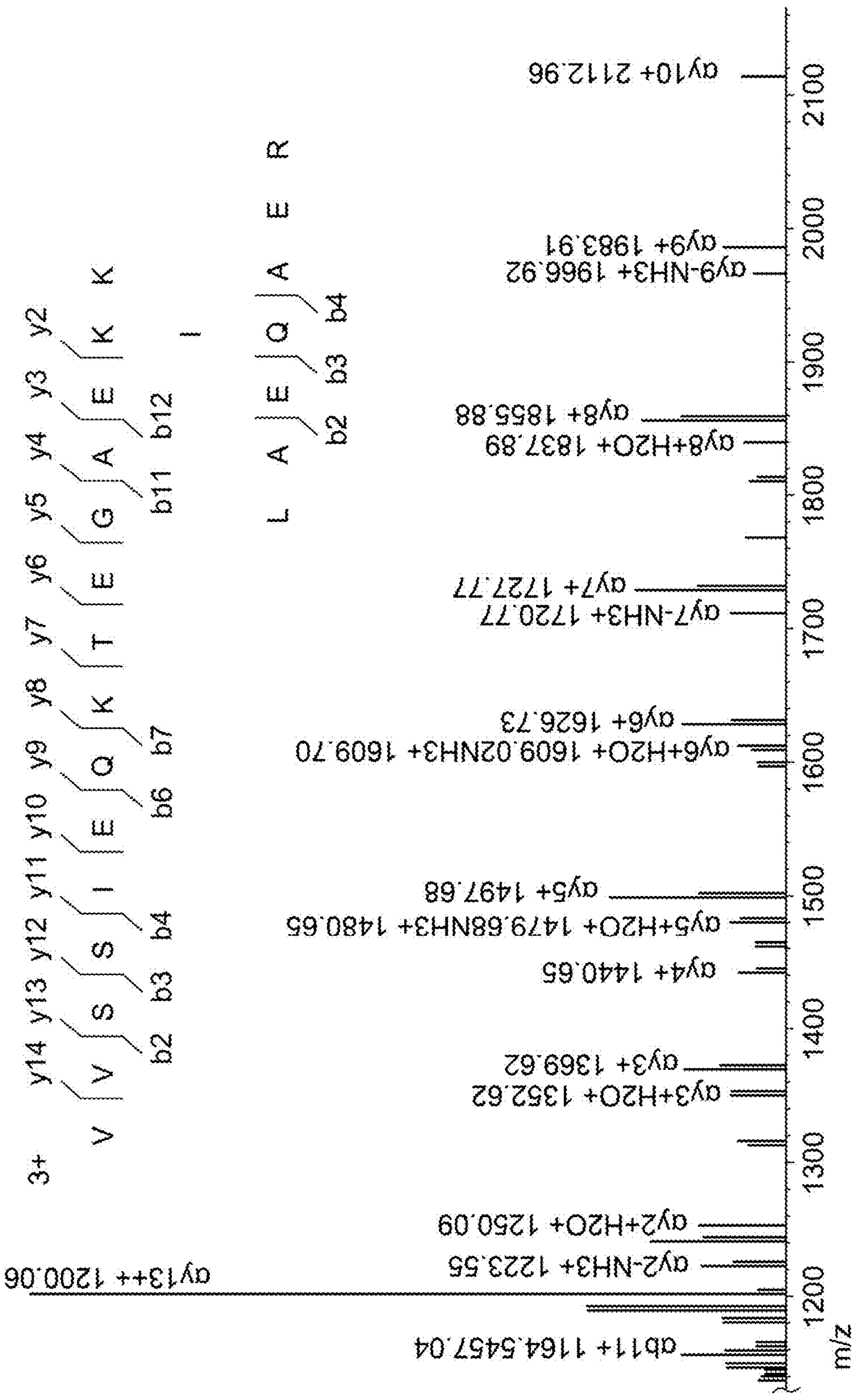
Figure 10C:
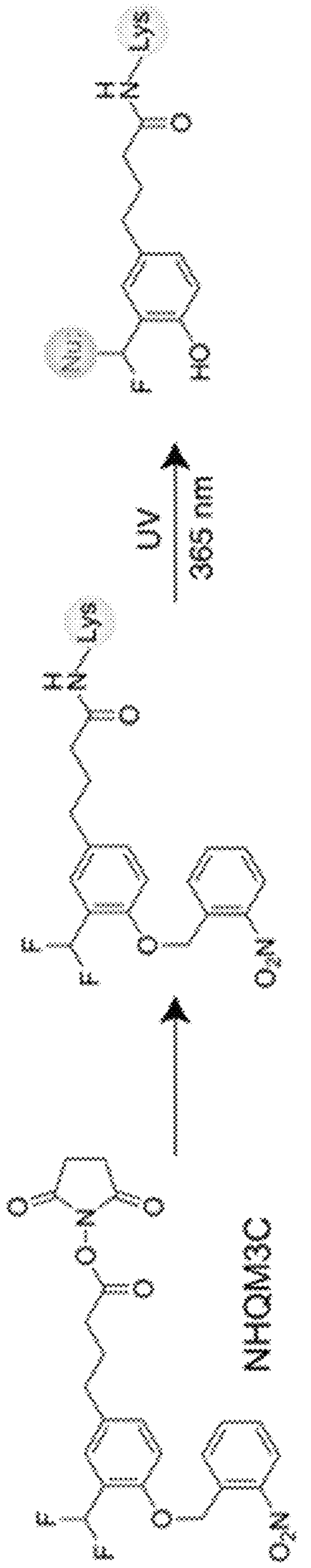
Figure 11A:
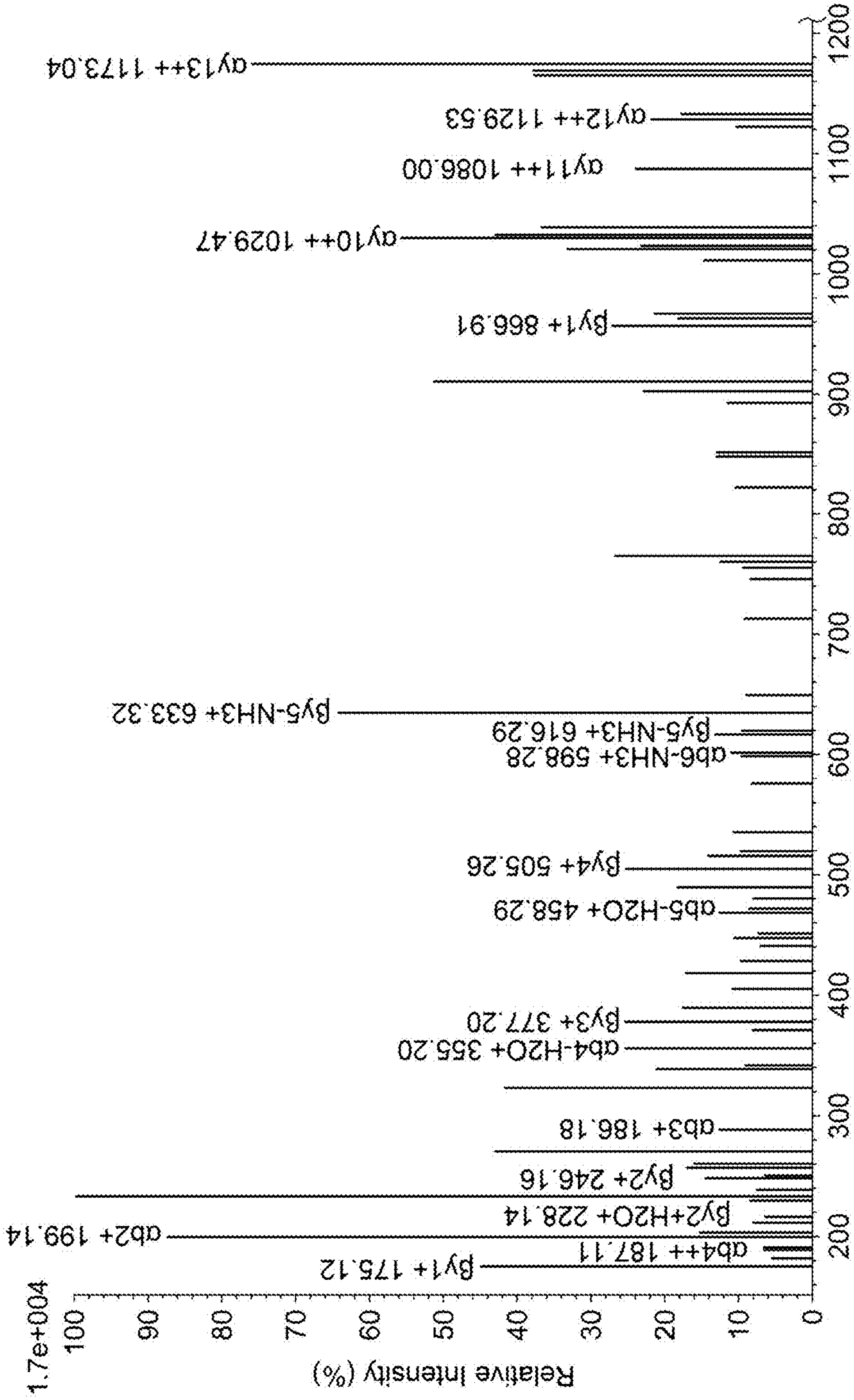
FIGS. 11A-11E. Tandem mass spectra of 14-3-3 crosslinked by NHQM. These spectra indicate that NHQM crosslinked Lys with Lys, Glu, Ser, Arg, Asn, respectively. Spectrum of Lys-Gln crosslinking is shown in FIG. 10B.
Figure 11A:
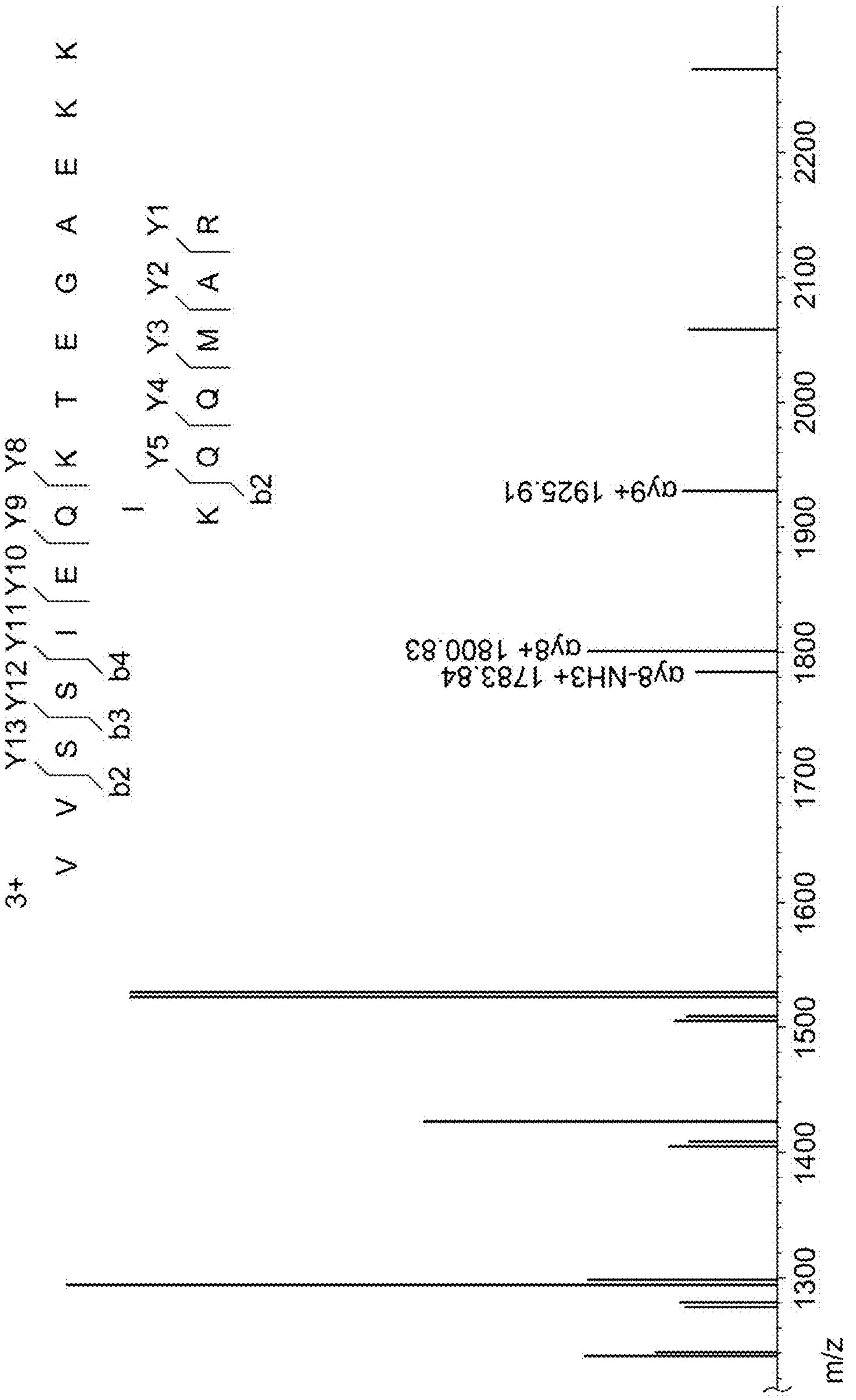
Figure 11B:
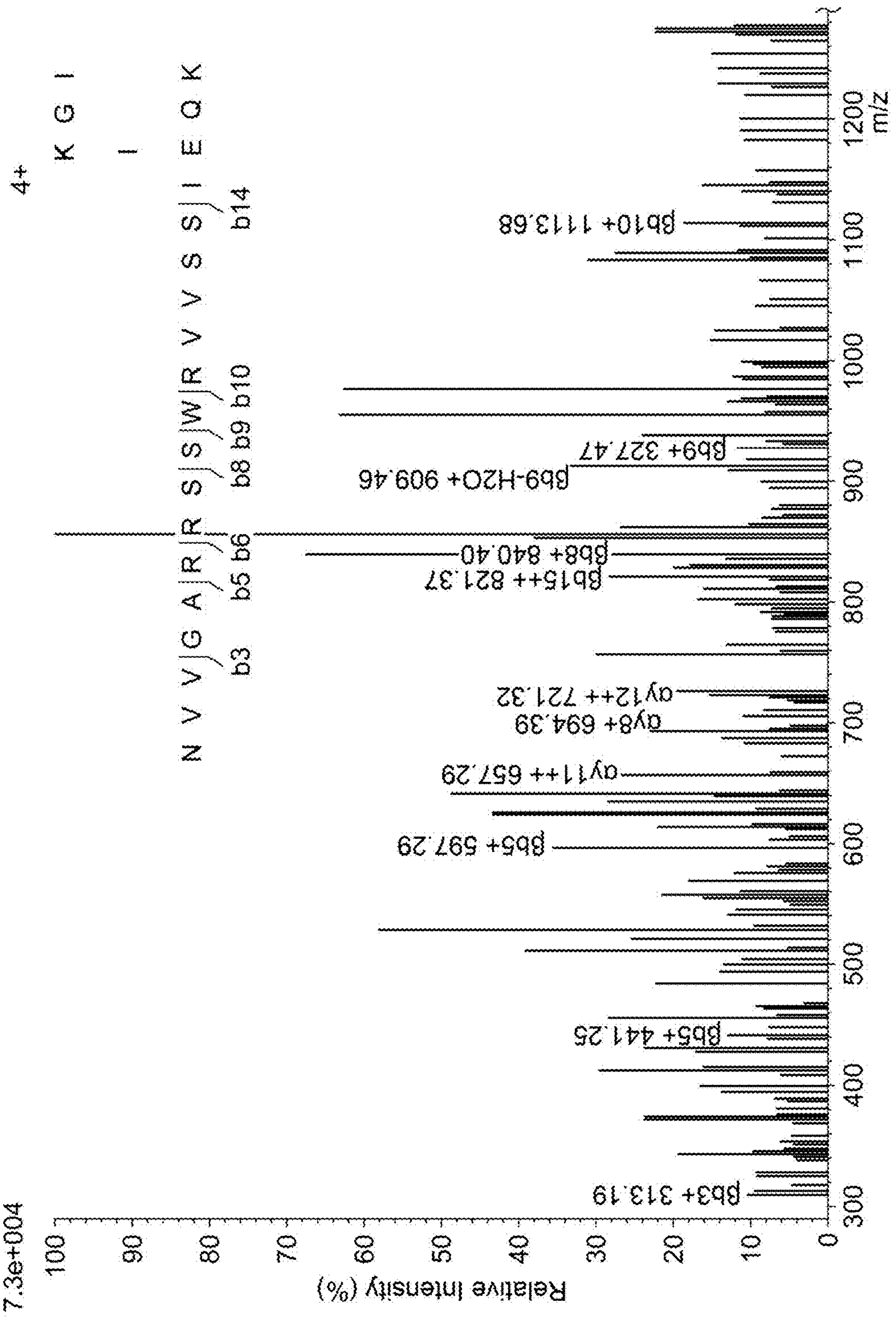
Figure 11B:
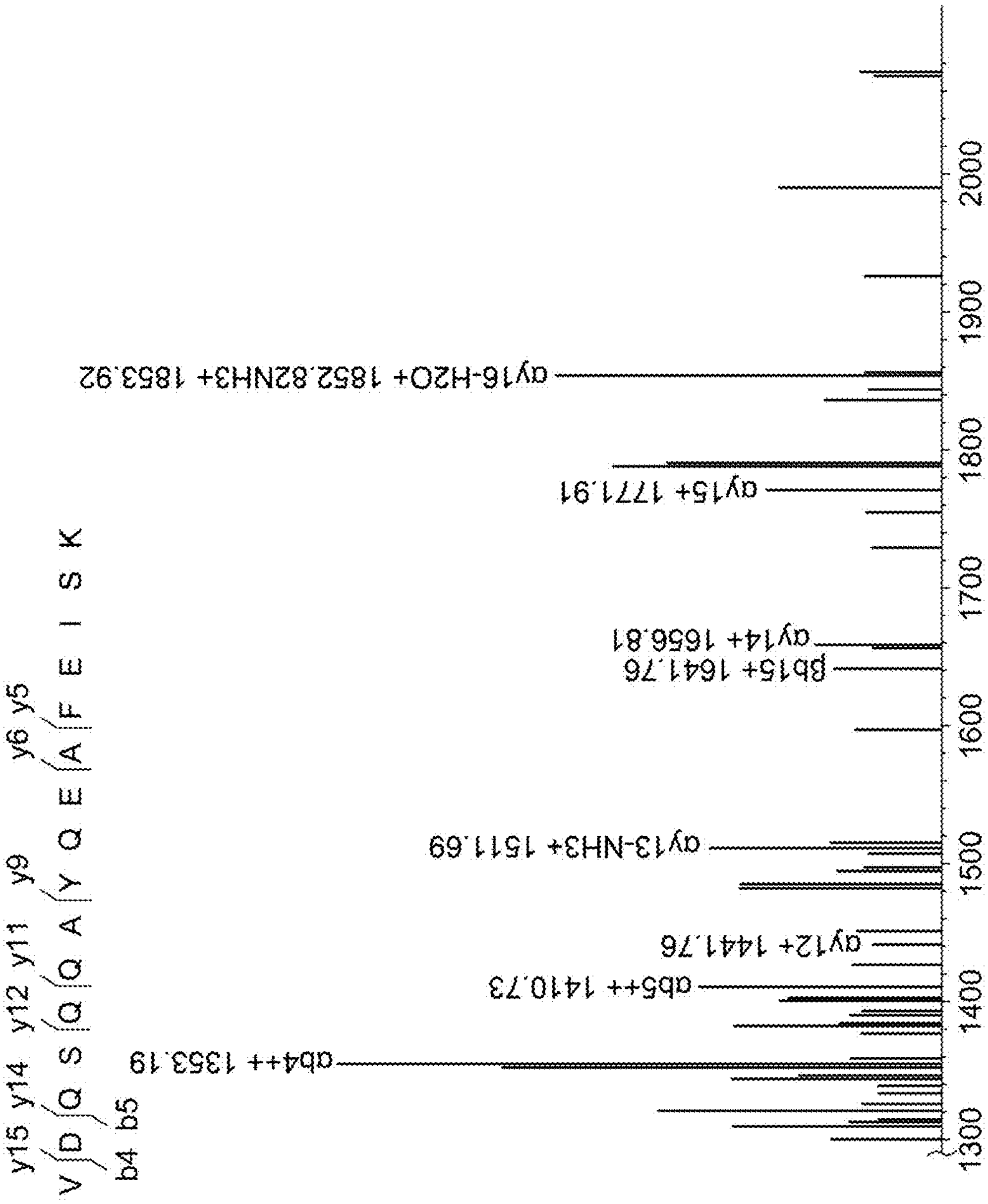
Figure 11C:
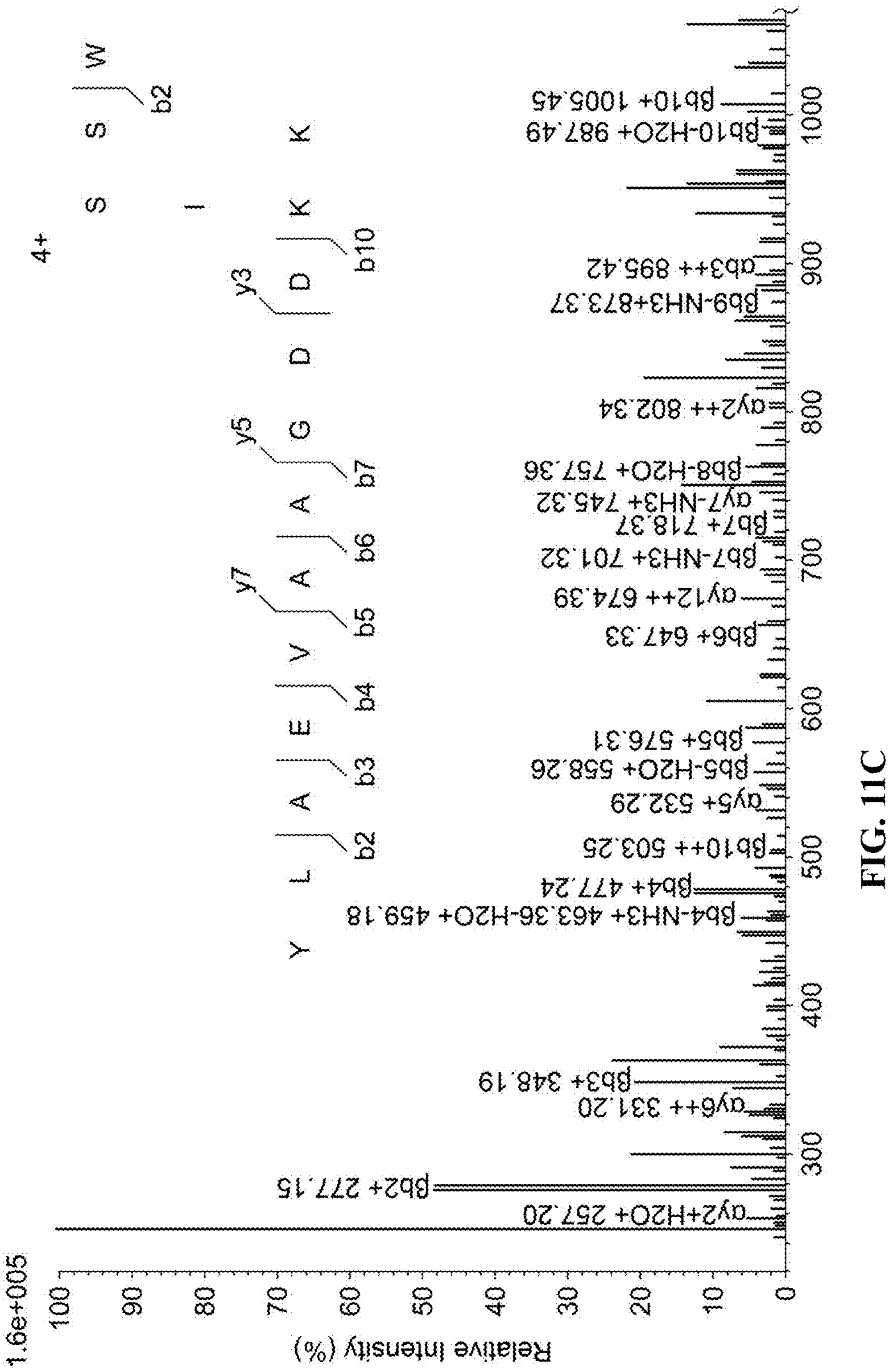
Figure 11C:
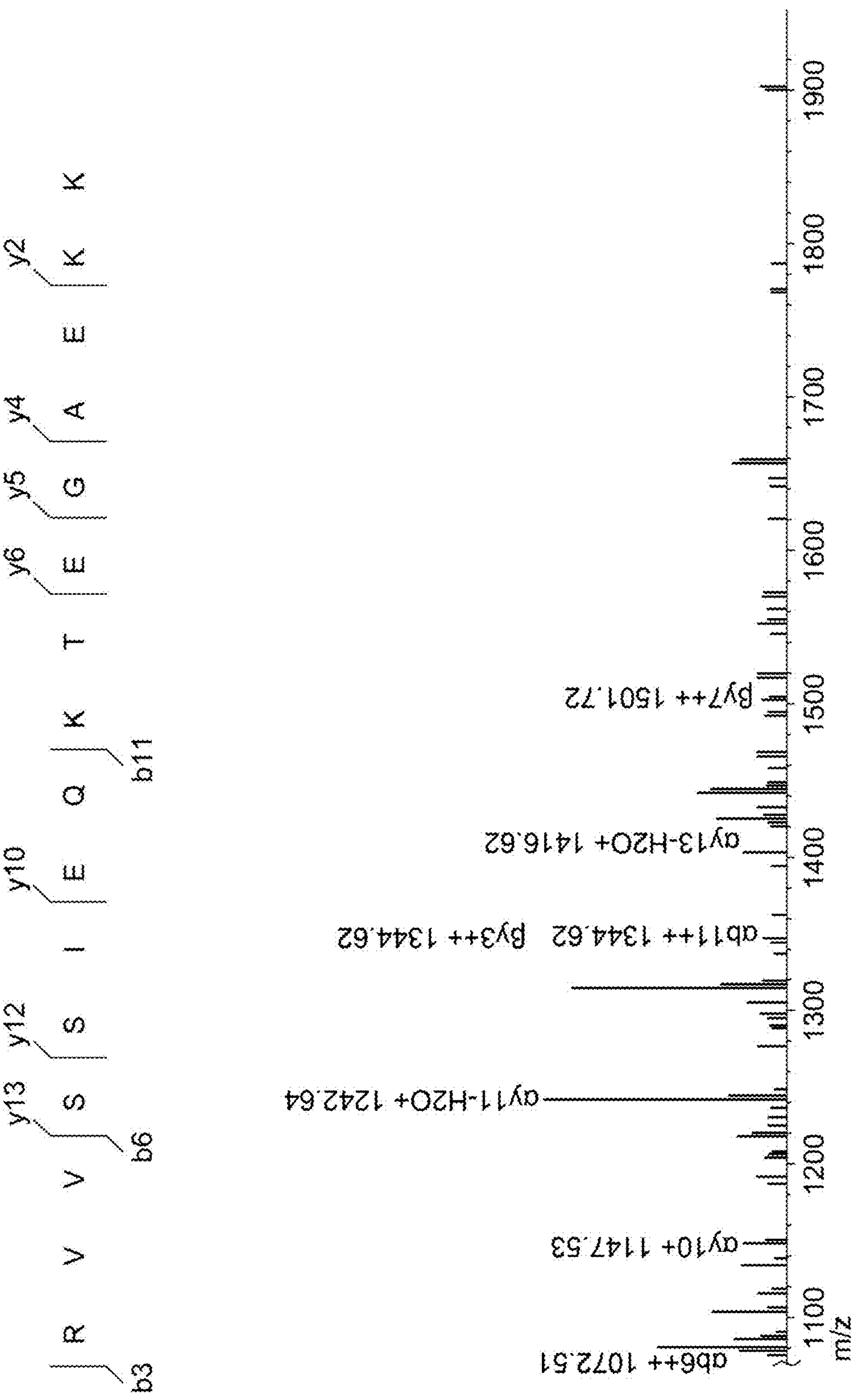
Figure 11D:
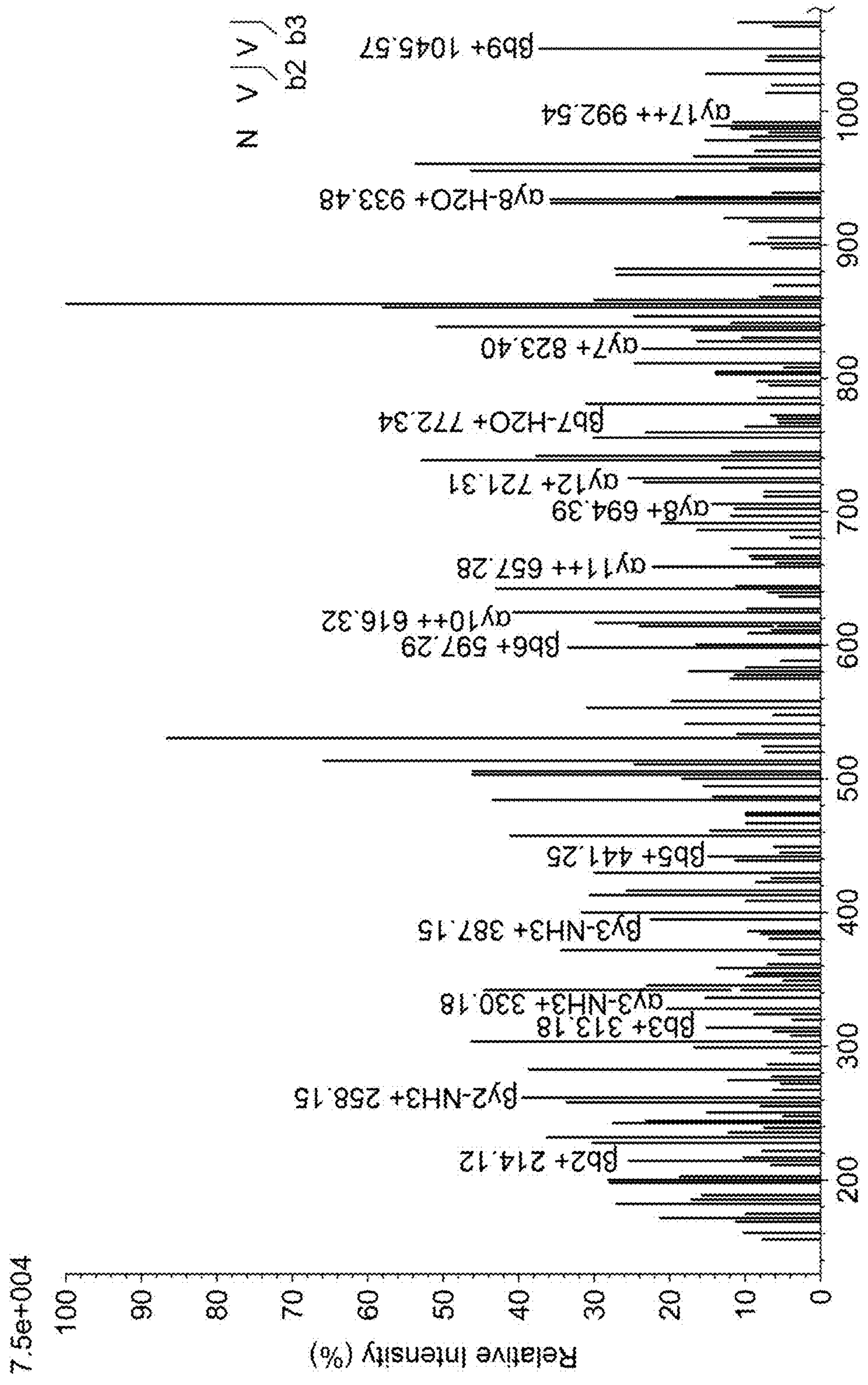
Figure 11D:
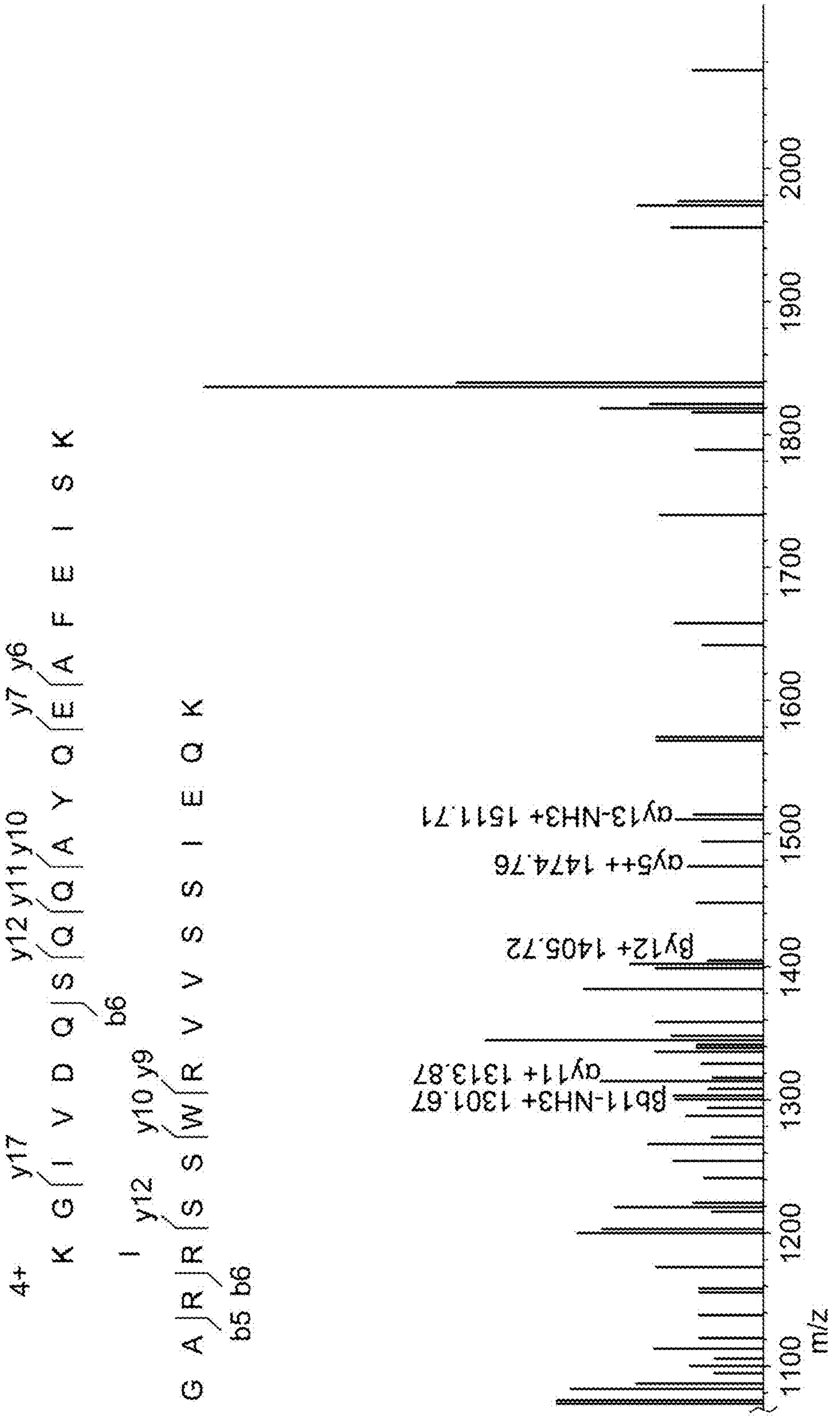
Figure 11E:
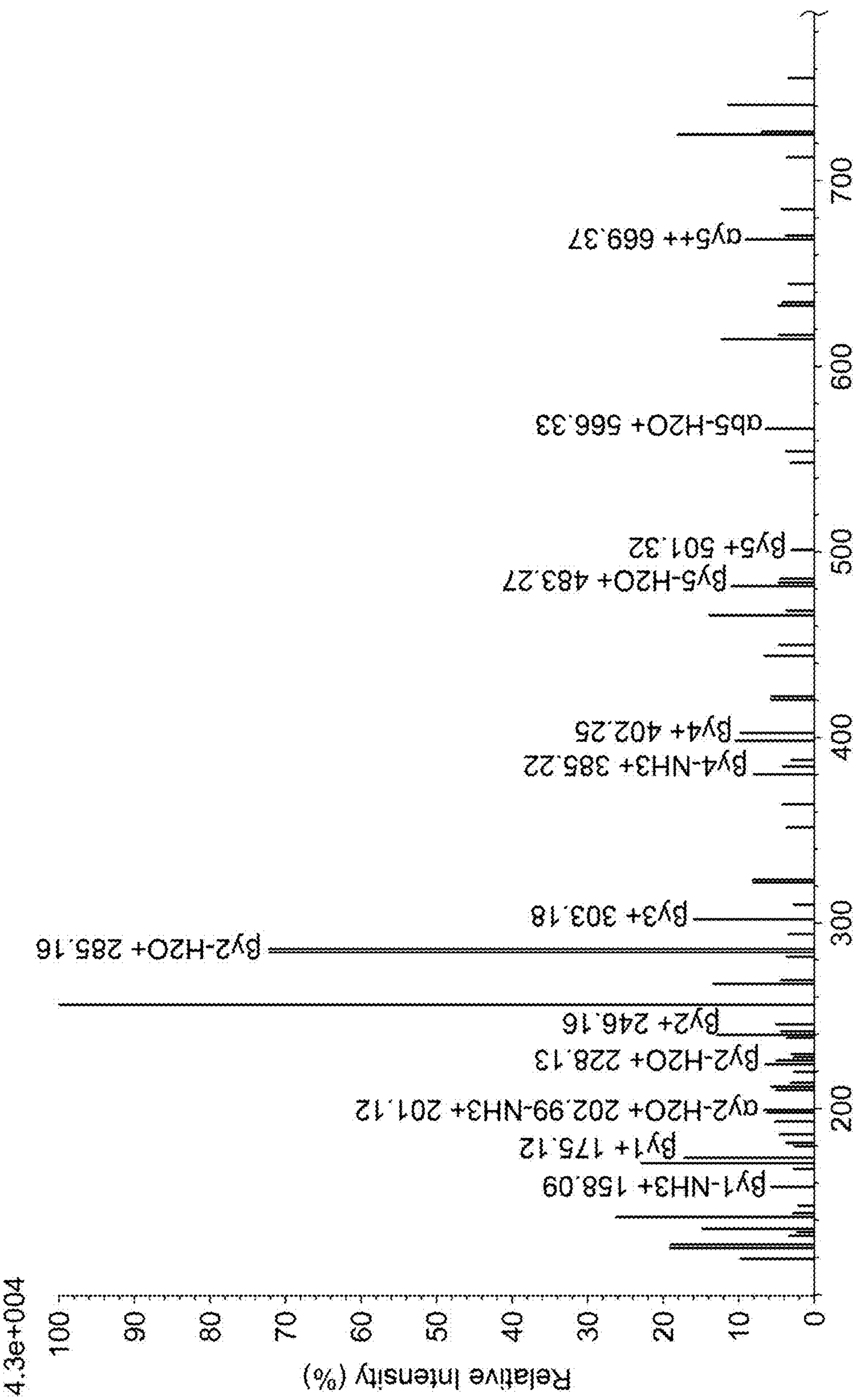
Figure 11E:
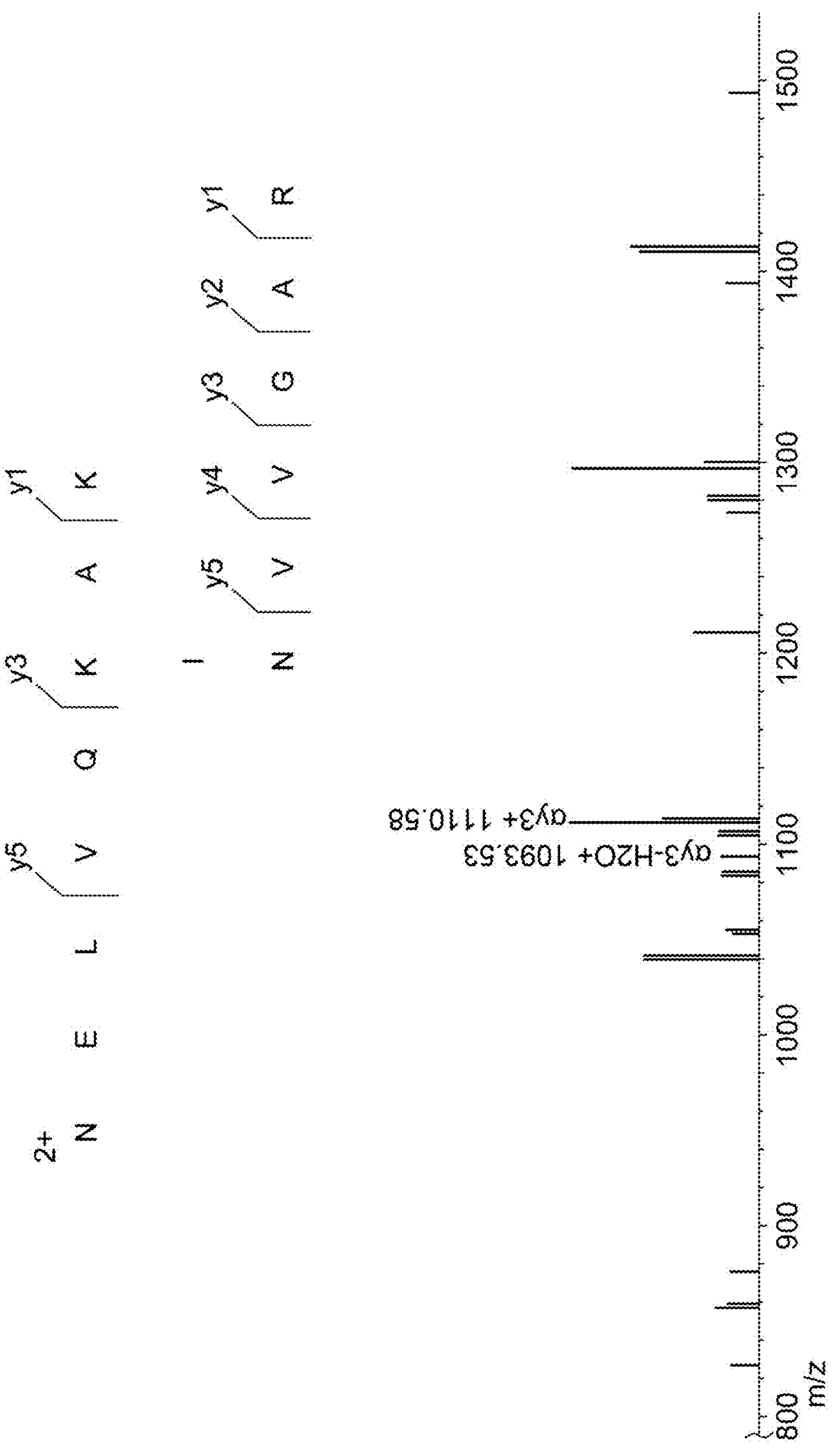
Figure 12:
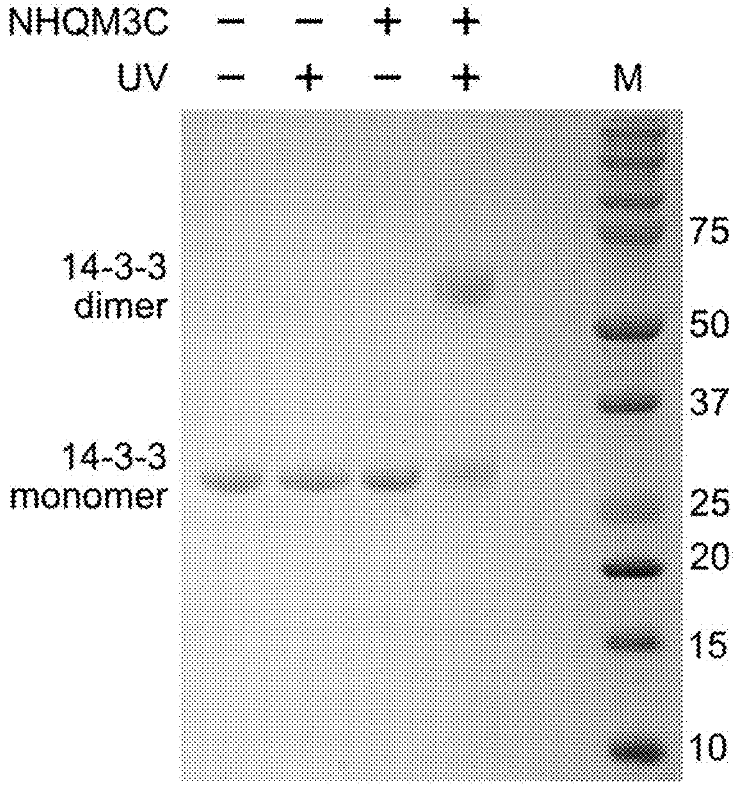
FIG. 12. NHQM3C crosslinked WT 14-3-3 protein into dimeric form in vitro. The WT 14-3-3 was treated with or without UV illumination in the presence or absence of NHQM3C cross linker, and the crosslinking was detected by analyzing the mass shift observed by 10% Tris-tricine SDS-PAGE.
Figure 13B:
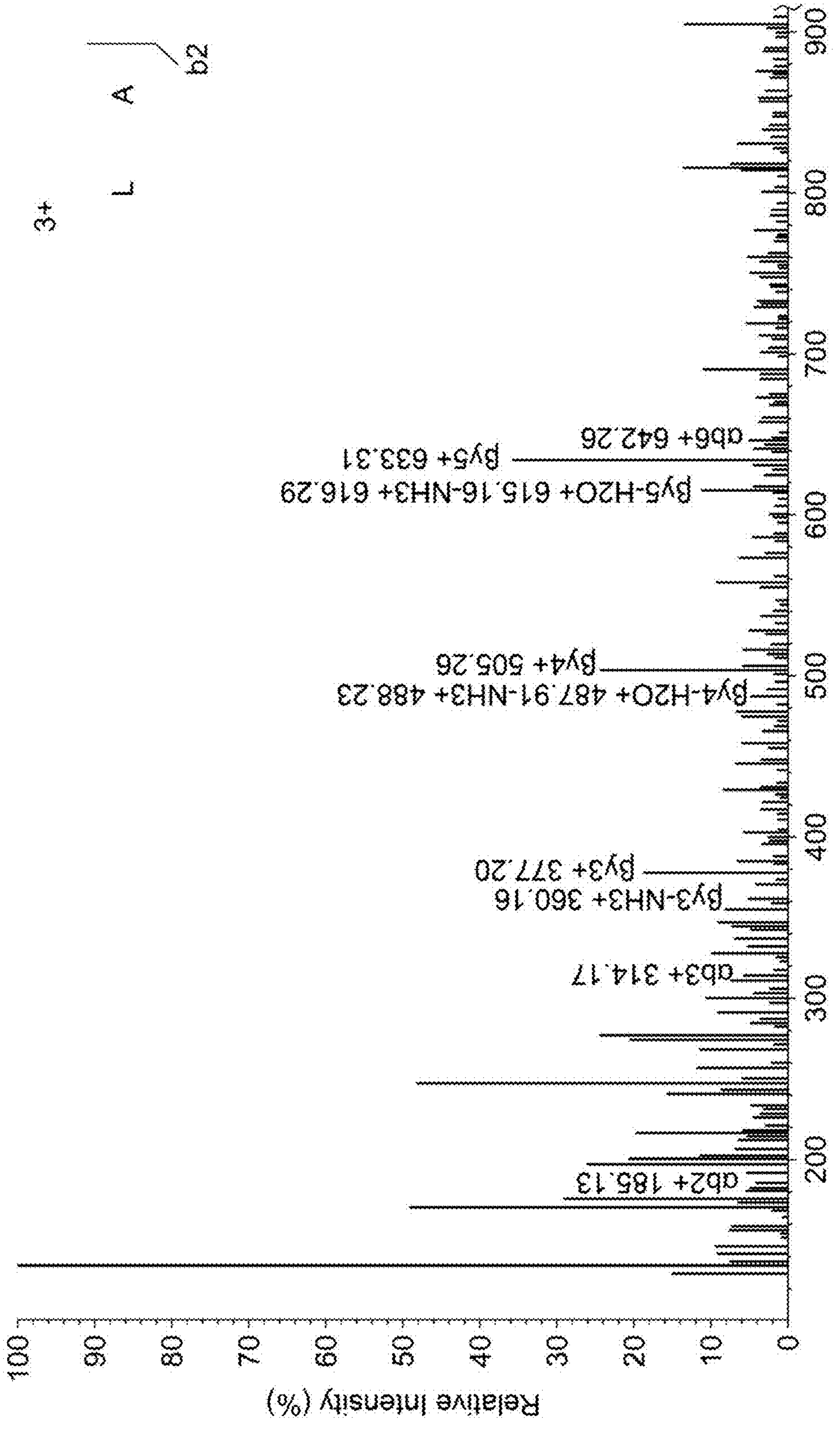
Figure 13B:
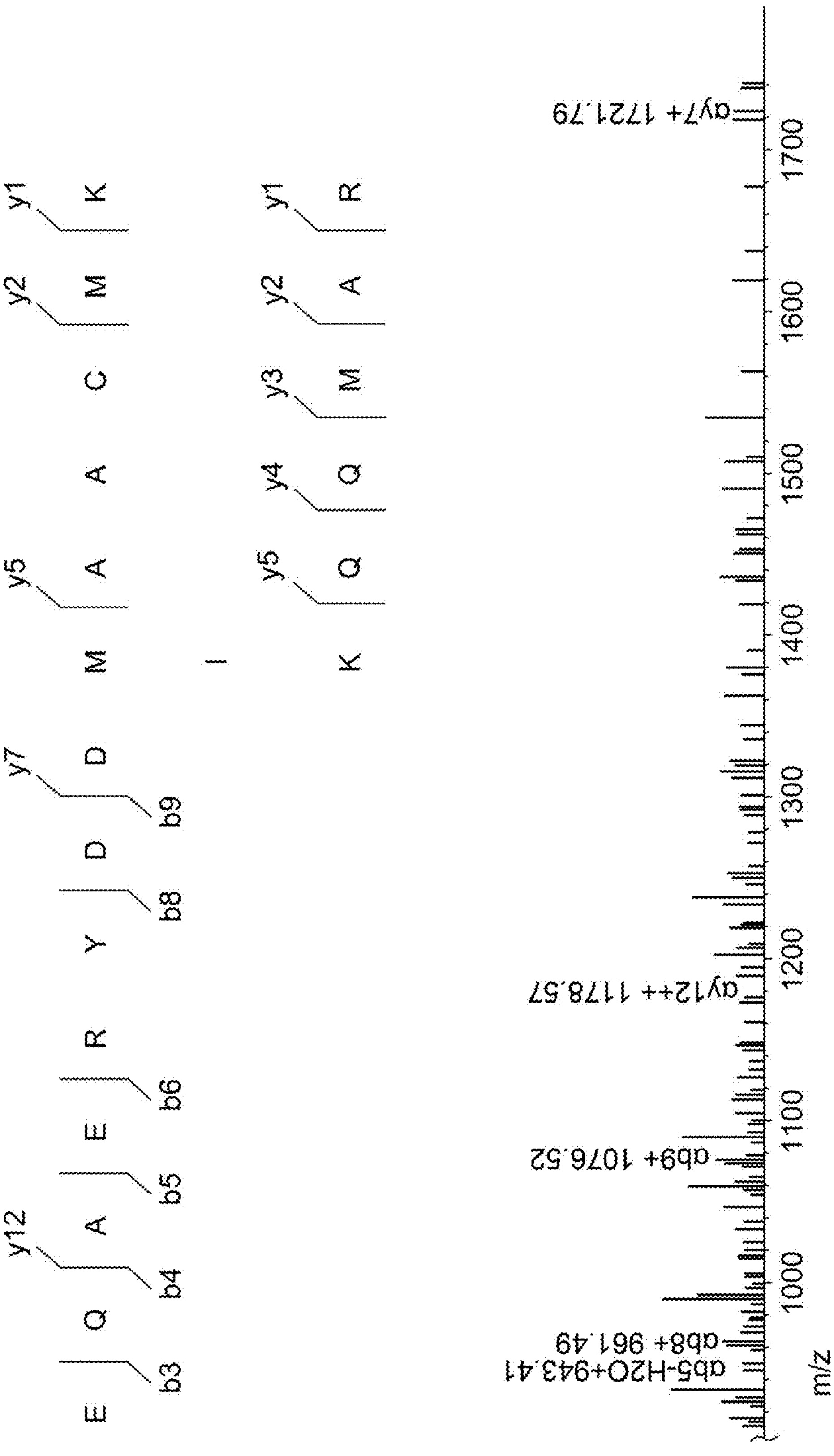
Figure 13C:
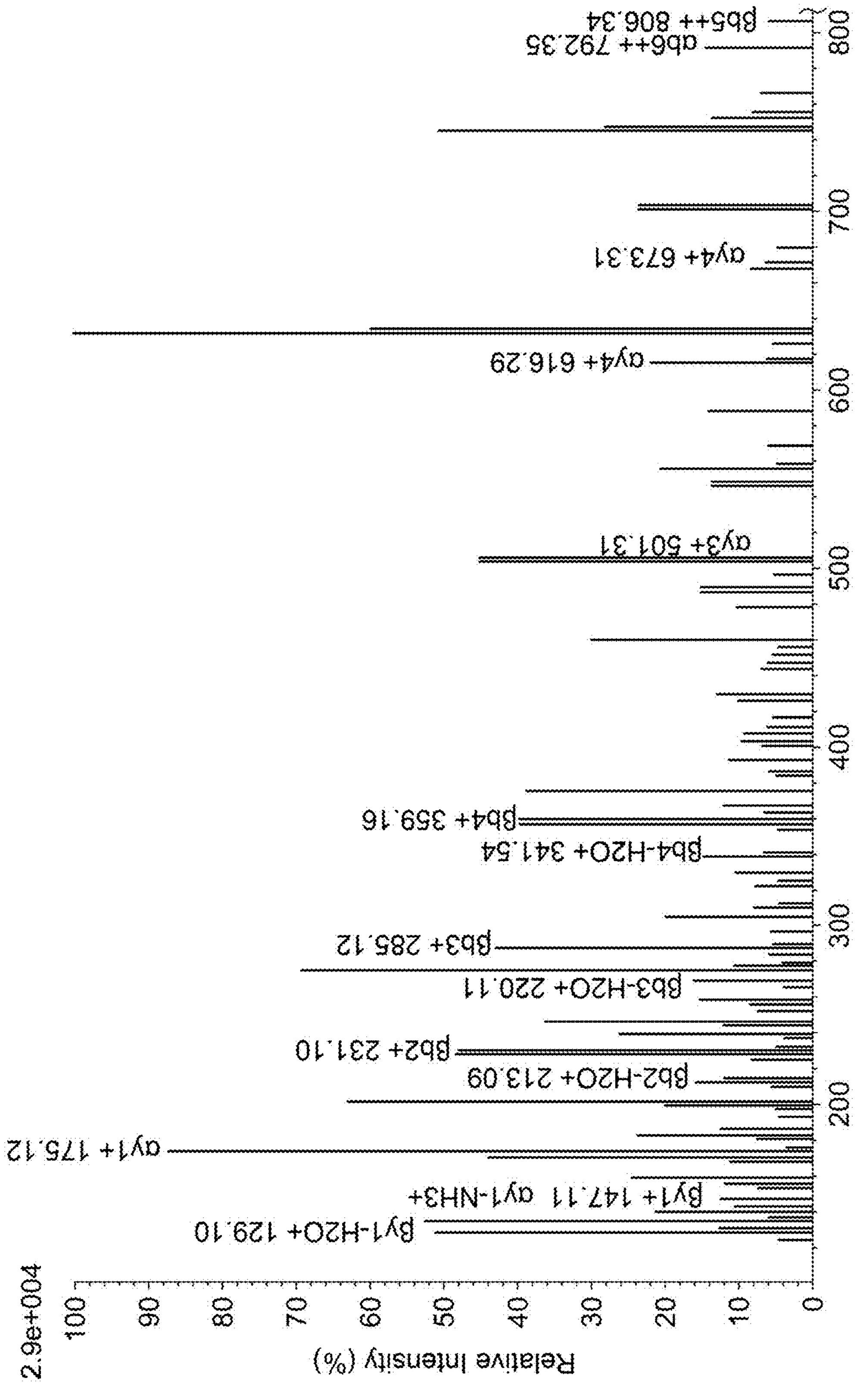
Figure 13C:
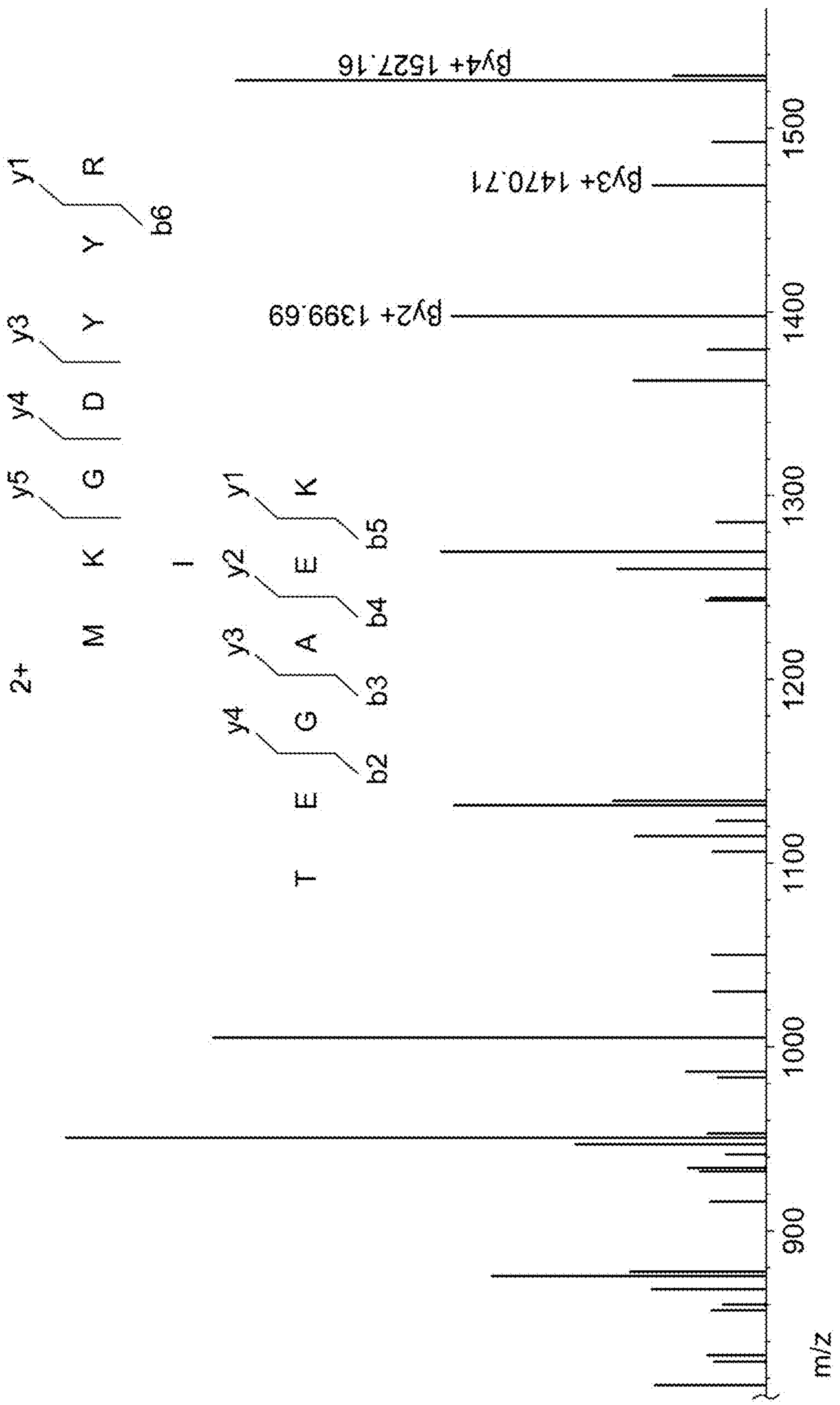
Figure 13D:
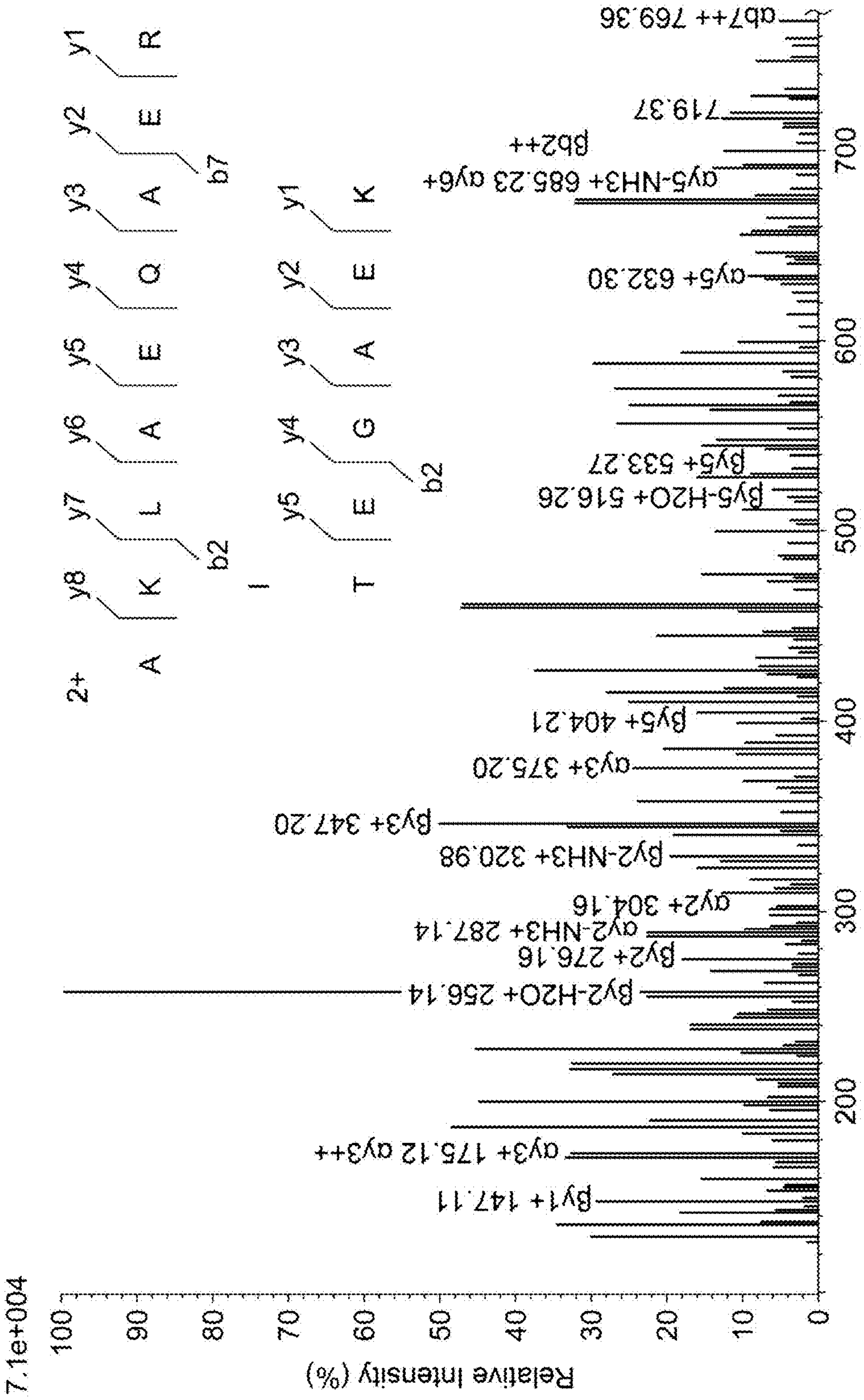
Figure 13D:
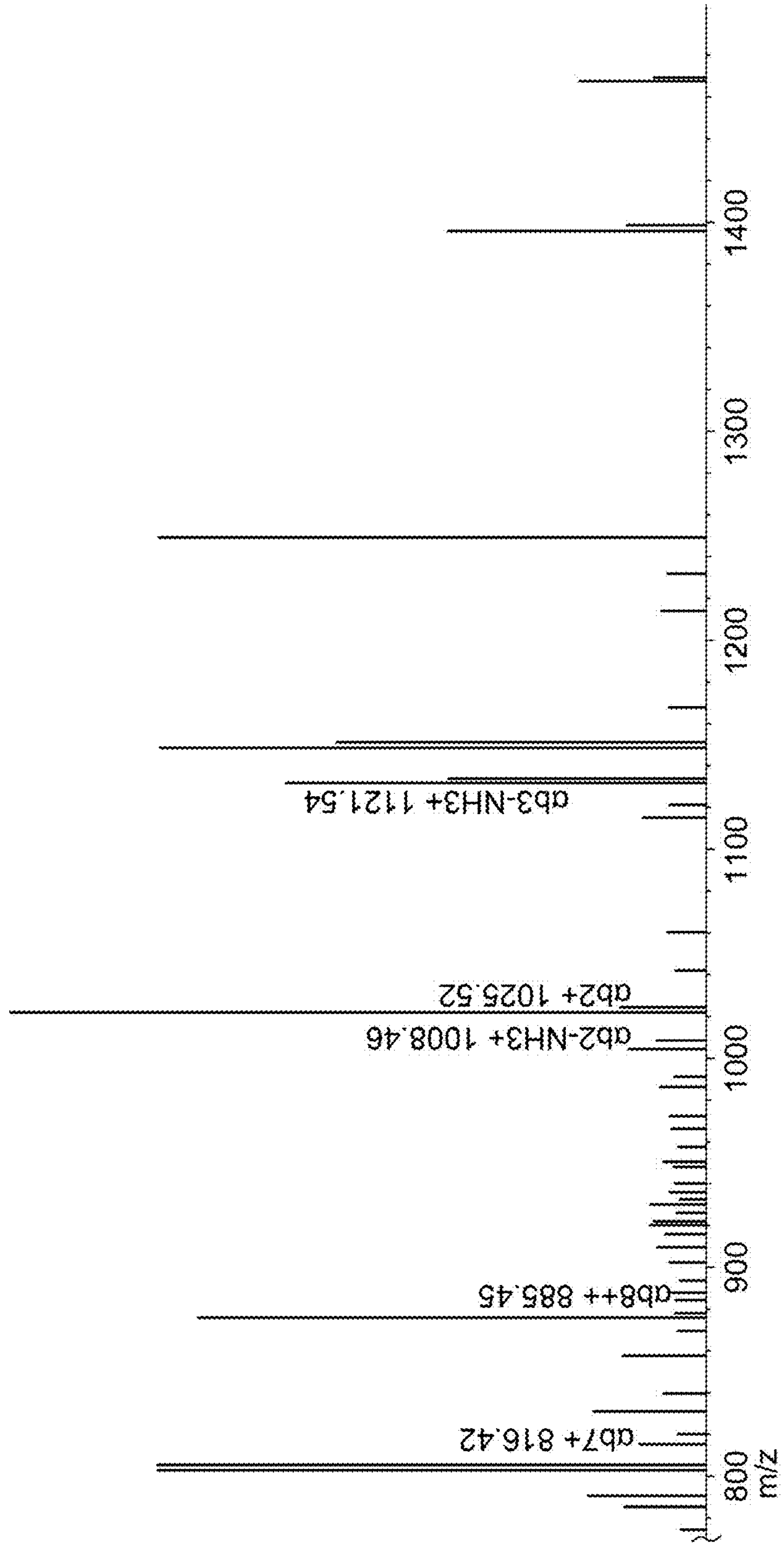
Figure 13E:
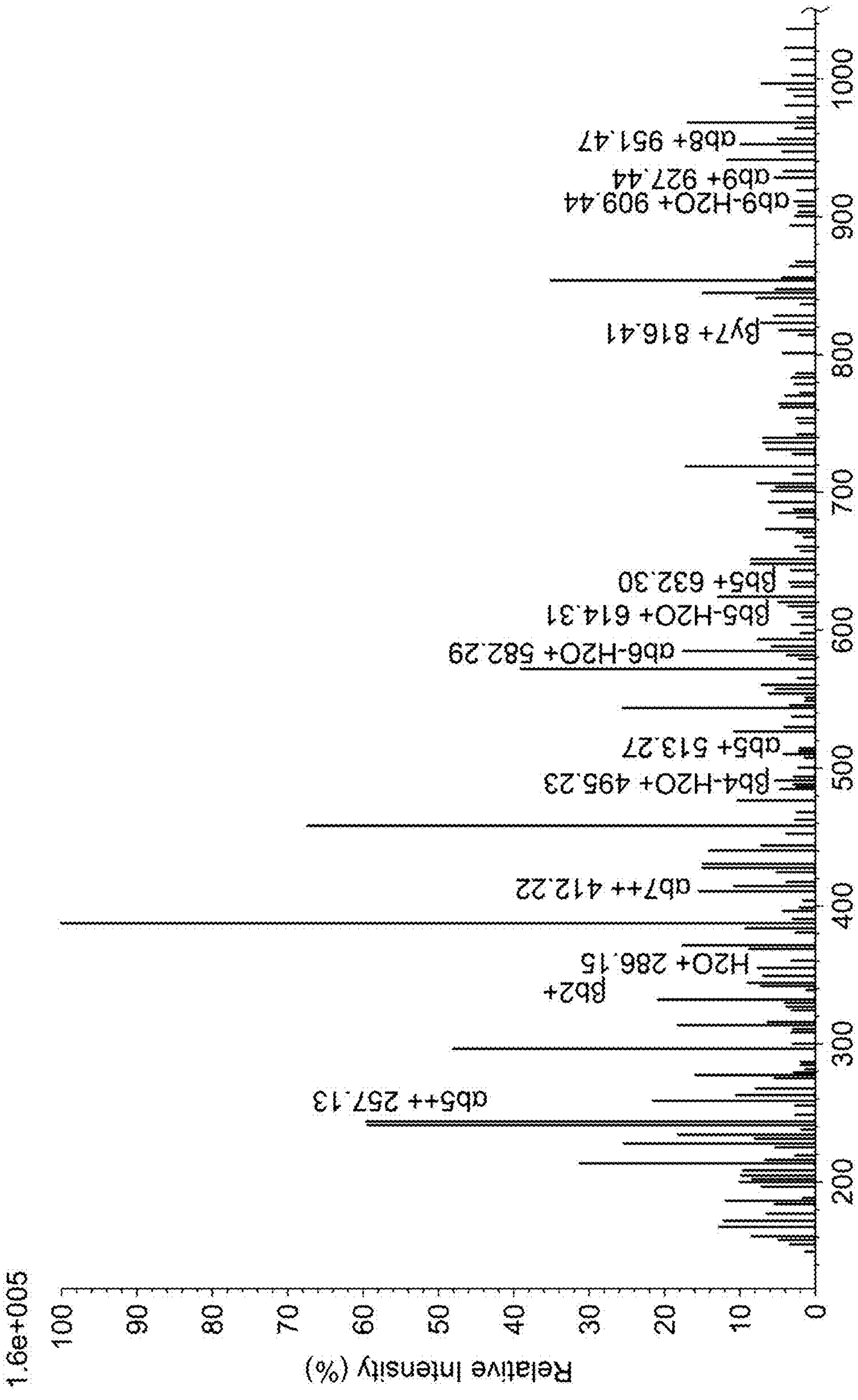
Figure 13E:
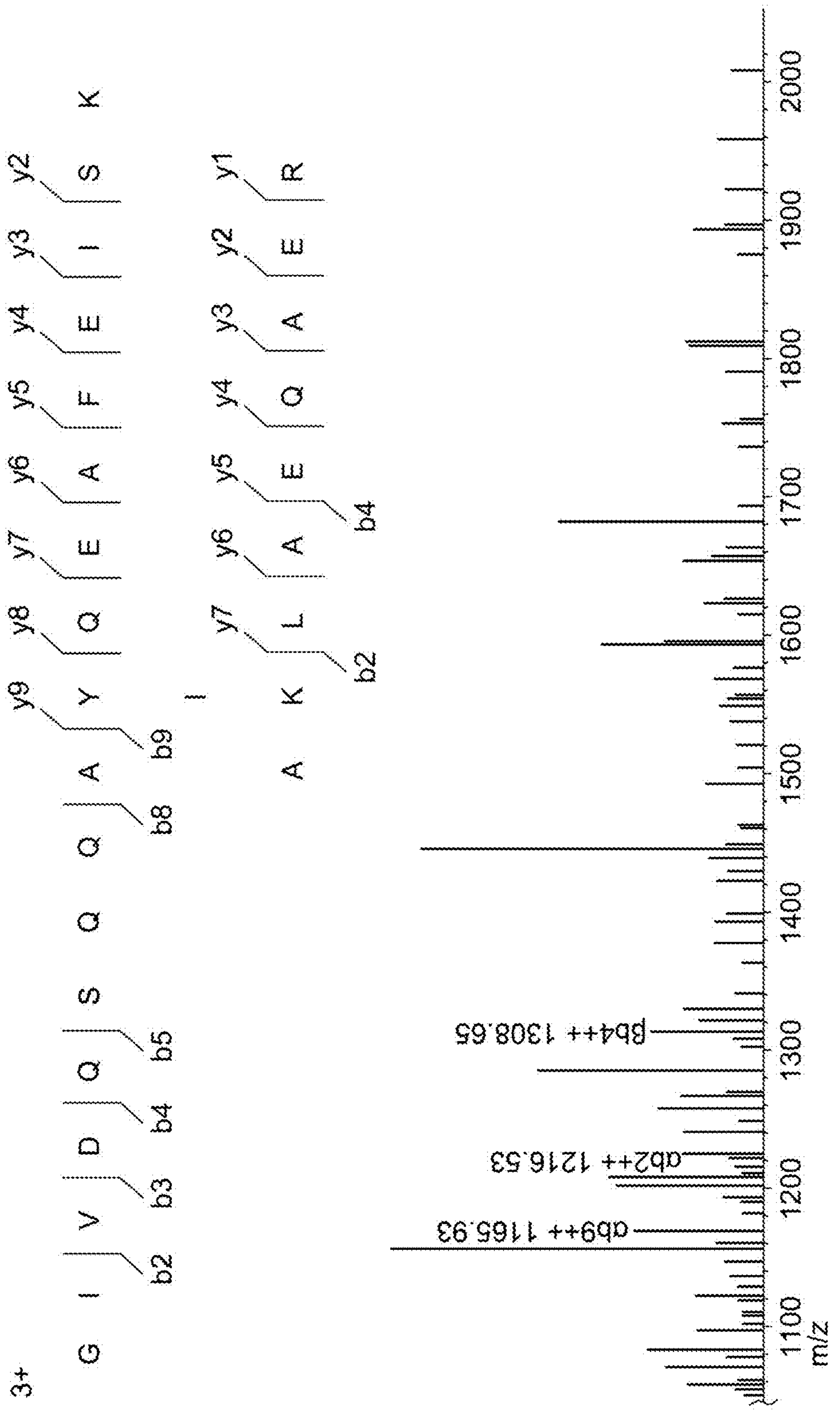
Figure 13F:
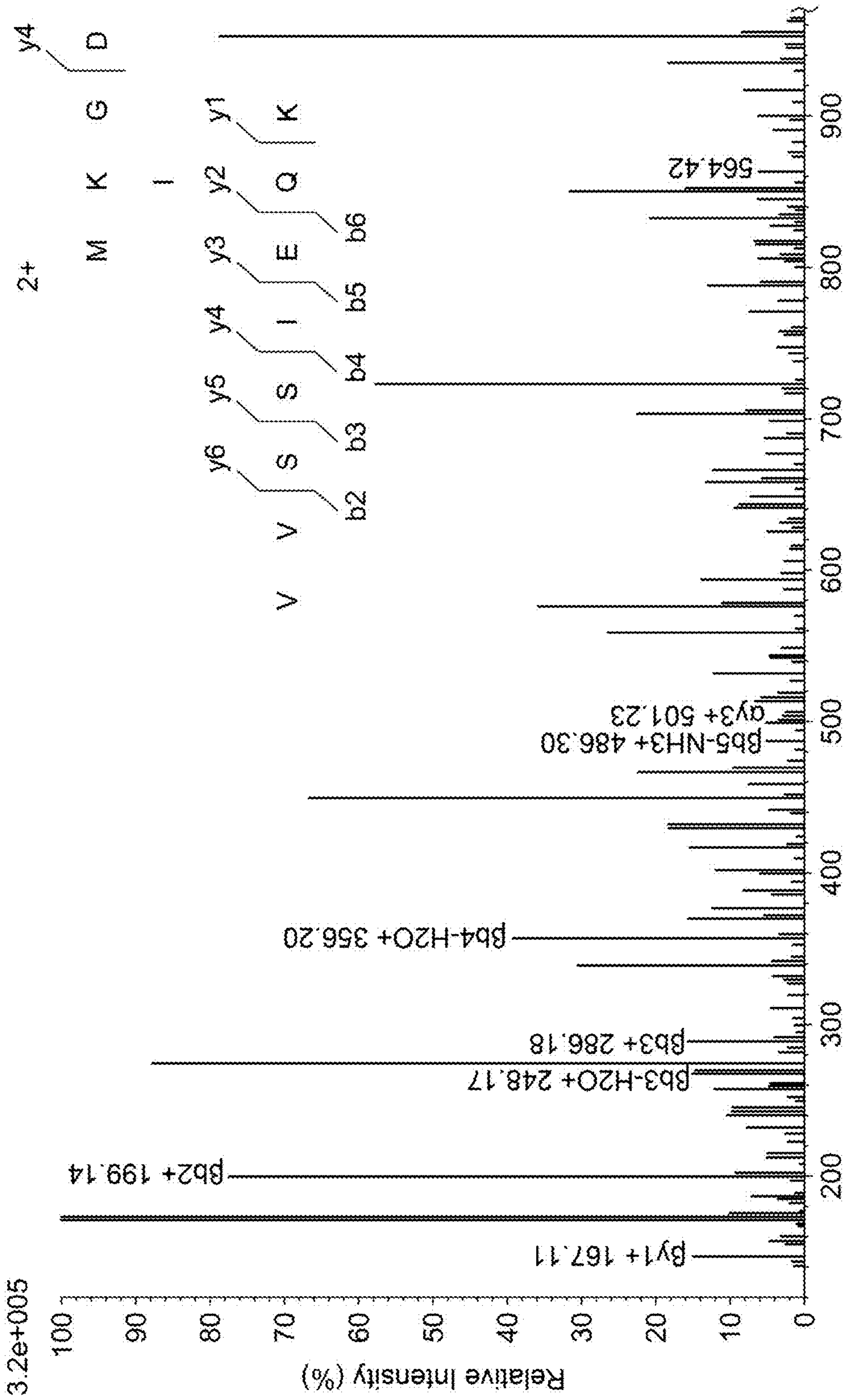
Figure 13F:
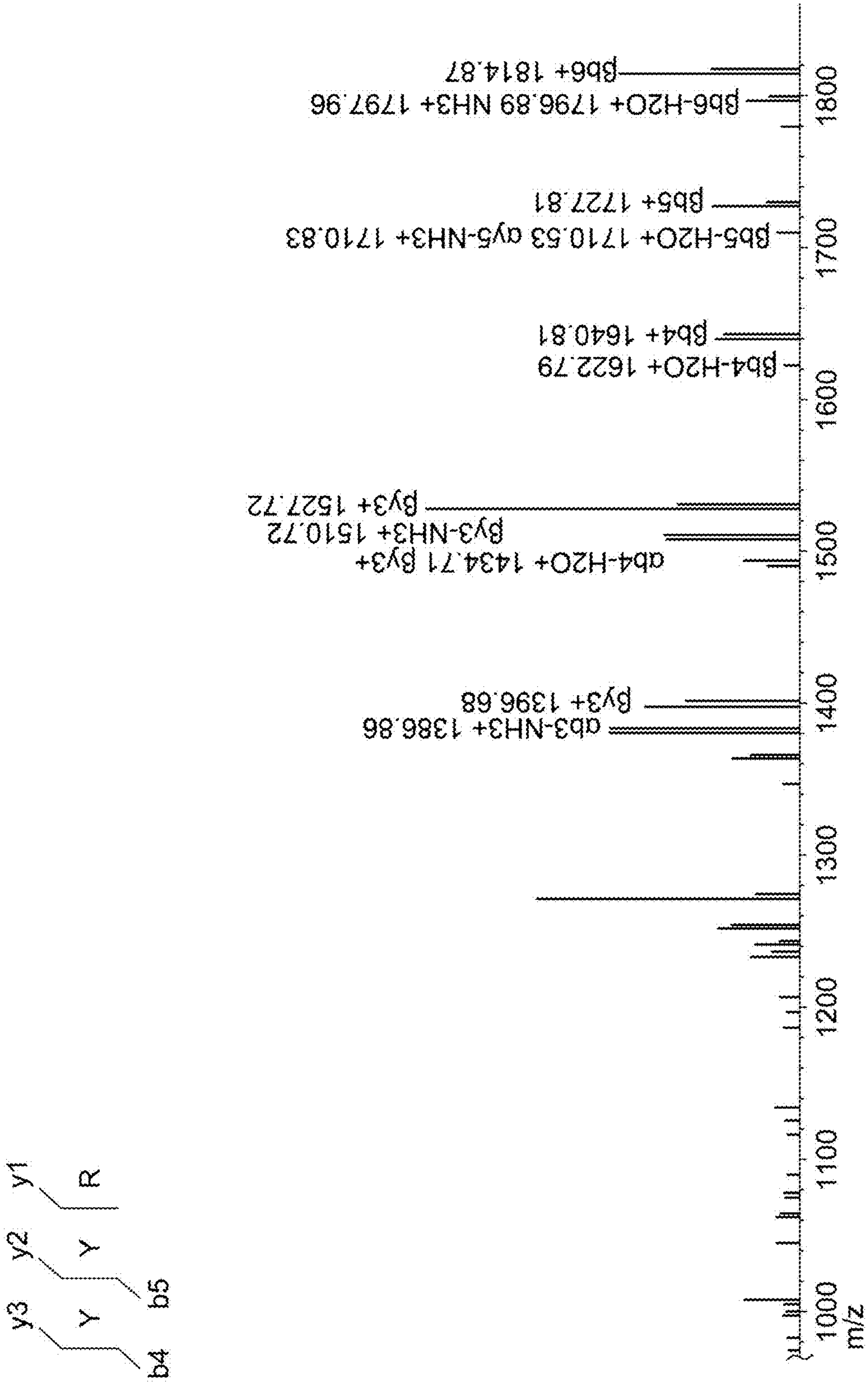
Figure 13G:
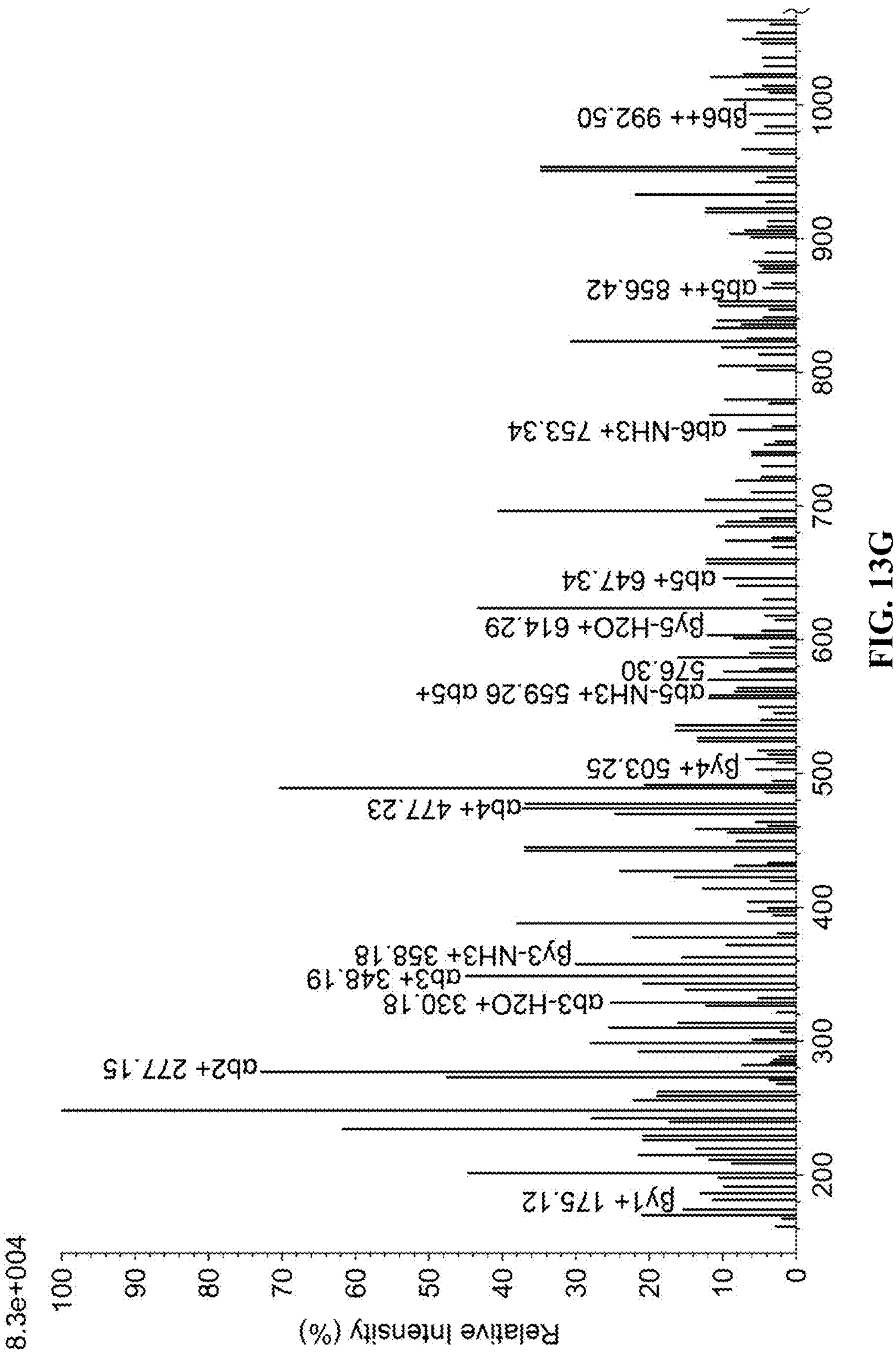
Figure 13G:
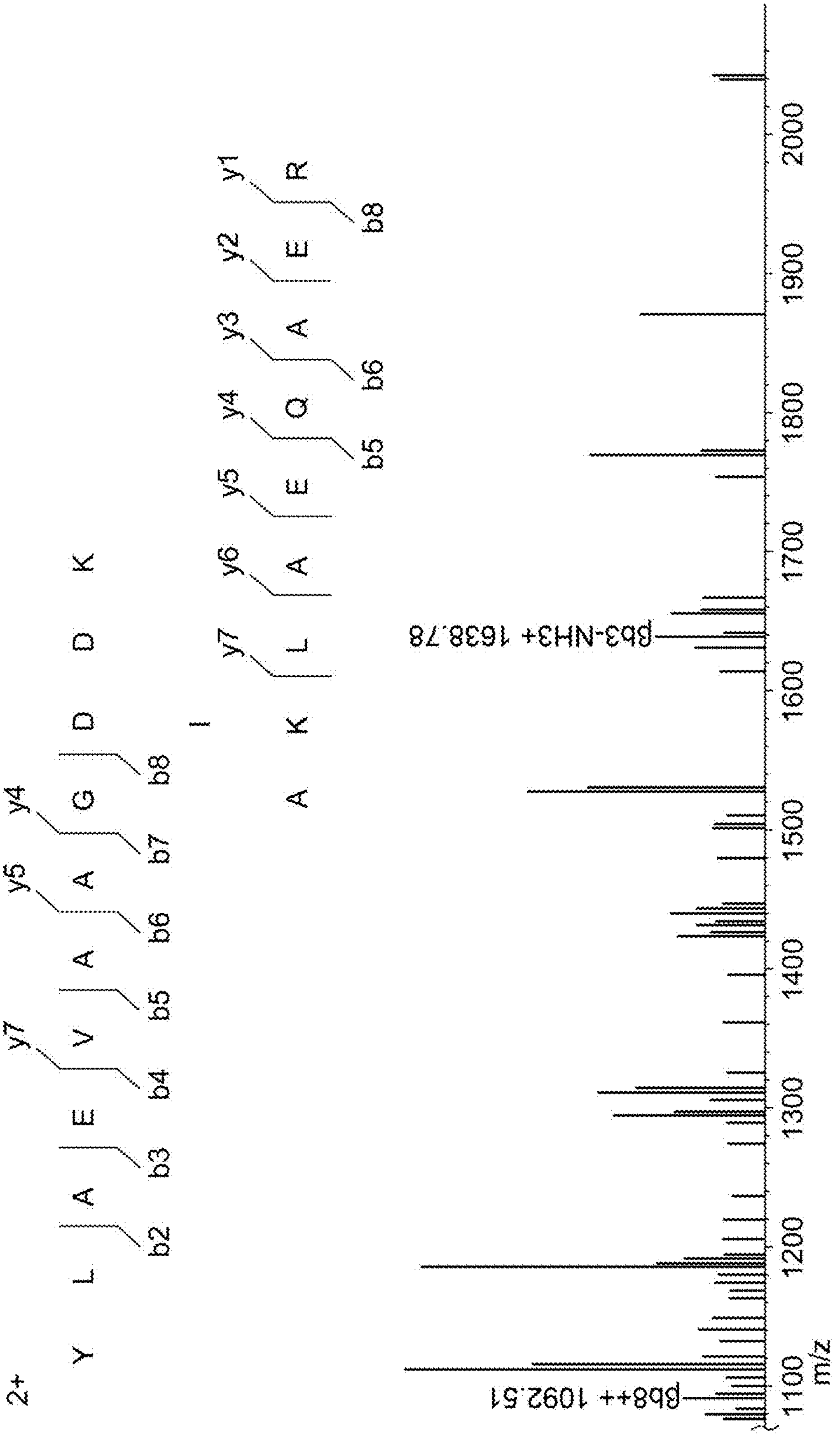

To identify which amino acid residues NHQM could crosslink, we analyzed the crosslinked 14-3-3 protein sample with tandem mass spectrometry. Eight pairs of crosslinked peptides were identified, showing that NHQM crosslinked Lys of one peptide with Arg, Asn, Gln, Glu, Lys, or Ser of the other peptide (FIGS. 10A-10B, FIGS. 11A-11E). These residues have nucleophilic side chains, consistent with the reaction mechanism of o-QM. The maximum Cα-Cα distance of NHQM crosslinker is ~22 Å considering the amino acid side chain length plus the covalently connected crosslinking agent. The Cα-Cα distances for the majority of crosslinked residues fall within this range, with only one slightly exceeding this limit and measured at 23.7 Å. To increase the flexibility of the crosslinker, we also synthesized cross-linker NHQM3C, which adds three methylene units to the spacer of NHQM (FIG. 10C, Example 5). When applied to the purified WT 14-3-3 protein, NHQM3C also crosslinked 14-3-3 into covalent dimers upon UV activation (FIG. 12). Tandem mass spectrometric analysis of the crosslinked 14-3-3 protein also identified eight pairs of crosslinked peptides, with Lys crosslinked with multiple nucleophilic amino acid residues including Asp, Gln, Glu, Met, Thr, and Tyr (FIGS. 13A-13G). The crosslinking pattern of each anchor Lys residue was different for NHQM and NHQM3C, and the Cα-Cα distances for NHQM3C were significantly longer than those for NHQM, reflecting their differences in rigidity and length. Taken together, these results show that NHQM and NHQM3C significantly expand the repertoire of natural amino acid residues targetable with small molecule crosslinkers, with a total of ten nucleophilic residues among which Asn, Gln, Met, and Arg have not been chemically crosslinked before.

Figure 14:
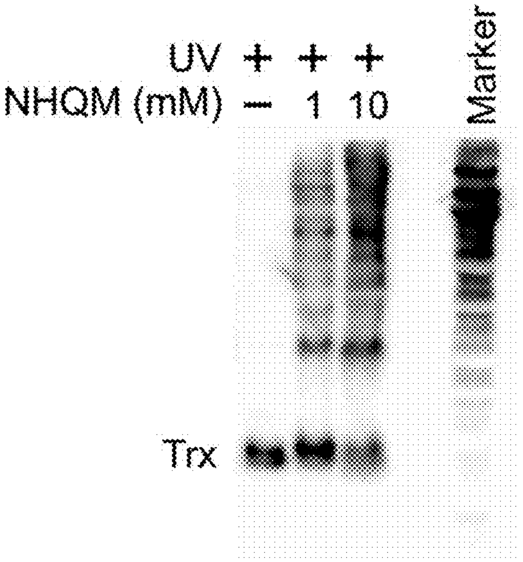
FIG. 14. NHQM crosslinked Trx with interacting proteins in *E. coli* cell lysate. Cell lysate of *E. coli* expressing Trx was added with 0, 1 or 10 mM NHQM, and treated with UV at wavelength 365 nm for 15 min. The samples were then analyzed with Western blot using an anti-His antibody to detect this His6 tag appended at the C-terminus of Trx.

We next explored potential applications of NHQM in various biological settings. We started by testing NHQM's ability to crosslink interacting proteins in *E. coli* cell lysates. Thioredoxin (Trx) is a ubiquitous oxidoreductase for the regulation of cellular redox and signaling by interacting with various proteins.[19] We expressed His-tagged Trx in *E. coli* cells, and then applied NHQM to the cell lysate followed by UV activation. Western blot analysis of the treated cell lysates showed that many endogenous proteins were crosslinked to Trx in the presence of 1 mM or 10 mM NHQM (FIG. 14). These results, together with the success of crosslinking 14-3-3 into dimer form in *E. coli* cell lysate (FIG. 9E), show that NHQM is compatible for crosslinking usage in *E. coli* cell lysate. We next attempted to apply NHQM directly to *E. coli* cells to crosslink the expressed 14-3-3 protein inside cells, but did not detect any 14-3-3 dimeric form on Western blot, possibly because NHQM could not enter *E. coli* cells efficiently.

Figure 15:
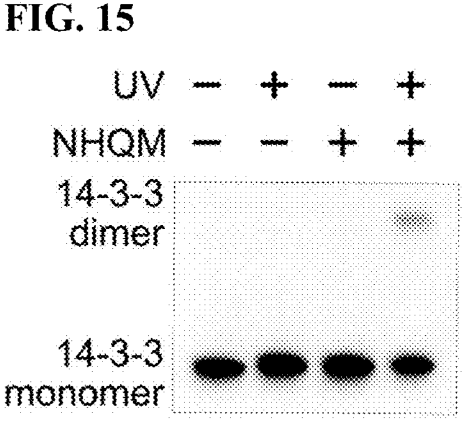
FIG. 15. NHQM mediated 14-3-3 crosslinking in mammalian cells detected by Western blot. The HEK 293T cells expressing 14-3-3 were treated with or without 4 mM NHQM, and with or without UV at wavelength 365 for 15 min. The samples were analyzed with Western blot using an anti-His antibody to detect 14-3-3 monomer and dimer.
Figure 16:
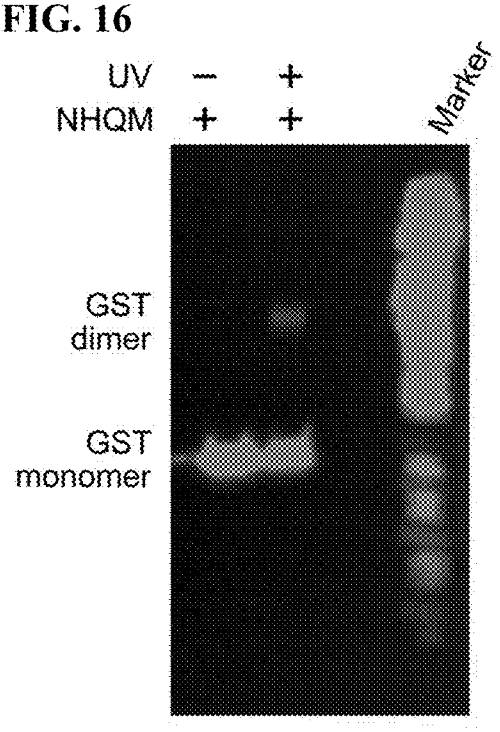
FIG. 16. NHQM mediated GST crosslinking in mammalian cells detected by Western blot. The HEK 293T cells expressing GST were treated with or without 4 mM NHQM, and with or without UV at wavelength 365 for 15 min. The samples were analyzed with Western blot using an anti-His antibody to detect GST monomer and dimer.
Figure 17:
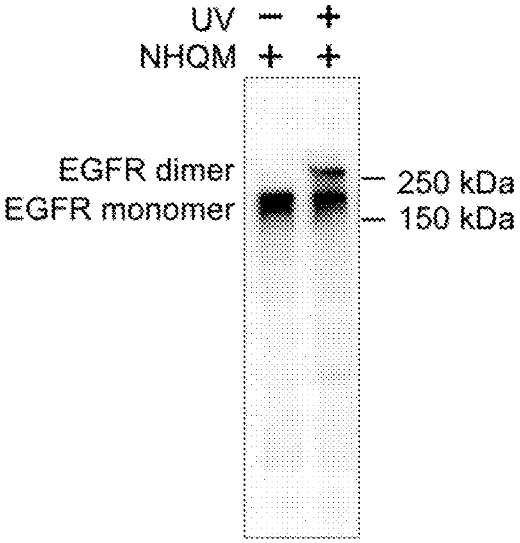
FIG. 17. NHQM mediated EGFR crosslinking in mammalian cells detected by Western blot. HEK 293T cells expressing EGFR via plasmid transfection were treated with 4 mM NHQM and with or without UV illumination (λ=365) for 15 min. The EGFR dimerization due to crosslinking was detected by Western blot using an anti-EGFR antibody.
Figure 18A:
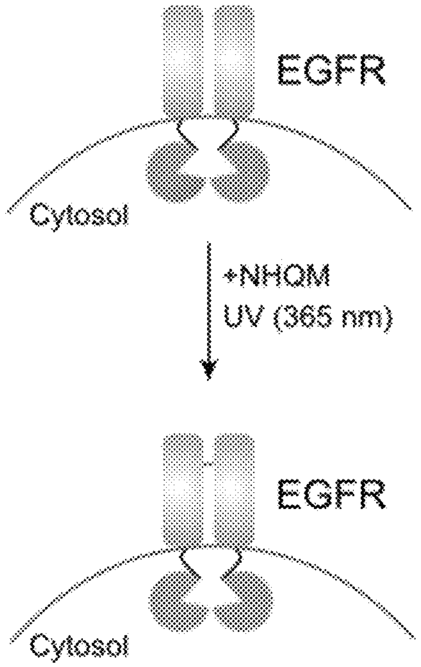
FIGS. 18A-18B. Photo-controlled dimeric crosslinking of EGFR on mammalian cell surface by NHQM.
Figure 18B:
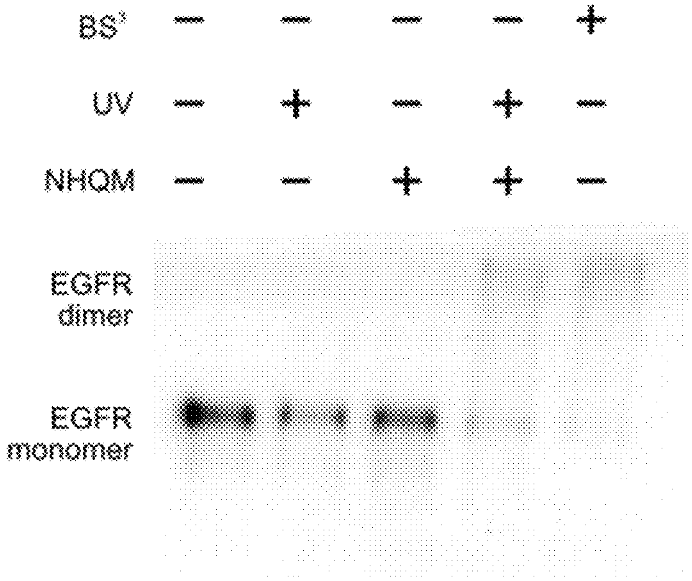

We subsequently tested NHQM's crosslinking ability in mammalian cells. We incubated NHQM with live mammalian cells expressing the dimeric glutathione transferase (GST)[9] or 14-3-3. In both cases, we detected crosslinking of a dimeric protein in response to light, albeit in low efficiency (<10%, FIGS. 15-16), suggesting NHQM could enter mammalian cells but at low efficiency. Therefore, we tested using NHQM to crosslink proteins on mammalian cell surfaces. NHQM was applied to HEK293T cells, which were transfected with plasmids to overexpress the epidermal growth factor receptor (EGFR). EGFR dimer was detected on Western blot in response to UV and NHQM, demonstrating NHQM crosslinking of the receptor with excellent optical control (FIG. 17). In addition, we further explored whether NHQM could probe endogenous mammalian proteins at physiologically relevant conditions. With this aim, we cultured MCF7 cells and treated them with or without NHQM, with or without UV, using the amine-reactive crosslinker bissulfosuccinimidyl suberate ($BS^3$) as a positive control. The EGFR dimerization was detected only in the presence of UV and NHQM, with crosslinking efficiency comparable to the commercial crosslinker $BS^3$ (FIGS. 18A-18B).

Figure 19A:
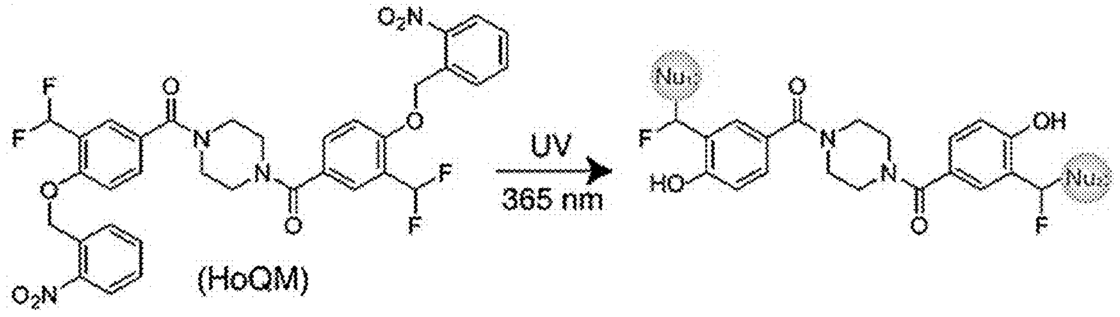
FIGS. 19A-19C. HoQM-mediated protein crosslinking in *E. coli* and mammalian cells.
Figure 19B:
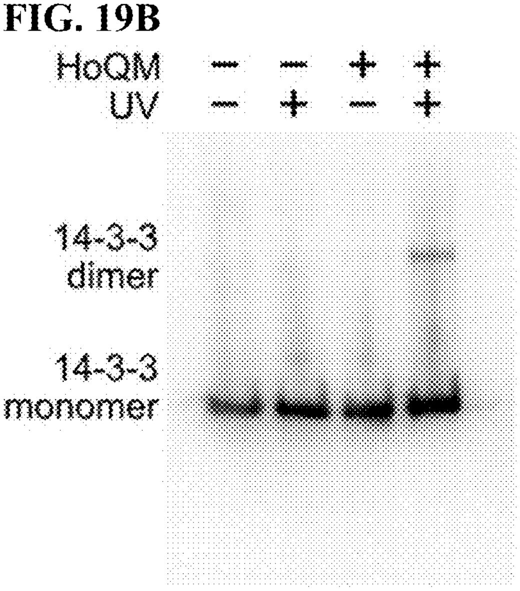
Figure 19C:
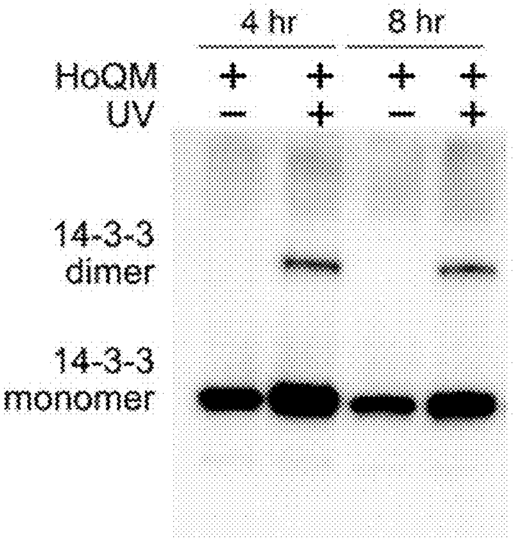
Figure 20:
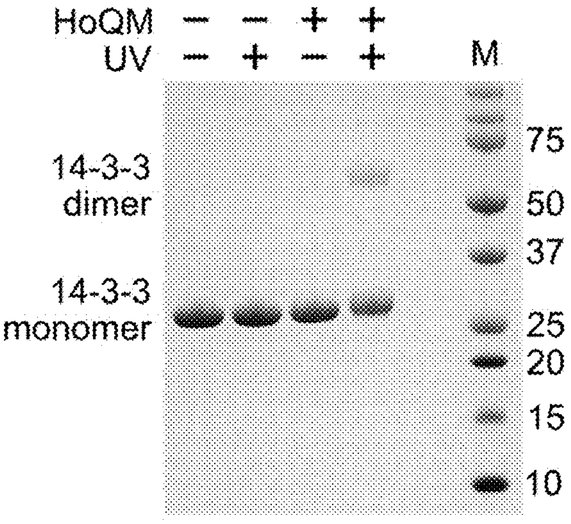
FIG. 20. HoQM crosslinked WT 14-3-3 into dimeric form in vitro. The WT 14-3-3 protein was treated with or without UV in the presence or absence of HoQM crosslinker, and the crosslinking was detected by running 10% Tris-tricine SDS-PAGE.

To enable efficient crosslinking in cells, we designed and synthesized a homobifunctional crosslinker HoQM, with photocaged o-QM at both ends (FIG. 19A). We reasoned that replacing NHS ester with the photocaged QM would remove chemical reactivity of the crosslinker prior to photoactivation, thus allowing it to enter cells without causing cytotoxicity. Additionally, QM at both ends could increase the diversity of crosslink types since QM reacts with more residues than NHS ester. As expected, HoQM crosslinked 14-3-3 into dimer in vitro upon light activation with comparable efficiency as NHQM (FIG. 20). We then incubated HoQM with *E. coli* cells for 1 h, and found it crosslinked 14-3-3 protein expressed in *E. coli* cells in dimeric form upon UV illumination (λ=365 nm) of intact cells for 15 min (FIG. 19B), which was infeasible with NHQM. In addition, we also incubated HoQM with HEK293T cells for different time duration without apparent toxicity; exposure of these cells to UV light (λ=365 nm) resulted in dimeric crosslinking of 14-3-3 protein expressed in the cells (FIG. 19C). These results demonstrated HoQM's ability to crosslink proteins inside live bacterial and mammalian cells.

Reagents to crosslink proteins with DNA remain sparse, because the reactivities of most crosslinkers favor protein-protein crosslinking over protein-DNA crosslinking. Formaldehyde is the primary reagent but fails to crosslink proteins not in close contact (2 Å) with DNA.[20] [21] [3] QM has been reported to alkylate deoxynucleosides efficiently.[22] We thus reasoned that NHQM should be able to crosslink protein with DNA. To test this possibility, we first incubated a single stranded DNA binding protein (SSB)[23] with a short DNA oligo of repeats, 19(3×)

(TGTAGCTGTTGATCTAAGTTGT

AGCTGTTGATCTAAGTTGTAGCT

GTTGATCTAAGT(SEQ ID NO: 4))
or

ATC(4x)
(AATTCGCCAATGACAAGACGCTG

GGCGGGGCCGGATCCATCATCATC

Figure 21A:
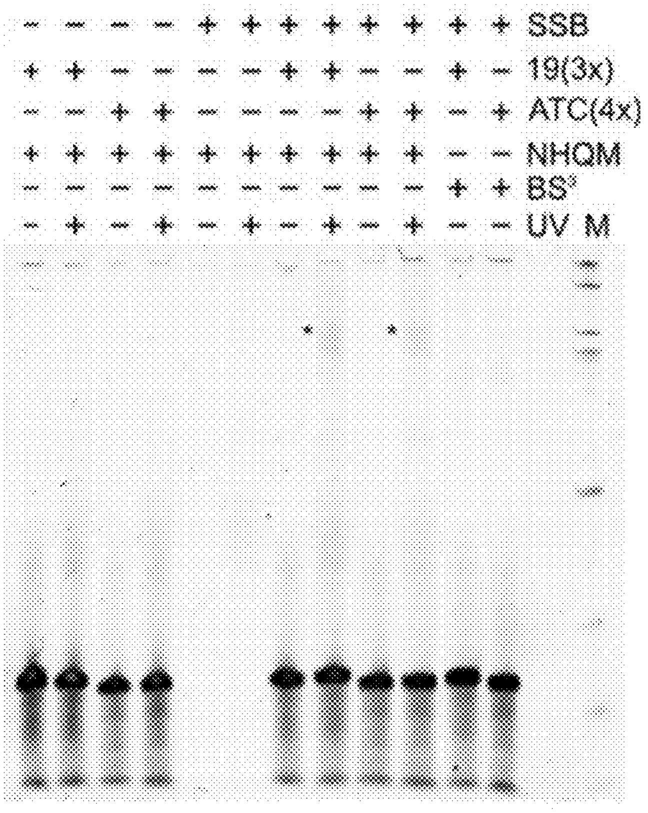
FIGS. 21A-21B. NHQM mediated protein-DNA crosslinking.
Figure 21B:
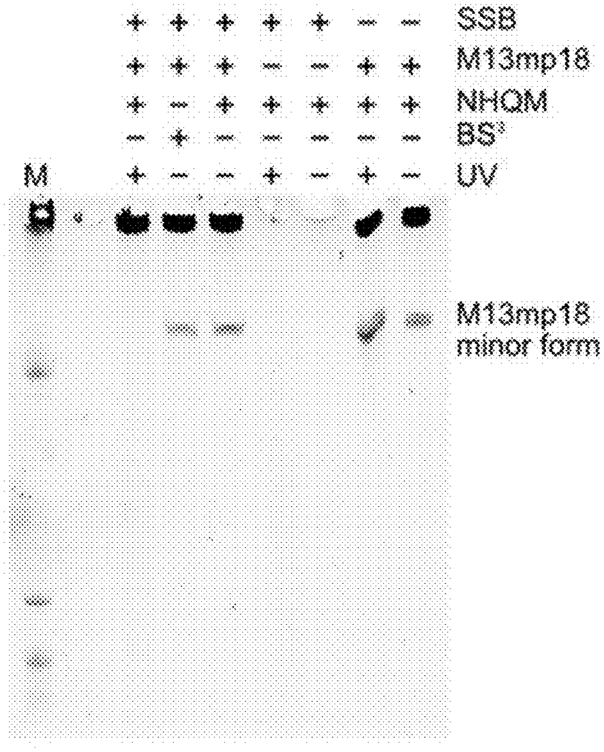
Figure 22A:
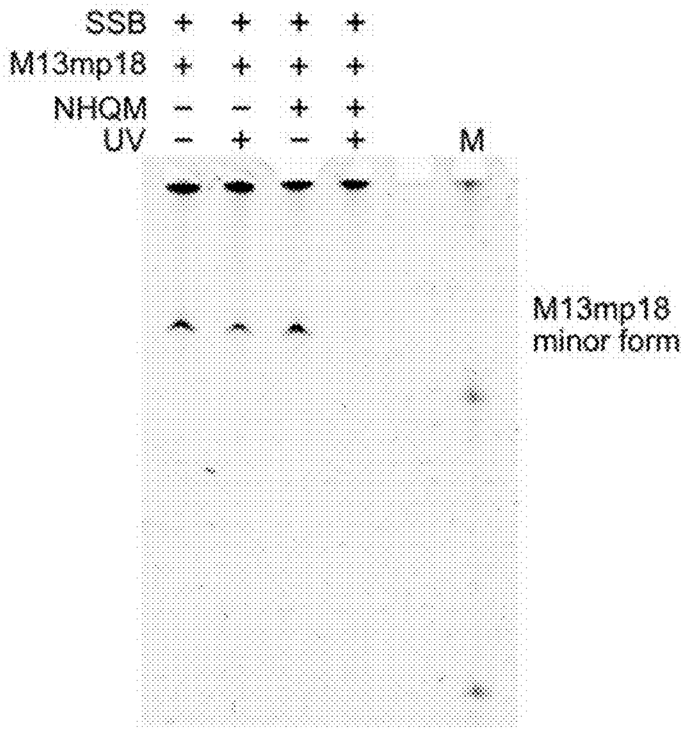
FIGS. 22A-22B. NHQM mediated protein-DNA crosslinking.
Figure 22B:
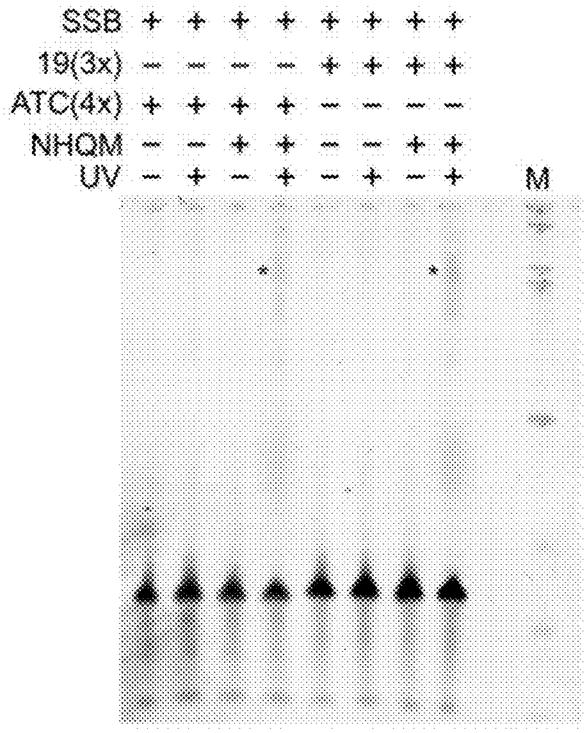
Figure 23:
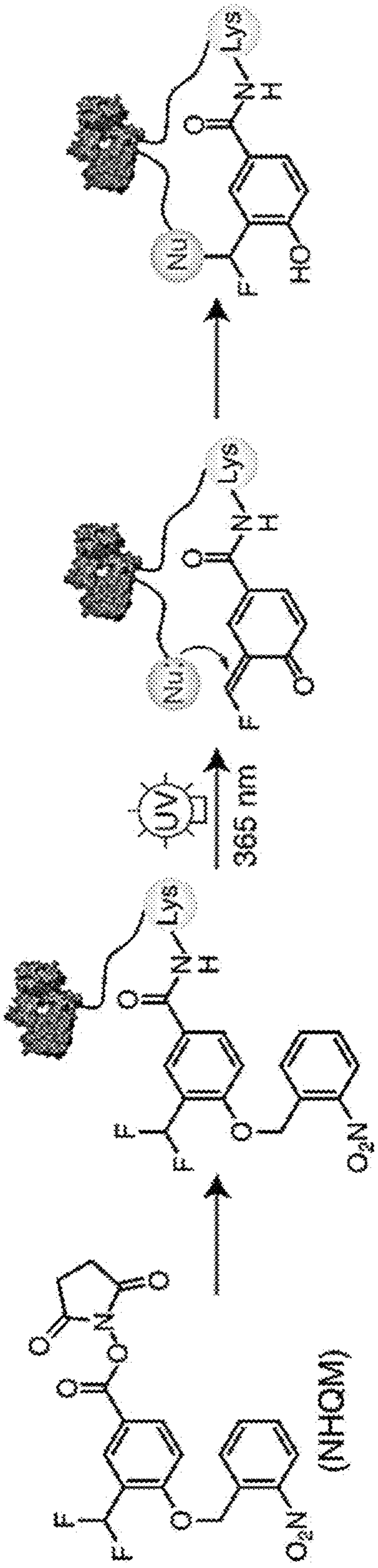
FIG. 23. Photocaged quinone methide crosslinkers for light-controlled chemical crosslinking of biomolecules strategy.

ATCTAGAAGCT(SEQ ID NO: 5))

that are reported to interact with SSB[24] [25] The SSB-DNA complex was treated with NHQM and UV activation, and analyzed by denaturing TBE-urea gel shift assay to detect covalent crosslinking between SSB and DNA. An upshifted band was only observed for the SSB-19(3×) or SSB-ATC (4×) complex treated with both NHQM and UV light (FIG. 21A), indicating successful protein-DNA crosslinking mediated by NHQM. As expected, the NHS ester-based amine reactive $BS^3$ crosslinker did not result in SSB-DNA crosslinking. We further investigated protein-DNA crosslinking by incubating a natural single stranded circular viral DNA M13mp18 with the SSB protein.[26] As shown in FIG. 21B (also FIGS. 22A-22B), the M13mp18 control DNA run as two isoforms in the denatured TBE-Urea gel due to its large size, a major form remained in the well and a minor form migrating in the gel. We found that only in the presence of both NHQM treatment and UV activation was the minor form of M13mp18 upshifted into the well, suggesting it was crosslinked with SSB, which further corroborates that NHQM has the potential for direct protein-DNA crosslinking.

In summary, we developed hetero- and homo-bifunctional photocaged quinone methide (PQM) crosslinkers for probing protein-protein and protein-DNA complexes. These PQM crosslinkers enable crosslinking Lys with a total of ten nucleophilic amino acid residues. In addition to Asp, Glu, Lys, Ser, Thr and Tyr, PQM crosslinkers notably crosslinked Gln, Arg, Asn, and Met residues hitherto untargetable by existing chemical crosslinkers, dramatically increasing the number of residues targetable with a single crosslinker. Such multiplicity of crosslinks will significantly expand the diversity of proteins amenable to CXMS and afford abundant restraints to facilitate structural modeling of challenging large protein complexes and intrinsically disordered proteins. PQM crosslinkers are photo-controlled, which can be utilized to gain spatiotemporal resolution. We demonstrated their usage in vitro, as well as in *E. coli* and mammalian cells to crosslink dimeric proteins and endogenous membrane integral receptors. We also showed that NHQM could directly crosslink proteins to DNA, for which few cross-linkers exist. We therefore expect that the photoactivatable and multitargeting reactivity of these PQM crosslinkers will be valuable for investigation of protein-protein and protein-DNA networks and structural biology through chemical crosslinking.

Example 5: Synthesis and Characterization of Compounds

Molecular cloning. Primers were synthesized and purified by Integrated DNA Technologies (IDT), and plasmids were sequenced by GENEWIZ. All molecular biology reagents were obtained from New England Biolabs. 14-3-3 gene were codon optimized for *E. coli* expression, and synthesized by GENEWIZ. EGFR-GFP was a gift from Alexander Sorkin (addgene plasmid #32751)[27]. Primers 14-3-3 NdeI for (GTTGTTCATATGGATAAAAATGAACTAGTA-CAAAAGGCTAAGTTG (SEQ ID NO:6)), 14-3-3 HindIII rev (GTTGTTAAGCTTTTAGTGATGGTGATGGT-GATGGTTTTCACCACCCTCACCCGCC TC (SEQ ID NO:7)) were used to clone 14-3-3 into pBAD vector; primers 14-3-3 QQR NdeI for (CATATGGATAAAAAT-GAACTAGTACAAAAGGCTAAGCAGCAGCGT-CAAGCTGA GCGCTAC (SEQ ID NO:8)) and 14-3-3 HindIII rev were used to obtain pBAD-14-3-3 QQR mutant; primers 14-3-3 HindIII for (GTTGTTAAGCTTGCCAC-CATGGATAAAAATGAACTAGTAC (SEQ ID NO:9)), 14-3-3 XhoI rev (GGTGGTCTCGAGTTAGTGATGGT-GATGGTGATGGTTTTCAC (SEQ ID NO:10)) were used to subclone 14-3-3 or 14-3-3 QQR from pBAD into pCDNA 3.1.

NHQM and HoQM Chemical Syntheses

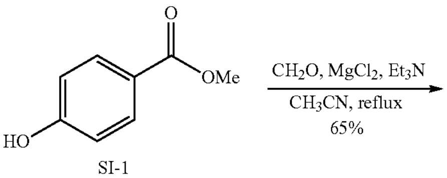

SI-1

-continued

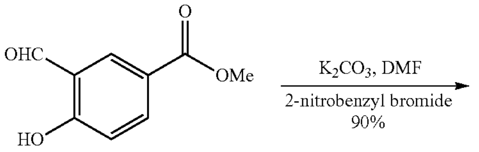

SI-2

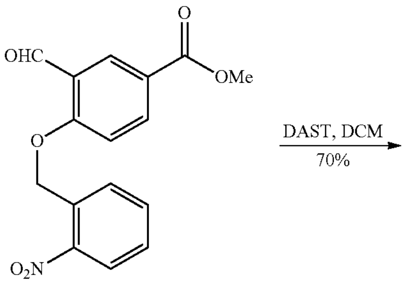

SI-3

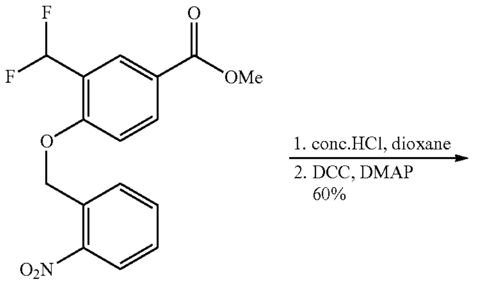

SI-4

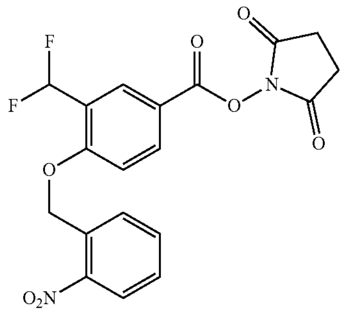

SI-5

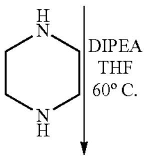

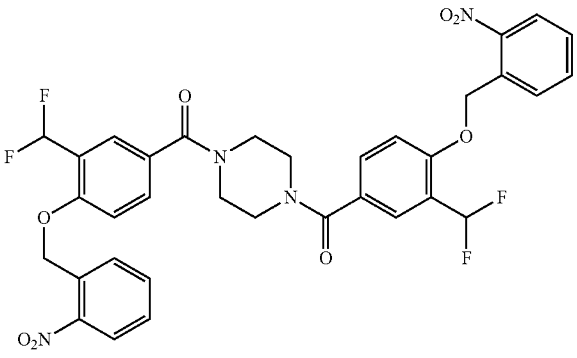

SI-6

-continued

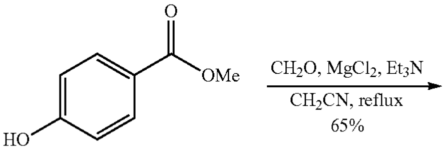

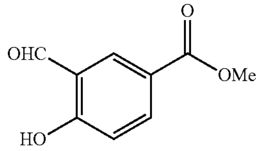

SI-2

Parafomaldehyde (2.1 g, 67.5 mmol, 6.75 equiv) was added to a mixture of the methyl 4-hydroxybenzoate (1.5 g, 10 mmol, 1.0 equiv), anhydrous $MgCl_2$ (1.4 g, 15 mmol, 1.5 equiv) and $Et_3N$ (5.3 mL, 37.5 mmol, 3.7 equiv) in $CH_3CN$ (50 mL), and the mixture was heated under reflux until consumption of the starting material as determined by TLC. After the reaction mixture was cooled to rt, the reaction was quenched with 1 M HCl and the product was extracted with EtOAc (50 mL×3). The organic layers were combined, washed with brine, dried over $Na_2SO_4$ and filtered. All volatiles were removed under reduced pressure and the product was isolated by flash chromatography (EtOAc/Hex) on silica gel (1.2 g, 65%). The NMR spectrum is the same as reported.

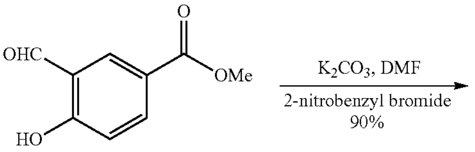

SI-2

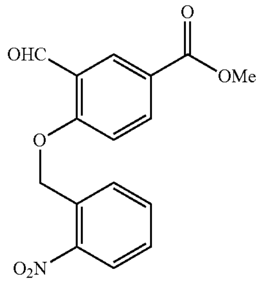

SI-3

Aldehyde SI-2 (2.00 g, 11.1 mmol, 1.0 equiv) from previous step in DMF was added $K_2CO_3$ (3.06 g, 22.2 mmol, 2.0 equiv). The reaction mixture was stirred at room temperature for 1 h. The reaction was quenched with saturated aqueous $NH_4Cl$ solution and the product was extracted with EtOAc (50 mL×3). The organic layers were combined, washed with brine, dried over $Na_2SO_4$ and filtered. All volatiles were removed under reduced pressure and the product was isolated by flash chromatography (EtOAc/Hex) on silica gel (3.1 g, 90%).

1H NMR (300 MHz, $CDCl_3$) δ 10.57 (s, 1H), 8.58 (d, J=2.1 Hz, 1H), 8.27 (t, J=7.7 Hz 1H), 7.97 (d, J=7.7 Hz, 1H), 7.79 (t, J=7.4 Hz, 1H), 7.59 (t, J=7.7 Hz, 1H), 7.17 (d, J=8.8 Hz, 1H), 5.72 (s, 2H), 3.95 (s, 3H); 13C NMR (75 MHz, $CDCl_3$): δ 188.5, 165.8, 162.9, 146.8, 137.2, 134.5, 132.1, 131.8, 129.0, 128.4, 125.4, 124.8, 123.8, 112.8, 67.7, 52.3.

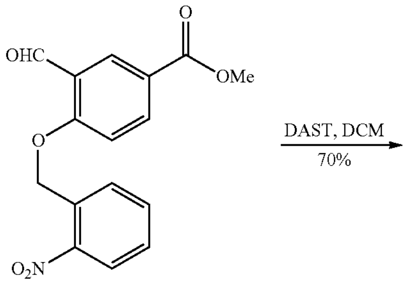

SI-3

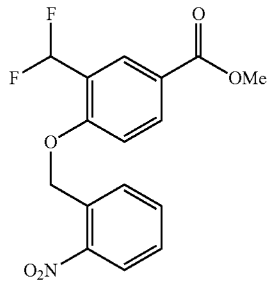

SI-4

Ester SI-3 (3.00 g, 9.52 mmol, 1.0 equiv) from previous step in DCM was slowly added DAST at 0° C. (3.37 g, 20.9 mmol, 2.2 equiv). The reaction mixture was slowly warmed to the room temperature and stirred for 2 h. The reaction was quenched with saturated aqueous $NH_4Cl$ solution and the product was extracted with EtOAc (50 mL×3). The organic layers were combined, washed with brine, dried over $Na_2SO_4$ and filtered. All volatiles were removed under reduced pressure and the product was isolated by flash chromatography (EtOAc/Hex) on silica gel (2.2 g, 90%).

1H NMR (300 MHz, $CDCl_3$) δ 8.32 (s, 1H), 8.24 (d, J=8.2 Hz, 1H), 8.17 (td, J=1.2, 8.5 Hz 1H), 7.85 (d, J=8.5 Hz, 1H), 7.75 (t, J=8.5 Hz, 1H), 7.57 (t, J=8.5 Hz, 1H), 7.08 (d, J=8.5 Hz, 1H), 7.03 (d, J=55.2 Hz, 1H), 5.66 (s, 2H), 3.94 (s, 3H); 13C NMR (75 MHz, $CDCl_3$): δ 165.9, 159.1, 146.7, 134.4, 134.1, 132.3, 128.8, 128.6 (t, J=6.8 Hz), 128.1, 125.2, 123.2 (t, J=43.9 Hz), 111.8, 111.4 (t, J=237.1 Hz), 67.3, 52.2.

-continued

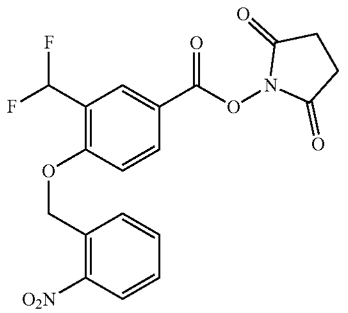

SI-5

The difluo SI-4 (100 mg, 0.3 mmol, 1.0 equiv) in 1,4-dioxane (5.00 mL) was added 0.5 mL of conc. HCl solution. The reaction mixture was stirred at 90° C. and monitored by TLC. After the starting material had been completely consumed by TLC, the mixture was cooled to room temperature. The white solid product was collected by filtration. The product was dried under high vacuum and then used directly for the next step.

The acid from previous step was dissolved in THE and added DCC (63.8 mg, 0.31 mmol, 1.01 equiv), N-hydroxysuccinimide (42.7 mg. 0.37 mmol, 1.2 equiv) and catalytic amount DMAP (1.84 mg, 0.015 mmol, 0.05 equiv). The reaction was stirred at room temperature for 12 h. The reaction was diluted with hexanes and remove the solid by filtration. The filtrate was concentrated under reduced pressure and the product was isolated by flash chromatography as white solid (78 mg, 60%).

1H NMR (300 MHz, $CDCl_3$) δ 8.41 (s, 1H), 8.26 (d, J=7.7 Hz, 2H), 7.82 (t, J=7.7 Hz 1H), 7.74 (d, J=7.7 Hz, 1H), 7.58 (t, J=7.7 Hz, 1H), 7.13 (d, J=8.5 Hz, 1H), 7.03 (d, J=55.2 Hz, 1H), 5.71 (s, 2H), 2.94 (s, 4H); 13C NMR (75 MHz, $CDCl_3$): δ 169.2, 160.7, 146.7, 135.3, 134.5, 131.8, 129.6 (t, J=6.8 Hz), 129.0, 128.1, 125.3, 118.1 (t, J=237.2 Hz), 112.3, 111.0, 67.6, 25.6.

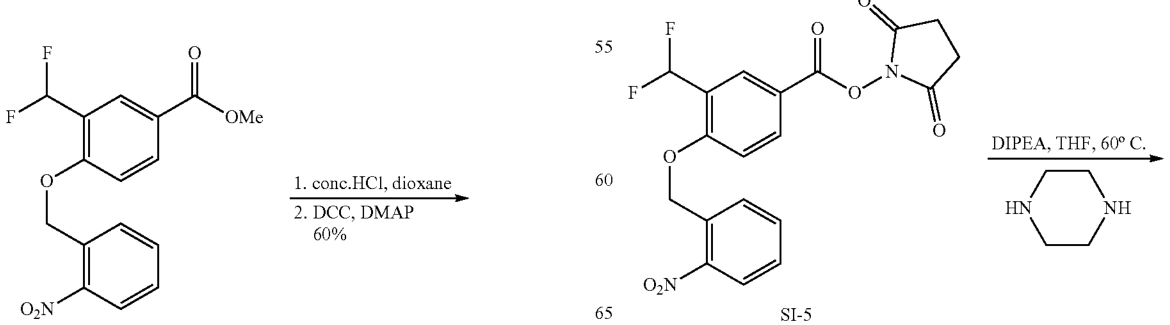

SI-4

SI-5

-continued

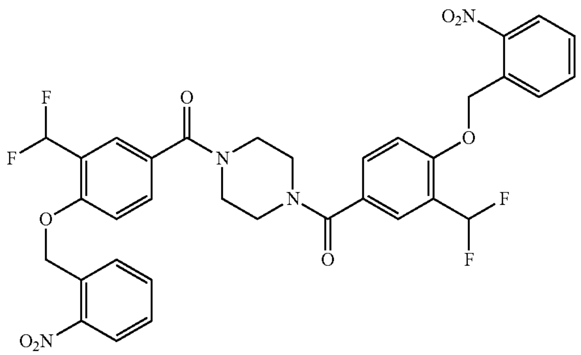

SI-6

The NHS ester SI-5 (38.0 mg, 90.4 μmol, 2.0 equiv.) in THF (5.00 mL) was added piperazine (3.8 mg, 45.2 μmol, 1.0 equiv.) and DIPEA (8.76 mg, 67.8 μmol, 1.5 equiv.). The reaction mixture was stirred overnight under reflux. After starting material was consumed, the reaction was cooled to the room temperature. The reaction was concentrated under reduced pressure and the product was isolated by flash chromatography as white solid (12.00 mg, 38.1%).

1H NMR (300 MHz, $CDCl_3$) δ 8.23 (d, J=8.0 Hz, 2H), 7.83 (d, J=8.0 Hz 2H), 7.76 (d, J=8.0 Hz, 2H), 7.70 (s, 2H), 7.58 (t, J=8.0 Hz, 4H), 7.09 (d, J=8.0 Hz, 2H), 7.03 (d, J=55.2 Hz, 2H), 5.63 (s, 4H), 3.69 (s, 8H); 13C NMR (75 MHz, $CDCl_3$): δ 169.4, 146.8, 134.3, 132.2, 131.7, 128.8 (t, J=6.8 Hz), 128.2, 126.2, 125.2, 123.2 (t, J=237.2 Hz), 112.3, 111.2, 67.3.

NHQM3C Chemical Synthesis

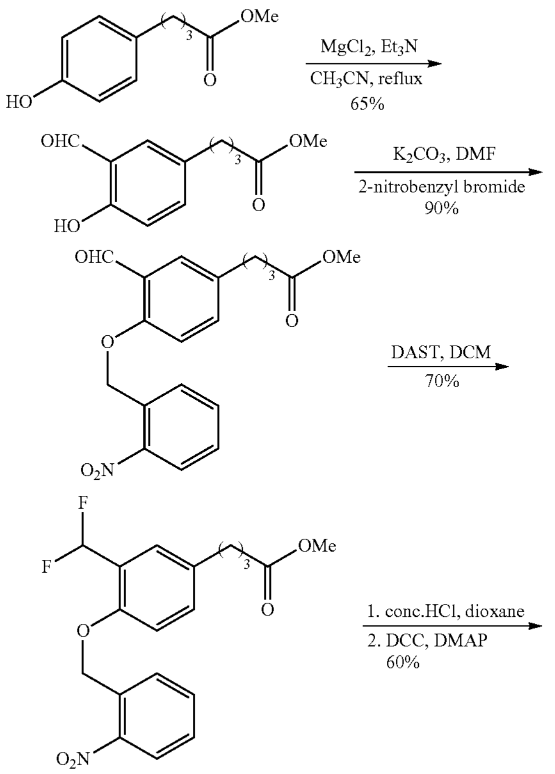

-continued

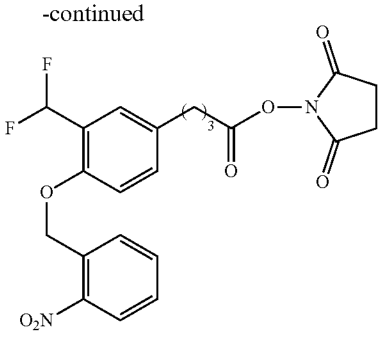

The NHQM3C chemical synthesis was carried out using the same procedures described in the above section for NHQM chemical synthesis, except for the different starting material shown in the scheme.

Protein expression and purification. For protein expression and purification of 14-3-3 WT or 14-3-3 QQR, plasmid pBAD-14-3-3 or pBAD-14-3-3 QQR was transformed into *E. coli* BL21(DE3), and plated on $L^{1B}$ argar plate supplemented with 100 μg/mL ampicillin. Several colonies were picked from above freshly transformed plate, and inoculated to 100 mL 2×YT (5 g/L NaCl, 16 g/L Tryptone, 10 g/L Yeast extract). The cells were grown at 37° C., 220 rpm to an OD 0.5, with good aeration and the relevant antibiotic selection. Then the medium was added with only 0.2% L-Arabinose, and the expression were carried out at 18° C., 220 rpm for 18-22 hr. The cells were harvested at 3000 g, 4° C. for 10 min. The cell pellet was washed with cold IMAC buffer (25 mM sodium phosphate, 20 mM imidazole, 500 mM NaCl, pH 7.5), and centrifuged again at 3000 g, 4° C. for 10 min, and resuspended in 15 mL IMAC buffer. The tube was then frozen on dry ice and stored in −80° C. For protein purification, the frozen cells were thawed quickly and resuspended well, and supplemented with EDTA free protease inhibitor cocktail, 0.5 mg/mL lysozyme, 1 μg/mL DNase, and vortex for 2 min. The cells then were opened by sonification, after which the cell lysis solution was centrifuged at 25,000 g at 4° C. for 40 min. The supernatant was collected and incubated with 1 mL TALON® Metal Affinity resin. After excessive wash with IMAC buffer, the protein was eluted five times with 1 mL 25 mM sodium phosphate, 500 mM imidazole, 500 mM NaCl, pH 7.5. The fractions containing the target protein were analyzed by running 10% Tris-tricine SDS-PAGE gel.

NHQM mediated 14-3-3 crosslinking in vitro. To test if NHQM could crosslink 14-3-3 protein in dimeric form, 8 μM WT 14-3-3 protein in PBS buffer, pH 7.4 were treated with or without 1 mM NHQM, with or without UV illumination for 15 mins at wavelength 365 nm. The reaction was then treated by adding 100 mM Tris-HCl, pH 7.5 and incubated at RT for 15 min. After that, the reaction mixture was immediately treated with SDS loading dye with 100 mM DTT, and samples were boiled at 95° C. for 5 mins and run in 10% Tris-tricine SDS-PAGE gel.

Utilizing NHQM to differentiate 14-3-3 dimer versus monomer. To test if NHQM crosslinking could differentiate dimer from monomer, 8 μM 14-3-3 WT or 14-3-3 QQR mutant in PBS buffer, pH 7.4 were treated with 0, 0.05, 0.1, 0.2, or 0.4 mM NHQM, and subjected to UV illumination for 15 min at wavelength 365 nm. The reaction was then treated by adding 100 mM Tris-HCl, pH 7.5 and incubated at RT for 15 min. The reaction mixture was immediately added with SDS loading dye containing 100 mM DTT, and the samples were boiled at 95° C. for 5 mins and run in 10% Tris-tricine SDS-PAGE gel.

NHQM mediated Trx crosslinking with interacting proteins in *E. coli* cell lysate. Plasmid pBAD-Trx was transformed into BL21(DE3) *E. coli* cells, and the Trx protein expression was carried out following procedures described above except that the cell culture volume was decreased to 20 mL. After protein expression, the cells were harvested and resuspended in 15 mL 50 mM sodium phosphate buffer containing 200 mM NaCI, pH 7.5. The cells were broken by sonification. 15 μL cell suspension were taken and added with 0, 1, or 10 mM NHQM and incubated at RT for 15 min, followed by UV illumination at wavelength 365 nm for another 15 min. The reaction was then treated by adding 100 mM Tris-HCI, pH 7.5 and incubated at RT for 15 min. The samples were then quickly treated with SDS loading dye containing 100 mM DTT, boiled at 95° C. for 5 min, and then analyzed with Western blot using anti-His antibody.

NHQM mediated 14-3-3, GST, or EGFR crosslinking in mammalian cells. Plasmid pCDNA3.1-14-3-3, pCDNA3.1-GST, or pCDNA3.1-EGFR (2 μg each) was transfected into one well of 6-well plate of HEK293T cells, respectively. After transfection, the cells were cultured at 37° C. for additional 24 hr. The cells were harvested and washed with PBS, pH 7.4 for one time, followed by resuspension in 50 μL PBS, pH 7.4. The cells were either added nothing or added with 4 mM NHQM and incubated at RT for 15 min. Then the cells were illuminated with or without UV at wavelength 365 nm for another 15 min. After that, the reaction was treated by adding 100 mM Tris-HCI, pH 7.5 and incubated at RT for 15 min. The samples were then quickly treated with 2×SDS loading dye containing 100 mM DTT, boiled at 95° C. for 5 mins, and analyzed by running Western blot using an anti-His antibody.

NHQM mediated endogenous EGFR crosslinking in MCF10A cells. The MCF10A cells were cultured in Mammary Epithelial Cell Growth Medium (PromoCell, C-21110). When the cell population reached 80% confluence, cells were harvested and washed with PBS, pH 7.4 for one time, followed by resuspension in four equal aliquots of 30 μL PBS, pH 7.4. The cells were treated with or without 1 mM NHQM and incubated at RT for 30 mins. Then the cells were illuminated with or without UV at wavelength 365 nm for another 15 min. After that, the reaction was treated by adding 100 mM Tris-HCI, pH 7.5 and incubated at RT for 15 min. The samples were then quickly treated with 2×SDS loading dye containing 100 mM DTT, boiled at 95° C. for 5 min, and analyzed with Western blot using an anti-His antibody.

HoQM mediated 14-3-3 crosslinking in vitro. To test if HoQM could crosslink 14-3-3 protein in dimeric form, 20 μM WT 14-3-3 in PBS buffer, pH 7.4 were treated with or without 1 mM HoQM, with or without UV illumination for 15 min at wavelength 365 nm. Then the reaction mixture was immediately treated with SDS loading dye containing 100 mM DTT, and the samples were boiled at 95° C. for 5 min followed by running in 10% Tris-tricine SDS-PAGE gel.

HoQM mediated 14-3-3 crosslinking in *E. coli* cells. To evaluate if HoQM could crosslink 14-3-3 directly in *E. coli* living cells, 100 μL *E. coli* BL21(DE3) cells expressing WT 14-3-3 protein with pBAD vector were spun down using a benchtop centrifuge. The cell pellet was then resuspended in 50 μL PBS, pH 7.4, and treated with or without 1 mM HoQM for 1 hr at RT, after which the samples were illuminated with or without UV at 365 nm for 15 min. Then the reaction mixture was immediately treated with 2×SDS loading dye containing 100 mM DTT, and the samples were vortexed for lysis, boiled at 95° C. for 5 min, and analyzed with Western blot using an anti-His antibody.

HoQM mediated 14-3-3 crosslinking in mammalian cells. Plasmid pCDNA3.1-14-3-3 (2 μg) was transfected into one well of 6-well plate of HEK293T cells. The media was changed to DMEM with 10% FBS after 15 hr. The cells were cultured at 37° C. for additional 24 hr. HoQM (0.6 mM) was directly added to the cell culture medium and incubated for an additional 4 hr or 8 hr. HoQM was removed by gently washing with PBS for one time. Then the cells in each time point were harvested, resuspended, and separated in 4 equals of 15 μL PBS, pH 7.4. The cells were subsequently illuminated with or without UV at wavelength 365 nm for another 10 min. The samples were then quickly treated with 2×SDS loading dye containing 100 mM DTT, boiled at 95° C. for 5 min, and analyzed with Western blot using an anti-His antibody.

NHQM mediated crosslinking of SSB protein with M13mp18 in vitro. To test crosslinking of M13mp18 DNA with the SSB protein using NHQM, in 10 μL reaction, 3 ng/μL M13mp18 was incubated with or without 0.7 mg/mL SSB protein at 37° C. for 30 min. The reaction mixture was then added with 1 mM NHQM and incubated at RT for 15 min, followed with or without UV illumination at wavelength 365 nm for another 15 min at RT. The reaction was treated by adding 100 mM Tris-HCI, pH 7.5 and incubated at RT for 15 min. The samples were then quickly treated with RNA loading dye containing 100 mM DTT, and were boiled at 95° C. for 5 min. The samples were quickly put on ice after boiling, and run in 5% TBE-Urea gel.

NHQM mediated crosslinking of SSB protein with 19(3×) or ATC(4×) in vitro. To test crosslinking of 19(3×) or ATC(4×) DNA with the SSB protein using NHQM, in 10 μL reaction, 1.5 μM 19(3×) or ATC(4×) was incubated with or without 0.2 mg/mL SSB protein at 37° C. for 30 min. The reaction mixture was then added with 1 mM NHQM and incubated at RT for 15 min, followed with or without UV illumination at wavelength 365 nm for another 15 min at RT. Then the reaction was treated by adding 100 mM Tris-HCI, pH 7.5 and incubated at RT for 15 min. The samples were then quickly treated with RNA loading dye containing 100 mM DTT, and were boiled at 95° C. for 5 min. The samples were quickly put on ice after boiling, and run in 5% TBE-Urea gel.

Tryptic digestion of cross-linked proteins. Protein digestion was carried out by following a procedure described previously.[28] Briefly, after crosslinking protein samples were quenched by adding 100 mM Tris-HCI, pH 7.4 for 15 min. The protein samples were then precipitated by adding six volumes of acetone at −20° C. for 30 min. Protein was collected by centrifugation for 10 min at 15,000 g. Precipitated proteins were dried in air and resuspended in 8 M urea, 100 mM Tris, pH 8.5. After reduction with 2 mM DTT for 20 min and alkylation with 10 mM iodoacetamide for 15 min in the dark, samples were diluted to 1 M urea with 100 mM Tris, pH 8.5, and digested with trypsin (at 50:1 protein: enzyme ratio) at 37° C. for 16 h. Digestion was terminated by adding formic acid at final concentration 5% (v/v). Digested peptides were desalted with C18 ZipTip, and eluted peptides were dried down with SpeedVac.

Mass spectrometry. Digested peptides were dissolved in 200 mM $NH_4HCO_3$ after clean-up and then subject to tandem mass spectrometry on a Thermo Q-Exactive Orbitrap. Crosslinked peptides. Peptides were separated by nano-LC Ultimate 3000 high-performance liquid chromatography system using an Acclaim PepMap C18 column (Thermo Scientific). Samples were analyzed with a 145 min 2%-95% acetonitrile gradient with 0.1% formic acid at flow rate 200 nL/min. The Q-Exactive mass spectrometer was operated in data-dependent mode with one full MS scan at R=70,000 (m/z=200) followed by ten HCD MS/MS scans at R=17,500 (m/z=200) using a stepped normalized collision energy of 28, 30, 35 eV. The AGC targets for the MS1 and MS2 scans were $3\times10^6$ and $1\times10^5$, respectively, and the maximum injection time for MS1 was 250 ms, and for MS2 was 200 ms. Precursors of the +1, +6 or above, or unassigned charge states were rejected; exclusion of isotopes was enabled; dynamic exclusion was set to 30 s. The crosslinking mass spectra were analyzed with pLink 2.3.[29]

REFERENCES FOR EXAMPLES 4-5

[1] C. Yu, L. Huang, *Anal. Chem.* 2017, 90, 144-165. [2] A. Sinz, *Angew. Chem. Int. Ed. Engl.* 2018, 57, 6390-6396. [3] E. A. Hoffman, B. L. Frey, L. M. Smith, D. T. Auble, *J. Biol. Chem.* 2015, 290, 26404-26411. [4] R. B. Bass, S. L. Butler, S. A. Chervitz, S. L. Gloor, J. J. Falke, *Methods Enzymol.* 2007, 423, 25-51. [5] P. Novak, G. H. Kruppa, 2008, 14, 355-365. [6] A. Leitner, L. A. Joachimiak, P. Unverdorben, T. Walzthoeni, J. Frydman, F. Förster, R. Aebersold, *Proc. Natl. Acad. Sci. U.S.A.* 2014, 111, 9455-9460. [7]C. B. Gutierrez, C. Yu, E. J. Novitsky, A. S. Huszagh, S. D. Rychnovsky, L. Huang, *Anal. Chem.* 2016, 88, 8315-8322. [8] B. Yang, H. Wu, P. D. Schnier, Y. Liu, J. Liu, N. Wang, W. F. DeGrado, L. Wang, *Proc. Natl. Acad. Sci. U.S.A.* 2018, 115, 11162-11167. [9] M. Suchanek, M. Suchanek, A. Radzikowska, A. Radzikowska, C. Thiele, C. Thiele, *Nat. Methods* 2005, 2, 261-267. [10] P. Lössl, A. Sinz, *Methods Mol. Biol.* 2016, 1394, 109-127. [11] M. M. Toteva, J. P. Richard, *Adv Phys Org Chem* 2011, 45, 39-91. [12] W.-J. Bai, J. G. David, Z.-G. Feng, M. G. Weaver, K.-L. Wu, T. R. R. Pettus, *Acc. Chem. Res.* 2014, 47, 3655-3664. [13] S. Gnaim, D. Shabat, *Acc. Chem. Res.* 2014, 47, 2970-2984. [14] A. Parra, M. Tortosa, *ChemCatChem* 2015, 7, 1524-1526. [15] J. Liu, S. Li, N. A. Aslam, F. Zheng, B. Yang, R. Cheng, N. Wang, S. Rozovsky, P. G. Wang, Q. Wang, et al., *J. Am. Chem. Soc.* 2019, 141, 9458-9462. [16] H. A. Fu, R. R. Subramanian, S. C. Masters, *Annu. Rev. Pharmacol. Toxicol.* 2000, 40, 617-647. [17] N. N. Sluchanko, M. V. Sudnitsyna, A. S. Seit-Nebi, A. A. Antson, N. B. Gusev, *Biochemistry* 2011, 50, 9797-9808. [18] N. N. Sluchanko, N. V. Artemova, M. V. Sudnitsyna, I. V. Safenkova, A. A. Antson, D. I. Levitsky, N. B. Gusev, *Biochemistry* 2012, 51, 6127-6138. [19] S. Lee, S. M. Kim, R. T. Lee, *Antioxid. Redox. Signal.* 2013, 18, 1165-1207. [20] D. E. Nowak, B. Tian, A. R. Brasier, *BioTechniques* 2005, 39, 715-725. [21] T. Aoki, D. Wolle, E. Preger-Ben Noon, Q. Dai, E. C. Lai, P. Schedl, *Fly* 2014, 8, 43-51. [22] P. Pande, J. Shearer, J. Yang, W. A. Greenberg, S. E. Rokita, *J. Am. Chem. Soc.* 1999, 121, 6773-6779. [23] S. Raghunathan, A. G. Kozlov, T. M. Lohman, G. Waksman, *Nat. Struct. Biol.* 2000, 7, 648-652. [24] M. Mitas, J. Y. Chock, M. Christy, *Biochem. J.* 1997, 324 (Pt 3), 957-961. [25] H. Steen, J. Petersen, M. Mann, O. N. Jensen, *Protein Sci.* 2001, 10, 1989-2001. [26] A. C. Syvanen, M. Alanen, H. Soderlund, *Nucleic Acids Res.* 1985, 13, 2789-2802. [27] R. E. Carter, A. Sorkin, *J. Biol. Chem.* 1998, 273, 35000-35007. [28] B. Yang, H. Wu, P. D. Schnier, Y. Liu, J. Liu, N. Wang, W. F. DeGrado, L. Wang, *Proc. Natl. Acad. Sci. U.S.A.* 2018, 115, 11162-11167. [29] a) B. Yang, Y. J. Wu, M. Zhu, S. B. Fan, J. Lin, K. Zhang, S. Li, H. Chi, Y. X. Li, H. F. Chen, S. K. Luo, Y. H. Ding, L. H. Wang, Z. Hao, L. Y. Xiu, S. Chen, K. Ye, S. M. He, M. Q. Dong, *Nat. Methods* 2012, 9, 904-906; b) S. Lu, S.-B. Fan, B. Yang, Y.-X. Li, J.-M. Meng, L. Wu, P. Li, K. Zhang, M.-J. Zhang, Y. Fu, J. Luo, R.-X. Sun, S.-M. He, M.-Q. Dong, *Nat. Methods* 2015, 12, 329.

What is claimed is:

1. A method of detecting a covalently conjugated biomolecule comprising a first biomolecule conjugated to a second biomolecule, said method comprising i) contacting the first biomolecule and the second biomolecule with a crosslinking agent to form the covalently conjugated biomolecule;

ii) identifying a first point of attachment of the crosslinking agent to the first biomolecule using mass spectroscopy; and iii) identifying a second point of attachment of the crosslinking agent to the second biomolecule using mass spectroscopy;

thereby detecting the covalently conjugated biomolecule; wherein the crosslinking agent has the formula:

$$R^1\text{-}L^1\text{-}R^2 \quad (I);$$

wherein $R^1$ is a bioconjugate reactive moiety;

$R^2$ is

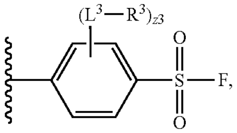 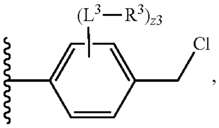 ,

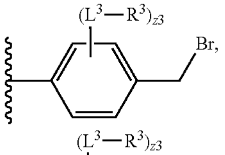 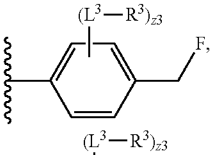

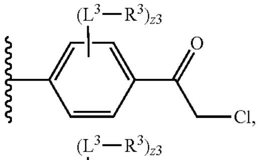 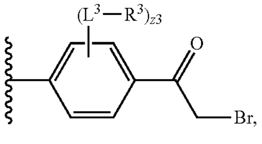

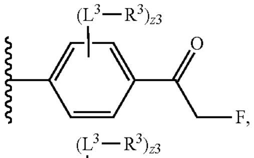

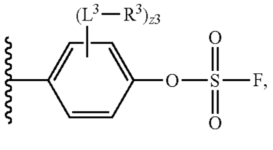 or 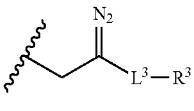 ;

$L^3$ is independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety;

z3 is an integer from 0 to 4;

L' is a covalent linker; and wherein the bonding reactivity of $R^1$ with said first biomolecule is greater than the bonding reactivity of $R^2$ with said second biomolecule.

2. A method of detecting an intramolecular crosslinked protein, said method comprising:

i) contacting the protein with a crosslinking agent, wherein said crosslinking agent bonds to a first amino acid of said protein and a second amino acid of said protein to form the intramolecular crosslinked protein;

ii) identifying a first point of attachment of said crosslinking agent to said protein using mass spectroscopy; and iii) identifying a second point of attachment of said crosslinking agent to said protein using mass spectroscopy;

wherein the crosslinking agent has the formula:

$$R^1\text{-}L^1\text{-}R^2 \quad (I);$$

wherein $R^1$ is a bioconjugate reactive moiety;

$R^2$ is

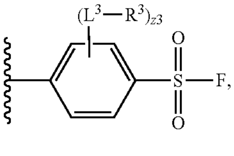 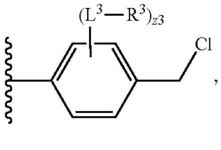 ,

-continued

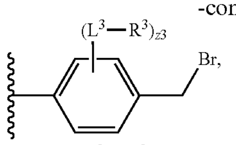
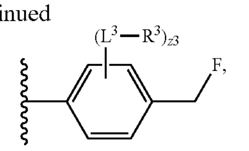
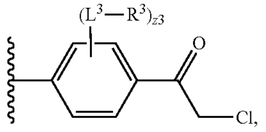
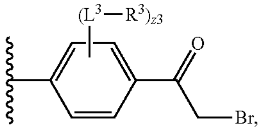
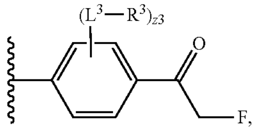
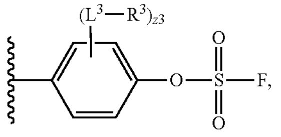 or 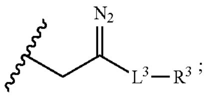

$L^3$ is independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety;

z3 is an integer from 0 to 4;

$L^1$ is a covalent linker; and wherein the bonding reactivity of $R^1$ with said first amino acid is greater than the bonding reactivity of $R^2$ with said second amino acid.

3. The method of claim 1, wherein $R^1$ is

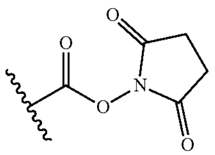 , 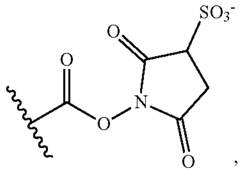 ,

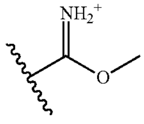 , 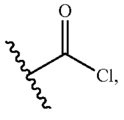 or 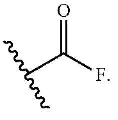

4. The method of claim 1, wherein $L^1$ has the formula:

$-L^{1A}-L^{1B}-L^{1C}-L^{1D}-$;

wherein $L^{1A}$ is connected directly to $R^1$;

$L^{1A}$, $L^{1B}$, $L^{1C}$, and $L^{1D}$ are independently a bond, —N($R^{10}$)—, —C(O)—, —C(O)N ($R^{10}$)—, —N($R^{10}$)C(O)—, —N(H)—, —C(O)N(H)—, —N(H)C(O)—, —C(O)O—, —OC(O)—, —$S(O)_2$—, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker; and $R^{10}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

5. A crosslinking agent having the formula $R^1-L^1-R^2$ (I);

wherein $R^1$ is a bioconjugate reactive moiety;

$R^2$ is

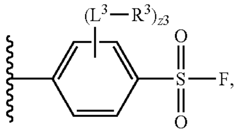 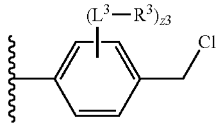 ,
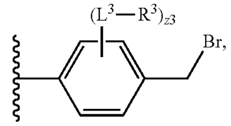 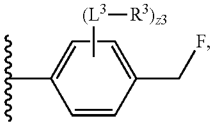
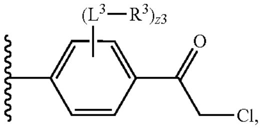 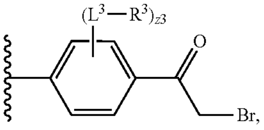
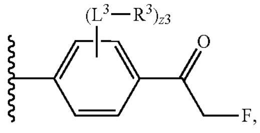 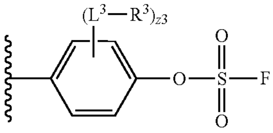 , or
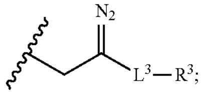

$L^3$ is independently a bond, —$S(O)_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a bioconjugate reactive moiety;

z3 is an integer from 0 to 4;

$L^1$ is a covalent linker; and wherein the bonding reactivity of $R^1$ with a first biomolecule is greater than the bonding reactivity of $R^2$ with a second biomolecule.

6. The method of claim 1, wherein $R^2$ is

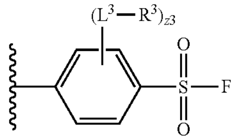

or

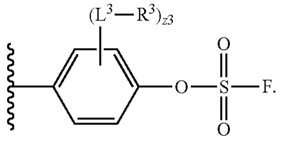

7. The method of claim 1, wherein $R^1$ is

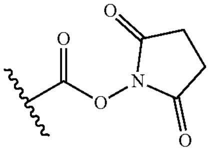

or

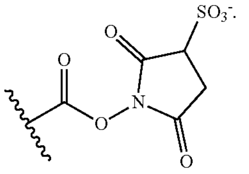

8. The method of claim 1, wherein $L^1$ is

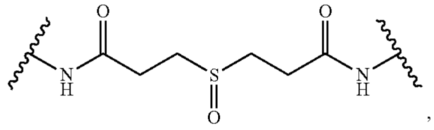

,

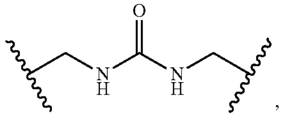

,

-continued

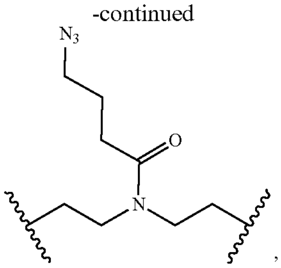

,

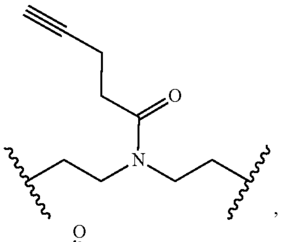

, or

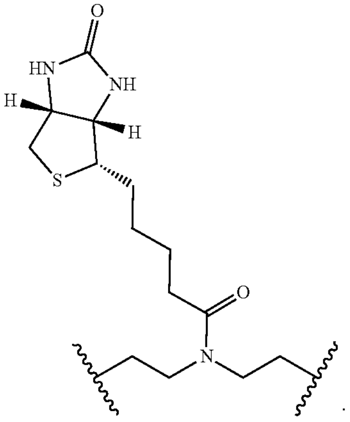

.

9. The method of claim 1, wherein the crosslinking agent has the formula:

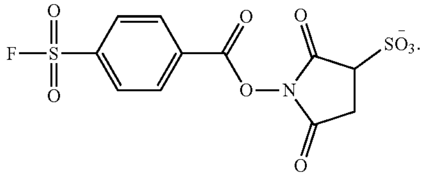

10. The method of claim 1, wherein the first biomolecule is a protein, nucleic acid, or glycan; and the second biomolecule is a protein, nucleic acid, or glycan.

11. The method of claim 1, wherein the first biomolecule is a first protein; and the second biomolecule is a second protein, $R^1$ is a bioconjugate reactive moiety reactive with a first amino acid of said first protein, and $R^2$ is a proximity enhanced bioconjugate reactive moiety reactive with said second amino acid of said second protein.

12. The method of claim 1, wherein $R^1$ reacts with an amine moiety of said first biomolecule, carboxylate moiety of said first biomolecule, or sulfhydryl moiety of said first biomolecule and $R^2$ reacts with an amine moiety of said second biomolecule, imidazolyl moiety of said second biomolecule, or hydroxyl moiety of said second biomolecule.

13. The method of claim 1, wherein $R^1$ reacts with an amino terminus of said first biomolecule, a lysine side chain of said first biomolecule, a glutamate side chain of said first amino acid of said first biomolecule, an aspartate side chain of said first amino acid of said first biomolecule, or a cysteine side chain of said first amino acid of said first biomolecule and $R^2$ reacts with an amino terminus of said second biomolecule, a lysine side chain of said second amino acid of said second biomolecule, a histidine side chain of said second amino acid of said second biomolecule, a serine side chain of said second amino acid of said second biomolecule, a threonine side chain of said second amino acid of said second biomolecule, or a tyrosine side chain of said second amino acid of said biomolecule.

14. The method of claim 1, wherein the first point of attachment is an amino terminus of said first biomolecule, a lysine side chain of said first biomolecule, a glutamate side chain of said first biomolecule, an aspartate side chain of said first biomolecule, or a cysteine side chain of said first biomolecule and wherein the second point of attachment is an amino terminus of said second biomolecule, a lysine side chain of said second biomolecule, a histidine side chain of said second biomolecule, a serine side chain of said second biomolecule, a threonine side chain of said second biomolecule, or a tyrosine side chain of said second biomolecule.

15. The method of claim 2, wherein $R^2$ is

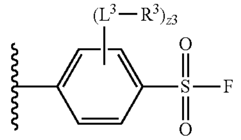

or

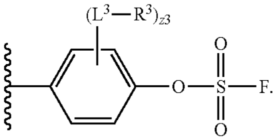

16. The method of claim 2, wherein $R^1$ is

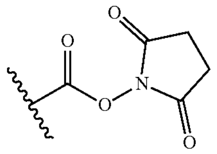

,

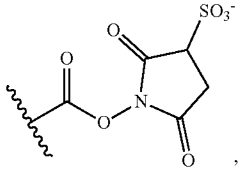

,

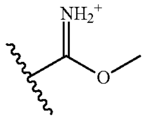

,

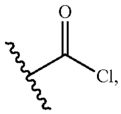

or

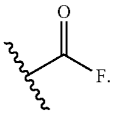

17. The method of claim 2, wherein $R^1$ is

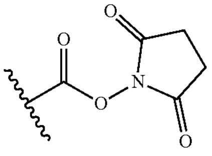

or

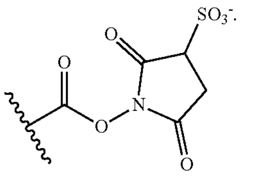

18. The method of claim 2, wherein $L^1$ has the formula:

$-L^{1A}-L^{1B}-L^{1C}-L^{1D}-$;

wherein $L^1A$ is connected directly to $R^1$;

$L^{1A}$, $L^{1B}$, $L^{1C}$, and $L^{1D}$ are independently a bond, $—N(R^{10})—$, —C(O)—, $—C(O)N(R^{10})—$, $—N(R^{10})C(O)—$, —N(H)—, —C(O)N(H)—, —N(H)C(O)—, —C(O)O—, —OC(O)—, $—S(O)_2—$, —S(O)—, —O—, —S—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker; and $R^{10}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

19. The method of claim 2, wherein $L^1$ is

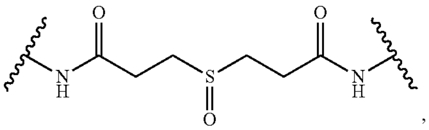

,

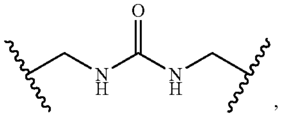

,

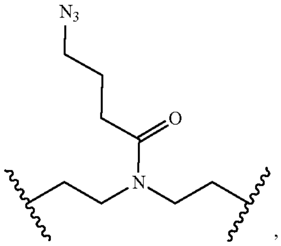

,

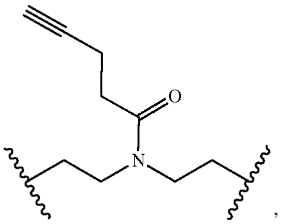

, or

-continued

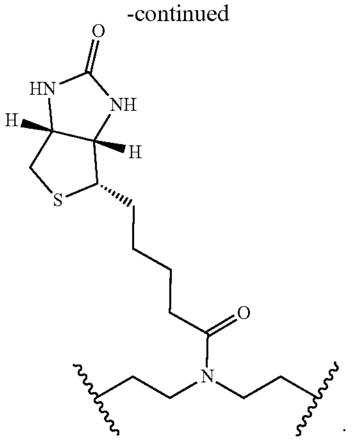

20. The method of claim 2, wherein the crosslinking agent has the formula:

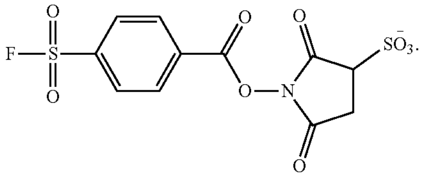

21. The method of claim 2, wherein $R^1$ reacts with an amine moiety of said protein, a carboxylate moiety of said protein, or a sulfhydryl moiety of said protein and wherein $R^2$ reacts with an amine moiety of said protein, imidazolyl moiety of said protein, or hydroxyl moiety of said protein.

22. The method of claim 2, wherein $R^1$ reacts with an amino terminus of said protein, a lysine side chain of said protein, a glutamate side chain of said first amino acid of said protein, an aspartate side chain of said first amino acid of said protein, or a cysteine side chain of said first amino acid of said protein, and $R^2$ reacts with an amino terminus of said protein, a lysine side chain of said second amino acid of said protein, a histidine side chain of said second amino acid of said protein, a serine side chain of said second amino acid of said protein, a threonine side chain of said second amino acid of said protein, or a tyrosine side chain of said second amino acid of said protein.

23. The method of claim 2, wherein the first point of attachment is an amino terminus of said protein, a lysine side chain of said protein, a glutamate side chain of said protein, an aspartate side chain of said protein, or a cysteine side chain of said protein and wherein the second point of attachment is an amino terminus of said protein, a lysine side chain of said protein, a histidine side chain of said protein, a serine side chain of said protein, a threonine side chain of said protein, or a tyrosine side chain of said protein.

24. The crosslinking agent of claim 5, wherein $R^2$ is

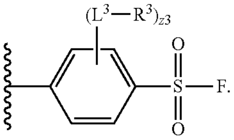

25. The crosslinking agent of claim 5, wherein $R^2$ is

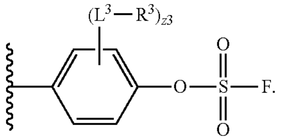

26. The crosslinking agent of claim 5, wherein $R^1$ is

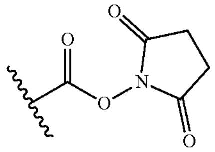 , 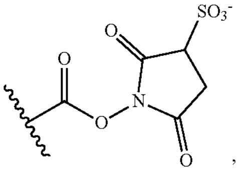 ,

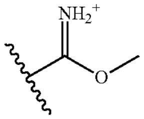 , 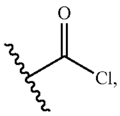 or 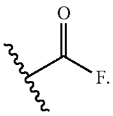

27. The crosslinking agent of claim 5, wherein $R^1$ is

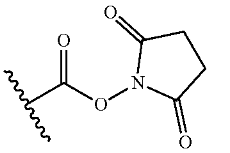 or 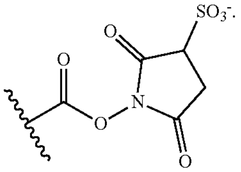

28. The crosslinking agent of claim 5, wherein $L^1$ has the formula:

$$-L^{1A}-L^{1B}-L^{1C}-L^{1D}-;$$

wherein $L^{1A}$ is connected directly to $R^1$;

$L^{1A}$, $L^{1B}$, $L^{1C}$, and $L^{1D}$ are independently a bond, $—N(R^{10})—$, $—C(O)—$, $—C(O)N(R^{10})—$, $—N(R^{10})C(O)—$, $—N(H)—$, $—C(O)N(H)—$, $—N(H)C(O)—$, $—C(O)O—$, $—OC(O)—$, $—S(O)_2—$, $—S(O)—$, $—O—$, $—S—$, $—NHC(O)NH—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker; and $R^{10}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

29. The crosslinking agent of claim 5, wherein $L^1$ is
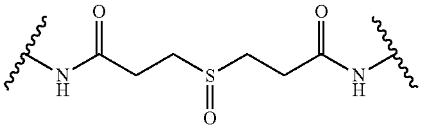
,
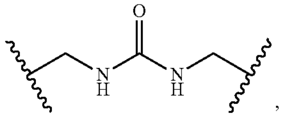
,
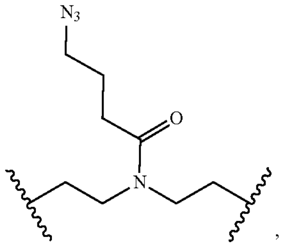
,
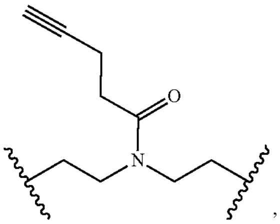
, or
-continued
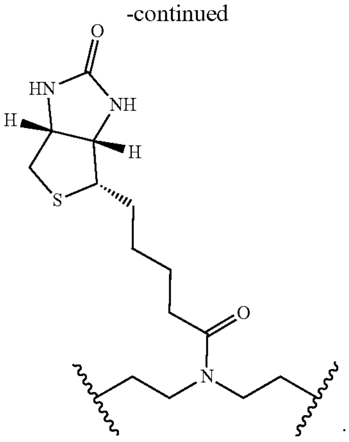
.
30. The crosslinking agent of claim 5, wherein the crosslinking agent has the formula:
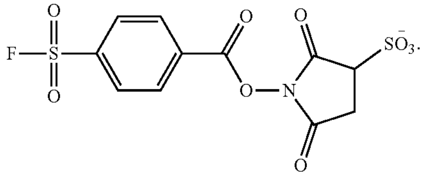
* * * * *